US 7,201,912 B2

(12) United States Patent
Park et al.

(10) Patent No.: US 7,201,912 B2
(45) Date of Patent: Apr. 10, 2007

(54) RECOMBINANT IMMUNOGENIC COMPOSITIONS AND METHODS FOR PROTECTING AGAINST LETHAL INFECTIONS FROM *BACILLUS ANTHRACIS*

(75) Inventors: Sukjoon Park, East Lansing, MI (US); Lallan Giri, Haslett, MI (US)

(73) Assignee: Emergent BioDefense Operation Lansing Inc., Lansing, MI (US)

(*) Notice: Subject to any disclaimer, the term of this patent is extended or adjusted under 35 U.S.C. 154(b) by 311 days.

(21) Appl. No.: 10/402,466

(22) Filed: Mar. 28, 2003

(65) Prior Publication Data

US 2004/0028695 A1 Feb. 12, 2004

Related U.S. Application Data

(60) Provisional application No. 60/372,152, filed on Apr. 12, 2002.

(51) Int. Cl.
*A61K 39/07* (2006.01)
(52) U.S. Cl. .............. 424/246.1; 424/234.1; 424/184.1; 424/190.1; 424/823
(58) Field of Classification Search ............... 530/350; 424/190.1
See application file for complete search history.

(56) References Cited

U.S. PATENT DOCUMENTS

| 5,591,631 A * | 1/1997 | Leppla et al. ............. 435/252.3 |
| 5,677,274 A * | 10/1997 | Leppla et al. ................. 514/2 |
| 5,840,312 A | 11/1998 | Mock et al. |
| 6,316,006 B1 | 11/2001 | Worsham et al. |
| 6,387,665 B1 | 5/2002 | Ivins et al. |
| 6,528,063 B2 | 3/2003 | Stram et al. |
| 6,592,872 B1 * | 7/2003 | Klimpel et al. ........ 424/197.11 |
| 2002/0034512 A1 | 3/2002 | Ivins et al. |
| 2002/0039588 A1 * | 4/2002 | Collier et al. ............ 424/246.1 |
| 2002/0051791 A1 * | 5/2002 | Galloway et al. ........ 424/190.1 |
| 2002/0197272 A1 | 12/2002 | Galloway et al. |
| 2003/0003109 A1 * | 1/2003 | Galloway et al. ........ 424/190.1 |

FOREIGN PATENT DOCUMENTS

| WO | 97/23236 | * | 7/1997 |
| WO | 98/11914 | * | 3/1998 |
| WO | WO 01/21656 A2 | * | 3/2001 |

OTHER PUBLICATIONS

Singh, Y et al, The Journal of Biological Chemistry, vol. 269 (46), Nov. 18, 1994, pp. 29039-29046, The Chymotrypsin-sensitive site, FFD315, in Anthrax toxin Protective antigen is required for translocation of lethal factor.*

(Continued)

Primary Examiner—Mark Navarro
Assistant Examiner—Ginny Allen Portner
(74) Attorney, Agent, or Firm—Finnegan, Henderson, Farabow, Garrett & Dunner LLP

(57) ABSTRACT

Recombinant immunogenic compositions and methods for protecting against lethal infections from *Bacillus anthracis* having a variant of recombinant *Bacillus anthracis* protective antigen (rPA) and a variant of recombinant *Bacillus anthracis* lethal factor (rLF). These proteins may be expressed separately or as a fusion protein. The recombinant proteins are produced in an avirulent strain of *Bacillus anthracis* that overproduces the desired antigens. The compositions and methods induce the animal host to produce antibodies against a virulent strain of *Bacillus anthracis*.

8 Claims, 83 Drawing Sheets

CANDIDATES

☒ Total anti-Pa IgG (μg/ml) after one vaccination
☐ Total anti-PA IgG (μg/ml) after two vaccinations

OTHER PUBLICATIONS

Arora, N et al, The Journal of Biological Chemistry, vol. 268(5), pp. 3334-3341, Feb. 15, 1993, Residues 1-254 of anthrax toxin lethal factor are sufficient to cause cellular uptake of fused polypeptides.*

Singh, A et al, FEMS Microbiology Letters, vol. 2098, 2002, pp. 301-305, Expression of anthrax lethal factor gene by osmolyte induction.*

Flick-Smith, HC et al, Infection and Immunity, Mar. 2002, pp. 1653-1656, vol. 70(3) A recombinant carboy-terminal domain of the protective antigen of *Bacillus anthracis* protects mice against anthrax infection.*

Park, S et al, Protein Expression and Purification, vol. 18, pp. 293-302, (20002) Optimized production and purification of *Bacillus anthracis* lethal factor.*

Alexeyev, O.A., V. G. Morozov, T. V. Suzdaltseva, A. S. Michukov, and L. A. Steinberg. 1994. Impaired neutrophil function in the cutaneous form of anthrax. Infection 22:281-282.

Brachman, P. S., H. Gold, S. A. Plotkin, F. R. Fekety, M. Werrin, and N. R. Ingraham. 1962. Field evaluation of a human anthrax vaccine. Am.J.Pub.Health 52:632-645.

Bradley, K. A., J. Mogridge, M. Mourez, R. J. Collier, and J. A. Young. 2001. Identification of the cellular receptor for anthrax toxin. Nature 414:160-161.

Bragg, T. S. and D. L. Robertson. 1989. Nucleotide sequence and analysis of the lethal factor gene (lef) from *Bacillus anthracis*. Gene 81:45-54.

Cieslak, T. J. and E. M. Eitzen. 1999. Clinical and epidemiologic principles of anthrax. Emerg.Infect.Dis. 5:552-555.

Dixon, T. C., M. Meselson, J. Guillemin, and P. C. Hanna. 1999. Medical Progress: Anthrax. N.Engl.J.Med. 341:815-826.

Drum, C. L., S. Z. Yan, J. Bard, Y. Q. Shen, D. Lu, S. Soelaiman, Z. Grabarek, A. Bohm, and W. J. Tang. 2002. Structural basis for the activation of anthrax adenylyl cyclase exotoxin by calmodulin. Nature Jan. 24, 2002;415(6870):396-402 415:396-402.

Duesbery, N. S., C. P. Webb, S. H. Leppla, V. M. Gordon, K. R. Klimpel, T. D. Copeland, N. G. Ahn, M. K. Oskarsson, K. Fukasawa, K. D. Paull, and G. F. Vande Woude. 1998. Proteolytic inactivation of MAP-kinase-kinase by anthrax lethal factor [see comments]. Science 280:734-737.

Flick-Smith, H. C., N. J. Walker, P. Gibson, H. Bullifent, S. Hayward, J. Miller, R. W. Titball, and E. D. williamson. 2002. A recombinant carbosy-terminal domain of the Protective Antigen of *Bacillus anthracis* protects mice against anthrax infection. Infect. Immun. 70:1653-1656.

Friedlander, A. M. and P. S. Brachman. 1998. Anthrax, p. 729-739. In S. A. Plotkin and E. A. Mortimer (eds.), Vaccines. W. B. Saunders, Philadelphia.

Friedlander, A. M., P. R. Pittman, and G. W. Parker. 1999. Anthrax vaccine—Evidence for safety and efficacy against inhalational anthrax. Jama-Journal Of The American Medical Association 282:2104-2106.

Gladstone, G. P. 1946. Immunity to anthrax. Protective antigen present in cell-free culture filtrates. Brit.J.exp.Path. 27:349-418.

Green, B. D., L. Battisti, T. M. Koehler, C. B. Thorne, and B. E. Ivins. 1985. Demonstration of a capsule plasmid in *Bacillus anthracis*. Infect.Immun. 49:291-297.

Hammond, S. E. and P. C. Hanna. 1998. Lethal factor active-site mutations affect catalytic activity in vitro. Infect.Immun. 66:2374-2378.

Hanna, P. C., B. A. Kruskal, R. A. Ezekowitz, B. R. Bloom, and R. J. Collier. 1994. Role of macrophage oxidative burst in the action of anthrax lethal toxin. Mol.Med. 1:7-18.

Ivins, B., P. Fellows, L. Pitt, J. Estep, J. Farchaus, A. Friedlander, and P. Gibbs. 1995. Experimental anthrax vaccines: efficacy of adjuvants combined with protective antigen against an aerosol *Bacillus anthracis* spore challenge in guinea pigs. Vaccine 13:1779-1784.

Ivins, B. E., J. W. Ezzell, Jr., J. Jemski, K. W. Hedlund, J. D. Ristroph, and S. H. Leppla. 1986. Immunization studies with attenuated strains of *Bacillus anthracis*. Infect.Immun. 52:454-458.

Ivins, B. E. and S. L. Welkos. 1986. Cloning and expression of the *Bacillus anthracis* protective antigen gene in *Bacillus subtilis*. Infect.Immun. 54:537-542.

Ivins, B. E. and S. L. Welkos. 1988. Recent advances in the development of an improved human anthrax vaccine. Eur.J. Epidemiol. 4:12-19.

Johnson-Winegar, A. 1984. Comparison of enzyme-linked immunosorbent and indirect hemagglutination assays for determining anthrax antibodies. J.Clin.Microbiol. 20:357-361.

Klimpel, K. R., N. Arora, and S. H. Leppla. 1994. Anthrax toxin lethal factor contains a zinc metalloprotease consensus sequence which is required for lethal toxin activity. Mol.Microbiol. 13:1093-1100.

Leppla, S. H. 1982. Anthrax toxin edema factor: a bacterial adenylate cyclase that increases cyclic AMP concentrations of eukaryotic cells. Proc.Natl.Acad.Sci.U.S.A. 79:3162-3166.

Leppla, S. H. 2000. Anthrax Toxin, p. 445-472. In K. Aktories and I. Just (eds.), Bacterial Protein Toxins. Springer, Berlin.

Liddington, R., A. Pannifer, P. Hanna, S. Leppla, and R. J. Collier. 1999. Crystallographic studies of the anthrax lethal toxin. J.Appl. Microbiol. 87:282.

Little, S. F. and G. B. Knudson. 1986. Comparative efficacy of *Bacillus anthracis* live spore vaccine and protective antigen vaccine against anthrax in the guinea pig. Infect.Immun. 52:509-512.

Little, S. F., S. H. Leppla, and A. M. Friedlander. 1990. Production and characterization of monoclonal antibodies against the lethal factor component of *Bacillus anthracis* lethal toxin. Infect.Immun. 58:1606-1613.

Makino, S., I. Uchida, N. Terakado, C. Sasakawa, and M. Yoshikawa. 1989. Molecular characterization and protein analysis of the cap region, which is essential for encapsulation in *Bacillus anthracis*. J.Bacterial. 171:722-730.

Meselson, M., J. Guillemin, M. Hugh-Jones, A. Langmuir, I. Popova, A. Shelokov, and O. Yampolskaya. 1994. The Sverdlovsk anthrax outbreak of 1979. Science 266:1202-1208.

Mikesell, P., B. E. Ivins, J. D. Ristroph, and T. M. Dreier. 1983. Evidence for plasmid-mediated toxin production in *Bacillus anthracis*. Infect.Immun. 39:371-376.

O'Brien, J., A. Friedlander, T. Dreier, J. Ezzell, and S. Leppla. 1985. Effects of anthrax toxin components on human neutrophils. Infect. Immun. 47:306-310.

Okinaka, R. T., K. Cloud, O. Hampton, A. R. Hoffmaster, K. K. Hill, P. Keim, T. M. Koehler, G. Lamke, S. Kumano, J. Mahillon, D. Manter, Y. Martinez, D. Ricke, R. Svensson, and P. J. Jackson. 1999. Sequence and organization of pXO1, the large *Bacillus anthracis* plasmid harboring the anthrax toxin genes. J.Bacteriol. 181:6509-6515.

Pannifer, A. D., T. Y. Wong, R. Schwarzenbacher, M. Renatus, C. Petosa, J. Blenkowska, D. B. Lacy, R. J. Collier, S. Park, S. H. Leppla, P. Hanna, and R. C. Liddington. 2001. Crystal structure of the anthrax lethal factor. Nature 414:229-233.

Park, S. and S. H. Leppla. 2000. Optimized production and purification of *Bacillus anthracis* Lethal Factor. Protein Expr.Purif. 18:293-302.

Pellizzari, R., C. Guidi-Rontani, G. Vitale, M. Mock, and C. Montecucco. 1999. Anthrax lethal factor cleaves MKK3 in macrophages and inhibits the LPS/IFNgamma-induced release of NO and TNFalpha. FEBS Lett. 462:199-204.

Petosa, C., R. J. Collier, K. R. Klimpel, S. H. Leppla, and R. C. Liddington. 1997. Crystal structure of the anthrax toxin protective antigen. Nature 385:833-838.

Pittman, P. R., G. Kim-Ahn, D. Y. Pifat, K. M. Coonan, P. Gibbs, S. Little, J. G. Pace-Templeton, R. Myers, G. W. Parker, and A. M. Friedlander. 2002. Anthrax vaccine: Immunogenicity and safety of a dose-reduction, route-change comparison study in humans. Vaccine 20:1412-1420.

Pittman, P. R., J. A. Mangiafico, C. A. Rossi, T. L. Cannon, P. H. Gibbs, G. W. Parker, and A. M. Friedlander. 2000. Anthrax vaccine: increasing intervals between the first two doses enhances antibody response in humans. Vaccine 19:213-216.

Robertson, D. L., T. S. Bragg, S. Simpson, R. Kaspar, W. Xie, and M. T. Tippetts. 1990. Mapping and characterization of *Bacillus anthracis* plasmids pXO1 and pXO2. Salisbury Med.Bull. 68, Spec. suppl.:55-58.

Robertson, D. L. and S. H. Leppla. 1986. Molecular cloning and expression in *Escherichia coli* of the lethal factor gene of *Bacillus anthracis*. Gene 44:71-78.

Singh, Y., V. K. Chaudhary, and S. H. Leppla. 1989. A deleted variant of *Bacillus anthracis* protective antigen is non-toxic and blocks anthrax toxin action in vivo. J.Biol.Chem. 264:19103-19107.

Smith, H., J. Keppie, and J. L. Stanley. 1955. The chemical basis of the virulence of *Bacillus anthracis*. V. the specific toxin produced by *B. anthracis* in vivo. Brit.J.exp.Path. 36:460-472.

Thorne, C. B. 1985. Genetics of *Bacillus anthracis*, p. 56-62. In L. Lieve, P. F. Bonventre, J. A. Morello, S. Schlessinger, S. D. Silver, and H. C. Wu (eds.), Microbiology-85. American Society for Microbiology, Washington, D.C.

Tippetts, M. T. and D. L. Robertson. 1988. Molecular cloning and expression of the *Bacillus anthracis* edema factor toxin gene: a calmodulin-dependent adenylate cyclase. J.Bacteriol. 170:2263-2266.

Uchida, I., K. Hashimoto, and N. Terakado. 1986. Virulence and immunogenicity in experimental animals of *Bacillus anthracis* strains harbouring or lacking 110 MDa and 60 MDa plasmids. J.Gen.Microbiol. 132:557-559.

Uchida, I., T. Sekizaki, K. Hashimoto, and N. Terakado. 1985. Association of the encapsulation of *Bacillus anthracis* with a 60 megadalton plasmid. J.Gen.Microbiol. 131:363-367.

Vital, G., R. Pellizzari, C. Recchi, G. Napolitani, M. Mock, and C. Montecucco. 1998. Anthrax lethal factor cleaves the N-terminus of MAPKKs and induces tyrosine/threonine phosphorylation of MAPKs in cultured macrophages. Biochem.Biophy.Res.Comm. 248:706-711.

Vodkin, M. H. and S. H. Leppla. 1983. Cloning of the protective antigen gene of *Bacillus anthracis*. Cell 34:693-697.

Welkos, S. L. and A. M. Friedlander. 1988. Comparative safety and efficacy against *Bacillus anthracis* of protective antigen and live vaccines in mice. Microb.Pathog. 5:127-139.

Welkos, S. L., J. R. Lowe, F. Eden-McCutchan, M. Vodkin, S. H. Leppla, and J. J. Schmidt. 1988. Sequence and analysis of the DNA encoding protective antigen of *Bacillus anthracis*. Gene 69:287-300.

Wright, G. G., T. W. Green, and R. G. Kanode. 1954. Studies on immunity in anthrax. V. Immunizing activity of alum-precipitated protective antigen. J.Immunol. 73:387-391.

* cited by examiner

FIG. 1B

```
   1 catatgggat cccgggtaag aattcggctg ctaacaaagc ccgaaaggaa
  51 gctgagttgg ctgctgccac cgctgagcaa taactagcat aaccccttgg
 101 ggcctctaaa cgggtcttga ggggttttttt gctgaaagga ggaactatat
 151 ccggatcgag atcaattctg gcgtaatagc gaagaggccc gcaccgatcg
 201 cccttcccaa cagttgcgca gcctgaatgg cgaatgggac gcgccctgta
 251 gcggcgcatt aagcgcggcg ggtgtggtgg ttacgcgcag cgtgaccgct
 301 acacttgcca gcgccctagc gcccgctcct ttcgctttct tcccttcctt
 351 tctcgccacg ttcgccggct ttccccgtca agctctaaat cgggggctcc
 401 ctttagggtt ccgatttagt gctttacggc acctcgaccc caaaaaactt
 451 gattagggtg atggttcacg tagtgggcca tcgccctgat agacggtttt
 501 tcgccctttg acgttggagt ccacgttctt taatagtgga ctcttgttcc
 551 aaactggaac aacactcaac cctatctcgg tctattcttt tgatttataa
 601 gggattttgc cgatttcggc ctattggtta aaaaatgagc tgatttaaca
 651 aaaatttaac gcgaatttta acaaaatatt aacgcttaca atttaggtgg
 701 cacttttcgg ggaaatgtgc gcggaacccc tatttgttta ttttttctaaa
 751 tacattcaaa tatgtatccg ctcatgagac aataaccctg ataaatgctt
 801 caataatatt gaaaaggaa gagtatgagt attcaacatt tccgtgtcgc
 851 ccttattccc ttttttgcgg cattttgcct tcctgttttt gctcacccag
 901 aaacgctggt gaaagtaaaa gatgctgaag atcagttggg tgcacgagtg
 951 ggttacatcg aactggatct caacagcggt aagatccttg agagttttcg
1001 ccccgaagaa cgttttccaa tgatgagcac ttttaaagtt ctgctatgtg
1051 gcgcggtatt atcccgtatt gacgccgggc aagagcaact cggtcgccgc
1101 atacactatt ctcagaatga cttggttgag tactcaccag tcacagaaaa
1151 gcatcttacg gatggcatga cagtaagaga attatgcagt gctgccataa
1201 ccatgagtga taacactgcg gccaacttac ttctgacaac gatcggagga
1251 ccgaaggagc taaccgcttt tttgcacaac atgggggatc atgtaactcg
1301 ccttgatcgt tgggaaccgg agctgaatga agccatacca aacgacgagc
1351 gtgacaccac gatgcctgta gcaatggcaa caacgttgcg caaactatta
1401 actggcgaac tacttactct agcttcccgg caacaattaa tagactggat
1451 ggaggcggat aaagttgcag gaccacttct gcgctcggcc cttccggctg
1501 gctggtttat tgctgataaa tctggagccg gtgagcgtgg gtctcgcggt
1551 atcattgcag cactggggcc agatggtaag ccctcccgta tcgtagttat
1601 ctacacgacg gggagtcagg caactatgga tgaacgaaat agacagatcg
1651 ctgagatagg tgcctcactg attaagcatt ggtaactgtc agaccaagtt
1701 tactcatata tactttagat tgatttaaaa cttcattttt aatttaaaag
1751 gatctaggtg aagatccttt ttgataatct catgaccaaa atcccttaac
1801 gtgagttttc gttccactga gcgtcagacc ccgtagaaaa gatcaaagga
1851 tcttcttgag atcctttttt tctgcgcgta atctgctgct tgcaaacaaa
1901 aaaccaccgc taccagcgg tggtttgttt gccggatcaa gagctaccaa
1951 ctctttttcc gaaggtaact ggcttcagca gagcgcagat accaaatact
2001 gttcttctag tgtagccgta gttaggccac cacttcaaga actctgtagc
2051 accgcctaca tacctcgctc tgctaatcct gttaccagtg gctgctgcca
2101 gtggcgataa gtcgtgtctt accgggttgg actcaagacg atagttaccg
```

FIG. 1B cont.

```
2151 gataaggcgc agcggtcggg ctgaacgggg ggttcgtgca cacagcccag
2201 cttggagcga acgacctaca ccgaactgag atacctacag cgtgagctat
2251 gagaaagcgc cacgcttccc gaagggagaa aggcggacag gtatccggta
2301 agcggcaggg tcggaacagg agagcgcacg agggagcttc caggggaaa
2351 cgcctggtat ctttatagtc ctgtcgggtt tcgccacctc tgacttgagc
2401 gtcgatttttt gtgatgctcg tcaggggggc ggagcctatg gaaaaacgcc
2451 agcaacgcgg cctttttacg gttcctggcc ttttgctggc cttttgctca
2501 catgttcttt cctgcgttat ccctgattc tgtggataac cgtattaccg
2551 cctttgagtg agctgatacc gctcgccgca gccgaacgac cgagcgcagc
2601 gagtcagtga gcgaggaagc ggaagagcgc ctgatgcggt attttctcct
2651 tacgcatctg tgcggtattt cacaccgcaa tggtgcactc tcagtacaat
2701 ctgctctgat gccgcatagt taagccagta tacactccgc tatcgctacg
2751 tgactgcaag gagatggcgc ccaacagtcc cccggccacg gggcctgcca
2801 ccatacccac gccgaaacaa gcgctcatga gcccgaagtg gcgagcccga
2851 tcttccccat cggtgatgtc ggcgatatag gcgccagcaa ccgcacctgt
2901 ggcgccggtg atgccggcca cgatgcgtcc ggcgtagagg atcgagatcc
2951 aggagaacaa aaacgatttt ttgaggaaag ttataaatta ttttccgaac
3001 gatatggcaa gcaaaatatt gcttatgcaa cagttcataa tgatgagcaa
3051 accoctcaca tgcatttagg tgttgtgcct atgcgtgatg gaaaactgca
3101 aggaaaaaat gtgtttaatc gtcaagaact gttatggcta caagataaat
3151 tccccgagca catgaaaaaa cagggttttg agttgaagcg tggtgaacgt
3201 ggctctgacc gtaaacatat tgagacagct aaatttaaaa aacaaacttt
3251 ggaaaaagag attgattttc tagaaaaaaa tttagcagtt aaaaaagatg
3301 aatggactgc ttatagcgat aaagttaaat cagatttaga agtaccagcg
3351 aaacgacaca tgaaaagtgt tgaagtgcca acgggtgaaa agtccatgtt
3401 tggtttggga aagaaataa tgaaaacaga aagaaacca accaaaaatg
3451 ttgttatatc ggagcgtgat tataaaaact tagtgactgc tgcgagagat
3501 aacgataggt taaaacagca tgttagaaat ctcatgagta ctgatatggc
3551 gagagaatat aaaaaattaa gtaaagaaca tgggcaagtt aaagaaaaat
3601 atagtggtct tgtagagcga tttaatgaaa atgtaaatga ttataatgag
3651 ttgcttgaag aaaacaagtc tttaaagtct aaaataagcg atttaaagcg
3701 tgatgtgagt ttaatctatg aaagcactaa ggaattcctt aaggaacgta
3751 cagacggctt aaaagccttt aaaaacgttt taagggggtt tgtagacaag
3801 gtaaaggata aacagcaca attccaagaa aaacacgatt tagaacctaa
3851 aaagaacgaa tttgaactaa ctcataaccg agaggtaaaa aagaacgaa
3901 gtcgagatca gggaatgagt ttataaaata aaaaaagcac ctgaaaaggt
3951 gtcttttttt gatggttttg aacttgttct ttcttatctt gatacatata
4001 gaaataacgt catttttatt ttagttgctg aaaggtgcgt tgaagtgttg
4051 gtatgtatgt gttttaaagt attgaaaacc cttaaaattg gttgcacaga
4101 aaaccccat ctgttaaagt tataagtgac taaacaaata actaaataga
4151 tgggggtttc ttttaatatt atgtgtccta atagtagcat ttattcagat
4201 gaaaaatcaa gggttttagt ggacaagaca aaaagtggaa aagtgagacc
```

FIG. 1B cont.

```
4251 atggagagaa aagaaaatcg ctaatgttga ttactttgaa cttctgcata
4301 ttcttgaatt taaaaaggct gaaagagtaa aagattgtgc tgaaatatta
4351 gagtataaac aaaatcgtga aacaggcgaa agaaagttgt atcgagtgtg
4401 gttttgtaaa tccaggcttt gtccaatgtg caactggagg agagcaatga
4451 aacatggcat tcagtcacaa aaggttgttg ctgaagttat taaacaaaag
4501 ccaacagttc gttggttgtt tctcacatta acagttaaaa atgtttatga
4551 tggcgaagaa ttaaataaga gtttgtcaga tatggctcaa ggatttcgcc
4601 gaatgatgca atataaaaaa attaataaaa atcttgttgg ttttatgcgt
4651 gcaacggaag tgacaataaa taataaagat aattcttata atcagcacat
4701 gcatgtattg gtatgtgtgg aaccaactta ttttaagaat acagaaaact
4751 acgtgaatca aaaacaatgg attcaatttt ggaaaaaggc aatgaaatta
4801 gactatgatc caaatgtaaa agttcaaatg attcgaccga aaaataaata
4851 taaatcggat atacaatcgg caattgacga aactgcaaaa tatcctgtaa
4901 aggatacgga ttttatgacc gatgatgaag aaaagaattt gaacgtttg
4951 tctgatttgg aggaaggttt acaccgtaaa aggttaatct cctatggtgg
5001 tttgttaaaa gaaatacata aaaaattaaa ccttgatgac acagaagaag
5051 gcgatttgat tcatacagat gatgacgaaa aagccgatga agatggattt
5101 tctattattg caatgtggaa ttgggaacgg aaaaattatt ttattaaaga
5151 gtagttcaac aaacgggcca gtttgttgaa gattagatgc tataattgtt
5201 attaaaagga ttgaaggatg cttaggaaga cgagttatta atagctgaat
5251 aagaacggtg ctctccaaat attcttattt agaaaagcaa atctaaaatt
5301 atctgaaaag ggaatgagaa tagtgaatgg accaataata atgactagag
5351 aagaaagaat gaagattgtt catgaaatta aggaacgaat attggataaa
5401 tatggggatg atgttaaggc tattggtgtt tatggctctc ttggtcgtca
5451 gactgatggg ccctattcgg atattgagat gatgtgtgtc atgtcaacag
5501 aggaagcaga gttcagccat gaatggacaa ccggtgagtg gaaggtggaa
5551 gtgaattttg atagcgaaga gattctacta gattatgcat ctcaggtgga
5601 atcagattgg ccgcttacac atggtcaatt tttctctatt tgccgattt
5651 atgattcagg tggatactta gagaaagtgt atcaaactgc taaatcggta
5701 gaagcccaaa cgttccacga tgcgatttgt gcccttatcg tagaagagct
5751 gtttgaatat gcaggcaaat ggcgtaatat tcgtgtgcaa ggaccgacaa
5801 catttctacc atccttgact gtacaggtag caatggcagg tgccatgttg
5851 attggtctgc atcatcgcat ctgttatacg acgagcgctt cggtcttaac
5901 tgaagcagtt aagcaatcag atcttccttc aggttatgac catctgtgcc
5951 agttcgtaat gtctggtcaa ctttccgact ctgagaaact tctggaatcg
6001 ctagagaatt tctggaatgg gattcaggag tggacagaac gacacggata
6051 tatagtggat gtgtcaaaac gcataccatt ttgaacgatg acctctaata
6101 attgttaatc atgttggtta cgtatttatt aacttctcct agtattagta
6151 attatcatgg ctgtcatggc gcattaacgg aataaagggt gtgcttaaat
6201 cgggccattt tgcgtaataa gaaaaaggat taattatgag cgaattgaat
6251 taataataag gtaatagatt tacattagaa aatgaagggg gattttatgc
6301 gtgagaatgt tacagtctat cccggcattg ccagtcgggg atattaaaaa
```

FIG. 1B cont.

```
6351 gagtataggt ttttattgcg ataaactagg tttcactttg gttcaccatg
6401 aagatggatt cgcagttcta atgtgtaatg aggttcggat tcatctatta
6451 aacatataaa ttcttttta tgttatatat ttataaaagt tctgtttaaa
6501 aagccaaaaa taaataatta tctcttttta tttatattat attgaaacta
6551 aagtttatta atttcaatat aatataaatt taattttata caaaaaggag
6601 aacgtatatg aaaaaacgaa aagtgttaat accattaatg gcattgtcta
6651 cgatattagt ttcaagcaca ggtaatttag aggtgattca ggca
```

FIG. 2B

```
   1 catatgggat ccggctgcta acaaagcccg aaaggaagct gagttggctg
  51 ctgccaccgc tgagcaataa ctagcataac cccttgggc  ctctaaacgg
 101 gtcttgaggg gtttttttgct gaaaggagga actatatccg gatatcccgc
 151 aagaggcccg gcagtaccgg cataaccaag cctatgccta cagcatccag
 201 ggtgacggtg ccgaggatga cgatgagcgc attgttagat ttcatacacg
 251 gtgcctgact gcgttagcaa tttaactgtg ataaactacc gcattaaagc
 301 ttatcgatga taagctgtca aacatgagaa ttcttgaaga cgaaagggcc
 351 tcgtgatacg cctatttta  taggttaatg tcatgataat aatggtttct
 401 tagacgtcag gtggcacttt tcggggaaat gtgcgcggaa cccctatttg
 451 tttattttc  taaatacatt caaatatgta tccgctcatg agacaataac
 501 cctgataaat gcttcaataa tattgaaaaa ggaagagtat gagtattcaa
 551 catttccgtg tcgcccttat tcccttttt  gcggcatttt gccttcctgt
 601 ttttgctcac ccagaaacgc tggtgaaagt aaaagatgct gaagatcagt
 651 tgggtgcacg agtgggttac atcgaactgg atctcaacag cggtaagatc
 701 cttgagagtt ttcgccccga agaacgtttt ccaatgatga gcacttttaa
 751 agttctgcta tgtggcgcgg tattatcccg tgttgacgcc gggcaagagc
 801 aactcggtcg ccgcatacac tattctcaga atgacttggt tgagtactca
 851 ccagtcacag aaaagcatct tacggatggc atgacagtaa gagaattatg
 901 cagtgctgcc ataaccatga gtgataacac tgcggccaac ttacttctga
 951 caacgatcgg aggaccgaag gagctaaccg cttttttgca caacatgggg
1001 gatcatgtaa ctcgccttga tcgttgggaa ccggagctga atgaagccat
1051 accaaacgac gagcgtgaca ccacgatgcc tgcagcaatg gcaacaacgt
1101 tgcgcaaact attaactggc gaactactta ctctagcttc ccggcaacaa
1151 ttaatagact ggatggaggc ggataaagtt gcaggaccac ttctgcgctc
1201 ggcccttccg gctggctggt ttattgctga taaatctgga gccggtgagc
1251 gtgggtctcg cggtatcatt gcagcactgg ggccagatgg taagccctcc
1301 cgtatcgtag ttatctacac gacggggagt caggcaacta tggatgaacg
1351 aaatagacag atcgctgaga taggtgcctc actgattaag cattggtaac
1401 tgtcagacca agtttactca tatatacttt agattgattt aaaacttcat
1451 ttttaattta aaaggatcta ggtgaagatc cttttttgata atctcatgac
1501 caaaatccct taacgtgagt tttcgttcca ctgagcgtca gacccgtag
1551 aaaagatcaa aggatcttct tgagatcctt ttttctgcg  cgtaatctgc
1601 tgcttgcaaa caaaaaaacc accgctacca gcggtggttt gtttgccgga
1651 tcaagagcta ccaactcttt tccgaaggt  aactggcttc agcagagcgc
1701 agataccaaa tactgtcctt ctagtgtagc cgtagttagg ccaccacttc
1751 aagaactctg tagcaccgcc tacatacctc gctctgctaa tcctgttacc
1801 agtggctgct gccagtggcg ataagtcgtg tcttaccggg ttggactcaa
1851 gacgatagtt accggataag gcgcagcggt cgggctgaac ggggggttcg
1901 tgcacacagc ccagcttgga gcgaacgacc tacaccgaac tgagatacct
1951 acagcgtgag ctatgagaaa gcgccacgct cccgaaggg  agaaaggcgg
2001 acaggtatcc ggtaagcggc agggtcggaa caggagagcg cacgagggag
```

FIG. 2B cont.

```
2051 cttccagggg gaaacgcctg gtatctttat agtcctgtcg ggtttcgcca
2101 cctctgactt gagcgtcgat ttttgtgatg ctcgtcaggg gggcggagcc
2151 tatggaaaaa cgccagcaac gcggcctttt tacggttcct ggccttttgc
2201 tggcctttg ctcacatgtt ctttcctgcg ttatccctg attctgtgga
2251 taaccgtatt accgcctttg agtgagctga taccgctcgc cgcagccgaa
2301 cgaccgagcg cagcgagtca gtgagcgagg aagcggaaga gcgcctgatg
2351 cggtattttc tccttacgca tctgtgcggt atttcacacc gcaatggtgc
2401 actctcagta caatctgctc tgatgccgca tagttaagcc agtaaaaaaa
2451 atttagcagt taaaaaagat gaatggactg cttatagcga taaagttaaa
2501 tcagatttag aagtaccagc gaaacgacac atgaaagtg ttgaagtgcc
2551 aacgggtgaa aagtccatgt ttggtttggg aaaagaaata atgaaaacag
2601 aaaagaaacc aaccaaaaat gttgttatat cggagcgtga ttataaaaac
2651 ttagtgactg ctgcgagaga taacgatagg ttaaaacagc atgttagaaa
2701 tctcatgagt actgatatgg cgagagaata taaaaaatta agtaaagaac
2751 atgggcaagt taaagaaaaa tatagtggtc ttgtagagcg atttaatgaa
2801 aatgtaaatg attataatga gttgcttgaa gaaacaagt ctttaaagtc
2851 taaataagc gatttaaagc gtgatgtgag tttaatctat gaaagcacta
2901 aggaattcct taaggaacgt acagacggct aaaagcctt taaaaacgtt
2951 tttaaggggt tgtagacaa ggtaaggat aaaacagcac aattccaaga
3001 aaaacacgat ttagaaccta aaagaacga atttgaacta actcataacc
3051 gagaggtaaa aaagaacga agtcgagatc agggaatgag tttataaaat
3101 aaaaaaagca cctgaaaagg tgtcttttt tgatggtttt gaacttgttc
3151 tttcttatct tgatacatat agaaataacg tcatttttat tttagttgct
3201 gaaaggtgcg ttgaagtgtt ggtatgtatg tgttttaaag tattgaaaac
3251 ccttaaaatt ggttgcacag aaaaaccccca tctgttaaag ttataagtga
3301 ctaaacaaat aactaaatag atgggggttt cttttaatat tatgtgtcct
3351 aatagtagca tttattcaga tgaaaaatca agggttttag tggacaagac
3401 aaaagtgga aaagtgagac catggagaga aagaaaatc gctaatgttg
3451 attactttga acttctgcat attcttgaat ttaaaaaggc tgaaagagta
3501 aaagattgtg ctgaaatatt agagtataaa caaaatcgtg aaacaggcga
3551 aagaaagttg tatcgagtgt ggttttgtaa atccaggctt tgtccaatgt
3601 gcaactggag gagagcaatg aaacatggca ttcagtcaca aaaggttgtt
3651 gctgaagtta ttaaacaaaa gccaacagtt cgttggttgt ttctcacatt
3701 aacagttaaa aatgtttatg atggcgaaga attaaataag agtttgtcag
3751 atatggctca aggatttcgc cgaatgatgc aatataaaaa aattaataaa
3801 aatcttgttg gttttatgcg tgcaacggaa gtgacaataa ataataaaga
3851 taattcttat aatcagcaca tgcatgtatt ggtatgtgtg gaaccaactt
3901 attttaagaa tacagaaaac tacgtgaatc aaaaacaatg gattcaattt
3951 tggaaaaagg caatgaaatt agactatgat ccaaatgtaa aagttcaaat
4001 gattcgaccg aaaaataaat ataaatcgga tatacaatcg gcaattgacg
4051 aaactgcaaa atatcctgta aaggatacgg attttatgac cgatgatgaa
```

FIG. 2B cont.

```
4101 gaaaagaatt tgaaacgttt gtctgatttg gaggaaggtt tacaccgtaa
4151 aaggttaatc tcctatggtg gtttgttaaa agaaatacat aaaaaattaa
4201 accttgatga cacagaagaa ggcgatttga ttcatacaga tgatgacgaa
4251 aaagccgatg aagatggatt ttctattatt gcaatgtgga attgggaacg
4301 gaaaaattat tttattaaag agtagttcaa caaacgggcc agtttgttga
4351 agattagatg ctataattgt tattaaaagg attgaaggat gcttaggaag
4401 acgagttatt aatagctgaa taagaacggt gctctccaaa tattcttatt
4451 tagaaaagca aatctaaaat tatctgaaaa gggaatgaga atagtgaatg
4501 gaccaataat aatgactaga aagaaagaa tgaagattgt tcatgaaatt
4551 aaggaacgaa tattggataa atatggggat gatgttaagg ctattggtgt
4601 ttatggctct cttggtcgtc agactgatgg gccctattcg gatattgaga
4651 tgatgtgtgt catgtcaaca gaggaagcag agttcagcca tgaatggaca
4701 accggtgagt ggaaggtgga agtgaatttt gatagcgaag agattctact
4751 agattatgca tctcaggtgg aatcagattg gccgcttaca catggtcaat
4801 ttttctctat tttgccgatt tatgattcag gtggatactt agagaaagtg
4851 tatcaaactg ctaaatcggt agaagcccaa acgttccacg atgcgatttg
4901 tgcccttatc gtagaagagc tgtttgaata tgcaggcaaa tggcgtaata
4951 ttcgtgtgca aggaccgaca acatttctac catccttgac tgtacaggta
5001 gcaatggcag gtgccatgtt gattggtctg catcatcgca tctgttatac
5051 gacgagcgct tcggtcttaa ctgaagcagt taagcaatca gatcttcctt
5101 caggttatga ccatctgtgc cagttcgtaa tgtctggtca actttccgac
5151 tctgagaaac ttctggaatc gctagagaat ttctggaatg ggattcagga
5201 gtggacagaa cgacacggat atatagtgga tgtgtcaaaa cgcataccat
5251 tttgaacgat gacctctaat aattgttaat catgttggtt acgtatttat
5301 taacttctcc tagtattagt aattatcatg gctgtcatgg cgcattaacg
5351 gaataaaggg tgtgcttaaa tcgggccatt ttgcgtaata agaaaaagga
5401 ttaattatga gcgaattgaa ttaataataa ggtaatagat ttacattaga
5451 aaatgaaagg ggattttatg cgtgagaatg ttacagtcta tcccggcatt
5501 gccagtcggg gatattaaaa agagtatagg tttttattgc gataaactag
5551 gtttcacttt ggttcaccat gaagatggat tcgcagttct aatgtgtaat
5601 gaggttcgga ttcatctatt aaacatataa attcttttt atgttatata
5651 tttataaaag ttctgtttaa aaagccaaaa ataataatt atctctttt
5701 atttatatta tattgaaact aaagtttatt aatttcaata taatataaat
5751 ttaattttat acaaaaagga gaacgtatat gaaaaaacga aaagtgttaa
5801 taccattaat ggcattgtct acgatattag tttcaagcac aggtaattta
5851 gaggtgattc aggca
```

FIG. 3B

```
3701 catat
3751 ggcgggcggt catggtgatg taggtatgca cgtaaaagag aaagagaaaa
3801 ataaagatga gaataagaga aaagatgaag aacgaaataa aacacaggaa
3851 gagcatttaa aggaaatcat gaaacacatt gtaaaaatag aagtaaaagg
3901 ggaggaagct gttaaaaaag aggcagcaga aaagctactt gagaaagtac
3951 catctgatgt tttagagatg tataaagcaa ttggaggaaa gatatatatt
4001 gtggatggtg atattacaaa acatatatct ttagaagcat tatctgaaga
4051 taagaaaaaa ataaaagaca tttatgggaa agatgcctta ttacatgaac
4101 attatgtata tgcaaaagaa ggatatgaac ccgtacttgt aatccaatct
4151 tcggaagatt atgtagaaaa tactgaaaag gcactgaacg tttattatga
4201 aataggtaag atattatcaa gggatatttt aagtaaaatt aatcaaccat
4251 atcagaaatt tttagatgta ttaaatacca ttaaaaatgc atctgattca
4301 gatggacaag atctttatt tactaatcag cttaaggaac atcccacaga
4351 cttttctgta gaattcttgg aacaaaatag caatgaggta caagaagtat
4401 ttgcgaaagc ttttgcatat tatatcgagc cacagcatcg tgatgtttta
4451 cagctttatg caccggaagc ttttaattac atggataaat ttaacgaaca
4501 agaaataaat ctataa
```

FIG. 3C

```
  1 His Met Ala Gly Gly His Gly Asp Val Gly Met His Val Lys Glu Lys Glu Lys
 19 Asn Lys Asp Glu Asn Lys Arg Lys Asp Glu Glu Arg Asn Lys Thr Gln Glu Glu
 37 His Leu Lys Glu Ile Met Lys His Ile Val Lys Ile Glu Val Lys Gly Glu Glu
 55 Ala Val Lys Lys Glu Ala Ala Glu Lys Leu Leu Glu Lys Val Pro Ser Asp Val
 73 Leu Glu Met Tyr Lys Ala Ile Gly Gly Lys Ile Tyr Ile Val Asp Gly Asp Ile
 91 Thr Lys His Ile Ser Leu Glu Ala Leu Ser Glu Asp Lys Lys Lys Ile Lys Asp
109 Ile Tyr Gly Lys Asp Ala Leu Leu His Glu His Tyr Val Tyr Ala Lys Glu Gly
127 Tyr Glu Pro Val Leu Val Ile Gln Ser Ser Glu Asp Tyr Val Glu Asn Thr Glu
145 Lys Ala Leu Asn Val Tyr Tyr Glu Ile Gly Lys Ile Leu Ser Arg Asp Ile Leu
163 Ser Lys Ile Asn Gln Pro Tyr Gln Lys Phe Leu Asp Val Leu Asn Thr Ile Lys
181 Asn Ala Ser Asp Ser Asp Gly Gln Asp Leu Leu Phe Thr Asn Gln Leu Lys Glu
199 His Pro Thr Asp Phe Ser Val Glu Phe Leu Glu Gln Asn Ser Asn Glu Val Gln
217 Glu Val Phe Ala Lys Ala Phe Ala Tyr Tyr Ile Glu Pro Gln His Arg Asp Val
235 Leu Gln Leu Tyr Ala Pro Glu Ala Phe Asn Tyr Met Asp Lys Phe Asn Glu Gln
253 Glu Ile Asn Leu
```

FIG. 4B

```
5851    catatgg   cgggcggtca  tggtgatgta  ggtatgcacg  taaaagagaa
        gtatacc   gcccgccagt  accactacat  ccatacgtgc  attttctctt
5901   agagaaaaat  aaagatgaga  ataagagaaa  agatgaagaa  cgaaataaaa
       tctctttta   tttctactct  tattctcttt  tctacttctt  gctttatttt
5951   cacaggaaga  gcatttaaag  gaaatcatga  aacacattgt  aaaaatagaa
       gtgtccttct  cgtaaatttc  ctttagtact  ttgtgtaaca  ttttttatctt
6001   gtaaaagggg  aggaagctgt  taaaaaagag  gcagcagaaa  agctacttga
       cattttcccc  tccttcgaca  attttttctc  cgtcgtcttt  tcgatgaact
6051   gaaagtacca  tctgatgttt  tagagatgta  taaagcaatt  ggaggaaaga
       ctttcatggt  agactacaaa  atctctacat  atttcgttaa  cctcctttct
6101   tatatattgt  ggatggtgat  attacaaaac  atatatcttt  agaagcatta
       atatataaca  cctaccacta  taatgttttg  tatatagaaa  tcttcgtaat
6151   tctgaagata  agaaaaaaat  aaaagacatt  tatgggaaag  atgccttatt
       agacttctat  tcttttttta  ttttctgtaa  atacccttttc  tacggaataa
6201   acatgaacat  tatgtatatg  caaaagaagg  atatgaaccc  gtacttgtaa
       tgtacttgta  atacatatac  gttttcttcc  tatacttggg  catgaacatt
6251   tccaatcttc  ggaagattat  gtagaaaata  ctgaaaaggc  actgaacgtt
       aggttagaag  ccttctaata  catctttttat  gacttttccg  tgacttgcaa
6301   tattatgaaa  taggtaagat  attatcaagg  gatattttaa  gtaaaattaa
       ataatacttt  atccattcta  taatagttcc  ctataaaatt  cattttaatt
6351   tcaaccatat  cagaaatttt  tagatgtatt  aaataccatt  aaaaatgcat
       agttggtata  gtcttttaaaa  atctacataa  tttatggtaa  ttttttacgta
6401   ctgattcaga  tggacaagat  cttttattta  ctaatcagct  taaggaacat
       gactaagtct  acctgttcta  gaaaataaat  gattagtcga  attccttgta
6451   cccacagact  ttctgtaga   attcttggaa  caaaatagca  atgaggtaca
       gggtgtctga  aaagacatct  taagaacctt  gttttatcgt  tactccatgt
6501   agaagtattt  gcgaaagctt  ttgcatatta  tatcgagcca  cagcatcgtg
       tcttcataaa  cgctttcgaa  aacgtataat  atagctcggt  gtcgtagcac
6551   atgttttaca  gctttatgca  ccggaagctt  ttaattacat  ggataaattt
       tacaaaatgt  cgaaatacgt  ggccttcgaa  aattaatgta  cctatttaaa
6601   aacgaacaag  aaataaatct  atccttggaa  gaacttaaag  atcaacggat
       ttgcttgttc  tttatttaga  taggaacctt  cttgaatttc  tagttgccta
6651   gctgtcaaga  tatgaaaaat  gggaaaagat  aaaacagcac  tatcaacact
       cgacagttct  atactttttta  ccctttttcta  ttttgtcgtg  atagttgtga
6701   ggagcgattc  tttatctgaa  gaaggaagag  gacttttaaa  aaagctgcag
       cctcgctaag  aaatagactt  cttccttctc  ctgaaaattt  tttcgacgtc
6751   attcctattg  agccaaagaa  agatgacata  attcattctt  tatctcaaga
       taaggataac  tcggtttctt  tctactgtat  taagtaagaa  atagagttct
6801   agaaaaagag  cttctaaaaa  gaatacaaat  tgatagtagt  gattttttat
       tcttttttctc  gaagattttt  cttatgttta  actatcatca  ctaaaaaata
```

FIG. 4B cont.

```
6851 ctactgagga aaaagagttt ttaaaaaagc tacaaattga tattcgtgat
     gatgactcct ttttctcaaa aatttttcg atgtttaact ataagcacta
6901 tctttatctg aagaagaaaa agagcttta aatagaatac aggtggatag
     agaaatagac ttcttcttt tctcgaaaat ttatcttatg tccacctatc
6951 tagtaatcct ttatctgaaa aagaaaaga gttttaaaa aagctgaaac
     atcattagga aatagacttt ttcttttct caaaaatttt ttcgactttg
7001 ttgatattca accatacgat attaatcaaa ggttgcaaga tacaggaggg
     aactataagt tggtatgcta taattagttt ccaacgttct atgtcctccc
7051 ttaattgata gtccgtcaat taatcttgat gtaagaaagc agtataaaag
     aattaactat caggcagtta attagaacta cattctttcg tcatatttc
7101 ggatattcaa aatattgatg ctttattaca tcaatccatt ggaagtacct
     cctataagtt ttataactac gaaataatgt agttaggtaa ccttcatgga
7151 tgtacaataa aatttatttg tatgaaaata tgaatatcaa taaccttaca
     acatgttatt taaataaac atactttat acttatagtt attggaatgt
7201 gcaacctag gtgcggattt agttgattcc actgataata ctaaaattaa
     cgttgggatc cacgcctaaa tcaactaagg tgactattat gattttaatt
7251 tagaggtatt ttcaatgaat tcaaaaaaaa tttcaaatat agtatttcta
     atctccataa aagttactta agttttttt aaagtttata tcataaagat
7301 gtaactatat gattgttgat ataatgaaa ggcctgcatt agataatgag
     cattgatata ctaacaacta tatttacttt ccggacgtaa tctattactc
7351 cgtttgaaat ggagaatcca attatcacca gatactcgag caggatattt
     gcaaacttta cctcttaggt taatagtggt ctatgagctc gtcctataaa
7401 agaaaatgga aagcttatat tacaaagaaa catcggtctg gaaataaagg
     tcttttacct ttcgaatata atgtttcttt gtagccagac ctttatttcc
7451 atgtacaaat aattaagcaa tccgaaaaag aatatataag gattgatgcg
     tacatgttta ttaattcgtt aggcttttc ttatatattc ctaactacgc
7501 aaagtagtgc caaagagtaa aatagataca aaaattcaag aagcacagtt
     tttcatcacg gtttctcatt ttatctatgt ttttaagttc ttcgtgtcaa
7551 aaatataaat caggaatgga ataaagcatt agggttacca aaatatacaa
     tttatattta gtccttacct tatttcgtaa tcccaatggt tttatatgtt
7601 agcttattac attcaacgtg cataatagat atgcatccaa tattgtagaa
     tcgaataatg taagttgcac gtattatcta tacgtaggtt ataacatctt
7651 agtgcttatt taatattgaa tgaatggaaa aataatattc aaagtgatct
     tcacgaataa attataactt acttaccttt ttattataag tttcactaga
7701 tataaaaaag gtaacaaatt acttagttga tggtaatgga agatttgttt
     atatttttc cattgtttaa tgaatcaact accattcct tctaaacaaa
7751 ttaccgatat tactctccct aatatagctg aacaatatac acatcaagat
     aatggctata atgagaggga ttatatcgac ttgttatatg tgtagttcta
7801 gagatatatg agcaagttca ttcaaagggg ttatatgttc cagaatcccg
     ctctatatac tcgttcaagt aagttttccc aatatacaag gtcttagggc
```

FIG. 4B cont.

```
7851 ttctatatta ctccatggac cttcaaaagg tgtagaatta aggaatgata
     aagatataat gaggtacctg gaagttttcc acatcttaat tccttactat
7901 gtgagggttt tatacacgaa tttggacatg ctgtggatga ttatgctgga
     cactcccaaa atatgtgctt aaacctgtac gacacctact aatacgacct
7951 tatctattag ataagaacca atctgattta gttacaaatt ctaaaaaatt
     atagataatc tattcttggt tagactaaat caatgtttaa gattttttaa
8001 cattgatatt tttaaggaag aagggagtaa tttaacttcg tatgggagaa
     gtaactataa aaattccttc ttccctcatt aaattgaagc atccctctt
8051 caaatgaagc ggaattttt gcagaagcct ttaggttaat gcattctacg
     gtttacttcg ccttaaaaaa cgtcttcgga aatccaatta cgtaagatgc
8101 gaccatgctg aacgtttaaa agttcaaaaa aatgctccga aaactttcca
     ctggtacgac ttgcaaattt tcaagttttt ttacgaggct tttgaaaggt
8151 atttattaac gatcagatta agttcattat taactcataa
     taaataattg ctagtctaat tcaagtaata attgagtatt
```

FIG. 4C

```
  1 His Met Ala Gly Gly His Gly Asp Val Gly Met His Val Lys Glu Lys Glu Lys
 19 Asn Lys Asp Glu Asn Lys Arg Lys Asp Glu Glu Arg Asn Lys Thr Gln Glu Glu
 37 His Leu Lys Glu Ile Met Lys His Ile Val Lys Ile Glu Val Lys Gly Glu Glu
 55 Ala Val Lys Lys Glu Ala Ala Glu Lys Leu Leu Glu Lys Val Pro Ser Asp Val
 73 Leu Glu Met Tyr Lys Ala Ile Gly Gly Lys Ile Tyr Ile Val Asp Gly Asp Ile
 91 Thr Lys His Ile Ser Leu Glu Ala Leu Ser Glu Asp Lys Lys Ile Lys Asp
109 Ile Tyr Gly Lys Asp Ala Leu Leu His Glu His Tyr Val Tyr Ala Lys Glu Gly
127 Tyr Glu Pro Val Leu Val Ile Gln Ser Ser Glu Asp Tyr Val Glu Asn Thr Glu
145 Lys Ala Leu Asn Val Tyr Tyr Glu Ile Gly Lys Ile Leu Ser Arg Asp Ile Leu
163 Ser Lys Ile Asn Gln Pro Tyr Gln Lys Phe Leu Asp Val Leu Asn Thr Ile Lys
181 Asn Ala Ser Asp Ser Asp Gly Gln Asp Leu Leu Phe Thr Asn Gln Leu Lys Glu
199 His Pro Thr Asp Phe Ser Val Glu Phe Leu Glu Gln Asn Ser Asn Glu Val Gln
217 Glu Val Phe Ala Lys Ala Phe Ala Tyr Tyr Ile Glu Pro Gln His Arg Asp Val
235 Leu Gln Leu Tyr Ala Pro Glu Ala Phe Asn Tyr Met Asp Lys Phe Asn Glu Gln
253 Glu Ile Asn Leu Ser Leu Glu Glu Leu Lys Asp Gln Arg Met Leu Ser Arg Tyr
271 Glu Lys Trp Glu Lys Ile Lys Gln His Tyr Gln His Trp Ser Asp Ser Leu Ser
289 Glu Glu Gly Arg Gly Leu Leu Lys Lys Leu Gln Ile Pro Ile Glu Pro Lys Lys
307 Asp Asp Ile His Ser Leu Ser Gln Glu Glu Lys Glu Leu Leu Lys Arg Ile
325 Gln Ile Asp Ser Ser Asp Phe Leu Ser Thr Glu Glu Lys Glu Phe Leu Lys Lys
343 Leu Gln Ile Asp Ile Arg Asp Ser Leu Ser Glu Glu Glu Lys Glu Leu Leu Asn
361 Arg Ile Gln Val Asp Ser Ser Asn Pro Leu Ser Glu Lys Glu Lys Glu Phe Leu
379 Lys Lys Leu Lys Leu Asp Ile Gln Pro Tyr Asp Ile Asn Gln Arg Leu Gln Asp
397 Thr Gly Gly Leu Ile Asp Ser Pro Ser Ile Asn Leu Asp Val Arg Lys Gln Tyr
415 Lys Arg Asp Ile Gln Asn Ile Asp Ala Leu Leu His Gln Ser Ile Gly Ser Thr
433 Leu Tyr Asn Lys Ile Tyr Leu Tyr Glu Asn Met Asn Ile Asn Asn Leu Thr Ala
451 Thr Leu Gly Ala Asp Leu Val Asp Ser Thr Asp Asn Thr Lys Ile Asn Arg Gly
469 Ile Phe Asn Glu Phe Lys Lys Asn Phe Lys Tyr Ser Ile Ser Ser Asn Tyr Met
487 Ile Val Asp Ile Asn Glu Arg Pro Ala Leu Asp Asn Glu Arg Leu Lys Trp Arg
505 Ile Gln Leu Ser Pro Asp Thr Arg Ala Gly Tyr Leu Glu Gly Lys Lys Leu Ile
523 Leu Gln Arg Asn Ile Gly Leu Glu Ile Lys Asp Val Gln Ile Ile Lys Gln Ser
541 Glu Lys Glu Tyr Ile Arg Ile Asp Ala Lys Val Val Pro Lys Ser Lys Ile Asp
559 Thr Lys Ile Gln Glu Ala Gln Leu Asn Ile Asn Gln Glu Trp Asn Lys Ala Leu
577 Gly Leu Pro Lys Tyr Thr Lys Leu Ile Thr Phe Asn Val His Asn Arg Tyr Ala
595 Ser Asn Ile Val Glu Ser Ala Tyr Leu Ile Leu Asn Glu Trp Lys Asn Asn Ile
613 Gln Ser Asp Leu Ile Lys Lys Val Thr Asn Tyr Leu Val Asp Gly Asn Gly Arg
631 Phe Val Phe Thr Asp Ile Thr Leu Pro Asn Ile Ala Glu Gln Tyr Thr His Gln
649 Asp Glu Ile Tyr Glu Gln Val His Ser Lys Gly Leu Tyr Val Pro Glu Ser Arg
667 Ser Ile Leu Leu His Gly Pro Ser Lys Gly Val Glu Leu Arg Asn Asp Ser Glu
685 Gly Phe Ile His Glu Phe Gly His Ala Val Asp Asp Tyr Ala Gly Tyr Leu Leu
703 Asp Lys Asn Gln Ser Asp Leu Val Thr Asn Ser Lys Lys Phe Ile Asp Ile Phe
721 Lys Glu Glu Gly Ser Asn Leu Thr Ser Tyr Gly Arg Thr Asn Glu Ala Glu Phe
739 Phe Ala Glu Ala Phe Arg Leu Met His Ser Thr Asp His Ala Glu Arg Leu Lys
757 Val Gln Lys Asn Ala Pro Lys Thr Phe Gln Phe Ile Asn Asp Gln Ile Lys Phe
775 Ile Ile Asn Ser
```

FIG. 5B

```
   1 tcgtcagggg ggcggagcct atggaaaaac gccagcaacg cggccttttt
  51 acggttcctg gccttttgct ggccttttgc tcacatgttc tttcctgcgt
 101 tatccctga ttctgtggat aaccgtatta ccgcctttga gtgagctgat
 151 accgctcgcc gcagccgaac gaccgagcgc agcgagtcag tgagcgagga
 201 agcggaagag cgcctgatgc ggtattttct ccttacgcat ctgtgcggta
 251 tttcacaccg caatggtgca ctctcagtac aatctgctct gatgccgcat
 301 agttaagcca gtaaaaaaaa tttagcagtt aaaaagatg aatggactgc
 351 ttatagcgat aaagttaaat cagatttaga agtaccagcg aaacgacaca
 401 tgaaaagtgt tgaagtgcca acgggtgaaa agtccatgtt tggtttggga
 451 aaagaaataa tgaaaacaga aagaaaacca accaaaaatg ttgttatatc
 501 ggagcgtgat tataaaaact tagtgactgc tgcgagagat aacgataggt
 551 taaaacagca tgttagaaat ctcatgagta ctgatatggc gagagaatat
 601 aaaaaattaa gtaaagaaca tgggcaagtt aaagaaaaat atagtggtct
 651 tgtagagcga tttaatgaaa atgtaaatga ttataatgag ttgcttgaag
 701 aaaacaagtc tttaaagtct aaaataagcg attaaagcg tgatgtgagt
 751 ttaatctatg aaagcactaa ggaattcctt aaggaacgta cagacggctt
 801 aaaagccttt aaaaacgttt ttaaggggtt tgtagacaag gtaaaggata
 851 aaacagcaca attccaagaa aaacacgatt tagaacctaa aagaacgaa
 901 tttgaactaa ctcataaccg agaggtaaaa aagaacgaa gtcgagatca
 951 gggaatgagt ttataaaata aaaaaagcac ctgaaaaggt gtcttttttt
1001 gatggttttg aacttgttct ttcttatctt gatacatata gaaataacgt
1051 catttttatt ttagttgctg aaaggtgcgt tgaagtgttg gtatgtatgt
1101 gttttaaagt attgaaaacc cttaaaattg gttgcacaga aaaacccat
1151 ctgttaaagt tataagtgac taaacaaata actaaataga tgggggtttc
1201 ttttaatatt atgtgtccta atagtagcat ttattcagat gaaaaatcaa
1251 gggttttagt ggacaagaca aaaagtggaa aagtgagacc atggagagaa
1301 aagaaaatcg ctaatgttga ttactttgaa cttctgcata ttcttgaatt
1351 taaaaaggct gaaagagtaa aagattgtgc tgaaatatta gagtataaac
1401 aaaatcgtga aacaggcgaa agaaagttgt atcgagtgtg gttttgtaaa
1451 tccaggcttt gtccaatgtg caactggagg agagcaatga acatggcat
1501 tcagtcacaa aaggttgttg ctgaagttat taaacaaaag ccaacagttc
1551 gttggttgtt tctcacatta acagttaaaa atgtttatga tggcgaagaa
1601 ttaaataaga gtttgtcaga tatggctcaa ggatttcgcc gaatgatgca
1651 atataaaaaa attaataaaa atcttgttgg ttttatgcgt gcaacggaag
1701 tgacaataaa taataaagat aattcttata atcagcacat gcatgtattg
1751 gtatgtgtgg aaccaactta ttttaagaat acagaaaact acgtgaatca
1801 aaacaatgg attcaatttt ggaaaaggc aatgaaatta gactatgatc
1851 caaatgtaaa agttcaaatg attcgaccga aaataaata taaatcggat
1901 atacaatcgg caattgacga aactgcaaaa tatcctgtaa aggatacgga
```

FIG. 5B cont.

```
1951 ttttatgacc gatgatgaag aaaagaattt gaaacgtttg tctgatttgg
2001 aggaaggttt acaccgtaaa aggttaatct cctatggtgg tttgttaaaa
2051 gaaatacata aaaattaaa ccttgatgac acagaagaag gcgatttgat
2101 tcatacagat gatgacgaaa aagccgatga agatggattt tctattattg
2151 caatgtggaa ttgggaacgg aaaaattatt ttattaaaga gtagttcaac
2201 aaacgggcca gtttgttgaa gattagatgc tataattgtt attaaaagga
2251 ttgaaggatg cttaggaaga cgagttatta atagctgaat aagaacggtg
2301 ctctccaaat attcttattt agaaaagcaa atctaaaatt atctgaaaag
2351 ggaatgagaa tagtgaatgg accaataata atgactagag aagaaagaat
2401 gaagattgtt catgaaatta aggaacgaat attggataaa tatggggatg
2451 atgttaaggc tattggtgtt tatggctctc ttggtcgtca gactgatggg
2501 ccctattcgg atattgagat gatgtgtgtc atgtcaacag aggaagcaga
2551 gttcagccat gaatggacaa ccggtgagtg gaaggtggaa gtgaattttg
2601 atagcgaaga gattctacta gattatgcat ctcaggtgga atcagattgg
2651 ccgcttacac atggtcaatt tttctctatt ttgccgattt atgattcagg
2701 tggatactta gagaaagtgt atcaaactgc taaatcggta gaagcccaaa
2751 cgttccacga tgcgatttgt gcccttatcg tagaagagct gtttgaatat
2801 gcaggcaaat ggcgtaatat tcgtgtgcaa ggaccgacaa catttctacc
2851 atccttgact gtacaggtag caatggcagg tgccatgttg attggtctgc
2901 atcatcgcat ctgttatacg acgagcgctt cggtcttaac tgaagcagtt
2951 aagcaatcag atcttccttc aggttatgac catctgtgcc agttcgtaat
3001 gtctggtcaa ctttccgact ctgagaaact tctggaatcg ctagagaatt
3051 tctggaatgg gattcaggag tggacagaac gacacggata tatagtggat
3101 gtgtcaaaac gcataccatt ttgaacgatg acctctaata attgttaatc
3151 atgttggtta cgtatttatt aacttctcct agtattagta attatcatgg
3201 ctgtcatggc gcattaacgg aataaagggt gtgcttaaat cgggccattt
3251 tgcgtaataa gaaaaggat taattatgag cgaattgaat taataataag
3301 gtaatagatt tacattagaa aatgaaaggg gattttatgc gtgagaatgt
3351 tacagtctat cccggcattg ccagtcgggg atattaaaaa gagtataggt
3401 ttttattgcg ataaactagg tttcactttg gttcaccatg aagatggatt
3451 cgcagttcta atgtgtaatg aggttcggat tcatctatta aacatataaa
3501 ttctttttta tgttatatat ttataaaagt tctgtttaaa aagccaaaaa
3551 taaataatta tctcttttta tttatattat attgaaacta agtttatta
3601 atttcaatat aatataaatt taattttata caaaaggag aacgtatatg
3651 aaaaaacgaa aagtgttaat accattaatg gcattgtcta cgatattagt
3701 ttcaagcaca ggtaatttag aggtgattca ggcagaagtt aaacaggaga
3751 accggttatt aaatgaatca gaatcaagtt cccaggggtt actaggatac
3801 tatttagtg atttgaattt tcaagcaccc atggtggtta cctcttctac
3851 tacaggggat ttatctattc ctagttctga gttagaaaat attccatcgg
```

FIG. 5B cont.

```
3901 aaaaccaata ttttcaatct gctatttggt caggatttat caaagttaag
3951 aagagtgatg aatatacatt tgctacttcc gctgataatc atgtaacaat
4001 gtgggtagat gaccaagaag tgattaataa agcttctaat tctaacaaaa
4051 tcagattaga aaaaggaaga ttatatcaaa taaaaattca atatcaacga
4101 gaaaatccta ctgaaaaagg attggatttc aagttgtact ggaccgattc
4151 tcaaaataaa aaagaagtga tttctagtga taacttacaa ttgccagaat
4201 taaaacaaaa atcttcgaac tcaagaaaaa agcgaagtac aagtgctgga
4251 cctacggttc cagaccgtga caatgatgga atccctgatt cattagaggt
4301 agaaggatat acggttgatg tcaaaaataa aagaactttt ctttcaccat
4351 ggatttctaa tattcatgaa aagaaaggat taaccaaata taaatcatct
4401 cctgaaaaat ggagcacggc ttctgatccg tacagtgatt tcgaaaaggt
4451 tacaggacgg attgataaga atgtatcacc agaggcaaga cacccccttg
4501 tggcagctta tccgattgta catgtagata tggagaatat tattctctca
4551 aaaatgagg atcaatccac acagaatact gatagtcaaa cgagaacaat
4601 aagtaaaaat acttctacaa gtaggacaca tactagtgaa gtacatggaa
4651 atgcagaagt gcatgcgtcg ttctttgata ttggtgggag tgtatctgca
4701 ggatttagta attcgaattc aagtacggtc gcaattgatc attcactatc
4751 tctagcaggg gaaagaactt gggctgaaac aatgggttta aataccgctg
4801 atacagcaag attaaatgcc aatattagat atgtaaatac tgggacggct
4851 ccaatctaca acgtgttacc aacgacttcg ttagtgttag gaaaaaatca
4901 aacactcgcg acaattaaag ctaaggaaaa ccaattaagt caaatacttg
4951 cacctaataa ttattatcct tctaaaaact tggcgccaat cgcattaaat
5001 gcacaagacg atttcagttc tactccaatt acaatgaatt acaatcaatt
5051 tcttgagtta gaaaaaacga acaattaag attagatacg gatcaagtat
5101 atgggaatat agcaacatac aattttgaaa atggaagagt gagggtggat
5151 acaggctcga actggagtga agtgttaccg caaattcaag aaacaactgc
5201 acgtatcatt tttaatggaa aagatttaaa tctggtagaa aggcggatag
5251 cggcggttaa tcctagtgat ccattagaaa cgactaaacc ggatatgaca
5301 ttaaagaag cccttaaaat agcatttgga tttaacgaac cgaatggaaa
5351 cttacaatat caagggaaag acataaccga atttgatttt aatttcgatc
5401 aacaaacatc tcaaaatatc aagaatcagt tagcggaatt aaacgcaact
5451 aacatatata ctgtattaga taaaatcaaa ttaaatgcaa aaatgaatat
5501 tttaataaga gataaacgtt ttcattatga tagaaataac atagcagttg
5551 gggcggatga gtcagtagtt aaggaggctc atagagaagt aattaattcg
5601 tcaacagagg gattattgtt aaatattgat aaggatataa gaaaaatatt
5651 atcaggttat attgtagaaa ttgaagatac tgaagggctt aaagaagtta
5701 taaatgacag atatgatatg ttgaatattt ctagtttacg gcaagatgga
5751 aaaacattta tagattttaa aaaatataat gataaattac cgttatatat
5801 aagtaatccc aattataagg taaatgtata tgctgttact aaagaaaaca
```

FIG. 5B cont.

```
5851 ctattattaa tcctagtgag aatggggata ctagtaccaa cgggatcaag
5901 aaaattttaa tcttttctaa aaaaggctat gagataggat aaggtaattc
5951 taggtgattt ttaaattatc taaaaaacag taaaattaaa acatactctt
6001 tttgtaagaa atacaaggag agtatgtttt aaacagtaat ctaaatcatc
6051 ataatccttt gagattgttt gtaggatccg gctgctaaca aagcccgaaa
6101 ggaagctgag ttggctgctg ccaccgctga gcaataacta gcataacccc
6151 ttggggcctc taaacgggtc ttgaggggtt ttttgctgaa aggaggaact
6201 atatccggat atcccgcaag aggcccggca gtaccggcat aaccaagcct
6251 atgcctacag catccaggt gacggtgccg aggatgacga tgagcgcatt
6301 gttagatttc atacacggtg cctgactgcg ttagcaattt aactgtgata
6351 aactaccgca ttaaagctta tcgatgataa gctgtcaaac atgagaattc
6401 ttgaagacga aagggcctcg tgatacgcct atttttatag gttaatgtca
6451 tgataataat ggtttcttag acgtcaggtg cacttttcg gggaaatgtg
6501 cgcggaaccc ctatttgttt attttctaa atacattcaa atatgtatcc
6551 gctcatgaga caataaccct gataaatgct tcaataatat tgaaaagga
6601 agagtatgag tattcaacat ttccgtgtcg cccttattcc cttttttgcg
6651 gcatttttgcc ttcctgtttt tgctcaccca gaaacgctgg tgaaagtaaa
6701 agatgctgaa gatcagttgg gtgcacgagt gggttacatc gaactggatc
6751 tcaacagcgg taagatcctt gagagttttc gccccgaaga acgttttcca
6801 atgatgagca cttttaaagt tctgctatgt ggcgcggtat tatcccgtgt
6851 tgacgccggg caagagcaac tcggtcgccg catacactat tctcagaatg
6901 acttggttga gtactcacca gtcacagaaa agcatcttac ggatggcatg
6951 acagtaagag aattatgcag tgctgccata accatgagtg ataacactgc
7001 ggccaactta cttctgacaa cgatcggagg accgaaggag ctaaccgctt
7051 ttttgcacaa catgggggat catgtaactc gccttgatcg ttgggaaccg
7101 gagctgaatg aagccatacc aaacgacgag cgtgacacca cgatgcctgc
7151 agcaatggca acaacgttgc gcaaactatt aactggcgaa ctacttactc
7201 tagcttcccg gcaacaatta atagactgga tggaggcgga taaagttgca
7251 ggaccacttc tgcgctcggc ccttccggct ggctggttta ttgctgataa
7301 atctggagcc ggtgagcgtg ggtctcgcgg tatcattgca gcactggggc
7351 cagatggtaa gccctcccgt atcgtagtta tctacacgac ggggagtcag
7401 gcaactatgg atgaacgaaa tagacagatc gctgagatag gtgcctcact
7451 gattaagcat tggtaactgt cagaccaagt ttactcatat atactttaga
7501 ttgatttaaa acttcatttt taatttaaaa ggatctaggt gaagatcctt
7551 tttgataatc tcatgaccaa aatcccttaa cgtgagtttt cgttccactg
7601 agcgtcagac cccgtagaaa agatcaaagg atcttcttga gatccttttt
7651 ttctgcgcgt aatctgctgc ttgcaaacaa aaaaaccacc gctaccagcg
7701 gtggtttgtt tgccggatca agagctacca actctttttc cgaaggtaac
7751 tggcttcagc agagcgcaga taccaaatac tgtccttcta gtgtagccgt
7801 agttaggcca ccacttcaag aactctgtag caccgcctac atacctcgct
```

FIG. 5B cont.

```
7851 ctgctaatcc tgttaccagt ggctgctgcc agtggcgata agtcgtgtct
7901 taccgggttg gactcaagac gatagttacc ggataaggcg cagcggtcgg
7951 gctgaacggg gggttcgtgc acacagccca gcttggagcg aacgacctac
8001 accgaactga gatacctaca gcgtgagcta tgagaaagcg ccacgcttcc
8051 cgaagggaga aaggcggaca ggtatccggt aagcggcagg gtcggaacag
8101 gagagcgcac gagggagctt ccaggggggaa acgcctggta tctttatagt
8151 cctgtcgggt ttcgccacct ctgacttgag cgtcgatttt tgtgatgc
```

FIG. 5C

```
3701 gaagtt       aaacaggaga
3751 accggttatt aaatgaatca gaatcaagtt cccaggggtt actaggatac
3801 tattttagtg atttgaattt tcaagcaccc atggtggtta cctcttctac
3851 tacaggggat ttatctattc ctagttctga gttagaaaat attccatcgg
3901 aaaaccaata ttttcaatct gctatttggt caggatttat caaagttaag
3951 aagagtgatg aatatacatt tgctacttcc gctgataatc atgtaacaat
4001 gtgggtagat gaccaagaag tgattaataa agcttctaat tctaacaaaa
4051 tcagattaga aaaaggaaga ttatatcaaa taaaaattca atatcaacga
4101 gaaaatccta ctgaaaaagg attggatttc aagttgtact ggaccgattc
4151 tcaaaataaa aagaagtga tttctagtga taacttacaa ttgccagaat
4201 taaaacaaaa atcttcgaac tcaagaaaaa agcgaagtac aagtgctgga
4251 cctacggttc cagaccgtga caatgatgga atccctgatt cattagaggt
4301 agaaggatat acggttgatg tcaaaaataa agaactttt ctttcaccat
4351 ggatttctaa tattcatgaa agaaaggat taaccaaata taaatcatct
4401 cctgaaaaat ggagcacggc ttctgatccg tacagtgatt tcgaaaaggt
4451 tacaggacgg attgataaga atgtatcacc agaggcaaga cacccccttg
4501 tggcagctta tccgattgta catgtagata tggagaatat tattctctca
4551 aaaaatgagg atcaatccac acagaatact gatagtcaaa cgagaacaat
4601 aagtaaaaat acttctacaa gtaggacaca tactagtgaa gtacatggaa
4651 atgcagaagt gcatgcgtcg ttctttgata ttggtgggag tgtatctgca
4701 ggatttagta attcgaattc aagtacggtc gcaattgatc attcactatc
4751 tctagcaggg gaaagaactt gggctgaaac aatgggttta aataccgctg
4801 atacagcaag attaaatgcc aatattagat atgtaaatac tgggacggct
4851 ccaatctaca acgtgttacc aacgacttcg ttagtgttag gaaaaaatca
4901 aacactcgcg acaattaaag ctaaggaaaa ccaattaagt caaatacttg
4951 cacctaataa ttattatcct tctaaaaact ggcgccaat cgcattaaat
5001 gcacaagacg atttcagttc tactccaatt acaatgaatt acaatcaatt
5051 tcttgagtta gaaaaaacga acaattaag attagatacg gatcaagtat
5101 atgggaatat agcaacatac aattttgaaa atggaagagt gagggtggat
5151 acaggctcga actggagtga agtgttaccg caaattcaag aaacaactgc
5201 acgtatcatt tttaatggaa aagatttaaa tctggtagaa aggcggatag
5251 cggcggttaa tcctagtgat ccattagaaa cgactaaacc ggatatgaca
5301 ttaaaagaag cccttaaaat agcatttgga tttaacgaac cgaatgaaaa
5351 cttacaatat caagggaaag ataaccga atttgatttt aatttcgatc
5401 aacaaacatc tcaaaatatc aagaatcagt tagcggaatt aaacgcaact
5451 aacatatata ctgtattaga taaaatcaaa ttaaatgcaa aatgaatat
5501 tttaataaga gataaacgtt ttcattatga tagaaataac atagcagttg
```

FIG. 5C cont.

```
5551 gggcggatga gtcagtagtt aaggaggctc atagagaagt aattaattcg
5601 tcaacagagg gattattgtt aaatattgat aaggatataa gaaaaatatt
5651 atcaggttat attgtagaaa ttgaagatac tgaagggctt aaagaagtta
5701 taaatgacag atatgatatg ttgaatattt ctagtttacg gcaagatgga
5751 aaaacattta tagattttaa aaaatataat gataaattac cgttatatat
5801 aagtaatccc aattataagg taaatgtata tgctgttact aaagaaaaca
5851 ctattattaa tcctagtgag aatggggata ctagtaccaa cgggatcaag
5901 aaaattttaa tcttttctaa aaaggctat gagataggat aa
```

FIG. 5D

```
  1 Glu Val Lys Gln Glu Asn Arg Leu Leu Asn Glu Ser Glu Ser Ser Ser Gln Gly
 19 Leu Leu Gly Tyr Tyr Phe Ser Asp Leu Asn Phe Gln Ala Pro Met Val Val Thr
 37 Ser Ser Thr Thr Gly Asp Leu Ser Ile Pro Ser Ser Glu Leu Glu Asn Ile Pro
 55 Ser Glu Asn Gln Tyr Phe Gln Ser Ala Ile Trp Ser Gly Phe Ile Lys Val Lys
 73 Lys Ser Asp Glu Tyr Thr Phe Ala Thr Ser Ala Asp Asn His Val Thr Met Trp
 91 Val Asp Asp Gln Glu Val Ile Asn Lys Ala Ser Asn Ser Asn Lys Ile Arg Leu
109 Glu Lys Gly Arg Leu Tyr Gln Ile Lys Ile Gln Tyr Gln Arg Glu Asn Pro Thr
127 Glu Lys Gly Leu Asp Phe Lys Leu Tyr Trp Thr Asp Ser Gln Asn Lys Lys Glu
145 Val Ile Ser Ser Asp Asn Leu Gln Leu Pro Glu Leu Lys Gln Lys Ser Ser Asn
163 Ser Arg Lys Lys Arg Ser Thr Ser Ala Gly Pro Thr Val Pro Asp Arg Asp Asn
181 Asp Gly Ile Pro Asp Ser Leu Glu Val Glu Gly Tyr Thr Val Asp Val Lys Asn
199 Lys Arg Thr Phe Leu Ser Pro Trp Ile Ser Asn Ile His Glu Lys Lys Gly Leu
217 Thr Lys Tyr Lys Ser Ser Pro Glu Lys Trp Ser Thr Ala Ser Asp Pro Tyr Ser
235 Asp Phe Glu Lys Val Thr Gly Arg Ile Asp Lys Asn Val Ser Pro Glu Ala Arg
253 His Pro Leu Val Ala Ala Tyr Pro Ile Val His Val Asp Met Glu Asn Ile Ile
271 Leu Ser Lys Asn Glu Asp Gln Ser Thr Gln Asn Thr Asp Ser Gln Thr Arg Thr
289 Ile Ser Lys Asn Thr Ser Thr Ser Arg Thr His Thr Ser Glu Val His Gly Asn
307 Ala Glu Val His Ala Ser Phe Phe Asp Ile Gly Gly Ser Val Ser Ala Gly Phe
325 Ser Asn Ser Asn Ser Ser Thr Val Ala Ile Asp His Ser Leu Ser Leu Ala Gly
343 Glu Arg Thr Trp Ala Glu Thr Met Gly Leu Asn Thr Ala Asp Thr Ala Arg Leu
361 Asn Ala Asn Ile Arg Tyr Val Asn Thr Gly Thr Ala Pro Ile Tyr Asn Val Leu
379 Pro Thr Thr Ser Leu Val Leu Gly Lys Asn Gln Thr Leu Ala Thr Ile Lys Ala
397 Lys Glu Asn Gln Leu Ser Gln Ile Leu Ala Pro Asn Asn Tyr Tyr Pro Ser Lys
415 Asn Leu Ala Pro Ile Ala Leu Asn Ala Gln Asp Asp Phe Ser Ser Thr Pro Ile
433 Thr Met Asn Tyr Asn Gln Phe Leu Glu Leu Glu Lys Thr Lys Gln Leu Arg Leu
451 Asp Thr Asp Gln Val Tyr Gly Asn Ile Ala Thr Tyr Asn Phe Glu Asn Gly Arg
469 Val Arg Val Asp Thr Gly Ser Asn Trp Ser Glu Val Leu Pro Gln Ile Gln Glu
487 Thr Thr Ala Arg Ile Ile Phe Asn Gly Lys Asp Leu Asn Leu Val Glu Arg Arg
505 Ile Ala Ala Val Asn Pro Ser Asp Pro Leu Glu Thr Thr Lys Pro Asp Met Thr
523 Leu Lys Glu Ala Leu Lys Ile Ala Phe Gly Phe Asn Glu Pro Asn Gly Asn Leu
541 Gln Tyr Gln Gly Lys Asp Ile Thr Glu Phe Asp Phe Asn Phe Asp Gln Gln Thr
559 Ser Gln Asn Ile Lys Asn Gln Leu Ala Glu Leu Asn Ala Thr Asn Ile Tyr Thr
577 Val Leu Asp Lys Ile Lys Leu Asn Ala Lys Met Asn Ile Leu Ile Arg Asp Lys
595 Arg Phe His Tyr Asp Arg Asn Asn Ile Ala Val Gly Ala Asp Glu Ser Val Val
613 Lys Glu Ala His Arg Glu Val Ile Asn Ser Ser Thr Glu Gly Leu Leu Leu Asn
631 Ile Asp Lys Asp Ile Arg Lys Ile Leu Ser Gly Tyr Ile Val Glu Ile Glu Asp
649 Thr Glu Gly Leu Lys Glu Val Ile Asn Asp Arg Tyr Asp Met Leu Asn Ile Ser
667 Ser Leu Arg Gln Asp Gly Lys Thr Phe Ile Asp Phe Lys Lys Tyr Asn Asp Lys
685 Leu Pro Leu Tyr Ile Ser Asn Pro Asn Tyr Lys Val Asn Val Tyr Ala Val Thr
703 Lys Glu Asn Thr Ile Ile Asn Pro Ser Glu Asn Gly Asp Thr Ser Thr Asn Gly
721 Ile Lys Lys Ile Leu Ile Phe Ser Lys Lys Gly Tyr Glu Ile Gly
```

FIG. 5E

| Analysis | Entire Protein |
|---|---|
| Length | 735 aa |
| Molecular Weight | 82779.09 m.w. |
| 1 microgram = | 12.080 pMoles |
| Molar Extinction coefficient | 75670 |
| 1 A[280] corr. to | 1.09 mg/ml |
| A[280] of 1 mg/ml | 0.91 AU |
| Isoelectric Point | 5.64 |
| Charge at pH 7 | -10.26 |

FIG. 6B

```
  1 tcgtcagggg ggcggagcct atggaaaaac gccagcaacg cggccttttt
    agcagtcccc ccgcctcgga tacctttttg cggtcgttgc gccggaaaaa
 51 acggttcctg gccttttgct ggccttttgc tcacatgttc tttcctgcgt
    tgccaaggac cggaaaacga ccggaaaacg agtgtacaag aaaggacgca
101 tatcccctga ttctgtggat aaccgtatta ccgcctttga gtgagctgat
    atagggact aagacaccta ttggcataat ggcggaaact cactcgacta
151 accgctcgcc gcagccgaac gaccgagcgc agcgagtcag tgagcgagga
    tggcgagcgg cgtcggcttg ctggctcgcg tcgctcagtc actcgctcct
201 agcggaagag cgcctgatgc ggtattttct ccttacgcat ctgtgcggta
    tcgccttctc gcggactacg ccataaaaga ggaatgcgta gacacgccat
251 tttcacaccg caatggtgca ctctcagtac aatctgctct gatgccgcat
    aaagtgtggc gttaccacgt gagagtcatg ttagacgaga ctacggcgta
301 agttaagcca gtaaaaaaaa tttagcagtt aaaaagatg aatggactgc
    tcaattcggt catttttttt aaatcgtcaa ttttttctac ttacctgacg
351 ttatagcgat aaagttaaat cagatttaga agtaccagcg aaacgacaca
    aatatcgcta tttcaattta gtctaaatct tcatggtcgc tttgctgtgt
401 tgaaaagtgt tgaagtgcca acgggtgaaa agtccatgtt tggtttggga
    acttttcaca acttcacggt tgcccacttt tcaggtacaa accaaaccct
451 aaagaaataa tgaaaacaga aaagaaacca accaaaaatg ttgttatatc
    tttctttatt acttttgtct tttctttggt tggttttttac aacaatatag
501 ggagcgtgat tataaaaact tagtgactgc tgcgagagat aacgataggt
    cctcgcacta atattttga atcactgacg acgctctcta ttgctatcca
551 taaaacagca tgttagaaat ctcatgagta ctgatatggc gagagaatat
    attttgtcgt acaatctttta gagtactcat gactataccg ctctcttata
601 aaaaattaa gtaaagaaca tgggcaagtt aagaaaaat atagtggtct
    tttttaatt catttcttgt acccgttcaa tttctttta tatcaccaga
651 tgtagagcga tttaatgaaa atgtaaatga ttataatgag ttgcttgaag
    acatctcgct aaattacttt tacatttact aatattactc aacgaacttc
701 aaaacaagtc tttaaagtct aaaataagcg atttaaagcg tgatgtgagt
    ttttgttcag aaatttcaga ttttattcgc taaatttcgc actacactca
751 ttaatctatg aaagcactaa ggaattcctt aaggaacgta cagacggctt
    aattagatac tttcgtgatt ccttaaggaa ttccttgcat gtctgccgaa
801 aaaagccttt aaaaacgttt ttaaggggtt tgtagacaag gtaaaggata
    ttttcggaaa ttttttgcaaa aattccccaa acatctgttc catttcctat
851 aaacagcaca attccaagaa aaacacgatt tagaacctaa aaagaacgaa
    tttgtcgtgt taaggttctt tttgtgctaa atcttggatt tttcttgctt
901 tttgaactaa ctcataaccg agaggtaaaa aaagaacgaa gtcgagatca
    aaacttgatt gagtattggc tctccatttt tttcttgctt cagctctagt
951 gggaatgagt ttataaaata aaaaaagcac ctgaaaaggt gtcttttttt
    cccttactca aatattttat ttttttcgtg gacttttcca cagaaaaaaa
```

FIG. 6B cont.

```
1001 gatggttttg aacttgttct ttcttatctt gatacatata gaaataacgt
     ctaccaaaac ttgaacaaga aagaatagaa ctatgtatat ctttattgca
1051 cattttatt ttagttgctg aaaggtgcgt tgaagtgttg gtatgtatgt
     gtaaaaataa aatcaacgac tttccacgca acttcacaac catacataca
1101 gttttaaagt attgaaaacc cttaaaattg gttgcacaga aaaccccat
     caaaatttca taacttttgg gaattttaac caacgtgtct ttttggggta
1151 ctgttaaagt tataagtgac taaacaaata actaaataga tggggttttc
     gacaatttca atattcactg atttgtttat tgatttatct accccaaag
1201 ttttaatatt atgtgtccta atagtagcat ttattcagat gaaaaatcaa
     aaaattataa tacacaggat tatcatcgta aataagtcta cttttagtt
1251 gggttttagt ggacaagaca aaagtggaa aagtgagacc atggagagaa
     cccaaaatca cctgttctgt ttttcacctt ttcactctgg tacctctctt
1301 aagaaaatcg ctaatgttga ttactttgaa cttctgcata ttcttgaatt
     ttcttttagc gattacaact aatgaaactt gaagacgtat aagaacttaa
1351 taaaaaggct gaaagagtaa aagattgtgc tgaaatatta gagtataaac
     attttccga ctttctcatt ttctaacacg actttataat ctcatatttg
1401 aaaatcgtga acaggcgaa agaaagttgt atcgagtgtg gttttgtaaa
     ttttagcact ttgtccgctt tctttcaaca tagctcacac caaaacattt
1451 tccaggcttt gtccaatgtg caactggagg agagcaatga aacatggcat
     aggtccgaaa caggttacac gttgacctcc tctcgttact ttgtaccgta
1501 tcagtcacaa aaggttgttg ctgaagttat taaacaaaag ccaacagttc
     agtcagtgtt ttccaacaac gacttcaata atttgttttc ggttgtcaag
1551 gttggttgtt tctcacatta acagttaaaa atgttatga tggcgaagaa
     caaccaacaa agagtgtaat tgtcaatttt tacaaatact accgcttctt
1601 ttaaataaga gtttgtcaga tatggctcaa ggatttcgcc gaatgatgca
     aatttattct caaacagtct ataccgagtt cctaaagcgg cttactacgt
1651 atataaaaaa attaataaaa atcttgttgg ttttatgcgt gcaacggaag
     tatatttttt taattatttt tagaacaacc aaaatacgca cgttgccttc
1701 tgacaataaa taataaagat aattcttata atcagcacat gcatgtattg
     actgttattt attatttcta ttaagaatat tagtcgtgta cgtacataac
1751 gtatgtgtgg aaccaactta ttttaagaat acagaaaact acgtgaatca
     catacacacc ttggttgaat aaaattctta tgtcttttga tgcacttagt
1801 aaaacaatgg attcaatttt ggaaaaggc aatgaaatta gactatgatc
     ttttgttacc taagttaaaa ccttttccg ttactttaat ctgatactag
1851 caaatgtaaa agttcaaatg attcgaccga aaaataaata taaatcggat
     gtttacattt tcaagtttac taagctggct tttatttat atttagccta
1901 atacaatcgg caattgacga aactgcaaaa tatcctgtaa aggatacgga
     tatgttagcc gttaactgct ttgacgtttt ataggacatt tcctatgcct
```

FIG 6B cont.

```
1951 ttttatgacc gatgatgaag aaaagaattt gaaacgtttg tctgatttgg
     aaaatactgg ctactacttc ttttcttaaa ctttgcaaac agactaaacc
2001 aggaaggttt acaccgtaaa aggttaatct cctatggtgg tttgttaaaa
     tccttccaaa tgtggcattt tccaattaga ggataccacc aaacaatttt
2051 gaaatacata aaaaattaaa ccttgatgac acagaagaag gcgatttgat
     cttatgtat tttttaattt ggaactactg tgtcttcttc cgctaaacta
2101 tcatacagat gatgacgaaa aagccgatga agatggattt tctattattg
     agtatgtcta ctactgcttt ttcggctact tctacctaaa agataataac
2151 caatgtggaa ttgggaacgg aaaaattatt ttattaaaga gtagttcaac
     gttacacctt aacccttgcc tttttaataa aataatttct catcaagttg
2201 aaacgggcca gtttgttgaa gattagatgc tataattgtt attaaaagga
     tttgcccggt caaacaactt ctaatctacg atattaacaa taatttttcct
2251 ttgaaggatg cttaggaaga cgagttatta atagctgaat aagaacggtg
     aacttcctac gaatccttct gctcaataat tatcgactta ttcttgccac
2301 ctctccaaat attcttattt agaaaagcaa atctaaaatt atctgaaaag
     gagaggttta taagaataaa tcttttcgtt tagattttaa tagacttttc
2351 ggaatgagaa tagtgaatgg accaataata atgactagag aagaaagaat
     ccttactctt atcacttacc tggttattat tactgatctc ttctttctta
2401 gaagattgtt catgaaatta aggaacgaat attggataaa tatggggatg
     cttctaacaa gtactttaat tccttgctta taacctattt ataccctac
2451 atgttaaggc tattggtgtt tatggctctc ttggtcgtca gactgatggg
     tacaattccg ataaccacaa ataccgagag aaccagcagt ctgactaccc
2501 ccctattcgg atattgagat gatgtgtgtc atgtcaacag aggaagcaga
     gggataagcc tataactcta ctacacacag tacagttgtc tccttcgtct
2551 gttcagccat gaatggacaa ccggtgagtg gaaggtggaa gtgaattttg
     caagtcggta cttacctgtt ggccactcac cttccacctt cacttaaaac
2601 atagcgaaga gattctacta gattatgcat ctcaggtgga atcagattgg
     tatcgcttct ctaagatgat ctaatacgta gagtccacct tagtctaacc
2651 ccgcttacac atggtcaatt tttctctatt ttgccgattt atgattcagg
     ggcgaatgtg taccagttaa aaagagataa aacggctaaa tactaagtcc
2701 tggatactta gagaaagtgt atcaaactgc taaatcggta gaagcccaaa
     acctatgaat ctctttcaca tagtttgacg atttagccat cttcgggttt
2751 cgttccacga tgcgatttgt gcccttatcg tagaagagct gtttgaatat
     gcaaggtgct acgctaaaca cgggaatagc atcttctcga caaacttata
2801 gcaggcaaat ggcgtaatat tcgtgtgcaa ggaccgacaa catttctacc
     cgtccgttta ccgcattata agcacacgtt cctggctgtt gtaaagatgg
2851 atccttgact gtacaggtag caatggcagg tgccatgttg attggtctgc
     taggaactga catgtccatc gttaccgtcc acggtacaac taaccagacg
2901 atcatcgcat ctgttatacg acgagcgctt cggtcttaac tgaagcagtt
     tagtagcgta gacaatatgc tgctcgcgaa gccagaattg acttcgtcaa
```

FIG. 6B cont.

```
2951 aagcaatcag atcttccttc aggttatgac catctgtgcc agttcgtaat
     ttcgttagtc tagaaggaag tccaatactg gtagacacgg tcaagcatta
3001 gtctggtcaa ctttccgact ctgagaaact tctggaatcg ctagagaatt
     cagaccagtt gaaaggctga gactctttga agaccttagc gatctcttaa
3051 tctggaatgg gattcaggag tggacagaac gacacggata tatagtggat
     agaccttacc ctaagtcctc acctgtcttg ctgtgcctat atatcaccta
3101 gtgtcaaaac gcataccatt ttgaacgatg acctctaata attgttaatc
     cacagttttg cgtatggtaa aacttgctac tggagattat taacaattag
3151 atgttggtta cgtattatt aacttctcct agtattagta attatcatgg
     tacaaccaat gcataaataa ttgaagagga tcataatcat taatagtacc
3201 ctgtcatggc gcattaacgg aataaagggt gtgcttaaat cgggccattt
     gacagtaccg cgtaattgcc ttatttccca cacgaattta gcccggtaaa
3251 tgcgtaataa gaaaaggat taattatgag cgaattgaat taataataag
     acgcattatt cttttcctc attaatactc gcttaactta attattattc
3301 gtaatagatt tacattagaa aatgaaaggg gattttatgc gtgagaatgt
     cattatctaa atgtaatctt ttactttccc ctaaaatacg cactcttaca
3351 tacagtctat cccggcattg ccagtcgggg atattaaaaa gagtataggt
     atgtcagata gggccgtaac ggtcagcccc tataattttt ctcatatcca
3401 ttttattgcg ataaactagg tttcactttg gttcaccatg aagatggatt
     aaaataacgc tatttgatcc aaagtgaaac caagtggtac ttctacctaa
3451 cgcagttcta atgtgtaatg aggttcggat tcatctatta aacatataaa
     gcgtcaagat tacacattac tccaagccta agtagataat ttgtatattt
3501 ttcttttta tgttatatat ttataaaagt tctgtttaaa aagccaaaaa
     aagaaaaaat acaatatata aatatttca agacaaattt tcggttttt
3551 taaataatta tctctttta tttatattat attgaaacta agtttatta
     atttattaat agagaaaaat aaatataata taactttgat ttcaaataat
3601 atttcaatat aatataaatt taattttata caaaaaggag aacgtatatg
     taaagttata ttatatttaa attaaaatat gttttcctc ttgcatatac
3651 aaaaaacgaa aagtgttaat accattaatg gcattgtcta cgatattagt
     tttttgctt ttcacaatta tggtaattac cgtaacagat gctataatca
3701 ttcaagcaca ggtaatttag aggtgattca ggcagaagtt aaacaggaga
     aagttcgtgt ccattaaatc tccactaagt ccgtcttcaa tttgtcctct
3751 accggttatt aaatgaatca gaatcaagtt cccaggggtt actaggatac
     tggccaataa tttacttagt cttagttcaa gggtccccaa tgatcctatg
3801 tattttagtg atttgaattt tcaagcaccc atggtggtta cctcttctac
     ataaaatcac taaacttaaa agttcgtggg taccaccaat ggagaagatg
3851 tacaggggat ttatctattc ctagttctga gttagaaaat attccatcgg
     atgtccccta aatagataag gatcaagact caatctttta taaggtagcc
```

FIG 6B cont.

```
3901 aaaaccaata ttttcaatct gctatttggt caggatttat caaagttaag
     ttttggttat aaagttaga cgataaacca gtcctaaata gtttcaattc
3951 aagagtgatg aatatacatt tgctacttcc gctgataatc atgtaacaat
     ttctcactac ttatatgtaa acgatgaagg cgactattag tacattgtta
4001 gtgggtagat gaccaagaag tgattaataa agcttctaat tctaacaaaa
     cacccatcta ctggttcttc actaattatt tcgaagatta agattgtttt
4051 tcagattaga aaaggaaga ttatatcaaa taaaaattca atatcaacga
     agtctaatct ttttccttct aatatagttt attttaagt tatagttgct
4101 gaaaatccta ctgaaaagg attggatttc aagttgtact ggaccgattc
     cttttaggat gacttttcc taacctaaag ttcaacatga cctggctaag
4151 tcaaaataaa aagaagtga tttctagtga taacttacaa ttgccagaat
     agttttattt tttcttcact aaagatcact attgaatgtt aacggtctta
4201 taaaacaaaa atcttcgaac tcaagaaaaa agcgaagtac aagtgctgga
     attttgtttt tagaagcttg agttcttttt tcgcttcatg ttcacgacct
4251 cctacggttc cagaccgtga caatgatgga atccctgatt cattagaggt
     ggatgccaag gtctggcact gttactacct tagggactaa gtaatctcca
4301 agaaggatat acggttgatg tcaaaaataa aagaactttt ctttcaccat
     tcttcctata tgccaactac agtttttatt ttcttgaaaa gaaagtggta
4351 ggatttctaa tattcatgaa agaaaggat taaccaaata taaatcatct
     cctaaagatt ataagtactt ttctttccta attggtttat atttagtaga
4401 cctgaaaaat ggagcacggc ttctgatccg tacagtgatt tcgaaaaggt
     ggactttta cctcgtgccg aagactaggc atgtcactaa agcttttcca
4451 tacaggacgg attgataaga atgtatcacc agaggcaaga cacccccttg
     atgtcctgcc taactattct tacatagtgg tctccgttct gtggggaac
4501 tggcagctta tccgattgta catgtagata tggagaatat tattctctca
     accgtcgaat aggctaacat gtacatctat acctcttata ataagagagt
4551 aaaaatgagg atcaatccac acagaatact gatagtcaaa cgagaacaat
     ttttactcc tagttaggtg tgtcttatga ctatcagttt gctcttgtta
4601 aagtaaaaat acttctacaa gtaggacaca tactagtgaa gtacatggaa
     ttcatttta tgaagatgtt catcctgtgt atgatcactt catgtacctt
4651 atgcagaagt gcatgcgtcg ttctttgata ttggtgggag tgtatctgca
     tacgtcttca cgtacgcagc aagaaactat aaccaccctc acatagacgt
4701 ggatttagta attcgaattc aagtacggtc gcaattgatc attcactatc
     cctaaatcat taagcttaag ttcatgccag cgttaactag taagtgatag
4751 tctagcaggg gaaagaactt gggctgaaac aatgggttta aataccgctg
     agatcgtccc ctttcttgaa cccgactttg ttacccaaat ttatggcgac
4801 atacagcaag attaaatgcc aatattagat atgtaaatac tgggacggct
     tatgtcgttc taatttacgg ttataatcta tacatttatg accctgccga
```

FIG. 6B cont.

```
4851 ccaatctaca acgtgttacc aacgacttcg ttagtgttag gaaaaaatca
     ggttagatgt tgcacaatgg ttgctgaagc aatcacaatc cttttttagt
4901 aacactcgcg acaattaaag ctaaggaaaa ccaattaagt caaatacttg
     ttgtgagcgc tgttaatttc gattccttt ggttaattca gtttatgaac
4951 cacctaataa ttattatcct tctaaaaact tggcgccaat cgcattaaat
     gtggattatt aataatagga agattttga accgcggtta gcgtaattta
5001 gcacaagacg atttcagttc tactccaatt acaatgaatt acaatcaatt
     cgtgttctgc taaagtcaag atgaggttaa tgttacttaa tgttagttaa
5051 tcttgagtta gaaaaaacga acaattaag attagatacg gatcaagtat
     agaactcaat ctttttgct ttgttaattc taatctatgc ctagttcata
5101 atgggaatat agcaacatac aattttgaaa atggaagagt gagggtggat
     taccttata tcgttgtatg ttaaaacttt taccttctca ctcccaccta
5151 acaggctcga actggagtga agtgttaccg caaattcaag aaacaactgc
     tgtccgagct tgacctcact tcacaatggc gtttaagttc tttgttgacg
5201 acgtatcatt tttaatggaa aagatttaaa tctggtagaa aggcggatag
     tgcatagtaa aaattacctt ttctaaattt agaccatctt tccgcctatc
5251 cggcggttaa tcctagtgat ccattagaaa cgactaaacc ggatatgaca
     gccgccaatt aggatcacta ggtaatcttt gctgatttgg cctatactgt
5301 ttaaaagaag cccttaaaat agcatttgga tttaacgaac cgaatggaaa
     aattttcttc gggaatttta tcgtaaacct aaattgcttg cttaccttt
5351 cttacaatat caagggaaag acataaccga atttgatttt aatttcgatc
     gaatgttata gttccctttc tgtattggct taaactaaaa ttaaagctag
5401 aacaaacatc tcaaaatatc aagaatcagt tagcggaatt aaacgcaact
     ttgtttgtag agttttatag ttcttagtca atcgccttaa tttgcgttga
5451 aacatatata ctgtattaga taaaatcaaa ttaaatgcaa aaatgaatat
     ttgtatatat gacataatct attttagttt aatttacgtt tttacttata
5501 tttaataaga gataaacgtt tcattatga tagaaataac atagcagttg
     aaattattct ctatttgcaa aagtaatact atctttattg tatcgtcaac
5551 gggcggatga gtcagtagtt aaggaggctc atagagaagt aattaattcg
     cccgcctact cagtcatcaa ttcctccgag tatctcttca ttaattaagc
5601 tcaacagagg gattattgtt aaatattgat aaggatataa gaaaaatatt
     agttgtctcc ctaataacaa tttataacta ttcctatatt cttttataa
5651 atcaggttat attgtagaaa ttgaagatac tgaagggctt aaagaagtta
     tagtccaata taacatcttt aacttctatg acttcccgaa ttcttcaat
5701 taaatgacag atatgatatg ttgaatattt ctagtttacg gcaagatgga
     atttactgtc tatactatac aacttataaa gatcaaatgc cgttctacct
5751 aaaacattta tagatttaa aaaatataat gataaattac cgttatatat
     ttttgtaaat atctaaaatt ttttatatta ctatttaatg gcaatatata
```

FIG. 6B cont.

```
5801 aagtaatccc aattataagg taaatgtata tgctgttact aaagaaaaca
     ttcattaggg ttaatattcc atttacatat acgacaatga tttcttttgt
5851 ctattattaa tcctagtgag aatggggata ctagtaccaa cgggatcaag
     gataataatt aggatcactc ttacccctat gatcatggtt gccctagttc
5901 aaaattttaa tcttttctaa aaaaggctat gagataggat aaggtaattc
     ttttaaaatt agaaaagatt ttttccgata ctctatccta ttccattaag
5951 taggtgattt ttaaattatc taaaaaacag taaaattaaa acatactctt
     atccactaaa aatttaatag attttttgtc attttaattt tgtatgagaa
6001 tttgtaagaa atacaaggag agtatgtttt aaacagtaat ctaaatcatc
     aaacattctt tatgttcctc tcatacaaaa tttgtcatta gatttagtag
6051 ataatccttt gagattgttt gtaggatccc actttggttc accatgaaga
     tattaggaaa ctctaacaaa catcctaggg tgaaaccaag tggtacttct
6101 tggattcgca gttctaatgt gtaatgaggt tcggattcat ctattaaaca
     acctaagcgt caagattaca cattactcca agcctaagta gataatttgt
6151 tataaattct tttttatgtt atatatttat aaaagttctg tttaaaaagc
     atatttaaga aaaatacaa tatataaata ttttcaagac aaattttcg
6201 caaaaataaa taattatctc tttttattta tattatattg aaactaaagt
     gttttattt attaatagag aaaaataaat ataatataac tttgatttca
6251 ttattaattt caatataata taaatttaat tttatacaaa aaggagaacg
     aataattaaa gttatattat atttaaatta aaatatgttt ttcctcttgc
6301 tatatgaaaa aacgaaaagt gttaatacca ttaatggcat tgtctacgat
     atatactttt ttgcttttca caattatggt aattaccgta acagatgcta
6351 attagtttca agcacaggta atttagaggt gattcaggca catatggcgg
     taatcaaagt tcgtgtccat taaatctcca ctaagtccgt gtataccgcc
6401 gcggtcatgg tgatgtaggt atgcacgtaa aagagaaaga gaaaaataaa
     cgccagtacc actacatcca tacgtgcatt ttctctttct cttttattt
6451 gatgagaata agagaaaaga tgaagaacga aataaaacac aggaagagca
     ctactcttat tctctttct acttcttgct ttatttgtg tccttctcgt
6501 tttaaaggaa atcatgaaac acattgtaaa aatagaagta aaaggggagg
     aaatttcctt tagtactttg tgtaacattt ttatcttcat tttcccctcc
6551 aagctgttaa aaaagaggca gcagaaaagc tacttgagaa agtaccatct
     ttcgacaatt ttttctccgt cgtctttcg atgaactctt tcatggtaga
6601 gatgttttag agatgtataa agcaattgga ggaaagatat atattgtgga
     ctacaaaatc tctacatatt tcgttaacct cctttctata tataacacct
6651 tggtgatatt acaaaacata tatctttaga agcattatct gaagataaga
     accactataa tgttttgtat atagaaatct tcgtaataga cttctattct
6701 aaaaaataaa agacatttat gggaaagatg ccttattaca tgaacattat
     ttttttattt tctgtaaata cccttttctac ggaataatgt acttgtaata
```

FIG. 6B cont.

```
6751 gtatatgcaa aagaaggata tgaacccgta cttgtaatcc aatcttcgga
     catatacgtt ttcttcctat acttgggcat gaacattagg ttagaagcct
6801 agattatgta gaaaatactg aaaaggcact gaacgtttat tatgaaatag
     tctaatacat cttttatgac ttttccgtga cttgcaaata atactttatc
6851 gtaagatatt atcaagggat attttaagta aaattaatca accatatcag
     cattctataa tagttcccta taaaattcat tttaattagt tggtatagtc
6901 aaattttag atgtattaaa taccattaaa aatgcatctg attcagatgg
     tttaaaaatc tacataattt atggtaattt ttacgtagac taagtctacc
6951 acaagatctt ttatttacta atcagcttaa ggaacatccc acagactttt
     tgttctagaa aataaatgat tagtcgaatt ccttgtaggg tgtctgaaaa
7001 ctgtagaatt cttggaacaa aatagcaatg aggtacaaga agtatttgcg
     gacatcttaa gaaccttgtt ttatcgttac tccatgttct tcataaacgc
7051 aaagcttttg catattatat cgagccacag catcgtgatg ttttacagct
     tttcgaaaac gtaaatata gctcggtgtc gtagcactac aaaatgtcga
7101 ttatgcaccg gaagctttta attacatgga taaatttaac gaacaagaaa
     aatacgtggc cttcgaaaat taatgtacct atttaaattg cttgttcttt
7151 taaatctata aggatccggc tgctaacaaa gcccgaaagg aagctgagtt
     atttagatat tcctaggccg acgattgttt cgggctttcc ttcgactcaa
7201 ggctgctgcc accgctgagc aataactagc ataacccctt ggggcctcta
     ccgacgacgg tggcgactcg ttattgatcg tattggggaa ccccggagat
7251 aacgggtctt gaggggtttt ttgctgaaag gaggaactat atccggatat
     ttgcccagaa ctccccaaaa aacgactttc ctccttgata taggcctata
7301 cccgcaagag gcccggcagt accggcataa ccaagcctat gcctacagca
     gggcgttctc cgggccgtca tggccgtatt ggttcggata cggatgtcgt
7351 tccagggtga cggtgccgag gatgacgatg agcgcattgt tagatttcat
     aggtcccact gccacggctc ctactgctac tcgcgtaaca atctaaagta
7401 acacggtgcc tgactgcgtt agcaatttaa ctgtgataaa ctaccgcatt
     tgtgccacgg actgacgcaa tcgttaaatt gacactattt gatggcgtaa
7451 aaagcttatc gatgataagc tgtcaaacat gagaattctt gaagacgaaa
     tttcgaatag ctactattcg acagtttgta ctcttaagaa cttctgcttt
7501 gggcctcgtg atacgcctat ttttataggt taatgtcatg ataataatgg
     cccggagcac tatgcggata aaaatatcca attacagtac tattattacc
7551 tttcttagac gtcaggtggc acttttcggg gaaatgtgcg cggaaccccct
     aaagaatctg cagtccaccg tgaaaagccc ctttacacgc gccttgggga
7601 atttgtttat ttttctaaat acattcaaat atgtatccgc tcatgagaca
     taaacaaata aaagattta tgtaagttta tacataggcg agtactctgt
7651 ataaccctga taaatgcttc aataatattg aaaaggaag agtatgagta
     tattgggact atttacgaag ttattataac ttttccttc tcatactcat
7701 ttcaacattt ccgtgtcgcc cttattccct ttttgcggc attttgcctt
     aagttgtaaa ggcacagcgg gaataaggga aaaacgccg taaaacggaa
```

FIG. 6B cont.

```
7751 cctgtttttg ctcacccaga aacgctggtg aaagtaaaag atgctgaaga
     ggacaaaaac gagtgggtct ttgcgaccac tttcattttc tacgacttct
7801 tcagttgggt gcacgagtgg gttacatcga actggatctc aacagcggta
     agtcaaccca cgtgctcacc caatgtagct tgacctagag ttgtcgccat
7851 agatccttga gagttttcgc cccgaagaac gttttccaat gatgagcact
     tctaggaact ctcaaaagcg gggcttcttg caaaaggtta ctactcgtga
7901 tttaaagttc tgctatgtgg cgcggtatta tcccgtgttg acgccgggca
     aaatttcaag acgatacacc gcgccataat agggcacaac tgcggcccgt
7951 agagcaactc ggtcgccgca tacactattc tcagaatgac ttggttgagt
     tctcgttgag ccagcggcgt atgtgataag agtcttactg aaccaactca
8001 actcaccagt cacagaaaag catcttacgg atggcatgac agtaagagaa
     tgagtggtca gtgtcttttc gtagaatgcc taccgtactg tcattctctt
8051 ttatgcagtg ctgccataac catgagtgat aacactgcgg ccaacttact
     aatacgtcac gacggtattg gtactcacta ttgtgacgcc ggttgaatga
8101 tctgacaacg atcggaggac cgaaggagct aaccgctttt ttgcacaaca
     agactgttgc tagcctcctg gcttcctcga ttggcgaaaa aacgtgttgt
8151 tgggggatca tgtaactcgc cttgatcgtt gggaaccgga gctgaatgaa
     acccctagt acattgagcg gaactagcaa cccttggcct cgacttactt
8201 gccataccaa acgacgagcg tgacaccacg atgcctgcag caatggcaac
     cggtatggtt tgctgctcgc actgtggtgc tacggacgtc gttaccgttg
8251 aacgttgcgc aaactattaa ctggcgaact acttactcta gcttcccggc
     ttgcaacgcg tttgataatt gaccgcttga tgaatgagat cgaagggccg
8301 aacaattaat agactggatg gaggcggata agttgcagg accacttctg
     ttgttaatta tctgacctac ctccgcctat ttcaacgtcc tggtgaagac
8351 cgctcggccc ttccggctgg ctggtttatt gctgataaat ctggagccgg
     gcgagccggg aaggccgacc gaccaaataa cgactattta gacctcggcc
8401 tgagcgtggg tctcgcggta tcattgcagc actggggcca gatggtaagc
     actcgcaccc agagcgccat agtaacgtcg tgacccggt ctaccattcg
8451 cctcccgtat cgtagttatc tacacgacgg ggagtcaggc aactatggat
     ggagggcata gcatcaatag atgtgctgcc cctcagtccg ttgatacca
8501 gaacgaaata gacagatcgc tgagataggt gcctcactga ttaagcattg
     cttgctttat ctgtctagcg actctatcca cggagtgact aattcgtaac
8551 gtaactgtca gaccaagttt actcatatat actttagatt gatttaaaac
     cattgacagt ctggttcaaa tgagtatata tgaaatctaa ctaaattttg
8601 ttcatttta atttaaaagg atctaggtga agatcctttt tgataatctc
     aagtaaaaat taaattttcc tagatccact tctaggaaaa actattagag
8651 atgaccaaaa tcccttaacg tgagttttcg ttccactgag cgtcagaccc
     tactggtttt agggaattgc actcaaaagc aaggtgactc gcagtctggg
```

FIG. 6B cont.

```
8701 cgtagaaaag atcaaaggat cttcttgaga tccttttttt ctgcgcgtaa
     gcatcttttc tagtttccta gaagaactct aggaaaaaaa gacgcgcatt
8751 tctgctgctt gcaaacaaaa aaaccaccgc taccagcggt ggtttgtttg
     agacgacgaa cgtttgtttt tttggtggcg atggtcgcca ccaaacaaac
8801 ccggatcaag agctaccaac tcttttccg aaggtaactg gcttcagcag
     ggcctagttc tcgatggttg agaaaaggc ttccattgac cgaagtcgtc
8851 agcgcagata ccaaatactg tccttctagt gtagccgtag ttaggccacc
     tcgcgtctat ggtttatgac aggaagatca catcggcatc aatccggtgg
8901 acttcaagaa ctctgtagca ccgcctacat acctcgctct gctaatcctg
     tgaagttctt gagacatcgt ggcggatgta tggagcgaga cgattaggac
8951 ttaccagtgg ctgctgccag tggcgataag tcgtgtctta ccgggttgga
     aatggtcacc gacgacggtc accgctattc agcacagaat ggcccaacct
9001 ctcaagacga tagttaccgg ataaggcgca gcggtcgggc tgaacggggg
     gagttctgct atcaatggcc tattccgcgt cgccagcccg acttgccccc
9051 gttcgtgcac acagcccagc ttggagcgaa cgacctacac cgaactgaga
     caagcacgtg tgtcgggtcg aacctcgctt gctggatgtg gcttgactct
9101 tacctacagc gtgagctatg agaaagcgcc acgcttcccg aagggagaaa
     atggatgtcg cactcgatac tctttcgcgg tgcgaagggc ttccctcttt
9151 ggcggacagg tatccggtaa gcggcagggt cggaacagga gagcgcacga
     ccgcctgtcc ataggccatt cgccgtccca gccttgtcct ctcgcgtgct
9201 gggagcttcc aggggggaaac gcctggtatc tttatagtcc tgtcgggttt
     ccctcgaagg tccccctttg cggaccatag aaatatcagg acagcccaaa
9251 cgccacctct gacttgagcg tcgatttttg tgatgc
```

FIG. 6C

```
   1 gaagttaaac aggagaaccg gttattaaat gaatcagaat caagttccca
  51 ggggttacta ggatactatt ttagtgattt gaattttcaa gcacccatgg
 101 tggttacctc ttctactaca ggggatttat ctattcctag ttctgagtta
 151 gaaatattc catcggaaaa ccaatatttt caatctgcta tttggtcagg
 201 atttatcaaa gttaagaaga gtgatgaata tacatttgct acttccgctg
 251 ataatcatgt aacaatgtgg gtagatgacc aagaagtgat taataaagct
 301 tctaattcta acaaaatcag attagaaaaa ggaagattat atcaaataaa
 351 aattcaatat caacgagaaa atcctactga aaaaggattg gatttcaagt
 401 tgtactggac cgattctcaa aataaaaaag aagtgatttc tagtgataac
 451 ttacaattgc cagaattaaa acaaaaatct tcgaactcaa gaaaaaagcg
 501 aagtacaagt gctggaccta cggttccaga ccgtgacaat gatggaatcc
 551 ctgattcatt agaggtagaa ggatatacgg ttgatgtcaa aaataaaaga
 601 acttttcttt caccatggat ttctaatatt catgaaaaga aaggattaac
 651 caaatataaa tcatctcctg aaaaatggag cacggcttct gatccgtaca
 701 gtgatttcga aaaggttaca ggacggattg ataagaatgt atcaccagag
 751 gcaagacacc cccttgtggc agcttatccg attgtacatg tagatatgga
 801 gaatattatt ctctcaaaaa atgaggatca atccacacag aatactgata
 851 gtcaaacgag aacaataagt aaaaatactt ctacaagtag gacacatact
 901 agtgaagtac atggaaatgc agaagtgcat gcgtcgttct ttgatattgg
 951 tgggagtgta tctgcaggat ttagtaattc gaattcaagt acggtcgcaa
1001 ttgatcattc actatctcta gcaggggaaa gaacttgggc tgaaacaatg
1051 ggtttaaata ccgctgatac agcaagatta aatgccaata ttagatatgt
1101 aaatactggg acggctccaa tctacaacgt gttaccaacg acttcgttag
1151 tgttaggaaa aaatcaaaca ctcgcgacaa ttaaagctaa ggaaaaccaa
1201 ttaagtcaaa tacttgcacc taataattat tatccttcta aaaacttggc
1251 gccaatcgca ttaaatgcac aagacgattt cagttctact ccaattacaa
1301 tgaattacaa tcaatttctt gagttagaaa aaacgaaaca attaagatta
1351 gatacggatc aagtatatgg gaatatagca acatacaatt ttgaaaatgg
1401 aagagtgagg gtggatacag gctcgaactg gagtgaagtg ttaccgcaaa
1451 ttcaagaaac aactgcacgt atcatttta atggaaaaga tttaaatctg
1501 gtagaaaggc ggatagcggc ggttaatcct agtgatccat tagaaacgac
1551 taaccggat atgacattaa aagaagccct taaaatagca tttggattta
1601 acgaaccgaa tggaaactta caatatcaag ggaaagacat aaccgaattt
1651 gattttaatt tcgatcaaca aacatctcaa aatatcaaga atcagttagc
1701 ggaattaaac gcaactaaca tatatactgt attagataaa atcaaattaa
1751 atgcaaaaat gaatatttta ataagagata aacgttttca ttatgataga
1801 aataacatag cagttggggc ggatgagtca gtagttaagg aggctcatag
1851 agaagtaatt aattcgtcaa cagagggatt attgttaaat attgataagg
1901 atataagaaa aatattatca ggttatattg tagaaattga agatactgaa
1951 gggcttaaag aagttataaa tgacagatat gatatgttga atatttctag
2001 tttacggcaa gatggaaaaa catttataga ttttaaaaaa tataatgata
2051 aattaccgtt atatataagt aatcccaatt ataaggtaaa tgtatatgct
2101 gttactaaag aaaacactat tattaatcct agtgagaatg gggatactag
2151 taccaacggg atcaagaaaa ttttaatctt ttctaaaaaa ggctatgaga
2201 taggataa
```

FIG. 6D

```
  1 catatggcgg gcggtcatgg tgatgtaggt atgcacgtaa aagagaaaga
 51 gaaaaataaa gatgagaata agagaaaaga tgaagaacga aataaaacac
101 aggaagagca tttaaaggaa atcatgaaac acattgtaaa aatagaagta
151 aaaggggagg aagctgttaa aaaagaggca gcagaaaagc tacttgagaa
201 agtaccatct gatgttttag agatgtataa agcaattgga ggaaagatat
251 atattgtgga tggtgatatt acaaaacata tatctttaga agcattatct
301 gaagataaga aaaaaataaa agacatttat gggaaagatg ccttattaca
351 tgaacattat gtatatgcaa aagaaggata tgaacccgta cttgtaatcc
401 aatcttcgga agattatgta gaaaatactg aaaaggcact gaacgtttat
451 tatgaaatag gtaagatatt atcaagggat attttaagta aaattaatca
501 accatatcag aaattttag atgtattaaa taccattaaa aatgcatctg
551 attcagatgg acaagatctt ttatttacta atcagcttaa ggaacatccc
601 acagactttt ctgtagaatt cttggaacaa aatagcaatg aggtacaaga
651 agtatttgcg aaagcttttg catattatat cgagccacag catcgtgatg
701 ttttacagct ttatgcaccg gaagcttta attacatgga taaatttaac
751 gaacaagaaa taaatctata a
```

FIG. 6E

```
  1 Glu Val Lys Gln Glu Asn Arg Leu Leu Asn Glu Ser Glu Ser Ser Gln Gly
 19 Leu Leu Gly Tyr Tyr Phe Ser Asp Leu Asn Phe Gln Ala Pro Met Val Val Thr
 37 Ser Ser Thr Thr Gly Asp Leu Ser Ile Pro Ser Ser Glu Leu Glu Asn Ile Pro
 55 Ser Glu Asn Gln Tyr Phe Gln Ser Ala Ile Trp Ser Gly Phe Ile Lys Val Lys
 73 Lys Ser Asp Glu Tyr Thr Phe Ala Thr Ser Ala Asp Asn His Val Thr Met Trp
 91 Val Asp Asp Gln Glu Val Ile Asn Lys Ala Ser Asn Ser Asn Lys Ile Arg Leu
109 Glu Lys Gly Arg Leu Tyr Gln Ile Lys Ile Gln Tyr Gln Arg Glu Asn Pro Thr
127 Glu Lys Gly Leu Asp Phe Lys Leu Tyr Trp Thr Asp Ser Gln Asn Lys Lys Glu
145 Val Ile Ser Ser Asp Asn Leu Gln Leu Pro Glu Leu Lys Gln Lys Ser Ser Asn
163 Ser Arg Lys Lys Arg Ser Thr Ser Ala Gly Pro Thr Val Pro Asp Arg Asp Asn
181 Asp Gly Ile Pro Asp Ser Leu Glu Val Glu Gly Tyr Thr Val Asp Val Lys Asn
199 Lys Arg Thr Phe Leu Ser Pro Trp Ile Ser Asn Ile His Glu Lys Lys Gly Leu
217 Thr Lys Tyr Lys Ser Ser Pro Glu Lys Trp Ser Thr Ala Ser Asp Pro Tyr Ser
235 Asp Phe Glu Lys Val Thr Gly Arg Ile Asp Lys Asn Val Ser Pro Glu Ala Arg
253 His Pro Leu Val Ala Ala Tyr Pro Ile Val His Val Asp Met Glu Asn Ile Ile
271 Leu Ser Lys Asn Glu Asp Gln Ser Thr Gln Asn Thr Asp Ser Gln Thr Arg Thr
289 Ile Ser Lys Asn Thr Ser Thr Ser Arg Thr His Thr Ser Glu Val His Gly Asn
307 Ala Glu Val His Ala Ser Phe Phe Asp Ile Gly Gly Ser Val Ser Ala Gly Phe
325 Ser Asn Ser Asn Ser Ser Thr Val Ala Ile Asp His Ser Leu Ser Leu Ala Gly
343 Glu Arg Thr Trp Ala Glu Thr Met Gly Leu Asn Thr Ala Asp Thr Ala Arg Leu
361 Asn Ala Asn Ile Arg Tyr Val Asn Thr Gly Thr Ala Pro Ile Tyr Asn Val Leu
379 Pro Thr Thr Ser Leu Val Leu Gly Lys Asn Gln Thr Leu Ala Thr Ile Lys Ala
397 Lys Glu Asn Gln Leu Ser Gln Ile Leu Ala Pro Asn Asn Tyr Tyr Pro Ser Lys
415 Asn Leu Ala Pro Ile Ala Leu Asn Ala Gln Asp Asp Phe Ser Ser Thr Pro Ile
433 Thr Met Asn Tyr Asn Gln Phe Leu Glu Leu Glu Lys Thr Lys Gln Leu Arg Leu
451 Asp Thr Asp Gln Val Tyr Gly Asn Ile Ala Thr Tyr Asn Phe Glu Asn Gly Arg
469 Val Arg Val Asp Thr Gly Ser Asn Trp Ser Glu Val Leu Pro Gln Ile Gln Glu
487 Thr Thr Ala Arg Ile Ile Phe Asn Gly Lys Asp Leu Asn Leu Val Glu Arg Arg
505 Ile Ala Ala Val Asn Pro Ser Asp Pro Leu Glu Thr Thr Lys Pro Asp Met Thr
523 Leu Lys Glu Ala Leu Lys Ile Ala Phe Gly Phe Asn Glu Pro Asn Gly Asn Leu
541 Gln Tyr Gln Gly Lys Asp Ile Thr Glu Phe Asp Phe Asn Phe Asp Gln Gln Thr
559 Ser Gln Asn Ile Lys Asn Gln Leu Ala Glu Leu Asn Ala Thr Asn Ile Tyr Thr
577 Val Leu Asp Lys Ile Lys Leu Asn Ala Lys Met Asn Ile Leu Ile Arg Asp Lys
595 Arg Phe His Tyr Asp Arg Asn Asn Ile Ala Val Gly Ala Asp Glu Ser Val Val
613 Lys Glu Ala His Arg Glu Val Ile Asn Ser Ser Thr Glu Gly Leu Leu Leu Asn
631 Ile Asp Lys Asp Ile Arg Lys Ile Leu Ser Gly Tyr Ile Val Glu Ile Glu Asp
649 Thr Glu Gly Leu Lys Glu Val Ile Asn Asp Arg Tyr Asp Met Leu Asn Ile Ser
667 Ser Leu Arg Gln Asp Gly Lys Thr Phe Ile Asp Phe Lys Lys Tyr Asn Asp Lys
685 Leu Pro Leu Tyr Ile Ser Asn Pro Asn Tyr Lys Val Asn Val Tyr Ala Val Thr
703 Lys Glu Asn Thr Ile Ile Asn Pro Ser Glu Asn Gly Asp Thr Ser Thr Asn Gly
721 Ile Lys Lys Ile Leu Ile Phe Ser Lys Lys Gly Tyr Glu Ile Gly
```

FIG. 6F

```
  1 His Met Ala Gly Gly His Gly Asp Val Gly Met His Val Lys Glu Lys Glu Lys
 19 Asn Lys Asp Glu Asn Lys Arg Lys Asp Glu Glu Arg Asn Lys Thr Gln Glu Glu
 37 His Leu Lys Glu Ile Met Lys His Ile Val Lys Ile Glu Val Lys Gly Glu Glu
 55 Ala Val Lys Lys Glu Ala Ala Glu Lys Leu Leu Glu Lys Val Pro Ser Asp Val
 73 Leu Glu Met Tyr Lys Ala Ile Gly Gly Lys Ile Tyr Ile Val Asp Gly Asp Ile
 91 Thr Lys His Ile Ser Leu Glu Ala Leu Ser Glu Asp Lys Lys Lys Ile Lys Asp
109 Ile Tyr Gly Lys Asp Ala Leu Leu His Glu His Tyr Val Tyr Ala Lys Glu Gly
127 Tyr Glu Pro Val Leu Val Ile Gln Ser Ser Glu Asp Tyr Val Glu Asn Thr Glu
145 Lys Ala Leu Asn Val Tyr Tyr Glu Ile Gly Lys Ile Leu Ser Arg Asp Ile Leu
163 Ser Lys Ile Asn Gln Pro Tyr Gln Lys Phe Leu Asp Val Leu Asn Thr Ile Lys
181 Asn Ala Ser Asp Ser Asp Gly Gln Asp Leu Leu Phe Thr Asn Gln Leu Lys Glu
199 His Pro Thr Asp Phe Ser Val Glu Phe Leu Glu Gln Asn Ser Asn Glu Val Gln
217 Glu Val Phe Ala Lys Ala Phe Ala Tyr Tyr Ile Glu Pro Gln His Arg Asp Val
235 Leu Gln Leu Tyr Ala Pro Glu Ala Phe Asn Tyr Met Asp Lys Phe Asn Glu Gln
253 Glu Ile Asn Leu
```

FIG. 7B

```
3701 catat
3751 ggcgggcggt catggtgatg taggtatgca cgtaaaagag aaagagaaaa
3801 ataaagatga gaataagaga aaagatgaag aacgaaataa aacacaggaa
3851 gagcatttaa aggaaatcat gaaacacatt gtaaaaatag aagtaaaagg
3901 ggaggaagct gttaaaaaag aggcagcaga aaagctactt gagaaagtac
3951 catctgatgt tttagagatg tataaagcaa ttggaggaaa gatatatatt
4001 gtggatggtg atattacaaa acatatatct ttagaagcat tatctgaaga
4051 taagaaaaaa ataaaagaca tttatgggaa agatgcctta ttacatgaac
4101 attatgtata tgcaaaagaa ggatatgaac ccgtacttgt aatccaatct
4151 tcggaagatt atgtagaaaa tactgaaaag gcactgaacg tttattatga
4201 aataggtaag atattatcaa gggatatttt aagtaaaatt aatcaaccat
4251 atcagaaatt tttagatgta ttaaatacca ttaaaaatgc atctgattca
4301 gatggacaag atctttatt tactaatcag cttaaggaac atcccacaga
4351 cttttctgta gaattcttgg aacaaaatag caatgaggta caagaagtat
4401 ttgcgaaagc ttttgcatat tatatcgagc cacagcatcg tgatgtttta
4451 cagctttatg caccggaagc ttttaattac atggataaat ttaacgaaca
4501 agaaataaat ctaactgcac gtatcatttt taatggaaaa gatttaaatc
4551 tggtagaaag gcggatagcg gcggttaatc ctagtgatcc attagaaacg
4601 actaaaccgg atatgacatt aaaagaagcc cttaaaatag catttggatt
4651 taacgaaccg aatggaaact acaatatca agggaaagac ataaccgaat
4701 ttgatttaa tttcgatcaa caaacatctc aaaatatcaa gaatcagtta
4751 gcggaattaa acgcaactaa catatatact gtattagata aaatcaaatt
4801 aaatgcaaaa atgaatattt taataagaga taaacgtttt cattatgata
4851 gaaataacat agcagttggg gcggatgagt cagtagttaa ggaggctcat
4901 agagaagtaa ttaattcgtc aacagaggga ttattgttaa atattgataa
4951 ggatataaga aaaatattat caggttatat tgtagaaatt gaagatactg
5001 aagggcttaa agaagttata aatgacagat atgatatgtt gaatatttct
5051 agtttacggc aagatggaaa aacatttata gattttaaaa aatataatga
5101 taaattaccg ttatatataa gtaatcccaa ttataaggta aatgtatatg
5151 ctgttactaa agaaaacact attattaatc ctagtgagaa tggggatact
5201 agtaccaacg ggatcaagaa aattttaatc tttctaaaa aaggctatga
5251 gataggataa
```

FIG. 7C

```
  1 His Met Ala Gly Gly His Gly Asp Val Gly Met His Val Lys Glu Lys Glu Lys
 19 Asn Lys Asp Glu Asn Lys Arg Lys Asp Glu Glu Arg Asn Lys Thr Gln Glu Glu
 37 His Leu Lys Glu Ile Met Lys His Ile Val Lys Ile Glu Val Lys Gly Glu Glu
 55 Ala Val Lys Lys Glu Ala Ala Glu Lys Leu Leu Glu Lys Val Pro Ser Asp Val
 73 Leu Glu Met Tyr Lys Ala Ile Gly Gly Lys Ile Tyr Ile Val Asp Gly Asp Ile
 91 Thr Lys His Ile Ser Leu Glu Ala Leu Ser Glu Asp Lys Lys Lys Ile Lys Asp
109 Ile Tyr Gly Lys Asp Ala Leu Leu His Glu His Tyr Val Tyr Ala Lys Glu Gly
127 Tyr Glu Pro Val Leu Val Ile Gln Ser Ser Glu Asp Tyr Val Glu Asn Thr Glu
145 Lys Ala Leu Asn Val Tyr Tyr Glu Ile Gly Lys Ile Leu Ser Arg Asp Ile Leu
163 Ser Lys Ile Asn Gln Pro Tyr Gln Lys Phe Leu Asp Val Leu Asn Thr Ile Lys
181 Asn Ala Ser Asp Ser Asp Gly Gln Asp Leu Leu Phe Thr Asn Gln Leu Lys Glu
199 His Pro Thr Asp Phe Ser Val Glu Phe Leu Glu Gln Asn Ser Asn Glu Val Gln
217 Glu Val Phe Ala Lys Ala Phe Ala Tyr Tyr Ile Glu Pro Gln His Arg Asp Val
235 Leu Gln Leu Tyr Ala Pro Glu Ala Phe Asn Tyr Met Asp Lys Phe Asn Glu Gln
253 Glu Ile Asn Leu Thr Ala Arg Ile Ile Phe Asn Gly Lys Asp Leu Asn Leu Val
271 Glu Arg Arg Ile Ala Ala Val Asn Pro Ser Asp Pro Leu Glu Thr Thr Lys Pro
289 Asp Met Thr Leu Lys Glu Ala Leu Lys Ile Ala Phe Gly Phe Asn Glu Pro Asn
307 Gly Asn Leu Gln Tyr Gln Gly Lys Asp Ile Thr Glu Phe Asp Phe Asn Phe Asp
325 Gln Gln Thr Ser Gln Asn Ile Lys Asn Gln Leu Ala Glu Leu Asn Ala Thr Asn
343 Ile Tyr Thr Val Leu Asp Lys Ile Lys Leu Asn Ala Lys Met Asn Ile Leu Ile
361 Arg Asp Lys Arg Phe His Tyr Asp Arg Asn Asn Ile Ala Val Gly Ala Asp Glu
379 Ser Val Val Lys Glu Ala His Arg Glu Val Ile Asn Ser Ser Thr Glu Gly Leu
397 Leu Leu Asn Ile Asp Lys Asp Ile Arg Lys Ile Leu Ser Gly Tyr Ile Val Glu
415 Ile Glu Asp Thr Glu Gly Leu Lys Glu Val Ile Asn Asp Arg Tyr Asp Met Leu
433 Asn Ile Ser Ser Leu Arg Gln Asp Gly Lys Thr Phe Ile Asp Phe Lys Lys Tyr
451 Asn Asp Lys Leu Pro Leu Tyr Ile Ser Asn Pro Asn Tyr Lys Val Asn Val Tyr
469 Ala Val Thr Lys Glu Asn Thr Ile Ile Asn Pro Ser Glu Asn Gly Asp Thr Ser
487 Thr Asn Gly Ile Lys Lys Ile Leu Ile Phe Ser Lys Lys Gly Tyr Glu Ile Gly
```

FIG. 7D

| Analysis | Entire Protein |
|---|---|
| Length | 504 aa |
| Molecular Weight | 58000.98 m.w. |
| 1 microgram = | 17.241 pMoles |
| Molar Extinction coefficient | 30720 |
| 1 A[280] corr. to | 1.89 mg/ml |
| A[280] of 1 mg/ml | 0.53 AU |
| Isoelectric Point | 5.35 |
| Charge at pH 7 | -16.09 |

FIG. 8B

```
3701 catat
3751 ggcgggcggt catggtgatg taggtatgca cgtaaaagag aaagagaaaa
3801 ataaagatga gaataagaga aaagatgaag aacgaaataa aacacaggaa
3851 gagcatttaa aggaaatcat gaaacacatt gtaaaaatag aagtaaaagg
3901 ggaggaagct gttaaaaaag aggcagcaga aaagctactt gagaaagtac
3951 catctgatgt tttagagatg tataaagcaa ttggaggaaa gatatatatt
4001 gtggatggtg atattacaaa acatatatct ttagaagcat tatctgaaga
4051 taagaaaaaa ataaaagaca tttatgggaa agatgcttta ttacatgaac
4101 attatgtata tgcaaaagaa ggatatgaac ccgtacttgt aatccaatct
4151 tcggaagatt atgtagaaaa tactgaaaag gcactgaacg tttattatga
4201 aataggtaag atattatcaa gggatatttt aagtaaaatt aatcaaccat
4251 atcagaaatt tttagatgta ttaaatacca ttaaaaatgc atctgattca
4301 gatggacaag atcttttatt tactaatcag cttaaggaac atcccacaga
4351 cttttctgta gaattcttgg aacaaaatag caatgaggta caagaagtat
4401 ttgcgaaagc ttttgcatat tatatcgagc cacagcatcg tgatgtttta
4451 cagctttatg caccggaagc ttttaattac atggataaat taacgaaca
4501 agaaataaat ctatccttgg aagaacttaa agatcaacgg atgctgtcaa
4551 gatatgaaaa atgggaaaag ataaaacagc actatcaaca ctggagcgat
4601 tctttatctg aagaaggaag aggacttttaa aaaaagctgc agattcctat
4651 tgagccaaag aaagatgaca taattcattc tttatctcaa gaagaaaag
4701 agcttctaaa aagaatacaa attgatagta gtgatttttt atctactgag
4751 gaaaagagt ttttaaaaaa gctacaaatt gatattcgtg attctttatc
4801 tgaagaagaa aaagagcttt taaatagaat acaggtggat agtagtaatc
4851 ctttatctga aaaagaaaaa gagtttttaa aaaagctgaa acttgatatt
4901 caaccatacg atattaatca aaggttgcaa gatacaggag ggttaattga
4951 tagtccgcca attaatcttg aaactgcacg tatcattttt aatggaaaag
5001 atttaaatct ggtagaaagg cggatagcgg cggttaatcc tagtgatcca
5051 ttagaaacga ctaaaccgga tatgacatta aaagaagccc ttaaaatagc
5101 atttggattt aacgaaccga atggaaactt acaatatcaa gggaaagaca
5151 taaccgaatt tgattttaat ttcgatcaac aaacatctca aaatatcaag
5201 aatcagttag cggaattaaa cgcaactaac atatatactg tattagataa
5251 aatcaaatta aatgcaaaaa tgaatatttt aataagagat aaacgttttc
5301 attatgatag aaataacata gcagttgggg cggatgagtc agtagttaag
5351 gaggctcata gagaagtaat taattcgtca acagagggat tattgttaaa
5401 tattgataag gatataagaa aaatattatc aggttatatt gtagaaattg
5451 aagatactga agggcttaaa gaagttataa atgacagata tgatatgttg
5501 aatatttcta gtttacggca agatggaaaa acatttatag attttaaaaa
5551 ataatgat aaattaccgt tatatataag taatcccaat tataaggtaa
5601 atgtatatgc tgttactaaa gaaaacacta ttattaatcc tagtgagaat
5651 ggggatacta gtaccaacgg gatcaagaaa attttaatct tttctaaaaa
5701 aggctatgag ataggataa
```

FIG. 8C

```
  1 His Met Ala Gly Gly His Gly Asp Val Gly Met His Val Lys Glu Lys Glu Lys
 19 Asn Lys Asp Glu Asn Lys Arg Lys Asp Glu Glu Arg Asn Lys Thr Gln Glu Glu
 37 His Leu Lys Glu Ile Met Lys His Ile Val Lys Ile Glu Val Lys Gly Glu Glu
 55 Ala Val Lys Lys Glu Ala Ala Glu Lys Leu Leu Glu Lys Val Pro Ser Asp Val
 73 Leu Glu Met Tyr Lys Ala Ile Gly Gly Lys Ile Tyr Ile Val Asp Gly Asp Ile
 91 Thr Lys His Ile Ser Leu Glu Ala Leu Ser Glu Asp Lys Lys Lys Ile Lys Asp
109 Ile Tyr Gly Lys Asp Ala Leu Leu His Glu His Tyr Val Tyr Ala Lys Glu Gly
127 Tyr Glu Pro Val Leu Val Ile Gln Ser Ser Glu Asp Tyr Val Glu Asn Thr Glu
145 Lys Ala Leu Asn Val Tyr Tyr Glu Ile Gly Lys Ile Leu Ser Arg Asp Ile Leu
163 Ser Lys Ile Asn Gln Pro Tyr Gln Lys Phe Leu Asp Val Leu Asn Thr Ile Lys
181 Asn Ala Ser Asp Ser Asp Gly Gln Asp Leu Leu Phe Thr Asn Gln Leu Lys Glu
199 His Pro Thr Asp Phe Ser Val Glu Phe Leu Glu Gln Asn Ser Asn Glu Val Gln
217 Glu Val Phe Ala Lys Ala Phe Ala Tyr Tyr Ile Glu Pro Gln His Arg Asp Val
235 Leu Gln Leu Tyr Ala Pro Glu Ala Phe Asn Tyr Met Asp Lys Phe Asn Glu Gln
253 Glu Ile Asn Leu Ser Leu Glu Glu Leu Lys Asp Gln Arg Met Leu Ser Arg Tyr
271 Glu Lys Trp Glu Lys Ile Lys His Tyr Gln His Trp Ser Asp Ser Leu Ser
289 Glu Glu Gly Arg Gly Leu Leu Lys Lys Leu Gln Ile Pro Ile Glu Pro Lys Lys
307 Asp Asp Ile Ile His Ser Leu Ser Gln Glu Glu Lys Glu Leu Leu Lys Arg Ile
325 Gln Ile Asp Ser Ser Asp Phe Leu Ser Thr Glu Glu Lys Glu Phe Leu Lys Lys
343 Leu Gln Ile Asp Ile Arg Asp Ser Leu Ser Glu Glu Glu Lys Glu Leu Leu Asn
361 Arg Ile Gln Val Asp Ser Ser Asn Pro Leu Ser Glu Lys Glu Lys Glu Phe Leu
379 Lys Lys Leu Lys Leu Asp Ile Gln Pro Tyr Asp Ile Asn Gln Arg Leu Gln Asp
397 Thr Gly Gly Leu Ile Asp Ser Pro Pro Ile Asn Leu Glu Thr Ala Arg Ile Ile
415 Phe Asn Gly Lys Asp Leu Asn Leu Val Glu Arg Arg Ile Ala Ala Val Asn Pro
433 Ser Asp Pro Leu Glu Thr Thr Lys Pro Asp Met Thr Leu Lys Glu Ala Leu Lys
451 Ile Ala Phe Gly Phe Asn Glu Pro Asn Gly Asn Leu Gln Tyr Gln Gly Lys Asp
469 Ile Thr Glu Phe Asp Phe Asn Phe Asp Gln Gln Thr Ser Gln Asn Ile Lys Asn
487 Gln Leu Ala Glu Leu Asn Ala Thr Asn Ile Tyr Thr Val Leu Asp Lys Ile Lys
505 Leu Asn Ala Lys Met Asn Ile Leu Ile Arg Asp Lys Arg Phe His Tyr Asp Arg
523 Asn Asn Ile Ala Val Gly Ala Asp Glu Ser Val Val Lys Glu Ala His Arg Glu
541 Val Ile Asn Ser Ser Thr Glu Gly Leu Leu Leu Asn Ile Asp Lys Asp Ile Arg
559 Lys Ile Leu Ser Gly Tyr Ile Val Glu Ile Glu Asp Thr Glu Gly Leu Lys Glu
577 Val Ile Asn Asp Arg Tyr Asp Met Leu Asn Ile Ser Ser Leu Arg Gln Asp Gly
595 Lys Thr Phe Ile Asp Phe Lys Lys Tyr Asn Asp Lys Leu Pro Leu Tyr Ile Ser
613 Asn Pro Asn Tyr Lys Val Asn Val Tyr Ala Val Thr Lys Glu Asn Thr Ile Ile
631 Asn Pro Ser Glu Asn Gly Asp Thr Ser Thr Asn Gly Ile Lys Lys Ile Leu Ile
649 Phe Ser Lys Lys Gly Tyr Glu Ile Gly
```

FIG. 8D

| Analysis | Entire Protein |
|---|---|
| Length | 657 aa |
| Molecular Weight | 76140.63 m.w. |
| 1 microgram = | 13.134 pMoles |
| Molar Extinction coefficient | 45940 |
| 1 A[280] corr. to | 1.66 mg/ml |
| A[280] of 1 mg/ml | 0.60 AU |
| Isoelectric Point | 5.26 |
| Charge at pH 7 | -23.78 |

FIG. 9B

```
3701 catat
3751 ggcgggcggt catggtgatg taggtatgca cgtaaaagag aaagagaaaa
3801 ataaagatga gaataagaga aaagatgaag aacgaaataa aacacaggaa
3851 gagcatttaa aggaaatcat gaaacacatt gtaaaaatag aagtaaaagg
3901 ggaggaagct gttaaaaaag aggcagcaga aaagctactt gagaaagtac
3951 catctgatgt tttagagatg tataaagcaa ttggaggaaa gatatatatt
4001 gtggatggtg atattacaaa acatatatct ttagaagcat tatctgaaga
4051 taagaaaaaa ataaaagaca tttatgggaa agatgcttta ttacatgaac
4101 attatgtata tgcaaaagaa ggatatgaac ccgtacttgt aatccaatct
4151 tcggaagatt atgtagaaaa tactgaaaag gcactgaacg tttattatga
4201 aataggtaag atattatcaa gggatatttt aagtaaaatt aatcaaccat
4251 atcagaaatt tttagatgta ttaaatacca ttaaaaatgc atctgattca
4301 gatggacaag atcttttatt tactaatcag cttaaggaac atcccacaga
4351 cttttctgta gaattcttgg aacaaaatag caatgaggta caagaagtat
4401 ttgcgaaagc ttttgcatat tatatcgagc cacagcatcg tgatgtttta
4451 cagctttatg caccggaagc ttttaattac atggataaat taacgaaca
4501 agaaataaat ctatccttgg aagaacttaa agatcaacgg atgctgtcaa
4551 gatatgaaaa atgggaaaag ataaaacagc actatcaaca ctggagcgat
4601 tctttatctg aagaaggaag aggactttta aaaaagctgc agattcctat
4651 tgagccaaag aaagatgaca taattcattc tttatctcaa gaagaaaaag
4701 agcttctaaa aagaatacaa attgatagta gtgattttt atctactgag
4751 gaaaaagagt ttttaaaaaa gctacaaatt gatattcgtg attctttatc
4801 tgaagaagaa aaagagcttt taaatagaat acaggtggat agtagtaatc
4851 ctttatctga aaaagaaaaa gagttttttaa aaaagctgaa acttgatatt
4901 caaccatacg atattaatca aaggttgcaa gatacaggag ggttaattga
4951 tagtccgcca attaatcttg atgtaagaaa gcagtataaa agggatattc
5001 aaaatattga tgctttatta catcaatcca ttggaagtac cttgtacaat
5051 aaaatttatt tgtatgaaaa tatgaatatc aataaccta cagcaaccct
5101 aggtgcggat ttagttgatt ccactgataa tactaaaatt aatagaggta
5151 ttttcaatga attcaaaaaa aatttcaaat atagtatttc tagtaactat
5201 atgattgttg atataaatga aaggcctgca ttagataatg agcgtttgaa
5251 atggagaatc caattatcac cagatactcg agcaggaact gcacgtatca
5301 ttttaatgg aaaagattta atctggtag aaaggcggat agcggcggtt
5351 aatcctagtg atccattaga aacgactaaa ccggatatga cattaaaaga
5401 agcccttaaa atagcatttg gatttaacga accgaatgga aacttacaat
5451 atcaagggaa agacataacc gaatttgatt ttaatttcga tcaacaaaca
5501 tctcaaaata tcaagaatca gttagcggaa ttaaacgcaa ctaacatata
5551 tactgtatta gataaaatca aattaaatgc aaaaatgaat atttaataa
5601 gagataaacg ttttcattat gatagaaata acatagcagt tggggcggat
5651 gagtcagtag ttaaggaggc tcatagagaa gtaattaatt cgtcaacaga
```

FIG. 9B cont.

```
5701 gggattattg ttaaatattg ataaggatat aagaaaaata ttatcaggtt
5751 atattgtaga aattgaagat actgaagggc ttaaagaagt tataaatgac
5801 agatatgata tgttgaatat ttctagttta cggcaagatg gaaaaacatt
5851 tatagatttt aaaaaatata atgataaatt accgttatat ataagtaatc
5901 ccaattataa ggtaaatgta tatgctgtta ctaaagaaaa cactattatt
5951 aatcctagtg agaatgggga tactagtacc aacgggatca agaaaatttt
6001 aatcttttct aaaaaggct atgagatagg ataa
```

FIG. 9C

```
  1 His Met Ala Gly Gly His Gly Asp Val Gly Met His Val Lys Glu Lys Glu Lys
 19 Asn Lys Asp Glu Asn Lys Arg Lys Asp Glu Glu Arg Asn Lys Thr Gln Glu Glu
 37 His Leu Lys Glu Ile Met Lys His Ile Val Lys Ile Glu Val Lys Gly Glu Glu
 55 Ala Val Lys Lys Glu Ala Ala Glu Lys Leu Leu Glu Lys Val Pro Ser Asp Val
 73 Leu Glu Met Tyr Lys Ala Ile Gly Gly Lys Ile Tyr Ile Val Asp Gly Asp Ile
 91 Thr Lys His Ile Ser Leu Glu Ala Leu Ser Glu Asp Lys Lys Lys Ile Lys Asp
109 Ile Tyr Gly Lys Asp Ala Leu Leu His Glu His Tyr Val Tyr Ala Lys Glu Gly
127 Tyr Glu Pro Val Leu Val Ile Gln Ser Ser Glu Asp Tyr Val Glu Asn Thr Glu
145 Lys Ala Leu Asn Val Tyr Tyr Glu Ile Gly Lys Ile Leu Ser Arg Asp Ile Leu
163 Ser Lys Ile Asn Gln Pro Tyr Gln Lys Phe Leu Asp Val Leu Asn Thr Ile Lys
181 Asn Ala Ser Asp Ser Asp Gly Gln Asp Leu Leu Phe Thr Asn Gln Leu Lys Glu
199 His Pro Thr Asp Phe Ser Val Glu Phe Leu Glu Gln Asn Ser Asn Glu Val Gln
217 Glu Val Phe Ala Lys Ala Phe Ala Tyr Tyr Ile Glu Pro Gln His Arg Asp Val
235 Leu Gln Leu Tyr Ala Pro Glu Ala Phe Asn Tyr Met Asp Lys Phe Asn Glu Gln
253 Glu Ile Asn Leu Ser Leu Glu Glu Leu Lys Asp Gln Arg Met Leu Ser Arg Tyr
271 Glu Lys Trp Glu Lys Ile Lys Gln His Tyr Gln His Trp Ser Asp Ser Leu Ser
289 Glu Glu Gly Arg Gly Leu Leu Lys Lys Leu Gln Ile Pro Ile Glu Pro Lys Lys
307 Asp Asp Ile Ile His Ser Leu Ser Gln Glu Glu Lys Glu Leu Leu Lys Arg Ile
325 Gln Ile Asp Ser Ser Asp Phe Leu Ser Thr Glu Glu Lys Glu Phe Leu Lys Lys
343 Leu Gln Ile Asp Ile Arg Asp Ser Leu Ser Glu Glu Glu Lys Glu Leu Leu Asn
361 Arg Ile Gln Val Asp Ser Ser Asn Pro Leu Ser Glu Lys Glu Lys Glu Phe Leu
379 Lys Lys Leu Lys Leu Asp Ile Gln Pro Tyr Asp Ile Asn Gln Arg Leu Gln Asp
397 Thr Gly Gly Leu Ile Asp Ser Pro Pro Ile Asn Leu Asp Val Arg Lys Gln Tyr
415 Lys Arg Asp Ile Gln Asn Ile Asp Ala Leu Leu His Gln Ser Ile Gly Ser Thr
433 Leu Tyr Asn Lys Ile Tyr Leu Tyr Glu Asn Met Asn Ile Asn Asn Leu Thr Ala
451 Thr Leu Gly Ala Asp Leu Val Asp Ser Thr Asp Asn Thr Lys Ile Asn Arg Gly
469 Ile Phe Asn Glu Phe Lys Lys Asn Phe Lys Tyr Ser Ile Ser Ser Asn Tyr Met
487 Ile Val Asp Ile Asn Glu Arg Pro Ala Leu Asp Asn Glu Arg Leu Lys Trp Arg
505 Ile Gln Leu Ser Pro Asp Thr Arg Ala Gly Thr Ala Arg Ile Ile Phe Asn Gly
523 Lys Asp Leu Asn Leu Val Glu Arg Arg Ile Ala Ala Val Asn Pro Ser Asp Pro
541 Leu Glu Thr Thr Lys Pro Asp Met Thr Leu Lys Glu Ala Leu Lys Ile Ala Phe
559 Gly Phe Asn Glu Pro Asn Gly Asn Leu Gln Tyr Gln Gly Lys Asp Ile Thr Glu
577 Phe Asp Phe Asn Phe Asp Gln Gln Thr Ser Gln Asn Ile Lys Asn Gln Leu Ala
595 Glu Leu Asn Ala Thr Asn Ile Tyr Thr Val Leu Asp Lys Ile Lys Leu Asn Ala
613 Lys Met Asn Ile Leu Ile Arg Asp Lys Arg Phe His Tyr Asp Arg Asn Asn Ile
631 Ala Val Gly Ala Asp Glu Ser Val Val Lys Glu Ala His Arg Glu Val Ile Asn
649 Ser Ser Thr Glu Gly Leu Leu Leu Asn Ile Asp Lys Asp Ile Arg Lys Ile Leu
667 Ser Gly Tyr Ile Val Glu Ile Glu Asp Thr Glu Gly Leu Lys Glu Val Ile Asn
685 Asp Arg Tyr Asp Met Leu Asn Ile Ser Ser Leu Arg Gln Asp Gly Lys Thr Phe
703 Ile Asp Phe Lys Lys Tyr Asn Asp Lys Leu Pro Leu Tyr Ile Ser Asn Pro Asn
721 Tyr Lys Val Asn Val Tyr Ala Val Thr Lys Glu Asn Thr Ile Ile Asn Pro Ser
739 Glu Asn Gly Asp Thr Ser Thr Asn Gly Ile Lys Lys Ile Leu Ile Phe Ser Lys
757 Lys Gly Tyr Glu Ile Gly
```

FIG. 9D

| Analysis | Entire Protein |
|---|---:|
| Length | 762 aa |
| Molecular Weight | 88351.39 m.w. |
| 1 microgram = | 11.318 pMoles |
| Molar Extinction coefficient | 59310 |
| 1 A[280] corr. to | 1.49 mg/ml |
| A[280] of 1 mg/ml | 0.67 AU |
| Isoelectric Point | 5.42 |
| Charge at pH 7 | -20.69 |

FIG. 10B

```
   1 catatgaaaa agcgaagtac aagtgctgga cctacggttc cagaccgtga
  51 caatgatgga atccctgatt cattagaggt agaaggatat acggttgatg
 101 tcaaaaataa aagaactttt ctttcaccat ggatttctaa tattcatgaa
 151 aagaaaggat taaccaaata taaatcatct cctgaaaaat ggagcacggc
 201 ttctgatccg tacagtgatt tcgaaaaggt tacaggacgg attgataaga
 251 atgtatcacc agaggcaaga cacccccttg tggcagctta tccgattgta
 301 catgtagata tggagaatat tattctctca aaaaatgagg atcaatccac
 351 acagaatact gatagtcaaa cgagaacaat aagtaaaaat acttctacaa
 401 gtaggacaca tactagtgaa gtacatggaa atgcagaagt gcatgcgtcg
 451 ttctttgata ttggtgggag tgtatctgca ggatttagta attcgaattc
 501 aagtacggtc gcaattgatc attcactatc tctagcaggg gaaagaactt
 551 gggctgaaac aatgggttta ataccgctg atacagcaag attaaatgcc
 601 aatattagat atgtaaatac tgggacggct ccaatctaca acgtgttacc
 651 aacgacttcg ttagtgttag gaaaaaatca acactcgcg acaattaaag
 701 ctaaggaaaa ccaattaagt caaatacttg cacctaataa ttattatcct
 751 tctaaaaact tggcgccaat cgcattaaat gcacaagacg atttcagttc
 801 tactccaatt acaatgaatt acaatcaatt tcttgagtta gaaaaaacga
 851 aacaattaag attagatacg gatcaagtat atgggaatat agcaacatac
 901 aatttttgaaa atggaagagt gagggtggat acaggctcga actggagtga
 951 agtgttaccg caaattcaag aaacaactgc acgtatcatt tttaatggaa
1001 aagatttaaa tctggtagaa aggcggatag cggcggttaa tcctagtgat
1051 ccattagaaa cgactaaacc ggatatgaca ttaaaagaag cccttaaaat
1101 agcatttgga tttaacgaac cgaatggaaa cttacaatat caagggaaag
1151 acataaccga atttgatttt aatttcgatc aacaaacatc tcaaaatatc
1201 aagaatcagt tagcggaatt aaacgcaact aacatatata ctgtattaga
1251 taaatcaaa ttaaatgcaa aaatgaatat tttaataaga gataaacgtt
1301 ttcattatga tagaaataac atagcagttg gggcggatga gtcagtagtt
1351 aaggaggctc atagagaagt aattaattcg tcaacagagg gattattgtt
1401 aaatattgat aaggatataa gaaaaatatt atcaggttat attgtagaaa
1451 ttgaagatac tgaaggctt aagaagtta taaatgacag atatgatatg
1501 ttgaatattt ctagtttacg gcaagatgga aaaacattta tagattttaa
1551 aaaatataat gataaattac cgttatatat aagtaatccc aattataagg
1601 taaatgtata tgctgttact aaagaaaaca ctattattaa tcctagtgag
1651 aatggggata ctagtaccaa cgggatcaag aaaattttaa tctttctaa
1701 aaaggctat gagataggat aa
```

FIG. 10C

```
  1 His Met Lys Lys Arg Ser Thr Ser Ala Gly Pro Thr Val Pro Asp Arg Asp Asn
 19 Asp Gly Ile Pro Asp Ser Leu Glu Val Glu Gly Tyr Thr Val Asp Val Lys Asn
 37 Lys Arg Thr Phe Leu Ser Pro Trp Ile Ser Asn Ile His Glu Lys Lys Gly Leu
 55 Thr Lys Tyr Lys Ser Ser Pro Glu Lys Trp Ser Thr Ala Ser Asp Pro Tyr Ser
 73 Asp Phe Glu Lys Val Thr Gly Arg Ile Asp Lys Asn Val Ser Pro Glu Ala Arg
 91 His Pro Leu Val Ala Ala Tyr Pro Ile Val His Val Asp Met Glu Asn Ile Ile
109 Leu Ser Lys Asn Glu Asp Gln Ser Thr Gln Asn Thr Asp Ser Gln Thr Arg Thr
127 Ile Ser Lys Asn Thr Ser Thr Ser Arg Thr His Thr Ser Glu Val His Gly Asn
145 Ala Glu Val His Ala Ser Phe Phe Asp Ile Gly Gly Ser Val Ser Ala Gly Phe
163 Ser Asn Ser Asn Ser Ser Thr Val Ala Ile Asp His Ser Leu Ser Leu Ala Gly
181 Glu Arg Thr Trp Ala Glu Thr Met Gly Leu Asn Thr Ala Asp Thr Ala Arg Leu
199 Asn Ala Asn Ile Arg Tyr Val Asn Thr Gly Thr Ala Pro Ile Tyr Asn Val Leu
217 Pro Thr Thr Ser Leu Val Leu Gly Lys Asn Gln Thr Leu Ala Thr Ile Lys Ala
235 Lys Glu Asn Gln Leu Ser Gln Ile Leu Ala Pro Asn Asn Tyr Tyr Pro Ser Lys
253 Asn Leu Ala Pro Ile Ala Leu Asn Ala Gln Asp Asp Phe Ser Ser Thr Pro Ile
271 Thr Met Asn Tyr Asn Gln Phe Leu Glu Leu Glu Lys Thr Lys Gln Leu Arg Leu
289 Asp Thr Asp Gln Val Tyr Gly Asn Ile Ala Thr Tyr Asn Phe Glu Asn Gly Arg
307 Val Arg Val Asp Thr Gly Ser Asn Trp Ser Glu Val Leu Pro Gln Ile Gln Glu
325 Thr Thr Ala Arg Ile Ile Phe Asn Gly Lys Asp Leu Asn Leu Val Glu Arg Arg
343 Ile Ala Ala Val Asn Pro Ser Asp Pro Leu Glu Thr Thr Lys Pro Asp Met Thr
361 Leu Lys Glu Ala Leu Lys Ile Ala Phe Gly Phe Asn Glu Pro Asn Gly Asn Leu
379 Gln Tyr Gln Gly Lys Asp Ile Thr Glu Phe Asp Phe Asn Phe Asp Gln Gln Thr
397 Ser Gln Asn Ile Lys Asn Gln Leu Ala Glu Leu Asn Ala Thr Asn Ile Tyr Thr
415 Val Leu Asp Lys Ile Lys Leu Asn Ala Lys Met Asn Ile Leu Ile Arg Asp Lys
433 Arg Phe His Tyr Asp Arg Asn Asn Ile Ala Val Gly Ala Asp Glu Ser Val Val
451 Lys Glu Ala His Arg Glu Val Ile Asn Ser Ser Thr Glu Gly Leu Leu Leu Asn
469 Ile Asp Lys Asp Ile Arg Lys Ile Leu Ser Gly Tyr Ile Val Glu Ile Glu Asp
487 Thr Glu Gly Leu Lys Glu Val Ile Asn Asp Arg Tyr Asp Met Leu Asn Ile Ser
505 Ser Leu Arg Gln Asp Gly Lys Thr Phe Ile Asp Phe Lys Lys Tyr Asn Asp Lys
523 Leu Pro Leu Tyr Ile Ser Asn Pro Asn Tyr Lys Val Asn Val Tyr Ala Val Thr
541 Lys Glu Asn Thr Ile Ile Asn Pro Ser Glu Asn Gly Asp Thr Ser Thr Asn Gly
559 Ile Lys Lys Ile Leu Ile Phe Ser Lys Lys Gly Tyr Glu Ile Gly
```

FIG. 10D

| Analysis | Entire Protein |
|---|---|
| Length | 573 aa |
| Molecular Weight | 64235.03 m.w. |
| 1 microgram = | 15.568 pMoles |
| Molar Extinction coefficient | 49640 |
| 1 A[280] corr. to | 1.29 mg/ml |
| A[280] of 1 mg/ml | 0.77 AU |
| Isoelectric Point | 5.92 |
| Charge at pH 7 | -6.29 |

FIG. 11B

```
   1 catatggata ttggtgggag tgtatctgca ggatttagta attcgaattc
  51 aagtacggtc gcaattgatc attcactatc tctagcaggg gaaagaactt
 101 gggctgaaac aatgggttta ataccgctg atacagcaag attaaatgcc
 151 aatattagat atgtaaatac tgggacggct ccaatctaca acgtgttacc
 201 aacgacttcg ttagtgttag gaaaaaatca aacactcgcg acaattaaag
 251 ctaaggaaaa ccaattaagt caaatacttg cacctaataa ttattatcct
 301 tctaaaaact tggcgccaat cgcattaaat gcacaagacg atttcagttc
 351 tactccaatt acaatgaatt acaatcaatt tcttgagtta gaaaaaacga
 401 aacaattaag attagatacg gatcaagtat atgggaatat agcaacatac
 451 aattttgaaa atggaagagt gagggtggat acaggctcga actggagtga
 501 agtgttaccg caaattcaag aaacaactgc acgtatcatt tttaatggaa
 551 aagatttaaa tctggtagaa aggcggatag cggcggttaa tcctagtgat
 601 ccattagaaa cgactaaacc ggatatgaca ttaaaagaag cccttaaaat
 651 agcatttgga tttaacgaac cgaatggaaa cttacaatat caagggaaag
 701 acataaccga atttgatttt aatttcgatc aacaaacatc tcaaaatatc
 751 aagaatcagt tagcggaatt aaacgcaact aacatatata ctgtattaga
 801 taaatcaaa ttaaatgcaa aaatgaatat tttaataaga gataaacgtt
 851 ttcattatga tagaaataac atagcagttg gggcggatga gtcagtagtt
 901 aaggaggctc atagagaagt aattaattcg tcaacagagg gattattgtt
 951 aaatattgat aaggatataa gaaaaatatt atcaggttat attgtagaaa
1001 ttgaagatac tgaagggctt aaagaagtta taaatgacag atatgatatg
1051 ttgaatattt ctagtttacg gcaagatgga aaaacattta tagattttaa
1101 aaaatataat gataaattac cgttatatat aagtaatccc aattataagg
1151 taaatgtata tgctgttact aaagaaaaca ctattattaa tcctagtgag
1201 aatggggata ctagtaccaa cgggatcaag aaaattttaa tcttttctaa
1251 aaaaggctat gagataggat aa
```

FIG. 11C

```
  1 His Met Asp Ile Gly Gly Ser Val Ser Ala Gly Phe Ser Asn Ser Asn Ser Ser
 19 Thr Val Ala Ile Asp His Ser Leu Ser Leu Ala Gly Glu Arg Thr Trp Ala Glu
 37 Thr Met Gly Leu Asn Thr Ala Asp Thr Ala Arg Leu Asn Ala Asn Ile Arg Tyr
 55 Val Asn Thr Gly Thr Ala Pro Ile Tyr Asn Val Leu Pro Thr Thr Ser Leu Val
 73 Leu Gly Lys Asn Gln Thr Leu Ala Thr Ile Lys Ala Lys Glu Asn Gln Leu Ser
 91 Gln Ile Leu Ala Pro Asn Asn Tyr Tyr Pro Ser Lys Asn Leu Ala Pro Ile Ala
109 Leu Asn Ala Gln Asp Asp Phe Ser Ser Thr Pro Ile Thr Met Asn Tyr Asn Gln
127 Phe Leu Glu Leu Glu Lys Thr Lys Gln Leu Arg Leu Asp Thr Asp Gln Val Tyr
145 Gly Asn Ile Ala Thr Tyr Asn Phe Glu Asn Gly Arg Val Arg Val Asp Thr Gly
163 Ser Asn Trp Ser Glu Val Leu Pro Gln Ile Gln Glu Thr Thr Ala Arg Ile Ile
181 Phe Asn Gly Lys Asp Leu Asn Leu Val Glu Arg Arg Ile Ala Ala Val Asn Pro
199 Ser Asp Pro Leu Glu Thr Thr Lys Pro Asp Met Thr Leu Lys Glu Ala Leu Lys
217 Ile Ala Phe Gly Phe Asn Glu Pro Asn Gly Asn Leu Gln Tyr Gln Gly Lys Asp
235 Ile Thr Glu Phe Asp Phe Asn Phe Asp Gln Gln Thr Ser Gln Asn Ile Lys Asn
253 Gln Leu Ala Glu Leu Asn Ala Thr Asn Ile Tyr Thr Val Leu Asp Lys Ile Lys
271 Leu Asn Ala Lys Met Asn Ile Leu Ile Arg Asp Lys Arg Phe His Tyr Asp Arg
289 Asn Asn Ile Ala Val Gly Ala Asp Glu Ser Val Val Lys Glu Ala His Arg Glu
307 Val Ile Asn Ser Ser Thr Glu Gly Leu Leu Leu Asn Ile Asp Lys Asp Ile Arg
325 Lys Ile Leu Ser Gly Tyr Ile Val Glu Ile Glu Asp Thr Glu Gly Leu Lys Glu
343 Val Ile Asn Asp Arg Tyr Asp Met Leu Asn Ile Ser Ser Leu Arg Gln Asp Gly
361 Lys Thr Phe Ile Asp Phe Lys Lys Tyr Asn Asp Lys Leu Pro Leu Tyr Ile Ser
379 Asn Pro Asn Tyr Lys Val Asn Val Tyr Ala Val Thr Lys Glu Asn Thr Ile Ile
397 Asn Pro Ser Glu Asn Gly Asp Thr Ser Thr Asn Gly Ile Lys Lys Ile Leu Ile
415 Phe Ser Lys Lys Gly Tyr Glu Ile Gly
```

FIG. 11D

| Analysis | Entire Protein |
|---|---|
| Length | 423 aa |
| Molecular Weight | 47493.76 m.w. |
| 1 microgram = | 21.055 pMoles |
| Molar Extinction coefficient | 33140 |
| 1 A[280] corr. to | 1.43 mg/ml |
| A[280] of 1 mg/ml | 0.70 AU |
| Isoelectric Point | 5.50 |
| Charge at pH 7 | -5.84 |

FIG. 12B

```
  1 catatgttaa atctggtaga aaggcggata gcggcggtta atcctagtga
 51 tccattagaa acgactaaac cggatatgac attaaaagaa gcccttaaaa
101 tagcatttgg atttaacgaa ccgaatggaa acttacaata tcaagggaaa
151 gacataaccg aatttgattt taatttcgat caacaaacat ctcaaaatat
201 caagaatcag ttagcggaat taaacgcaac taacatatat actgtattag
251 ataaaatcaa attaaatgca aaatgaata tttttaataag agataaacgt
301 tttcattatg atagaaataa catagcagtt ggggcggatg agtcagtagt
351 taaggaggct catagagaag taattaattc gtcaacagag ggattattgt
401 taaatattga taaggatata agaaaaatat tatcaggtta tattgtagaa
451 attgaagata ctgaagggct taagaagtt ataaatgaca gatatgatat
501 gttgaatatt tctagtttac ggcaagatgg aaaaacattt atagatttta
551 aaaaatataa tgataaatta ccgttatata taagtaatcc caattataag
601 gtaaatgtat atgctgttac taaagaaaac actattatta tcctagtga
651 gaatggggat actagtacca acgggatcaa gaaaatttta ttctttctta
701 aaaaaggcta tgagatagga taa
```

FIG. 12C

```
  1 His Met Leu Asn Leu Val Glu Arg Arg Ile Ala Ala Val Asn Pro Ser Asp Pro
 19 Leu Glu Thr Thr Lys Pro Asp Met Thr Leu Lys Glu Ala Leu Lys Ile Ala Phe
 37 Gly Phe Asn Glu Pro Asn Gly Asn Leu Gln Tyr Gln Gly Lys Asp Ile Thr Glu
 55 Phe Asp Phe Asn Phe Asp Gln Gln Thr Ser Gln Asn Ile Lys Asn Gln Leu Ala
 73 Glu Leu Asn Ala Thr Asn Ile Tyr Thr Val Leu Asp Lys Ile Lys Leu Asn Ala
 91 Lys Met Asn Ile Leu Ile Arg Asp Lys Arg Phe His Tyr Asp Arg Asn Asn Ile
109 Ala Val Gly Ala Asp Glu Ser Val Val Lys Glu Ala His Arg Glu Val Ile Asn
127 Ser Ser Thr Glu Gly Leu Leu Leu Asn Ile Asp Lys Asp Ile Arg Lys Ile Leu
145 Ser Gly Tyr Ile Val Glu Ile Glu Asp Thr Glu Gly Leu Lys Glu Val Ile Asn
163 Asp Arg Tyr Asp Met Leu Asn Ile Ser Ser Leu Arg Gln Asp Gly Lys Thr Phe
181 Ile Asp Phe Lys Lys Tyr Asn Asp Lys Leu Pro Leu Tyr Ile Ser Asn Pro Asn
199 Tyr Lys Val Asn Val Tyr Ala Val Thr Lys Glu Asn Thr Ile Ile Asn Pro Ser
217 Glu Asn Gly Asp Thr Ser Thr Asn Gly Ile Lys Lys Ile Leu Ile Phe Ser Lys
235 Lys Gly Tyr Glu Ile Gly
```

FIG. 12D

| Analysis | Entire Protein |
|---|---|
| Length | 240 aa |
| Molecular Weight | 27505.06 m.w. |
| 1 microgram = | 36.357 pMoles |
| Molar Extinction coefficient | 12800 |
| 1 A[280] corr. to | 2.15 mg/ml |
| A[280] of 1 mg/ml | 0.47 AU |
| Isoelectric Point | 5.76 |
| Charge at pH 7 | -2.94 |

FIG. 13B

```
   1 catatggcgg gcggtcatgg tgatgtaggt atgcacgtaa aagagaaaga
  51 gaaaaataaa gatgagaata agagaaaaga tgaagaacga aataaaacac
 101 aggaagagca tttaaaggaa atcatgaaac acattgtaaa aatagaagta
 151 aaagggagg aagctgttaa aaaagaggca gcagaaaagc tacttgagaa
 201 agtaccatct gatgttttag agatgtataa agcaattgga ggaaagatat
 251 atattgtgga tggtgatatt acaaaacata tatctttaga agcattatct
 301 gaagataaga aaaaataaa agacatttat gggaaagatg ctttattaca
 351 tgaacattat gtatatgcaa aagaaggata tgaacccgta cttgtaatcc
 401 aatcttcgga agattatgta gaaaatactg aaaaggcact gaacgtttat
 451 tatgaaatag gtaagatatt atcaagggat attttaagta aaattaatca
 501 accatatcag aaattttag atgtattaaa taccattaaa aatgcatctg
 551 attcagatgg acaagatctt ttatttacta atcagcttaa ggaacatccc
 601 acagactttt ctgtagaatt cttggaacaa aatagcaatg aggtacaaga
 651 agtatttgcg aaagcttttg catattatat cgagccacag catcgtgatg
 701 ttttacagct ttatgcaccg gaagctttta attacatgga taaatttaac
 751 gaacaagaaa taaatctatc cttggaagaa cttaaagatc aacggatgct
 801 gtcaagatat gaaaaatggg aaaagataaa acagcactat caacactgga
 851 gcgattcttt atctgaagaa ggaagaggac ttttaaaaaa gctgcagatt
 901 cctattgagc caaagaaaga tgacataatt cattctttat ctcaagaaga
 951 aaaagagctt ctaaaaagaa tacaaattga tagtagtgat tttttatcta
1001 ctgaggaaaa agagttttta aaaagctac aaattgatat tcgtgattct
1051 ttatctgaag aagaaaaaga gcttttaaat agaatacagg tggatagtag
1101 taatcctta tctgaaaaag aaaaagagtt tttaaaaaag ctgaaacttg
1151 atattcaacc atacgatatt aatcaaaggt tgcaagatac aggagggtta
1201 attgatagtc cgccaattaa tcttgatgta agaaagcagt ataaaaggga
1251 tattcaaaat attgatgctt tattacatca atccattgga agtaccttgt
1301 acaataaaat ttatttgtat gaaaatatga atatcaataa ccttacagca
1351 accctaggtg cggatttagt tgattccact gataatacta aaattaatag
1401 aggtattttc aatgaattca aaaaaaattt caaatatagt atttctagta
1451 actatatgat tgttgatata aatgaaaggc ctgcattaga taatgagcgt
1501 ttgaaatgga gaatccaatt atcaccagat actcgagcag gatatttaga
1551 aaatggaaag cttatattac aaagaaacat cggtctggaa ataaaggatg
1601 tacaataat taagcaatcc gaaaaagaat atataaggat tgatgcgaaa
1651 gtagtgccaa agagtaaaat agatacaaaa attcaagaag cacagttaaa
1701 tataaatcag gaatggaata agcattagg gttaccaaaa tatacaaagc
1751 ttattacatt caacgtgcat aatagatatg catccaatat tgtagaaagt
1801 gcttatttaa tattgaatga atggaaaaat aatattcaaa gtgatcttat
1851 aaaaaaggta acaaattact tagttgatgg taatggaaga tttgttttta
1901 ccgatattac tctccctaat atagctgaac aatatacaca tcaagatgag
1951 atatatgagc aagttcattc aaaagggtta tatgttccag aatcccgttc
2001 tatattactc catggacctt caaaaggtgt agaattaagg aatgatagtg
2051 agggttttat acacgaataa
```

FIG. 13C

```
  1  His Met Ala Gly Gly His Gly Asp Val Gly Met His Val Lys Glu Lys Glu Lys
 19  Asn Lys Asp Glu Asn Lys Arg Lys Asp Glu Glu Arg Asn Lys Thr Gln Glu Glu
 37  His Leu Lys Glu Ile Met Lys His Ile Val Lys Ile Glu Val Lys Gly Glu Glu
 55  Ala Val Lys Lys Glu Ala Ala Glu Lys Leu Leu Glu Lys Val Pro Ser Asp Val
 73  Leu Glu Met Tyr Lys Ala Ile Gly Gly Lys Ile Tyr Ile Val Asp Gly Asp Ile
 91  Thr Lys His Ile Ser Leu Glu Ala Leu Ser Glu Asp Lys Lys Ile Lys Asp
109  Ile Tyr Gly Lys Asp Ala Leu Leu His Glu His Tyr Val Tyr Ala Lys Glu Gly
127  Tyr Glu Pro Val Leu Val Ile Gln Ser Ser Glu Asp Tyr Val Glu Asn Thr Glu
145  Lys Ala Leu Asn Val Tyr Tyr Glu Ile Gly Lys Ile Leu Ser Arg Asp Ile Leu
163  Ser Lys Ile Asn Gln Pro Tyr Gln Lys Phe Leu Asp Val Leu Asn Thr Ile Lys
181  Asn Ala Ser Asp Ser Asp Gly Gln Asp Leu Leu Phe Thr Asn Gln Leu Lys Glu
199  His Pro Thr Asp Phe Ser Val Glu Phe Leu Glu Gln Asn Ser Asn Glu Val Gln
217  Glu Val Phe Ala Lys Ala Phe Ala Tyr Tyr Ile Glu Pro Gln His Arg Asp Val
235  Leu Gln Leu Tyr Ala Pro Glu Ala Phe Asn Tyr Met Asp Lys Phe Asn Glu Gln
253  Glu Ile Asn Leu Ser Leu Glu Glu Leu Lys Asp Gln Arg Met Leu Ser Arg Tyr
271  Glu Lys Trp Glu Lys Ile Lys Gln His Tyr Gln His Trp Ser Asp Ser Leu Ser
289  Glu Glu Gly Arg Gly Leu Leu Lys Lys Leu Gln Ile Pro Ile Glu Pro Lys Lys
307  Asp Asp Ile Ile His Ser Leu Ser Gln Glu Glu Lys Glu Leu Leu Lys Arg Ile
325  Gln Ile Asp Ser Ser Asp Phe Leu Ser Thr Glu Glu Lys Glu Phe Leu Lys Lys
343  Leu Gln Ile Asp Ile Arg Asp Ser Leu Ser Glu Glu Glu Lys Glu Leu Leu Asn
361  Arg Ile Gln Val Asp Ser Ser Asn Pro Leu Ser Glu Lys Glu Lys Glu Phe Leu
379  Lys Lys Leu Lys Leu Asp Ile Gln Pro Tyr Asp Ile Asn Gln Arg Leu Gln Asp
397  Thr Gly Gly Leu Ile Asp Ser Pro Ser Ile Asn Leu Asp Val Arg Lys Gln Tyr
415  Lys Arg Asp Ile Gln Asn Ile Asp Ala Leu Leu His Gln Ser Ile Gly Ser Thr
433  Leu Tyr Asn Lys Ile Tyr Leu Tyr Glu Asn Met Asn Ile Asn Asn Leu Thr Ala
451  Thr Leu Gly Ala Asp Leu Val Asp Ser Thr Asp Asn Thr Lys Ile Asn Arg Gly
469  Ile Phe Asn Glu Phe Lys Lys Asn Phe Lys Tyr Ser Ile Ser Ser Asn Tyr Met
487  Ile Val Asp Ile Asn Glu Arg Pro Ala Leu Asp Asn Glu Arg Leu Lys Trp Arg
505  Ile Gln Leu Ser Pro Asp Thr Arg Ala Gly Tyr Leu Glu Asn Gly Lys Leu Ile
523  Leu Gln Arg Asn Ile Gly Leu Glu Ile Lys Asp Val Gln Ile Ile Lys Gln Ser
541  Glu Lys Glu Tyr Ile Arg Ile Asp Ala Lys Val Val Pro Lys Ser Lys Ile Asp
559  Thr Lys Ile Gln Glu Ala Gln Leu Asn Ile Asn Gln Glu Trp Asn Lys Ala Leu
577  Gly Leu Pro Lys Tyr Thr Lys Leu Ile Thr Phe Asn Val His Asn Arg Tyr Ala
595  Ser Asn Ile Val Glu Ser Ala Tyr Leu Ile Leu Asn Glu Trp Lys Asn Asn Ile
613  Gln Ser Asp Leu Ile Lys Lys Val Thr Asn Tyr Leu Val Asp Gly Asn Gly Arg
631  Phe Val Phe Thr Asp Ile Thr Leu Pro Asn Ile Ala Glu Gln Tyr Thr His Gln
649  Asp Glu Ile Tyr Glu Gln Val His Ser Lys Gly Leu Tyr Val Pro Glu Ser Arg
667  Ser Ile Leu Leu His Gly Pro Ser Lys Gly Val Glu Leu Arg Asn Asp Ser Glu
685  Gly Phe Ile His Glu
```

FIG. 13D

| analysis | entire protein |
|---|---|
| length | 689 aa |
| molecular weight | 80360.91 m.w. |
| 1 microgram = | 12.444 pmoles |
| molar extinction coefficient | 69410 |
| 1 a[280] corr. to | 1.16 mg/ml |
| a[280] of 1 mg/ml | 0.86 au |
| isoelectric point | 5.53 |
| charge at ph 7 | -19.43 |

FIG. 14B

```
   1 catatggcgg gcggtcatgg tgatgtaggt atgcacgtaa aagagaaaga
  51 gaaaaataaa gatgagaata agagaaaaga tgaagaacga aataaaacac
 101 aggaagagca tttaaaggaa atcatgaaac acattgtaaa aatagaagta
 151 aaaggggagg aagctgttaa aaaagaggca gcagaaaagc tacttgagaa
 201 agtaccatct gatgttttag agatgtataa agcaattgga ggaaagatat
 251 atattgtgga tggtgatatt acaaaacata tatctttaga agcattatct
 301 gaagataaga aaaaataaa agacatttat gggaaagatg ctttattaca
 351 tgaacattat gtatatgcaa aagaaggata tgaacccgta cttgtaatcc
 401 aatcttcgga agattatgta gaaaatactg aaaaggcact gaacgtttat
 451 tatgaaatag gtaagatatt atcaagggat attttaagta aaattaatca
 501 accatatcag aaattttag atgtattaaa taccattaaa aatgcatctg
 551 attcagatgg acaagatctt ttatttacta atcagcttaa ggaacatccc
 601 acagactttt ctgtagaatt cttggaacaa aatagcaatg aggtacaaga
 651 agtatttgcg aaagcttttg catattatat cgagccacag catcgtgatg
 701 ttttacagct ttatgcaccg gaagctttta attacatgga taaatttaac
 751 gaacaagaaa taaatctatc cttggaagaa cttaaagatc aacggatgct
 801 gtcaagatat gaaaaatggg aaaagataaa acagcactat caacactgga
 851 gcgattcttt atctgaagaa ggaagaggac ttttaaaaaa gctgcagatt
 901 cctattgagc caaagaaaga tgacataatt cattctttat ctcaagaaga
 951 aaaagagctt ctaaaaagaa tacaaattga tagtagtgat tttttatcta
1001 ctgaggaaaa agagttttta aaaaagctac aaattgatat tcgtgattct
1051 ttatctgaag aagaaaaaga gcttttaaat agaatacagg tggatagtag
1101 taatccttta tctgaaaaag aaaagagtt tttaaaaaag ctgaaacttg
1151 atattcaacc atacgatatt aatcaaaggt tgcaagatac aggagggtta
1201 attgatagtc cgccaattaa tcttgatgta agaaagcagt ataaaaggga
1251 tattcaaaat attgatgctt tattacatca atccattgga agtaccttgt
1301 acaataaaat ttatttgtat gaaaatatga atatcaataa ccttacagca
1351 accctaggtg cggatttagt tgattccact gataatacta aaattaatag
1401 aggtattttc aatgaattca aaaaaaattt caaatatagt atttctagta
1451 actatatgat tgttgatata aatgaaaggc ctgcattaga taattaa
```

FIG. 14C

```
  1  His Met Ala Gly Gly His Gly Asp Val Gly Met His Val Lys Glu Lys Glu Lys
 19  Asn Lys Asp Glu Asn Lys Arg Lys Asp Glu Glu Arg Asn Lys Thr Gln Glu Glu
 37  His Leu Lys Glu Ile Met Lys His Ile Val Lys Ile Glu Val Lys Gly Glu Glu
 55  Ala Val Lys Lys Glu Ala Ala Glu Lys Leu Leu Glu Lys Val Pro Ser Asp Val
 73  Leu Glu Met Tyr Lys Ala Ile Gly Gly Lys Ile Tyr Ile Val Asp Gly Asp Ile
 91  Thr Lys His Ile Ser Leu Glu Ala Leu Ser Glu Asp Lys Lys Lys Ile Lys Asp
109  Ile Tyr Gly Lys Asp Ala Leu Leu His Glu His Tyr Val Tyr Ala Lys Glu Gly
127  Tyr Glu Pro Val Leu Val Ile Gln Ser Ser Glu Asp Tyr Val Glu Asn Thr Glu
145  Lys Ala Leu Asn Val Tyr Tyr Glu Ile Gly Lys Ile Leu Ser Arg Asp Ile Leu
163  Ser Lys Ile Asn Gln Pro Tyr Gln Lys Phe Leu Asp Val Leu Asn Thr Ile Lys
181  Asn Ala Ser Asp Ser Asp Gly Gln Asp Leu Leu Phe Thr Asn Gln Leu Lys Glu
199  His Pro Thr Asp Phe Ser Val Glu Phe Leu Glu Gln Asn Ser Asn Glu Val Gln
217  Glu Val Phe Ala Lys Ala Phe Ala Tyr Tyr Ile Glu Pro Gln His Arg Asp Val
235  Leu Gln Leu Tyr Ala Pro Glu Ala Phe Asn Tyr Met Asp Lys Phe Asn Glu Gln
253  Glu Ile Asn Leu Ser Leu Glu Glu Leu Lys Asp Gln Arg Met Leu Ser Arg Tyr
271  Glu Lys Trp Glu Lys Ile Lys Gln His Tyr Gln His Trp Ser Asp Ser Leu Ser
289  Glu Glu Gly Arg Gly Leu Leu Lys Lys Leu Gln Ile Pro Ile Glu Pro Lys Lys
307  Asp Asp Ile Ile His Ser Leu Ser Gln Glu Glu Lys Glu Leu Leu Lys Arg Ile
325  Gln Ile Asp Ser Ser Asp Phe Leu Ser Thr Glu Glu Lys Glu Phe Leu Lys Lys
343  Leu Gln Ile Asp Ile Arg Asp Ser Leu Ser Glu Glu Glu Lys Glu Leu Leu Asn
361  Arg Ile Gln Val Asp Ser Ser Asn Pro Leu Ser Glu Lys Glu Lys Glu Phe Leu
379  Lys Lys Leu Lys Leu Asp Ile Gln Pro Tyr Asp Ile Asn Gln Arg Leu Gln Asp
397  Thr Gly Gly Leu Ile Asp Ser Pro Ser Ile Asn Leu Asp Val Arg Lys Gln Tyr
415  Lys Arg Asp Ile Gln Asn Ile Asp Ala Leu Leu His Gln Ser Ile Gly Ser Thr
433  Leu Tyr Asn Lys Ile Tyr Leu Tyr Glu Asn Met Asn Ile Asn Asn Leu Thr Ala
451  Thr Leu Gly Ala Asp Leu Val Asp Ser Thr Asp Asn Thr Lys Ile Asn Arg Gly
469  Ile Phe Asn Glu Phe Lys Lys Asn Phe Lys Tyr Ser Ile Ser Ser Asn Tyr Met
487  Ile Val Asp Ile Asn Glu Arg Pro Ala Leu Asp Asn
```

FIG. 14D

| Analysis | Entire Protein |
|---|---:|
| Length | 498 aa |
| Molecular Weight | 58219.30 m.w. |
| 1 microgram = | 17.176 pMoles |
| Molar Extinction coefficient | 40820 |
| 1 A[280] corr. to | 1.43 mg/ml |
| A[280] of 1 mg/ml | 0.70 AU |
| Isoelectric Point | 5.24 |
| Charge at pH 7 | -20.90 |

FIG. 15B

```
   1 catatggcgg gcggtcatgg tgatgtaggt atgcacgtaa aagagaaaga
  51 gaaaaataaa gatgagaata agagaaaaga tgaagaacga aataaaacac
 101 aggaagagca tttaaaggaa atcatgaaac acattgtaaa aatagaagta
 151 aaaggggagg aagctgttaa aaaagaggca gcagaaaagc tacttgagaa
 201 agtaccatct gatgttttag agatgtataa agcaattgga ggaaagatat
 251 atattgtgga tggtgatatt acaaaacata tatctttaga agcattatct
 301 gaagataaga aaaaaataaa agacatttat gggaaagatg ctttattaca
 351 tgaacattat gtatatgcaa aagaaggata tgaacccgta cttgtaatcc
 401 aatcttcgga agattatgta gaaaatactg aaaaggcact gaacgtttat
 451 tatgaaatag gtaagatatt atcaagggat attttaagta aaattaatca
 501 accatatcag aaattttag atgtattaaa taccattaaa aatgcatctg
 551 attcagatgg acaagatctt ttatttacta atcagcttaa ggaacatccc
 601 acagactttt ctgtagaatt cttggaacaa aatagcaatg aggtacaaga
 651 agtatttgcg aaagcttttg catattatat cgagccacag catcgtgatg
 701 ttttacagct tzatgcaccg gaagctttta attacatgga taaatztaac
 751 gaacaagaaa taaatctatc cttggaagaa cttaaagatc aacggatgct
 801 gtcaagatat gaaaaatggg aaaagataaa acagcactat caacactgga
 851 gcgattcttt atctgaagaa ggaagaggac ttttaaaaaa gctgcagatt
 901 cctattgagc caaagaaaga tgacataatt cattctttat ctcaagaaga
 951 aaaagagctt ctaaaaagaa tacaaattga tagtagtgat ttttatcta
1001 ctgaggaaaa agagttttta aaaaagctac aaattgatat tcgtgattct
1051 ttatctgaag aagaaaaaga gcttttaaat agaatacagg tggatagtag
1101 taatccıtta tctgaaaaag aaaaagagtt tttaaaaaag ctgaaacttg
1151 atattcaacc atacgatatt aatcaaaggt tgcaagatac aggagggtta
1201 atttaa
```

FIG. 15C

```
  1  His Met Ala Gly Gly His Gly Asp Val Gly Met His Val Lys Glu Lys Glu Lys
 19  Asn Lys Asp Glu Asn Lys Arg Lys Asp Glu Glu Arg Asn Lys Thr Gln Glu Glu
 37  His Leu Lys Glu Ile Met Lys His Ile Val Lys Ile Glu Val Lys Gly Glu Glu
 55  Ala Val Lys Lys Glu Ala Ala Glu Lys Leu Leu Glu Lys Val Pro Ser Asp Val
 73  Leu Glu Met Tyr Lys Ala Ile Gly Gly Lys Ile Tyr Ile Val Asp Gly Asp Ile
 91  Thr Lys His Ile Ser Leu Glu Ala Leu Ser Glu Asp Lys Lys Ile Lys Asp
109  Ile Tyr Gly Lys Asp Ala Leu Leu His Glu His Tyr Val Tyr Ala Lys Glu Gly
127  Tyr Glu Pro Val Leu Val Ile Gln Ser Ser Glu Asp Tyr Val Glu Asn Thr Glu
145  Lys Ala Leu Asn Val Tyr Tyr Glu Ile Gly Lys Ile Leu Ser Arg Asp Ile Leu
163  Ser Lys Ile Asn Gln Pro Tyr Gln Lys Phe Leu Asp Val Leu Asn Thr Ile Lys
181  Asn Ala Ser Asp Ser Asp Gly Gln Asp Leu Leu Phe Thr Asn Gln Leu Lys Glu
199  His Pro Thr Asp Phe Ser Val Glu Phe Leu Glu Gln Asn Ser Asn Glu Val Gln
217  Glu Val Phe Ala Lys Ala Phe Ala Tyr Tyr Ile Glu Pro Gln His Arg Asp Val
235  Leu Gln Leu Tyr Ala Pro Glu Ala Phe Asn Tyr Met Asp Lys Phe Asn Glu Gln
253  Glu Ile Asn Leu Ser Leu Glu Glu Leu Lys Asp Gln Arg Met Leu Ser Arg Tyr
271  Glu Lys Trp Glu Lys Ile Lys Gln His Tyr Gln His Trp Ser Asp Ser Leu Ser
289  Glu Glu Gly Arg Gly Leu Leu Lys Lys Leu Gln Ile Pro Ile Glu Pro Lys Lys
307  Asp Asp Ile Ile His Ser Leu Ser Gln Glu Glu Lys Glu Leu Leu Lys Arg Ile
325  Gln Ile Asp Ser Ser Asp Phe Leu Ser Thr Glu Glu Lys Glu Phe Leu Lys Lys
343  Leu Gln Ile Asp Ile Arg Asp Ser Leu Ser Glu Glu Glu Lys Glu Leu Leu Asn
361  Arg Ile Gln Val Asp Ser Ser Asn Pro Leu Ser Glu Lys Glu Lys Glu Phe Leu
379  Lys Lys Leu Lys Leu Asp Ile Gln Pro Tyr Asp Ile Asn Gln Arg Leu Gln Asp
397  Thr Gly Gly Leu Ile
```

FIG. 15D

| Analysis | Entire Protein |
|---|---|
| Length | 401 aa |
| Molecular Weight | 47050.76 m.w. |
| 1 microgram = | 21.254 pMoles |
| Molar Extinction coefficient | 33140 |
| 1 A[280] corr. to | 1.42 mg/ml |
| A[280] of 1 mg/ml | 0.70 AU |
| Isoelectric Point | 5.21 |
| Charge at pH 7 | -19.99 |

FIG. 16B

```
  1 catatggcgg gcggtcatgg tgatgtaggt atgcacgtaa aagagaaaga
 51 gaaaaataaa gatgagaata agagaaaaga tgaagaacga aataaaacac
101 aggaagagca tttaaaggaa atcatgaaac acattgtaaa aatagaagta
151 aaagggagg aagctgttaa aaaagaggca gcagaaaagc tacttgagaa
201 agtaccatct gatgttttag agatgtataa agcaattgga ggaaagatat
251 atattgtgga tggtgatatt acaaaacata tatctttaga agcattatct
301 gaagataaga aaaaaataaa agacatttat gggaaagatg ctttattaca
351 tgaacattat gtatatgcaa aagaaggata tgaacccgta cttgtaatcc
401 aatcttcgga agattatgta gaaaatactg aaaaggcact gaacgtttat
451 tatgaaatag gtaagatatt atcaagggat attttaagta aaattaatca
501 accatatcag aaatttttag atgtattaaa taccattaaa aatgcatctg
551 attcagatgg acaagatctt ttatttacta atcagcttaa ggaacatccc
601 acagactttt ctgtagaatt cttggaacaa aatagcaatg aggtacaaga
651 agtatttgcg aaagcttttg catattatat cgagccacag catcgtgatg
701 ttttacagct ttatgcaccg gaagctttta attacatgga taaatttaac
751 gaacaagaaa taaatctatc cttggaagaa cttaaagatc aacggatgct
801 gtcaagatat gaaaaatggg aaaagataaa acagcactat caacactgga
851 gcgattcttt atctgaagaa ggaagaggac ttttaaaaaa gctgcagatt
901 cctattgagc caagaaaaga ttaa
```

FIG. 16C

```
  1 His Met Ala Gly Gly His Gly Asp Val Gly Met His Val Lys Glu Lys Glu Lys
 19 Asn Lys Asp Glu Asn Lys Arg Lys Asp Glu Glu Arg Asn Lys Thr Gln Glu Glu
 37 His Leu Lys Glu Ile Met Lys His Ile Val Lys Ile Glu Val Lys Gly Glu Glu
 55 Ala Val Lys Lys Glu Ala Ala Glu Lys Leu Leu Glu Lys Val Pro Ser Asp Val
 73 Leu Glu Met Tyr Lys Ala Ile Gly Gly Lys Ile Tyr Ile Val Asp Gly Asp Ile
 91 Thr Lys His Ile Ser Leu Glu Ala Leu Ser Glu Asp Lys Lys Ile Lys Asp
109 Ile Tyr Gly Lys Asp Ala Leu His Glu His Tyr Val Tyr Ala Lys Glu Gly
127 Tyr Glu Pro Val Leu Val Ile Gln Ser Ser Asp Tyr Val Glu Asn Thr Glu
145 Lys Ala Leu Asn Val Tyr Tyr Glu Ile Gly Lys Ile Leu Ser Arg Asp Ile Leu
163 Ser Lys Ile Asn Gln Pro Tyr Gln Lys Phe Leu Asp Val Leu Asn Thr Ile Lys
181 Asn Ala Ser Asp Ser Asp Gly Gln Asp Leu Leu Phe Thr Asn Gln Leu Lys Glu
199 His Pro Thr Asp Phe Ser Val Glu Phe Leu Glu Gln Asn Ser Asn Glu Val Gln
217 Glu Val Phe Ala Lys Ala Phe Ala Tyr Tyr Ile Glu Pro Gln His Arg Asp Val
235 Leu Gln Leu Tyr Ala Pro Glu Ala Phe Asn Tyr Met Asp Lys Phe Asn Glu Gln
253 Glu Ile Asn Leu Ser Leu Glu Glu Leu Lys Asp Gln Arg Met Leu Ser Arg Tyr
271 Glu Lys Trp Glu Lys Ile Lys Gln His Tyr Gln His Trp Ser Asp Ser Leu Ser
289 Glu Glu Gly Arg Gly Leu Leu Lys Lys Leu Gln Ile Pro Ile Glu Pro Lys Lys
307 Asp
```

FIG. 16D

| Analysis | Entire Protein |
|---|---|
| Length | 307 aa |
| Molecular Weight | 36011.74 m.w. |
| 1 microgram = | 27.769 pMoles |
| Molar Extinction coefficient | 31860 |
| 1 A[280] corr. to | 1.13 mg/ml |
| A[280] of 1 mg/ml | 0.88 AU |
| Isoelectric Point | 5.43 |
| Charge at pH 7 | -13.11 |

SDS-PAGE of Purified Proteins

RECOMBINANT IMMUNOGENIC COMPOSITIONS AND METHODS FOR PROTECTING AGAINST LETHAL INFECTIONS FROM *BACILLUS ANTHRACIS*

CROSS-REFERENCE TO RELATED APPLICATIONS

This application claims priority to a U.S. Provisional Application Ser. No. 60/372,152 titled, "Recombinant Anthrax Vaccine," filed Apr. 12, 2002. The entire disclosure of Ser. No. 60/372,152 is incorporated hereby by reference in its entirety.

REFERENCE TO SEQUENCE LISTING

The material contained in the Sequence Listing attached hereto and also provided on compact disc is incorporated by reference herein. The compact disc contains the following file:
Seqlist.txt 109,000 Bytes Created Mar. 27, 2003.

FIELD OF THE INVENTION

The present invention generally relates to an immunogenic composition, methods for preparing a vaccine that protects an animal host against lethal infection *B. anthracis* and immunogenic, and methods of production, and specifically to compositions and methods having both purified recombinant and avirulent *Bacillus anthracis* (*B. anthracis*) protective antigen proteins and purified *B. anthracis* lethal factor proteins, or comprised of purified protective antigen-lethal factor fusion proteins, and to methods of production and purification of said proteins.

BACKGROUND OF THE INVENTION

Anthrax is a well-known infectious disease caused by a Gram-positive bacterium, purified *Bacillus anthracis* (*B. anthracis*). Among the three types of anthrax infection (cutaneous, gastrointestinal, and inhalation), cutaneous anthrax is the most common and is relatively easily treatable with various antibiotics (6). [It is noted that this numeral reference, and others that similarly follow, references a correspondingly numbered citation in the Literature Cited section, infra.] The other two types of anthrax are rare, but usually fatal even with aggressive anti-microbial therapy. For example, only about one fifth of those who contracted inhalation anthrax recovered in a reported outbreak that occurred in the former Soviet Union town of Sverdlovsk (28). Inhalation anthrax generally occurs after an incubation time of one to six days (10). After the incubation period, a nonspecific flu-like illness ensues for one to three days followed by a brief intervening period of improvement. Unfortunately, rapid deterioration follows and death is universal in untreated cases. Death may occur in as many as 95 percent of treated cases if therapy is not begun within 48 hours from the onset of initial symptoms (5).

Although well characterized as a disease, only in last twenty years has the molecular basis of *B. anthracis* virulence related to the disease been understood. The virulence of *B. anthracis* for animals and humans depends on the production of two types of virulence factors: the gamma-linked poly-D-glutamic acid capsule (27) and the three-component protein exotoxin that is termed anthrax toxin (23, 45). The genes related to virulence are located in two mega-plasmids: pXO1 and pXO2. The genes involved in toxin production are located in the 185 kilobase pair (kbp) pXO1 plasmid (29, 42, 46) and the genes required for capsule production are located in the 95 kbp pXO2 plasmid (13, 31, 42, 49). A *B. anthracis* strain that contains both plasmids is generally regarded as a virulent strain. There are many *B. anthracis* strains known in the art that lack virulence due to the absence of either or both of these plasmids. For example, strains lacking the pXO1 plasmid are avirulent (17, 48). Known strains without the pXO2 plasmid are at least $10^5$-fold less virulent than wild-type strains containing both plasmids (17, 52).

The major virulence factor, anthrax toxin, is composed of three proteins: protective antigen (PA, 83 kilo Dalton, kDa), edema factor (EF, 89 kDa), and lethal factor (LF, 90 kDa). The toxin components act in the binary combinations of PA+EF (edema toxin), and PA+LF (lethal toxin). PA is a cell receptor-binding protein and delivers the other two proteins (EF and LF) into the cytosol of infected cells (3, 39). EF is a calmodulin-dependent adenylate cyclase that disables phagocytes and other cells (22).

Increased cellular levels of cyclic adenosine monophosphate (cAMP) upset water homeostasis and are believed to be responsible for the massive edema seen in cutaneous anthrax infections. Edema toxin inhibits neutrophil function in vitro (30) and neutrophil function is impaired in patients with cutaneous anthrax infection (1). Lethal toxin can be fatal to animals and certain cultured cells due to the LF action. LF is a zinc metalloprotease (14, 15, 21) that inactivates mitogen-activated protein kinase kinase (8, 38, 50). The genes encoding PA (pagA), EF (cya), and LF (lef) have all been identified and cloned (43, 47, 51, 53). The crystal structures of all three proteins have also been identified (7, 24, 39).

The most effective known method for preventing anthrax is vaccination. The current and only FDA-approved anthrax vaccine in the United States (produced by BioPort Corporation of Lansing, Mich. under the trademark BIOTHRAX) is produced from a sterile culture filtrate from an avirulent *B. anthracis* V770-NP1-R strain. The vaccine primarily consists of PA, and aluminum hydroxide is used as an adjuvant (10). The vaccine was developed during the 1950s and 1960s (2, 54) and is licensed by the FDA to BioPort Corporation (and was formerly licensed to the Michigan Biologic Product Institute) since 1970. The vaccine is safe, showing less than 0.06% systemic reactions (11). The ability of the vaccine to elicit an immune response in humans is well-documented (20, 40, 41). The prior art BIOTHRAX vaccine is currently licensed for six doses over 18 months followed by annual boosts. Nevertheless, data indicate that all six doses may not be necessary to elicit full immune responses (41).

Although the prior art vaccine is effective and safe, there exists in the art a desire to develop new immunogenic compositions for preparing a vaccine which protects a subject against lethal a infection *B. anthracis* using current recombinant technologies. Such technologies could increase characterization of the vaccine protein components and allow use of new types of adjuvants that could elicit enhanced or more diverse immune responses.

Attempts in the art are known to develop new compositions to prepare a vaccine against anthrax using more current technologies. See for example, U.S. Patent Applications 2002/0051791, 2002/0197272, 2003/0003109, to Galloway et al. Unfortunately, Galloway et al. compositions to prepare vaccines are based on DNA vaccine technology and shows very low level of immune responses (both IgG1 and IgG2a) even after 4 vaccinations (3 DNA vaccinations plus one protein vaccination).

SUMMARY OF THE INVENTION

Accordingly, the present invention provides new compositions and methods to preparations to induce an immune response that protects an animal from a lethal infection of *Bacillus anthracis* (*B. anthracis*). The present invention increases the ability to characterize compositions to prepare vaccine protein components, decreases the number of doses required to complete immunization (thus saving costs and reducing risks of possible side effects), and allows use of new types of adjuvants that could elicit better and more diverse immune responses.

One embodiment of the present invention has two antigenic components, PA and LF. It is known that portions of EF and LF share high degree of homology due to the fact that both proteins bind to PA at the same location. As a result, many antibodies made against LF cross-react with EF, and vise versa. Therefore, by using LF and PA as antigens, the present invention can result in faster immune responses by targeting all three toxin proteins.

Another embodiment of the present invention targets all three proteins by making a fusion protein between LF and PA. The fusion protein streamlines the vaccine production by reducing the need for fermentation and purification procedures for each protein. By making a fusion protein, the same effect is achieved in a single production line.

Specifically, the present invention provides an immunogenic composition to prepare a vaccine against a lethal infection of *B. anthracis* in an animal and includes an effective immunizing amount of at least one recombinant *B. anthracis* PA (rPA) protein and at least one recombinant *B. anthracis* LF (rLF) protein. The composition may also include adjuvants such as aluminum hydroxide, immunostimulatory sequence (ISS), CpG, or calcium phosphate.

The recombinant rLF or rPA *B. anthracis* protein may be a variant rPA. The variant rPA and variant rLF may also be combined as fusion protein. Fusion may occur at the protein between the N-terminal domain 1 of rLF and the C-terminal domains 3 and 4 of rPA.

A method of the present invention to produce an immunogenic response against a lethal infection of *B. anthracis* in an animal includes administering a composition that comprises effective immunizing amount of at least one variant recombinant *B. anthracis* protein. Additional steps may also include administering at least one adjuvant such as aluminum hydroxide, immunostimulatory sequence (ISS), CpG, and calcium phosphate.

The method of the present invention to streamline manufacture of an immunogenic composition for producing an immunogenic response against a lethal infection of *B. anthracis* in an animal may include the step of fusing a rPA and a rLF. Optimizing protein fermentation, and purifying the protein may also be included.

The present invention also includes a composition comprising an expression vector that when incorporated into a suitable host allows over-expression of at least one recombinant *B. anthracis* protein.

Other features of the present invention will become more apparent to persons having ordinary skill in the art to which the present invention pertains from the following description and claims taken in conjunction with the accompanying figures.

BRIEF DESCRIPTION OF THE FIGURES

The foregoing features, as well as other features, will become apparent with reference to the description and figures below, in which like numerals represent like elements.

FIGS. 1A and 1B illustrate a graphic representation of the pBP I backbone vector (FIG. 1A) and DNA sequence (6694 base pairs, bp), SEQ ID NO: 1 (FIG. 1B).

FIGS. 2A and 2B illustrate a graphic representation of the pBP II backbone vector (FIG. 2A) and DNA sequence (5865 bp), SEQ ID NO: 2 (FIG. 2B).

FIGS. 3A, 3B, and 3C illustrate a graphic representation of the pBP101 expression vector for expression of LF30 (FIG. 3A), the DNA sequence of the LF30 coding region (771 bp from 3746 to 4516 of pBP101), SEQ ID NO: 3 (FIG. 3B), and the amino acid sequence of LF30 (256 amino acids), SEQ ID NO: 4 (FIG. 3C), derived therefrom.

FIGS. 4A, 4B, and 4C illustrate a graphic representation of the pBP102 expression vector for expression of full-length active recombinant LF (rLF) (FIG. 4A), the DNA sequence of the LF coding region (2337 bp from 5854 to 8190 of pBP102), SEQ ID NO: 5 (FIG. 4B), and the amino acid sequence of LF (778 amino acids), SEQ ID NO: 6 (FIG. 4C), derived therefrom.

FIGS. 5A, 5B, 5C, 5D, and 5E illustrate a graphic representation of the pBP103 expression vector for expression of full-length active recombinant PA (rPA) (FIG. 5A), the DNA sequence of pBP103 (entire sequence of pBP103 is shown since the vector is different from rest of the pBP vectors due to the lack of Nde I restriction site immediately after the PA signal sequence), SEQ ID NO: 7 (FIG. 5B), the DNA sequence of the rPA coding region (2208 bp from 3735 to 5942 of pBP103), SEQ ID NO: 8 (FIG. 5C), the amino acid sequence of rPA (735 amino acids), SEQ ID NO: 9 (FIG. 5D), and the calculated chemical properties of PA (FIG. 5E).

FIGS. 6A, 6B, 6C, 6D, 6E, and 6F illustrate a graphic representation of pBP105 expression vector for expression of full-length active rPA and LF30 (FIG. 6A); the DNA sequence of the entire vector (entire sequence of pBP105 is shown since there are two open reading frames in the vector), SEQ ID NO: 10 (FIG. 6B), the DNA sequence of the rPA and LF30 coding regions (the DNA sequence for rPA (2208 bp from 3735 to 5942 of pBP105) is the same as the rPA sequence in pBP103, SEQ ID NO: 11 (FIG. 6C); the DNA sequence for LF30 (771 bp from 6391 to 7161 of pBP105) is same as the LF30 sequence in pBP101 , SEQ ID NO: 12 (FIG. 6D)); the amino acid sequence of PA and LF30 (amino acids sequences of rPA (735 amino acids), SEQ ID NO: 13 (FIG. 6E), and LF30 (256 amino acids), SEQ ID NO: 14 (FIG. 6F), are identical to those sequences from pBP103 and pBP101 , respectively).

FIGS. 7A, 7B, 7C, and 7D illustrate a graphic representation of the pBP107 expression vector for expression of the fusion protein BP107 (FIG. 7A), the DNA sequence of the pBP107 coding region (1515 bp from 3746 to 5260 of pBP107), SEQ ID NO: 15 (FIG. 7B); the amino acid sequence of BP107 (504 amino acids), SEQ ID NO: 16 (FIG. 7C), derived therefrom; and the calculated chemical properties of BP107 (FIG. 7D).

FIGS. 8A, 8B, 8C, and 8D illustrate a graphic representation of the pBP108 expression vector for expression of the LF-PA fusion protein BP108 (FIG. 8A), the DNA sequence of the pBP108 coding region (1974 bp from 3746 to 5719 of pBP108), SEQ ID NO: 17 (FIG. 8B); the amino acid sequence of BP108 (657 amino acids), SEQ ID NO: 18

(FIG. 8C), derived therefrom; and the calculated chemical properties of BP108 (FIG. 8D).

FIGS. 9A, 9B, 9O, and 9D illustrate a graphic representation of the pBP109 expression vector for expression of the LF-PA fusion protein BP109 (FIG. 9A), the DNA sequence of the pBP109 coding region (2289 bp from 3746 to 6034 of pBP109), SEQ ID NO: 19 (FIG. 9B); the amino acid sequence of BP109 (762 amino acids), SEQ ID NO: 20 (FIG. 9C), derived therefrom; and the calculated chemical properties of BP109 (FIG. 9D).

FIGS. 10A, 10B, 10C, and 10D illustrate a graphic representation of the pBP111 expression vector for expression of a PA deletion mutant PA64 (FIG. 10A), the DNA sequence of the pBP111 coding region (1722 bp from 1 to 1722 of pBP111), SEQ ID NO: 21 (FIG. 10B); the amino acid sequence of PA64 (573 amino acids), SEQ ID NO: 22 (FIG. 10C), derived therefrom; and calculated chemical properties of PA64 (FIG. 10D).

FIGS. 11A, 11B, 11C, and 11D illustrate a graphic representation of the pBP113 expression vector for expression of a PA deletion mutant PA47 (FIG. 11A), the DNA sequence of the pBP113 coding region (1272 bp from 1 to 1272 of pBP113), SEQ ID NO: 23 (FIG. 11B); the amino acid sequence of PA47 (423 amino acids), SEQ ID NO: 24 (FIG. 11C), derived therefrom; and the calculated chemical properties of PA47 (FIG. 11D).

FIGS. 12A, 12B, 12C, and 12D illustrate a graphic representation of the pBP115 expression vector for expression of a PA deletion mutant PA27 (FIG. 12A); the DNA sequence of the pBP115 coding region (723 bp from 1 to 723 of pBP115), SEQ ID NO: 25 (FIG. 12B); the amino acid sequence of PA27 (240 amino acids), SEQ ID NO: 26 (FIG. 12C), derived therefrom; and the calculated chemical properties of PA27 (FIG. 12D).

FIGS. 13A, 13B, 13C, and 13D illustrate a graphic representation of pBP116 expression vector for expression of a LF C-terminal deletion mutant LF80 (FIG. 13A), the DNA sequence of the pBP116 coding region (2070 bp from 1 to 2070 of pBP116), SEQ ID NO: 27 (FIG. 13B); the amino acid sequence of LF80 (689 amino acids), SEQ ID NO: 28 (FIG. 13C); and calculated chemical properties of LF80 (FIG. 13D).

FIGS. 14A, 14B, 14C, and 14D illustrate a graphic representation of pBP118 expression vector for expression of a C-terminal LF deletion mutant LF60 (FIG. 14A), the DNA sequence of the pBP118 coding region (1497 bp from 1 to 1497 of pBP118), SEQ ID NO: 29 (FIG. 14B); the amino acid sequence of LF60 (498 amino acids), SEQ ID NO: 30 (FIG. 14C), derived therefrom; and the calculated chemical properties of LF60 (FIG. 14D).

FIGS. 15A, 15B, 15C, and 15D illustrate a graphic representation of the pBP119 expression vector for expression of a C-terminal LF deletion mutant LF50 (FIG. 15A); the DNA sequence of the pBP119 coding region (1206 bp from 1 to 1206 of pBP119), SEQ ID NO: 31 (FIG. 15B); the amino acid sequence of LF50 (401 amino acids), SEQ ID NO: 32 (FIG. 15C), derived therefrom; and the calculated chemical properties of LF50 (FIG. 15D).

FIGS. 16A, 16B, 16C, and 16D illustrate a graphic representation of the pBP120 expression vector for expression of a C-terminal LF deletion mutant LF40 (FIG. 16A), the DNA sequence of the pBP120 coding region (924 bp from 1 to 924 of pBP120), SEQ ID NO: 33 (FIG. 16B); the amino acid sequence of LF40 (307 amino acids), derived therefrom, SEQ ID NO: 34 (FIG. 16C); and the calculated chemical properties of LF40 (FIG. 16D).

DETAILED DESCRIPTION OF THE INVENTION

Figure 1A:
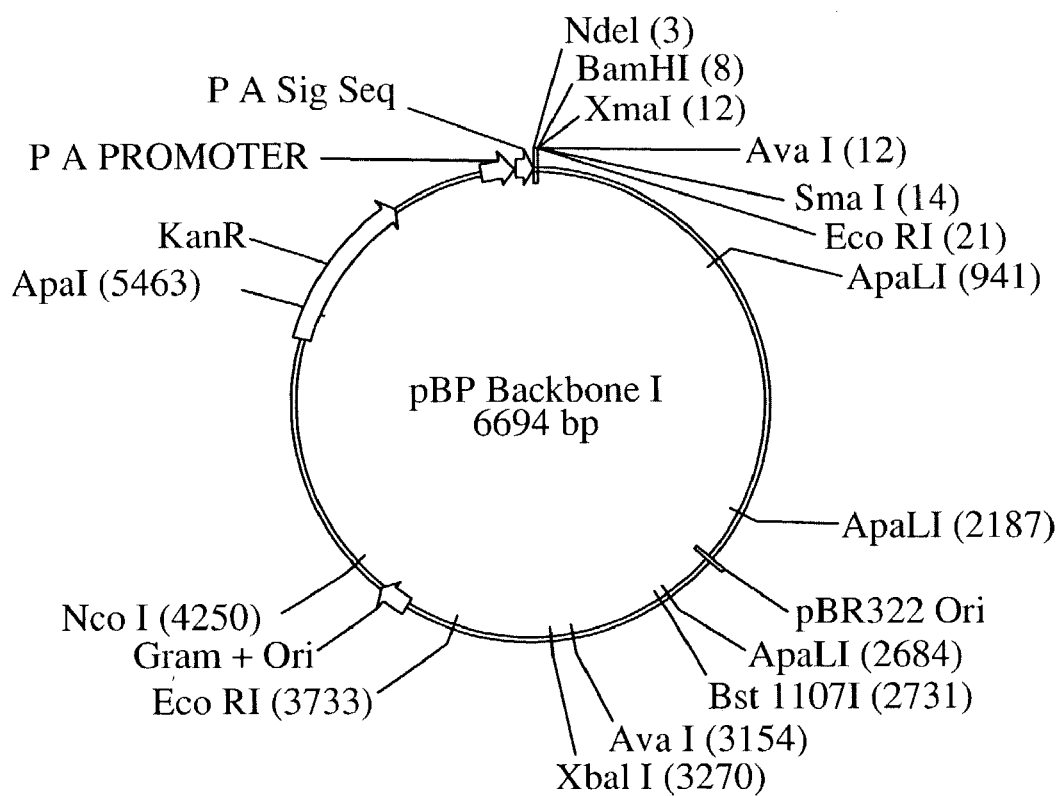

The present invention relates to compositions and methods to induce the animal host to produce antibodies against a virulent strain of *Bacillus anthracis* (*B. anthracis*). In general, the present invention provides an immunogenic composition, such as a new compositions to prepare a vaccine, including the use of two antigenic recombinant components derived from an avirulent strain of *B. anthracis*, namely the protective antigen (PA) and lethal factor (LF) proteins. Such recombinant proteins have an amino acid sequences that are at least 90% identical, preferably at least 95% identical to the amino acid sequences detailed below.

It is well established that both anti-PA and anti-LF antibodies will work as neutralizing antibodies and, therefore, will interrupt enzymatic activities of the anthrax toxin (16, 19, 25, 26). Additionally, it has been demonstrated that a booster by LF or the presence of LF antigen enhances the immunity of PA antigen (30). Furthermore, because LF and the edema factor (EF) protein share high N-terminal amino acid homology, some of the antibodies raised against the N-terminal of LF will also react with EF (4, 26). Therefore, the present invention, by using LF and PA as antigens, may result in faster immune responses by targeting all three toxin proteins since the presence of different antibodies allows attack of different proteins at the same time.

In another embodiment of the present invention, the immunogenic composition targeting all three proteins (i.e., PA, LF, and EF) is to make a fusion protein between LF and PA. In LF, the immuno-dominant region is domain 1 (32) which binds to PA. Many of the antibodies raised against LF may neutralize the toxic effect of the anthrax toxin by interrupting the binding of LF and PA (26). For PA, domain 4 (39) is the immuno-dominant region. A deletion mutant of PA containing only domain 4 is able to protect mice in a challenge study (9). One embodiment of the present invention fuses the protein between the N-terminal domain 1 of LF and the C-terminal domains 3 and 4 of PA. By using the domain 3 of PA as a spacer region, it is possible to keep the correct folding structures of the other two domains from LF and PA.

An important feature of the fusion protein of the present invention is streamlining the production of the composition. Production of two separate proteins may include fermentation and purification procedures for each protein. The fusion protein allows this to be performed in a single production line.

In the present invention, two antigenic B. anthracis proteins are over-expressed, either separately or together as a fusion protein, in an avirulent strain of B. anthracis BH441. The over-expressed proteins are produced in an optimized fermentation method and purified by column chromatography. The purified proteins are formulated as an immunogenic composition, namely a composition to prepare a vaccine.

Development of a B. anthracis over-expression system involves the development of series of expression vectors (plasmids) to express the target proteins from an avirulent strain (pX01⁻, pX02⁻) of B. anthracis. This system is designed to express and secrete the target proteins into the culture supernatant.

I. Host Strain

Avirulent B. anthracis strain BH441, lacking both pXO1 and pXO2 plasmids, may be used as the host strain for expression. Since the strain does not express any protein involved in virulence, issues related to the presence of various toxin components such as LF and EF are eliminated. Dr. Steve Leppla at the National Institute of Health is the inventor of the strain.

II. Expression Vector

Figure 2A:
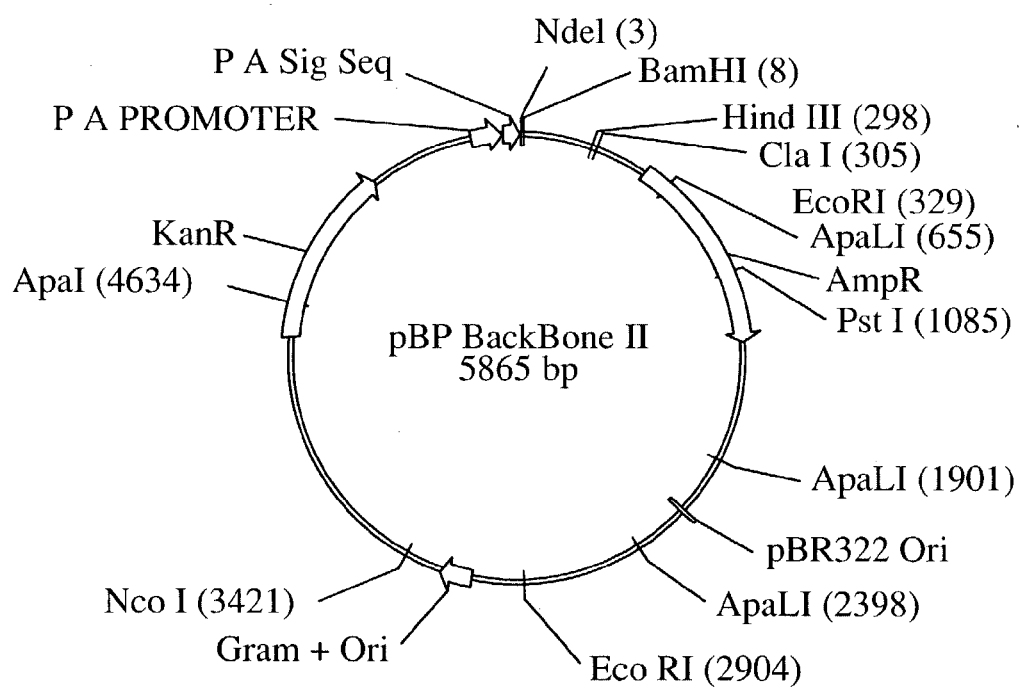

The present invention uses expression vectors (pBP I and pBP II vectors) to express the target proteins. The pBP II vector was developed as an E. coli-B. anthracis shuttle vector as illustrated in FIG. 2, SEQ ID NO: 2. In short, the vector was created using features of both pYS5 vector (44) and a commercially available E. coli expression vector pET16b (available from NOVAGEN, Madison, Wis.).

A difference of the new pBP vector from the two parent vectors is the fact that NdeI and BamHI restriction sites were used to insert a target gene right next to the PA signal sequence under the control of the PA promoter. As a result, the target gene will be expressed, processed, and secreted to the medium for easy purification. Thus, the target proteins may be purified easily from the culture supernatant without the need of lysing cells. Features of the resulting pBP vectors include origin of replication for both B. anthracis (18, 18, 44) and E. coli, two antibiotic resistant genes against ampicillin and kanamycin, PA promoter, and PA signal sequence for target protein secretion, and a cloning site containing NdeI and BamHI restriction sites. Two pBP expression vectors (I, SEQ ID NO: 1 and II, SEQ ID NO: 2) may be made utilizing the same principles.

The resulting difference between the two vectors is that pBP II (5865 bp), SEQ ID NO: 2, is smaller than pBP I (6694 bp), SEQ ID NO: 1, due to removal of sequences proved to be unnecessary for stability of the vector and the level of expression of the target proteins. FIGS. 1 and 2 illustrate the pBP vectors.

Using these expression vectors and the BH441 host strain, the following antigens were able to be cloned, expressed, and purified to be used as a component of the present invention's immunogenic composition. The 14 expression vectors that follow below, except pBP103 and pBP105, utilize NdeI and BamHI restriction sites for cloning the target gene into one of the two pBP expression vectors. DNA sequences of all of the resulting expression vectors described in this invention were verified by DNA sequencing using the ABI Prism 310 Genetic Analyzer (Applied Biosystems, Foster City, Calif.).

Figure 3A:
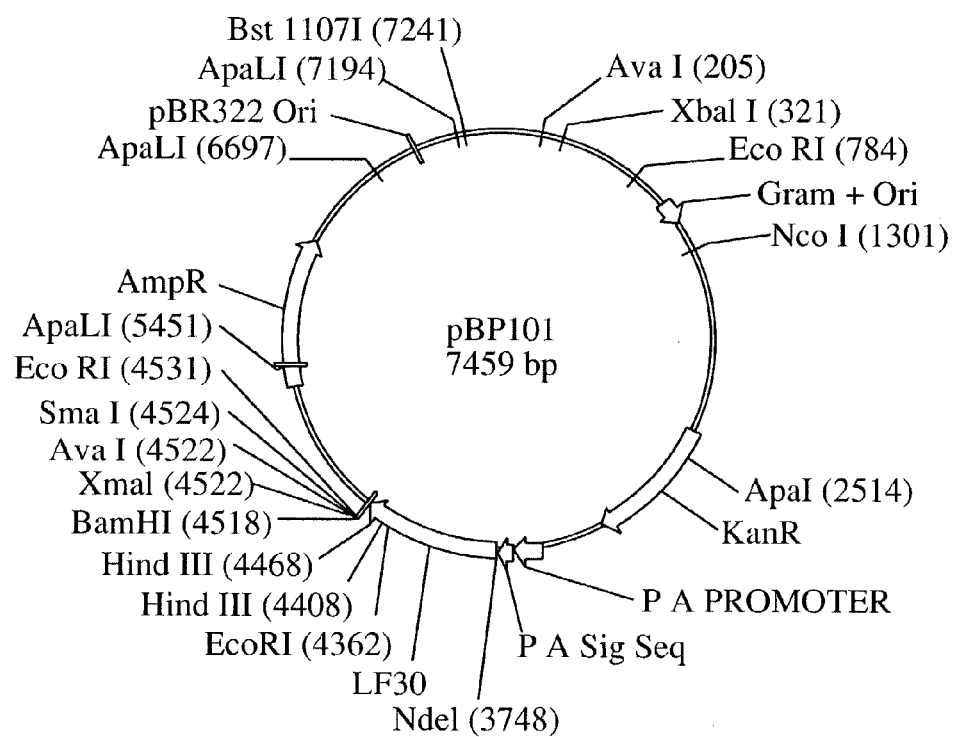

A. pBP101 pBP101 is an expression vector for LF30. LF30 is a truncated version of the anthrax lethal factor protein with deletions in its C-terminus. It consists of the first 254 amino acids of the 776 amino-acid wild-type protein. These first 254 amino acids represent the PA-binding domain of wild-type LF. There are two additional amino acids (histidine and methionine) at its N-terminus due to the addition of a NdeI restriction site at the beginning of the gene for cloning purposes. pBP I was used to create the vector. Please refer to FIG. 3 for the DNA sequence, SEQ ID NO: 3, and amino acid sequence, SEQ ID NO: 4, of LF30.

Figure 4A:
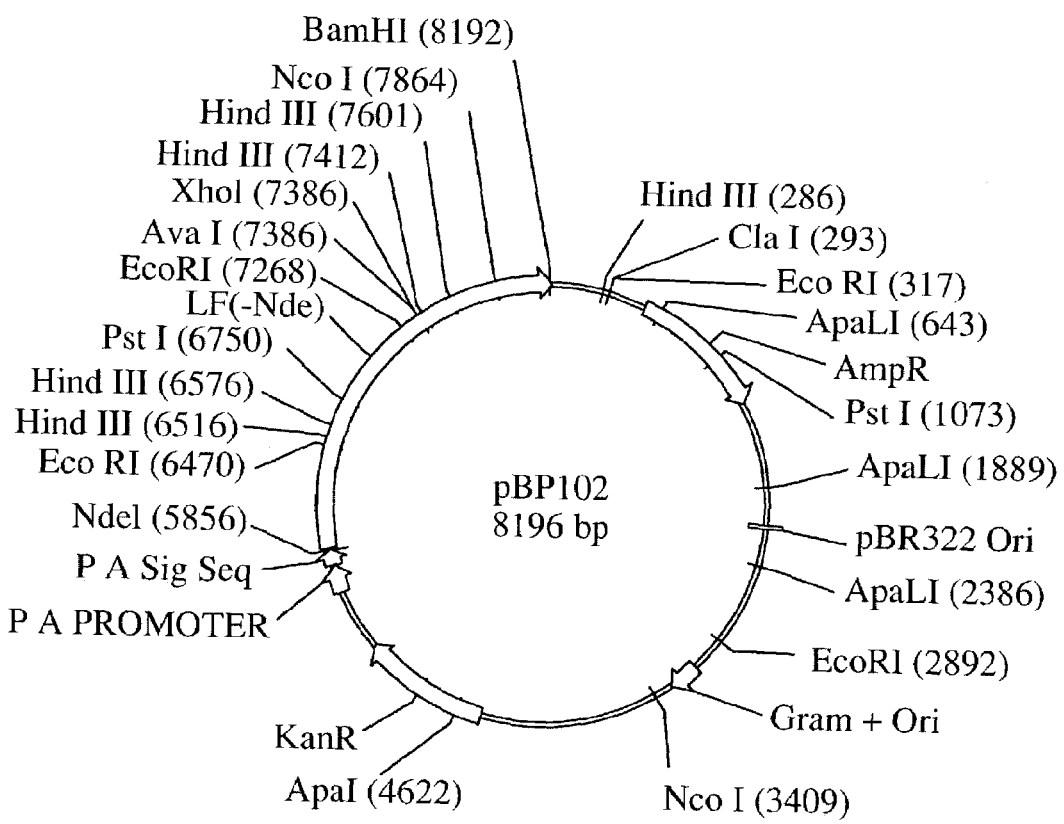

B. pBP102 pBP102 is an expression vector for full-length, active rLF. There are two differences between the sequence of the wild-type LF gene and the rLF gene in pBP102. First, rLF from pBP102 contains two additional amino acids (histidine and methionine) at its N-terminus due to the addition of a NdeI restriction site for cloning purposes. Second, the tyrosine codon (amino acid 388 counting the additional two amino acids at its N-terminus) TAT was changed to TAC to remove an internal NdeI site for cloning purposes (36). This vector was created using the pBP II. Please refer to FIG. 4 for detailed description for the DNA sequence, SEQ ID NO: 5, and amino acid sequence, SEQ ID NO: 6, of this vector.

Figure 5A:
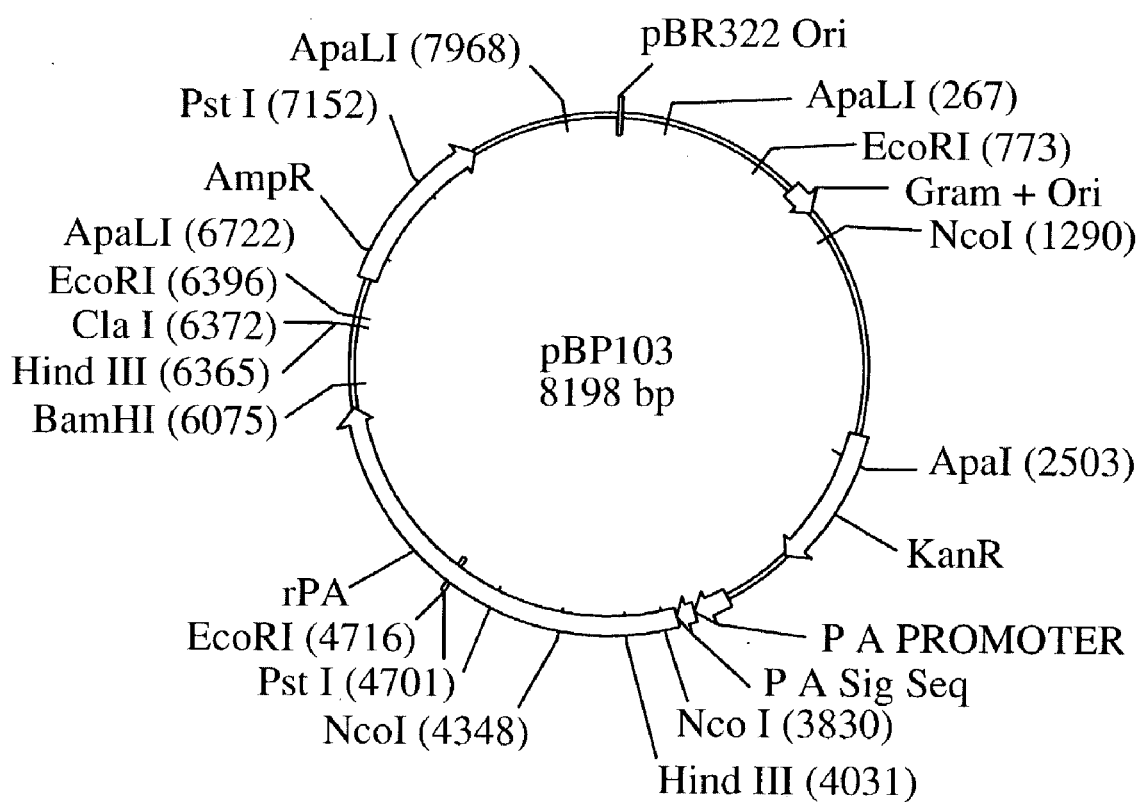

C. pBP103 pBP103 is an expression vector for full-length, wild-type rPA. This vector is different from the rest of the pBP vectors since there is no added amino acid in its N-terminus. The NdeI restriction site was not used to create this vector. Thus, the PA sequence from pBP103 is identical to that of wild-type PA. Expression vector pBP103 was created by ligating the 2436 base pair BamHI/Bst1107I fragment of plasmid pET16b with the 5765 base pair BamHI/XbaI fragment of plasmid pYS5. Please refer to FIG. 5 for the entire DNA sequence of pBP103, SEQ ID NO: 7; the DNA sequence of the pBP103 coding region, SEQ ID NO: 8; and amino acid sequence, SEQ ID NO: 9, of rPA. Please note the entire vector sequence, SEQ ID NO: 7, is shown in the figure since pBP103 is different from other pBP vectors.

Figure 6A:
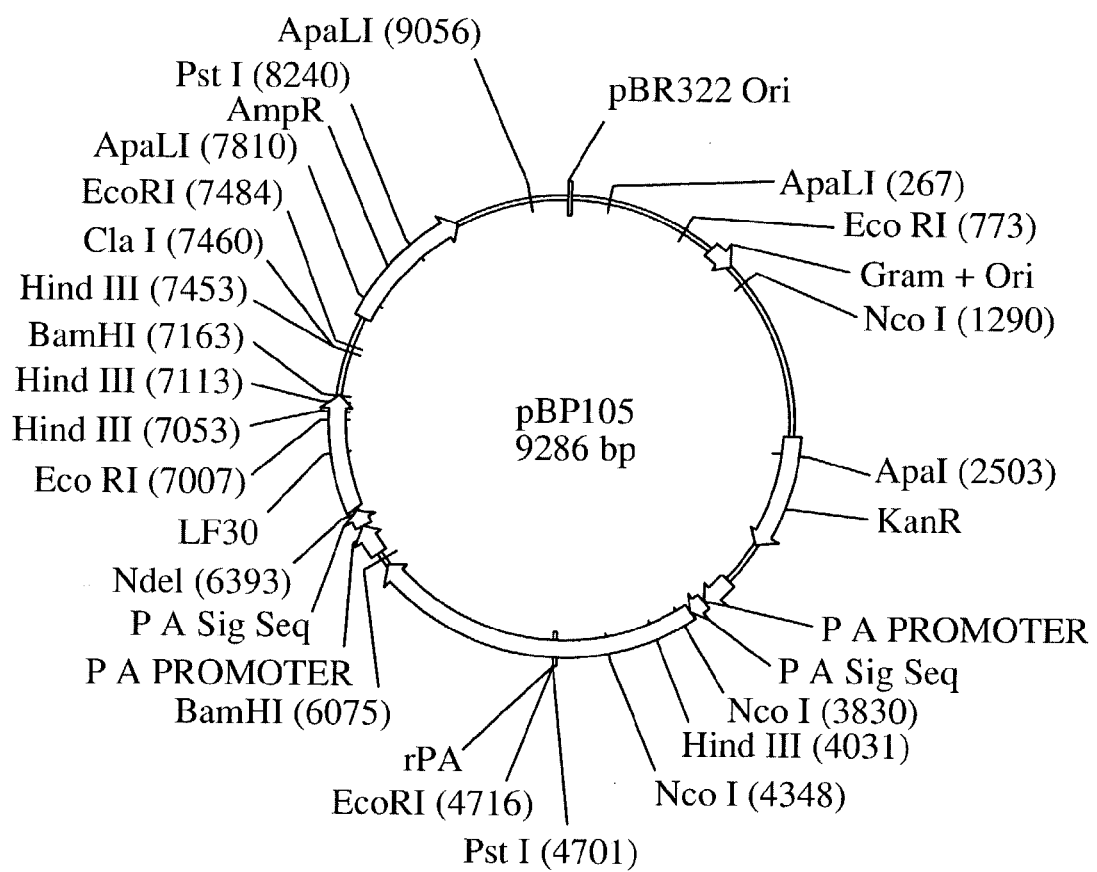

D. pBP105 pBP105 is a dual expression vector for both full-length rPA and LF30. This vector was created to express and purify both proteins from a single expression vector. Both open reading frames are under the control of separate PA promoters. This vector is also different from other pBP vectors since it was created from pBP101 and pBP103. To create two open reading frames, a second PA promoter and the LF30 gene from pBP101 are inserted into pBP103. Thus, the rPA protein sequence is the same as the wild-type PA sequence but the LF30 protein contains two additional amino acids as described in pBP101. Please refer to FIG. 6 for details. FIG. 6 illustrates a graphic representation of pBP105 expression vector for expression of full-length active rPA and LF30; the DNA sequence of the entire vector (entire sequence of pBP105 is shown since there are two open reading frames in the vector), SEQ ID NO: 10, the DNA sequence of the rPA and LF30 coding regions (the DNA sequence for rPA (2208 bp from 3735 to 5942 of pBP105) is the same as the rPA sequence in pBP103, SEQ ID NO: 11; the DNA sequence for LF30 (771 bp from 6391 to 7161 of pBP105) is same as the LF30 sequence in pBP101, SEQ ID NO: 12), and the amino acid sequence of PA and LF30 (amino acids sequences of rPA (735 amino acids), SEQ ID NO: 13, and LF30 (256 amino acids), SEQ ID NO: 14, are identical to those sequences from pBP103 and pBP101, respectively).

E. pBP107

Figure 7A:
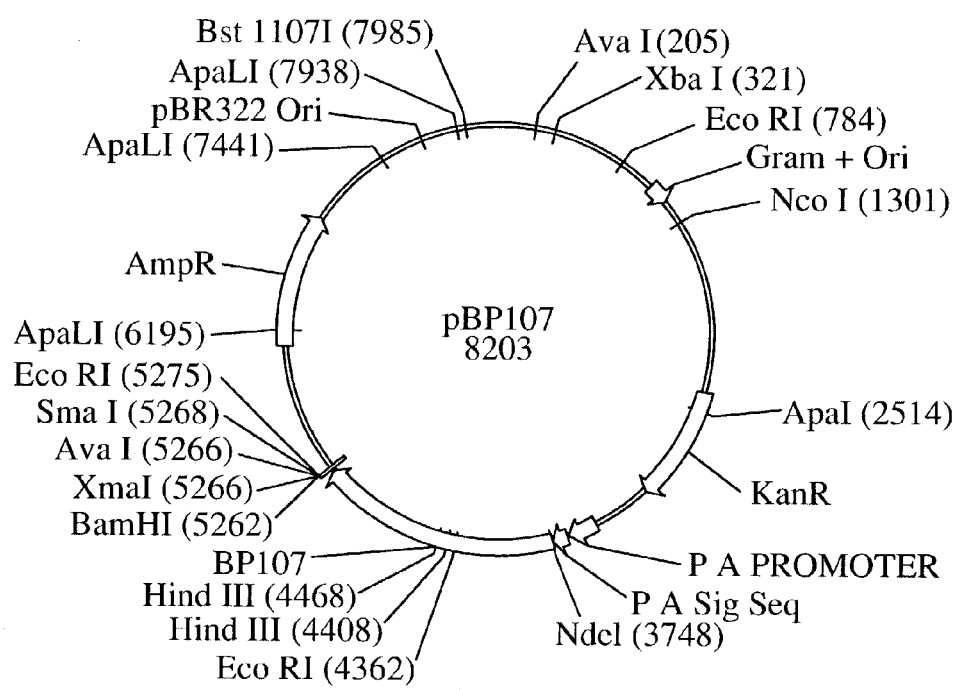

Expression vector pBP107 is a novel plasmid created for the purpose of over-expression of a recombinant *B. anthracis* LF-PA fusion protein. The 58 kDa LF-PA fusion protein contains domain 1 (residues 1 to 254) of LF (32) and domains 3 and 4 (residues 488 to 735) of PA (39). Domain 1 of LF is responsible for binding to PA and domain 4 of PA the receptor-binding region. Domain 3 of PA was used as a spacer for proper folding of LF domain 1 and PA domain 4. Two additional amino acids (His and Met) are added at the N-terminus for cloning purpose. Initially, the LF and PA fragments were generated from plasmids pBP102 and pBP103, respectively, by PCR. Next, the technique of overlap PCR was used to combine the LF and PA fragments. The pBP I backbone was used to insert the LF-PA fragment to generate pBP107. The resulting fusion protein is designated as BP107. FIG. 7 illustrates a graphic representation of the pBP107 expression vector for expression of the fusion protein BP107, the DNA sequence of the pBP107 coding region (1515 bp from 3746 to 5260 of pBP107), SEQ ID NO: 15; the amino acid sequence of BP107 (504 amino acids), SEQ ID NO: 16, derived therefrom; and the calculated chemical properties of BP107.

Figure 8A:
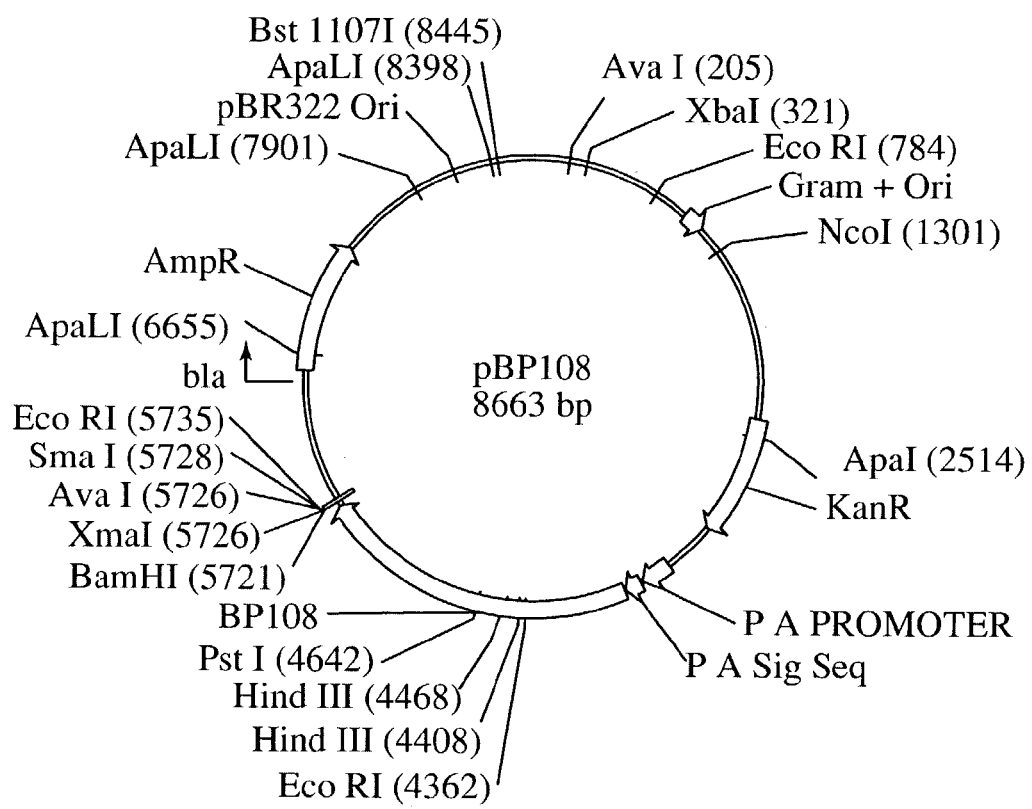

F. pBP108 pBP108 is an expression vector for a second PA-LF fusion protein BP108. This fusion protein is 76 kDa and represents the N-terminal LF amino acids 1 to 406 (domains 1, 3, and portion of domain 2) and PA amino acids 488-735 (domains 3 and 4 of PA). BP108 contains more LF sequences than BP107 to ensure proper folding of the LF domain 1. Like BP107, two additional amino acids (His and Met) are added at the N-terminus for cloning purposes. Initially, the LF and PA fragments were generated from plasmids pSJ115 (35) and pBP103, respectively, by PCR. Next, the technique of overlap PCR was used to combine the LF and PA fragments. The pBP I backbone was used to insert the LF-PA fragment to generate pBP108. FIG. 8 illustrates a graphic representation of the pBP108 expression vector for expression of the LF-PA fusion protein BP108, the DNA sequence of the BP108 coding region (1974 bp from 3746 to 5719 of pBP108), SEQ ID NO: 17, the amino acid sequence of BP108 (657 amino acids), SEQ ID NO: 18, derived therefrom, and the calculated chemical properties of BP108.

Figure 9A:
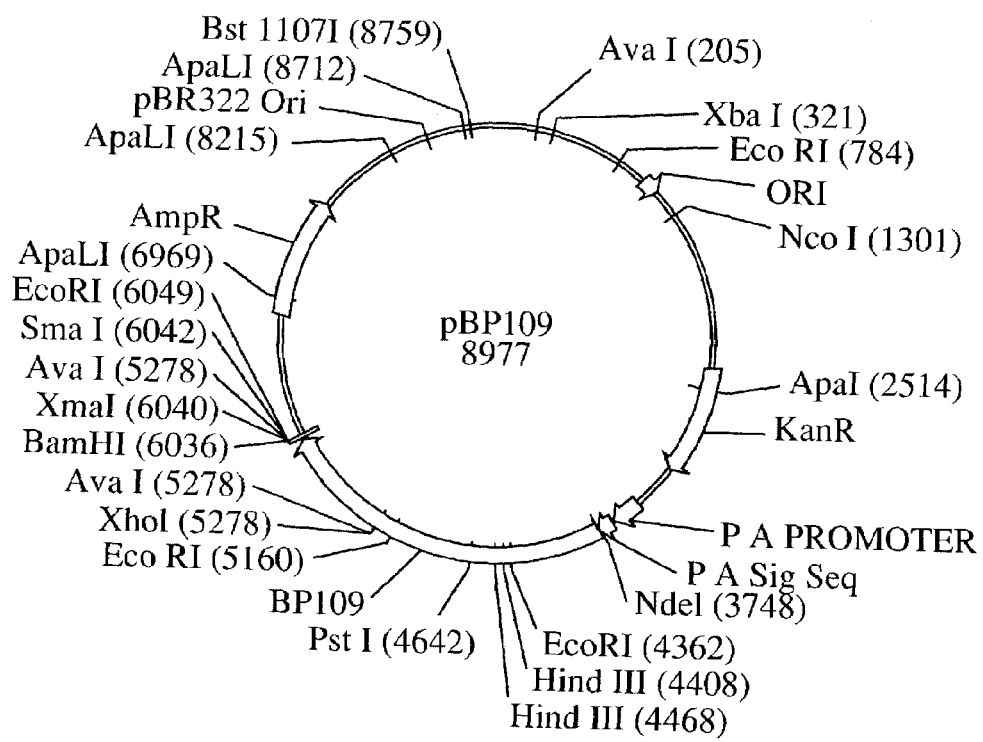

G. pBP109 pBP109 is an expression vector for a third PA-LF fusion protein BP109. This fusion protein is 88 kDa and represents the N-terminal LF amino acids 1 to 512 (domains 1, 3, and portion of domain 2) and PA amino acids 488-735 (domains 3 and 4 of PA). BP109 contains even more LF sequences than BP108 to ensure proper folding of the LF domain 1. Like BP107, two additional amino acids (His and Met) are added at the N-terminus for cloning purposes. Initially, the LF and PA fragments were generated from plasmids pSJ115 (34) and pBP103, respectively, by PCR. Next, the technique of overlap PCR was used to combine the LF and PA fragments. The pBP I backbone was used to insert the LF-PA fragment to generate pBP109. FIG. 9 illustrates a graphic representation of the pBP109 expression vector for expression of the LF-PA fusion protein BP109, the DNA sequence of the pBP109 coding region (2289 bp from 3746 to 6034 of pBP109), SEQ ID NO: 19; the amino acid sequence of BP109 (762 amino acids), SEQ ID NO: 20, derived therefrom; and the calculated chemical properties of BP109.

Figure 10A:
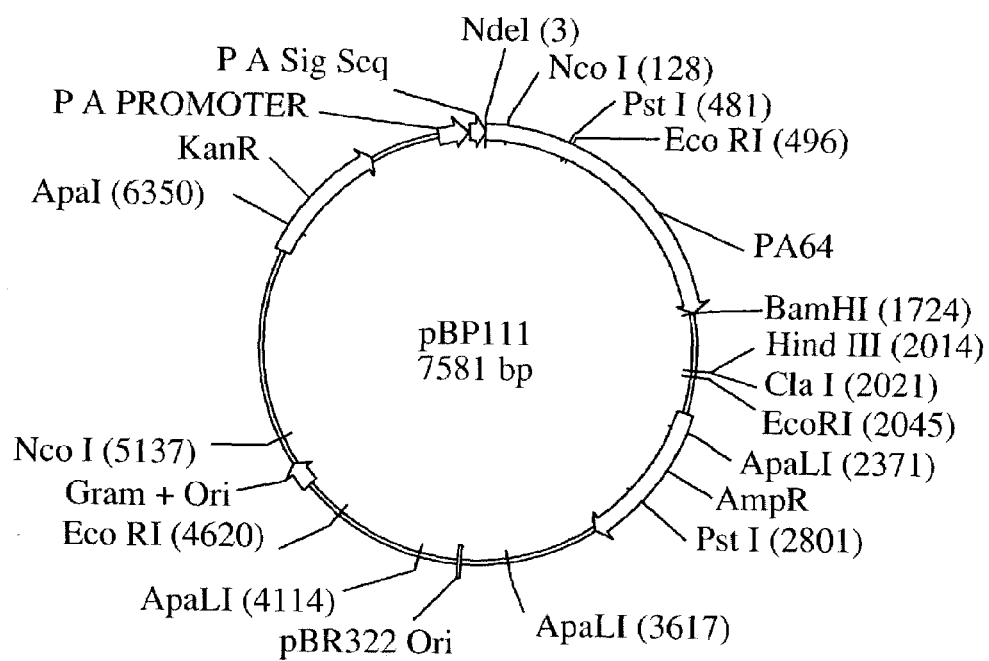

H. pBP111 pBP111 is an expression vector for a 64 kDa N-terminal PA deletion mutant PA64. This mutant contains amino acid 185-735 of PA and the purpose of this mutant is to create a stable PA molecule to be used as an antigen. The wild-type PA is not very stable due to the presence of a furin cleavage site at amino acid 164 (RKKR). By removing this site, PA64 is less vulnerable to degradation and other proteolytic activities. The vector pBP111 was made using the pBP backbone II. The resulting protein PA64 contains two additional amino acids (His and Met) at its N-terminus making the total number of amino acids 573. FIG. 10 illustrates a graphic representation of the pBP111 expression vector for expression of a PA deletion mutant PA64, the DNA sequence of the PBP111 coding region (1722 bp from 1 to 1722 of pBP111), SEQ ID NO: 21; the amino acid sequence of PA64 (573 amino acids), SEQ ID NO: 22, derived therefrom; and calculated chemical properties of PA64.

Figure 11A:
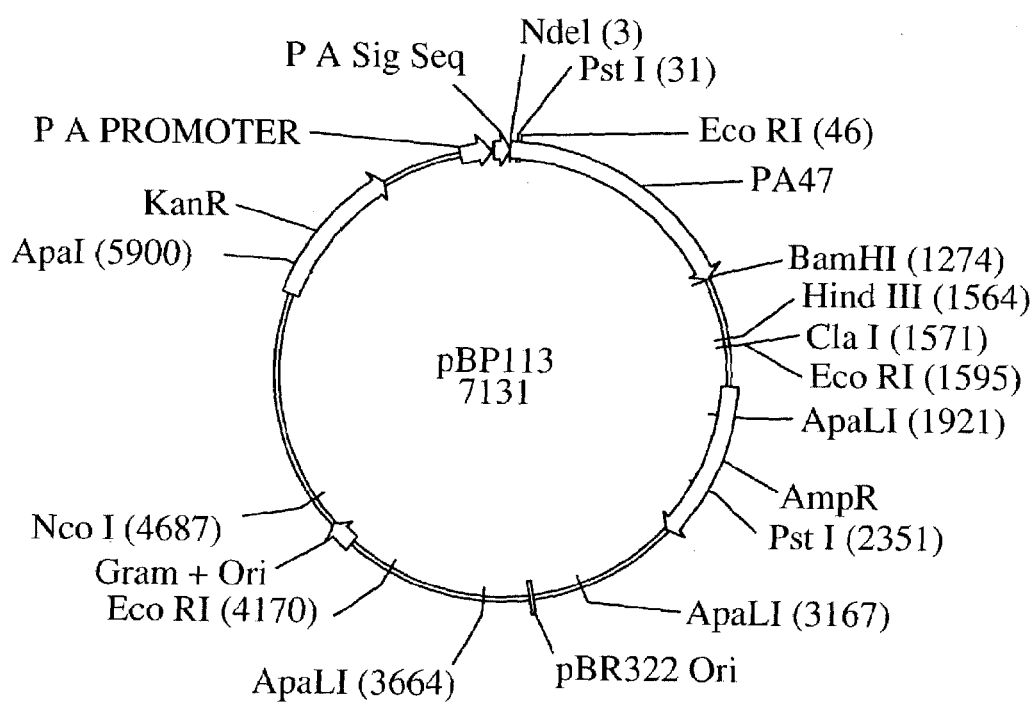

I. pBP113 pBP113 is an expression vector for a 47 kDa N-terminal PA deletion mutant PA47. This mutant contains amino acid 315-735 of PA and the purpose of this mutant is to create a stable PA molecule to be used as an antigen. The wild-type PA is not very stable due to the presence of a furin cleavage site at amino acid 164 (RKKR). Additionally, there is a chymotrypsin sensitive site at 313 (FF). By removing both sites, PA47 is less vulnerable to degradation and other proteolytic activities. The vector pBP1113 was made using the pBP II backbone. The resulting protein PA47 contains two additional amino acids (His and Met) at its N-terminus making the total number of amino acids 423. FIG. 11 illustrates a graphic representation of the pBP113 expression vector for expression of a PA deletion mutant PA47; the DNA sequence of the pBP113 coding region (1272 bp from 1 to 1272 of pBP113), SEQ ID NO: 23; the amino acid sequence of PA47 (423 amino acids), SEQ ID NO: 24, derived therefrom; and the calculated chemical properties of PA47.

Figure 12A:
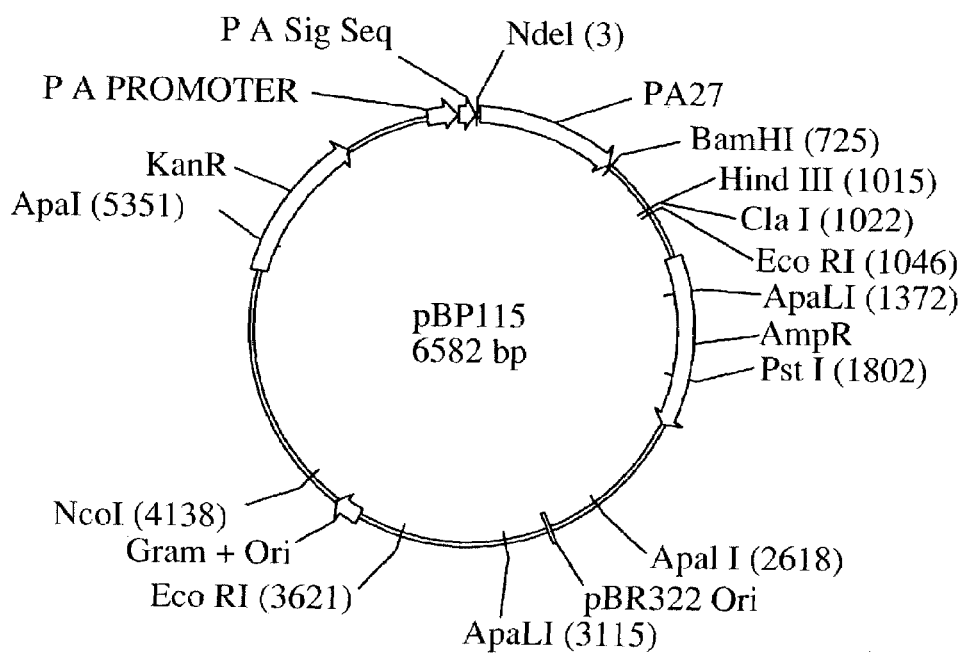

J. pBP115 pBP115 is an expression vector for a 27 kDa N-terminal PA deletion mutant PA27. This mutant contains amino acid 498-735 of PA and the purpose of this mutant is to create a smallest PA deletion mutant to be used as an effective antigen. It has been reported that the domain 4 by itself can protect mice from lethal dose of spore challenge (9). PA27 contains a part of domain 3 and full domain 4. The vector pBP1115 was created using the pBP II backbone. The resulting protein PA27 contains two additional amino acids (His and Met) at its N-terminus making the total number of amino acids 240. FIG. 12 illustrates a graphic representation of the pBP115 expression vector for expression of a PA deletion mutant PA27, the DNA sequence of the pBP115 coding region (723 bp from 1 to 723 of pBP115), SEQ ID NO: 25; the amino acid sequence of PA27 (240 amino acids), SEQ ID NO: 26, derived therefrom; and the calculated chemical properties of PA27.

Figure 13A:
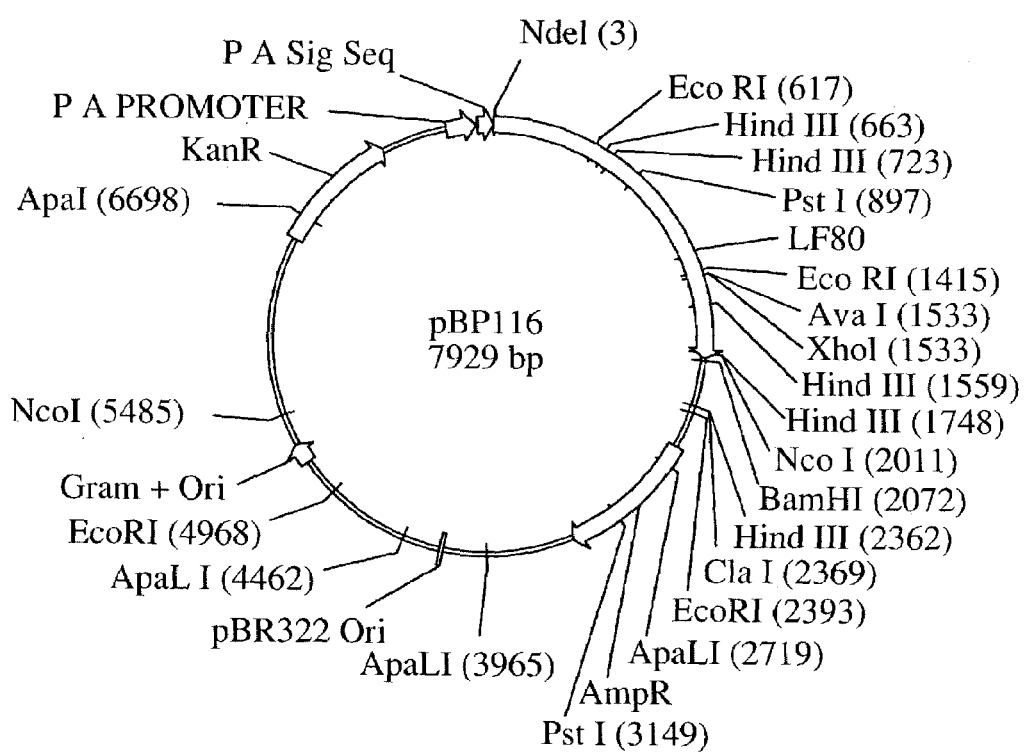
Figure 14A:
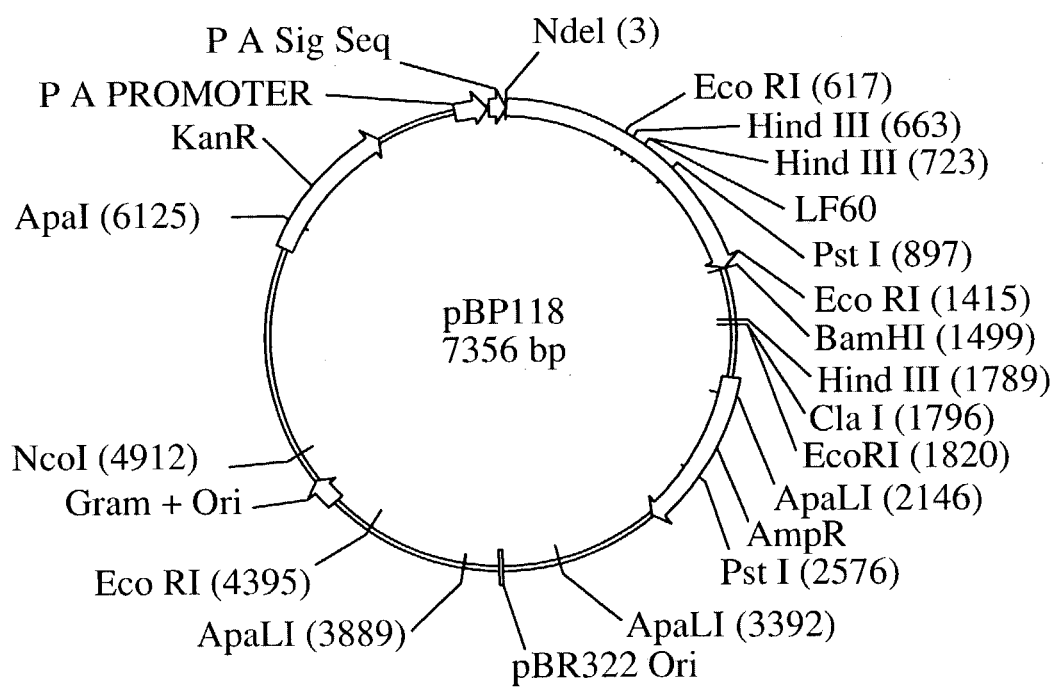
Figure 15A:
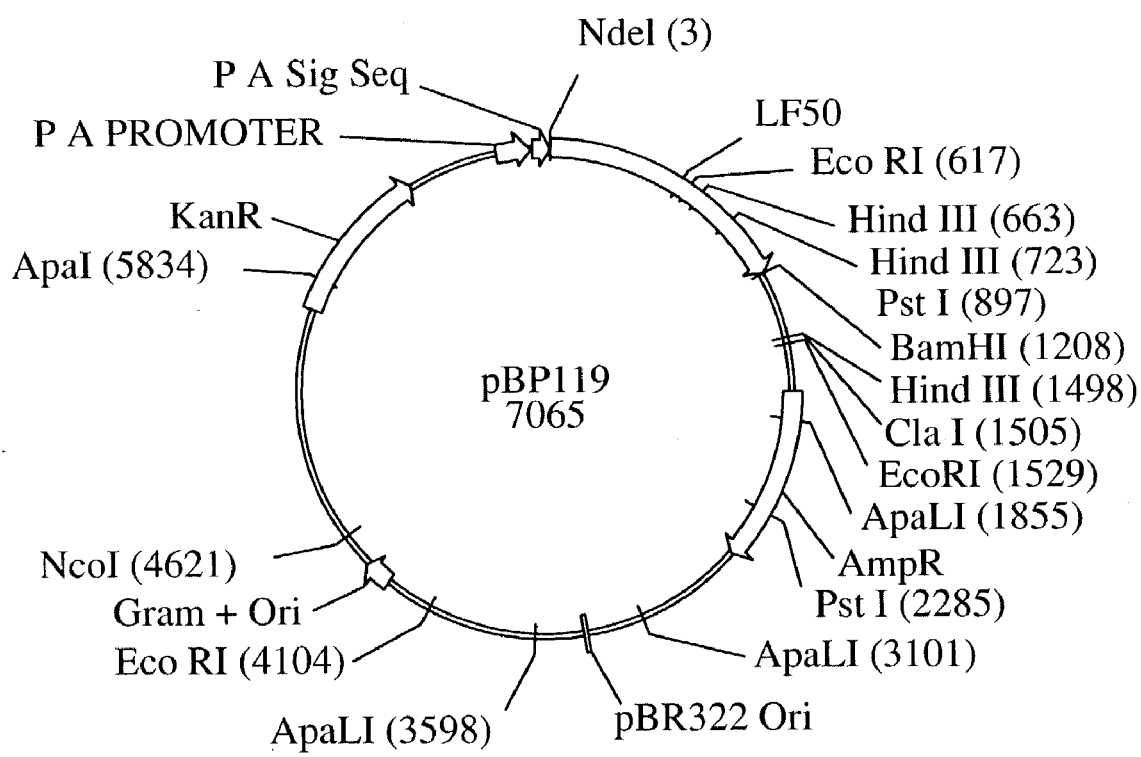
Figure 16A:
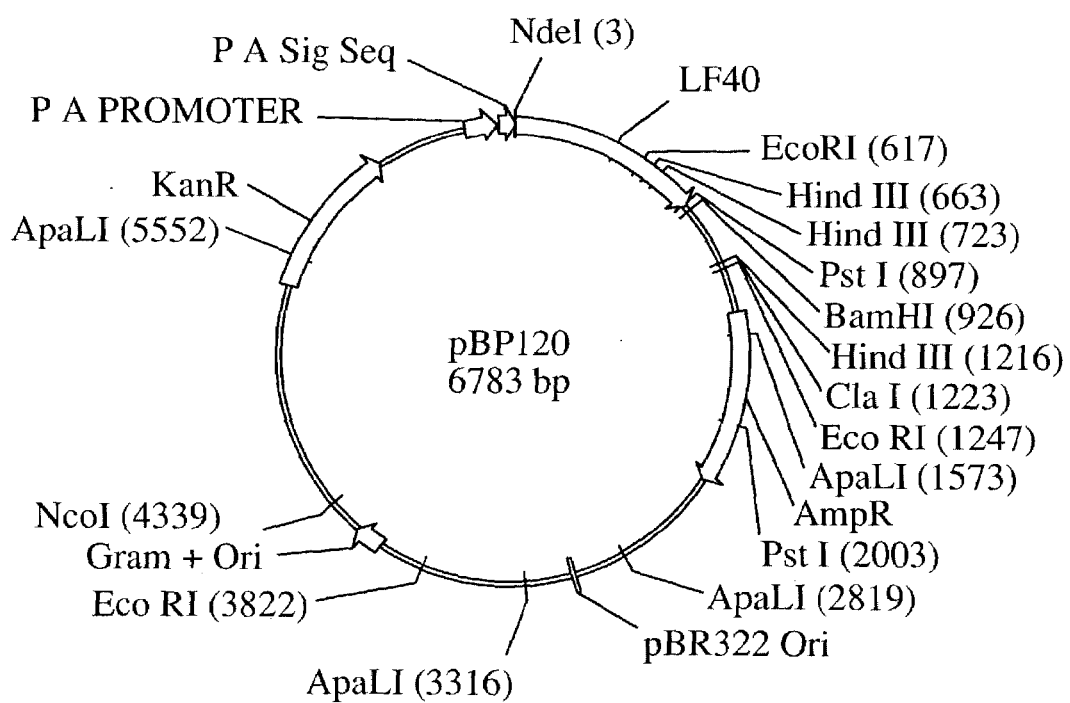

K. pBP116 pBP116 is an expression vector for an 80 kDa C-terminal LF deletion mutant LF80. LF80 contains amino acids 1 to 687 of LF representing most of the LF molecule except the C-terminal enzymatic domain. The vector pBP116 was created using the pBP II backbone. The resulting protein LF80 contains two additional amino acids (His and Met) at its N-terminus making the total number of amino acids 689. FIG. 13 illustrates a graphic representation of pBP116 expression vector for expression of a LF C-terminal deletion mutant LF80, the DNA sequence of the pBP116 coding region (2070 bp from 1 to 2070 of pBP116), SEQ ID NO:

27; the amino acid sequence of LF80 (689 amino acids), SEQ ID NO: 28; and calculated chemical properties of LF80.

L. pBP118 pBP118 is an expression vector for a 60 kDa C-terminal LF deletion mutant LF60. LF60 represents residues 1 to 496 of LF which represents domains I (residues 1–262), III (303–382), and portion of domain II (residues 263–297 and 385–550). The vector pBP118 was created using the pBP II backbone. The resulting protein LF60 contains two additional amino acids (His and Met) at its N-terminus making the total number of amino acids 498. FIG. 14 illustrates a graphic representation of pBP118 expression vector for expression of a C-terminal LF deletion mutant LF60; the DNA sequence of the pBP118 coding region (1497 bp from 1 to 1497 of pBP118), SEQ ID NO: 29; the amino acid sequence of LF60 (498 amino acids), SEQ ID NO: 30, derived therefrom; and the calculated chemical properties of LF60.

M. pBP119 pBP119 is an expression vector for a 50 kDa C-terminal LF deletion mutant LF50. LF50 represents residues 1 to 401 of LF that represents domains I, III, and portion of domain II. The vector pBP119 was created using the pBP II backbone. The resulting protein LF60 contains two additional amino acids (His and Met) at its N-terminus making the total number of amino acids 403. FIG. 15 illustrates a graphic representation of the pBP119 expression vector for expression of a C-terminal LF deletion mutant LF50; the DNA sequence of the pBP119 coding region (1206 bp from 1 to 1206 of pBP119), SEQ ID NO: 31; the amino acid sequence of LF50 (401 amino acids), SEQ ID NO: 32, derived therefrom; and the calculated chemical properties of LF50.

N. pBP120 pBP120 is an expression vector for a 40 kDa C-terminal LF deletion mutant LF40. LF40 represents residues 1 to 305 of LF which represents domain I and portions of domains II and III. The vector pBP120 was created using the pBP II backbone. The resulting protein LF40 contains two additional amino acids (His and Met) at its N-terminus making the total number of amino acids 307. FIG. 16 illustrates a graphic representation of the pBP120 expression vector for expression of a C-terminal LF deletion mutant LF40; the DNA sequence of the pBP120 coding region (924 bp from 1 to 924 of pBP120), SEQ ID NO: 33, the amino acid sequence of LF40 (307 amino acids), derived therefrom, SEQ ID NO: 34, and the calculated chemical properties of LF40.

III. Fermentation and Purification

The following procedure was based on typical fermentation and purification procedures of rPA preparation from pBP103 vector, SEQ ID NOS: 7 and 8, using BH441 as host cells. Fermentation and purification procedures of other proteins are known in the art and similar to that of rPA.

A. Bacterial Culture Conditions

A working stock of *B. anthracis* BH 441(pBP103) strain, stored at −80° C. in 50% (vol/vol) glycerol, was used. Two (2) liters of modified FA media, consisting of 35 g/L tryptone (BD Biosciences, San Jose, Calif.) and 20 g/L yeast extract (BD Biosciences, San Jose, Calif.), were formulated and sterilized at 121° C. for 15–20 minutes using a four (4) liter flask. Media was allowed to cool to room temperature before placing in a pre-sterilized two (2) liter polycarbonate bottle (NALGENE, Nalge Nunc International, Rochester, N.Y.).

One (1) liter of 10× FA media salt solution was formulated, consisting of 60 g/L $Na_2HPO_4{*}7H_2O$, 10 g/L $KH_2PO_4$, 55 g/L NaCl, 0.4 g/L L-Tryptophan, 0.4 g/L L-Methionine, 0.05 g/L Thiamine-HCl, and 0.25 g/L Uracil. The 10× salt solution was sterile filtered using 0.2 μm DURAPORE polyvinylidiene fluoride (PVDF) filter (Millipore Corporation, Bedford, Mass.) and placed into another pre-sterilized two (2) liter polycarbonate bottle (NALGENE) to be stored at room temperature.

After sterilizing the modified FA media without salt as described above, kanamycin (400 μL of 50 mg/mL kanamycin solution (Sigma) in 0.9% NaCl, final concentration of 0.01 mg/mL or 10 μg/mL) was added aseptically to the media. Additionally, 200 mL of the sterile 10× salt solution was also added aseptically to the 2L media. Ten (10) mL of the media was then aseptically transferred into each of five (5) sterile 50 mL polypropylene tubes. These tubes were inoculated with the frozen *B. anthracis* in BH441 (pBP103) strain, using a sterile inoculation loop. Sterile caps were placed onto the tubes and the tubes were allowed to incubate at 37° C. with a constant agitation rate of 250 rpm in the INNOVA 4000 shaker incubator (New Brunswick Scientific Co., Inc., Edison, N.J.) for approximately sixteen (16) hours. After incubation, the grown cultures were checked for sufficient turbidity and then stored at 2–8° C. temporarily (less than few hours) until the fermentor was ready. These were the cultures used to inoculate the fermentors during the study.

B. Fermentation Conditions

The fermentations were performed using the BIOFLO 2000 Bench-Top Fermentor (New Brunswick Scientific Co. Inc., Edison, N.J.) with a 9 L working volume. Two 6-blade Rushton impellers, connected to the bearing housing assembly (rotor) on the fermentor head plate, were used for agitation. The first impeller was positioned approximately 3 cm above the ring sparger. The second impeller was positioned in the center of the rotor, approximately 18 cm above the lower impeller. Stainless steal baffles were positioned at a 90° angle with the wall of the glass vessel.

The fermentor head-plate was equipped with a sample port designed for aseptic sampling during the fermentation. An exhaust system was set up using a 0.2 μm pharmaceutical grade exhaust filter (sold under the trademark ULTIPORE by Pall Ultrafine Filtration Corporation; "Pall") linked to a condensation collection bottle. A secondary exhaust filter (micro ACRODISC 50, 0.2 μm; Gelman Sciences, Ann Arbor, Mich.) was placed onto the head-plate. Medical grade silicon tubing and TYGON was used to make all connections on the head-plate. The head-plate was lowered onto the 9 L glass vessel and secured in place. Approximately 500 mL of water for injection (WFI) was added into the vessel to eliminate complete drying of the fermentor system during sterile autoclaving. The fermentor assembly was sterilized by autoclaving at 121° C. for 60 minutes and then allowed to cool to room temperature. The fermentor was then assembled onto the BIOFLO 2000 system.

Eight (8) liters of modified FA media was used during the fermentation. The formulated media was divided into four (4) liter flasks, each with 2 L of media. The flasks were autoclaved at 121° C. for 15 to 20 minutes. The media was allowed to cool to room temperature. Using a sterile glass funnel, the media was added aseptically to the fermentor via the addition port. The additional 800 mL of the 10× FA media salt solution was also added, along with 2 mL of 50 mg/mL kanamycin stock solution (0.01 mg/mL final concentration). Initial pH of the media was 6.7.

Aeration of the media was initiated at 9.0 L/min (1 L/min per L vessel volume) using an external compressed air tank (0.1 purity grade) and filtered through 0.2 μm ACRODISC 50 inlet filter line. Agitation of the media was initiated at 300 rpm using the motor-driven, rotor coupling agitator on the BIOFLO 2000. The media was equilibrated to 37° C. using an external circulating water bath system integrated to the head-plate, controlling the media temperature throughout the fermentation at a constant 37° C. Fermentation was initiated by inoculating the fermentor aseptically with the 50 mL initial culture prepared above.

C. Fermentation Harvest and Recovery

Sampling of the fermentor was done periodically throughout the growth cycle, and pH and $OD_{600}$ values were measured. As the $OD_{600}$ increased during log phase of the fermentation, a slight drop in the pH could be seen (initial pH 6.7 falls to pH 6.6). As the $OD_{600}$ approached stationary phase, a transient increase was observed in the pH between 10 and 14 hours (pH 6.6 increased to pH 7.3). These two key parameters (unchanging $OD_{600}$ and pH 7.3) were used to determine a suitable harvest time of 12–14 hours. At 12–14 hours, $OD_{600}$ of the sample was found to be 13, and the pH was 7.3. The fermentor culture was harvested.

The 9 L fermentation culture was placed on ice and then poured into 1 L polycarbonate bottles with rubber O-ring caps. Bottles were balanced using the OHAUS (Pine Brook, N.J.) opposing balance, and then centrifuged at 5,000 rpm for 30–40 minutes in a SORVALL RC12BP (Kendro laboratory Products, Asheville, N.C.) swing-bucket rotor centrifuge. After centrifugation, clarified supernatant was collected in a sterile 9 L bottle and cell debris pellets were discarded. 120 mL of 0.5 M EDTA was added to the 9 L clarified supernatant to inhibit protease activity (final concentrated 6.66 mM EDTA).

At 4° C., the 9 L culture was concentrated by tangential-flow ultrafiltration using a PELLICON II cassette system (Millipore, Billerica, Mass.) with a 10 kDa molecular weight cutoff membrane. Once the volume reached 600 mL, diafiltration was initiated against 6 L of 10 mM Tris, pH 8.0. The volume was held constant at 600 mL during the buffer exchange. After diafiltration, the volume was further concentrated to 500 mL. 125 g of solid ammonium sulfate (25 g per 100 mL) was added to achieve 40% saturation (1.89 M final concentration), and the sample was allowed to roll at 4° C. for approximately 16 hours. After 16 hours, the 500 mL sample was centrifuged at 5,000 rpm for 30 minutes. The supernatant was collected into a pre-sterilized polycarbonate bottle (NALGENE) for FPLC column purification.

D. Column Purification

The 500 mL sample was loaded onto a manually packed Fast Flow Phenyl Sepharose hydrophobic interaction chromatography column (100 mL column volume, c.v.) using a fully automated sample pump integrated onto an AKTA FPLC system with UNICORN software (PHARMACIA, Piscataway, N.J.). Sample was loaded at 2.5 mL/min with no significant back-pressure observed. The column was pre-equilibrated with buffer consisting of 1.5 M ammonium sulfate, 20 mM HEPES, and 1 mM EDTA (pH adjusted to 7.5). After the sample was loaded, a run cycle was executed using UNICORN pre-programmed with a 100 mL (1 c.v.) wash-out of unbound sample using the same buffer. The program then eluted the sample with an extended (9 c.v.) ammonium sulfate gradient from 1.5 M to 0 M at 2.0 mL/min. 0–70% gradient was achieved after 800 mL of buffer with the additional 100 mL used between 70–100% gradient. The 10 mL fractions were collected and analyzed by an 8–25% native polyacrylamide gel using the PHAST-GEL System (PHARMACIA).

The Phenyl Sepharose pool material was diafiltered by tangential-flow ultrafiltration using a small lab-scale TFF system (Millipore PELLICON XL) equipped with a BIOMAX 50 (50,000 kDa cutoff membrane, Millipore Corporation, Bedford, Mass.). Holding the volume constant, the buffer exchange was against approximately 700 mL to 1 L of 10 mM Tris, 1 mM EDTA, pH 8.0. The sample was concentrated further to 100 mL final volume.

The 100 mL dialyzed sample was loaded via a superloop onto a 50 mL Q-Sepharose Fast Flow column (PHARMACIA) pre-equilibrated with 10 mM Tris, 0.5 mM EDTA (pH 8.0), and then eluted with a 0–0.5 M NaCl extended gradient at 2.0 mL/min. Elongated gradient strategy was similar to the Phenyl Sepharose run with 0–70% being achieved through 8 c.v. and 70–100% through 1 c.v. Fractions (10 mL) were collected and analyzed again by an 8–25% native gel.

Finally, the pooled material was filtered again by tangential-flow ultrafiltration using the small lab-scale TFF system (Millipore PELLICON XL). A BIOMAX 10 (10,000 kDa cutoff membrane) was used for final dialysis. Holding the volume constant, the buffer exchange was against approximately 700 mL to 1 L of 10 mM Tris, pH 8.0, without EDTA. Small amount of sample is aliquoted for analyses and the rest of the purified protein is stored at −80° C.

Figure 17:
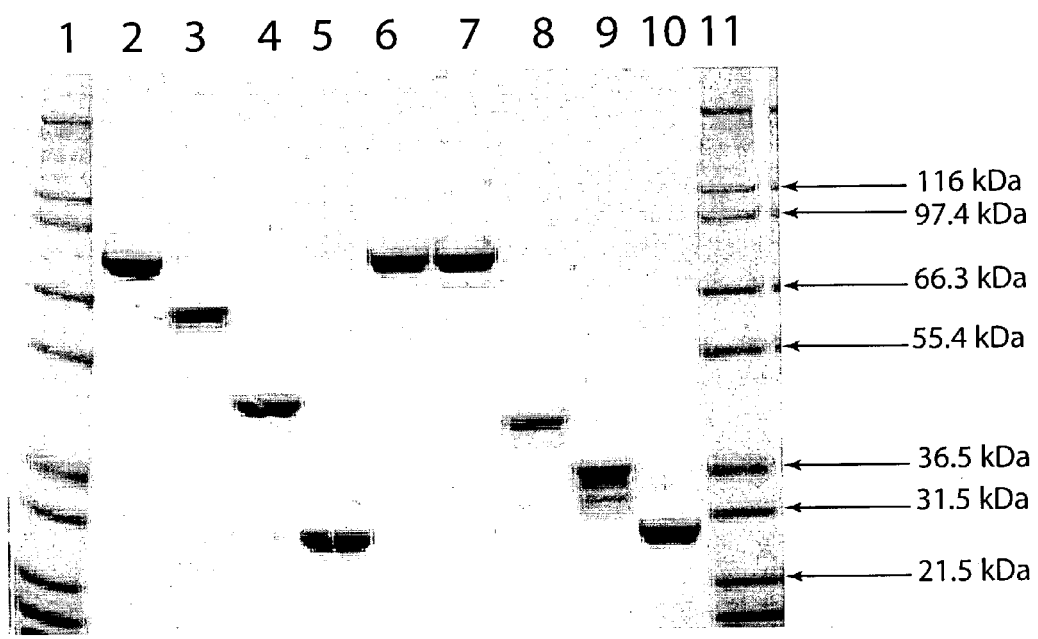
FIG. 17 illustrates a photograph of a SDS-PAGE analysis of purified proteins.

The purity of the purified proteins was greater than 95% by densitometer measurements and FIG. 17 shows SDS-PAGE of several of the purified proteins. Lanes 1 and 11, Mark 12 molecular weight standard (INVITROGEN, San Diego, Calif.):

Lane 2: PA
Lane 3: PA64
Lane 4: PA47
Lane 5: PA27
Lane 6: LF
Lane 7: LF-E687C*
Lane 8: LF50
Lane 9: LF40
Lane 10: LF30

*LF-E687C is a full-length inactive LF. The glutamic acid in the active site was mutated to cysteine by genetic manipulation. This molecule was created previously (33).

III. Compositions to Prepare Vaccine Formulations and Testing

A. Formulations

The new composition to prepare a vaccine candidate may be formulated using different types of adjuvants. Possible adjuvants for the vaccine formulation includes, but are not limited to, aluminum hydroxide, ImmunoStimulatory Sequences (ISS, CpG), and calcium phosphate.

For aluminum hydroxide, vaccine candidates were formulated to comprise either a combination of a variant of PA with a variant of LF or of a purified fusion protein combining the two antigens. Purified antigenic proteins were prepared singly or in combination such that each antigen was present at a concentration of 50 µg/ml in 10 mM Tris, pH 8.0. Proteins were then adsorbed to aluminum hydroxide (Alhydrogel). The adsorbed proteins were pelleted and resuspended in a preservative solution (9.36 g/L NaCl, 0.033 g/L phemerol, 218 µl/L formaldehyde) at a final concentration of 50 µg/ml per protein.

For ISS, protein samples were purified and resuspended separately in the preservative solution at a concentration of 200 µg/ml. To formulate a 100 ml vaccine candidate, either 25 ml of fusion protein preparation or 25 ml of each protein preparation is transferred to a sterile 200 ml bottle. Then, appropriate amount of ISS is added to the bottle and the volume is adjusted to 100 ml using the preservative solution. As a result, final protein concentration is 50 µg/ml per protein.

B. Animal Testing

1. Relative Potency Test

Some of the vaccine candidates formulated with aluminum hydroxide were tested for potency using BioPort's relative potency assay. Guinea pigs were immunized once with 0.5 ml of each vaccine candidates and challenged two weeks later with a virulent strain of *B. anthracis*. The relative potency was calculated after the number of survived animals in each group is compared to the result of a BioPort's reference vaccine. Table 1 below is the result of one the potency tests for few of the vaccine candidates.

TABLE 1

| Group | Amount of Antigen Per Dose (0.5 ml) | Relative Potency |
|---|---|---|
| 1 | 5 µg rPA | 0.49 |
| 2 | 25 µg rPA | 1.08 |
| 3 | 50 µg rPA | 1.12 |
| 4 | BioPort Reference Vaccine | NA |
| 5 | 5 µg rPA + 2 µg LF30 | 0.38 |
| 6 | 25 µg rPA + 10 µg LF30 | 0.9 |
| 7 | 50 µg rPA + 20 µg LF30 | 2.35 |

These test results indicate that the vaccine candidate group 7 containing 50 µg PA and 20 µg LF30 shows significantly better relative potency values than the reference vaccine and this higher value is statistically significant.

2. Immunogenicity Study in Mice

CD1 mice were used to determine immunogenicity of the vaccine candidates. In short, groups of mice were vaccinated one to three times with 0.5 ml of aluminum hydroxide-adsorbed vaccine candidates containing 25 µg of each protein component at days 0, 28, and 42. Bloods were drawn from mice two weeks after the final vaccination and the amount of anti-PA and anti-LF antibodies were measured. Table 2 explains statistical evaluation of total anti-PA IgG (µg/ml) and total anti-LF titer in mice after one or two immunizations with few of the vaccine candidates. Each 0.5 ml dose consists of 25 µg of each antigen adsorbed to 1.4 µg of aluminum hydroxide in a preservative solution. The vaccination was done by the intraperitoneal route in days 0 and 28 and the bleedings were done in days 28 and 42, respectively.

Figure 18:
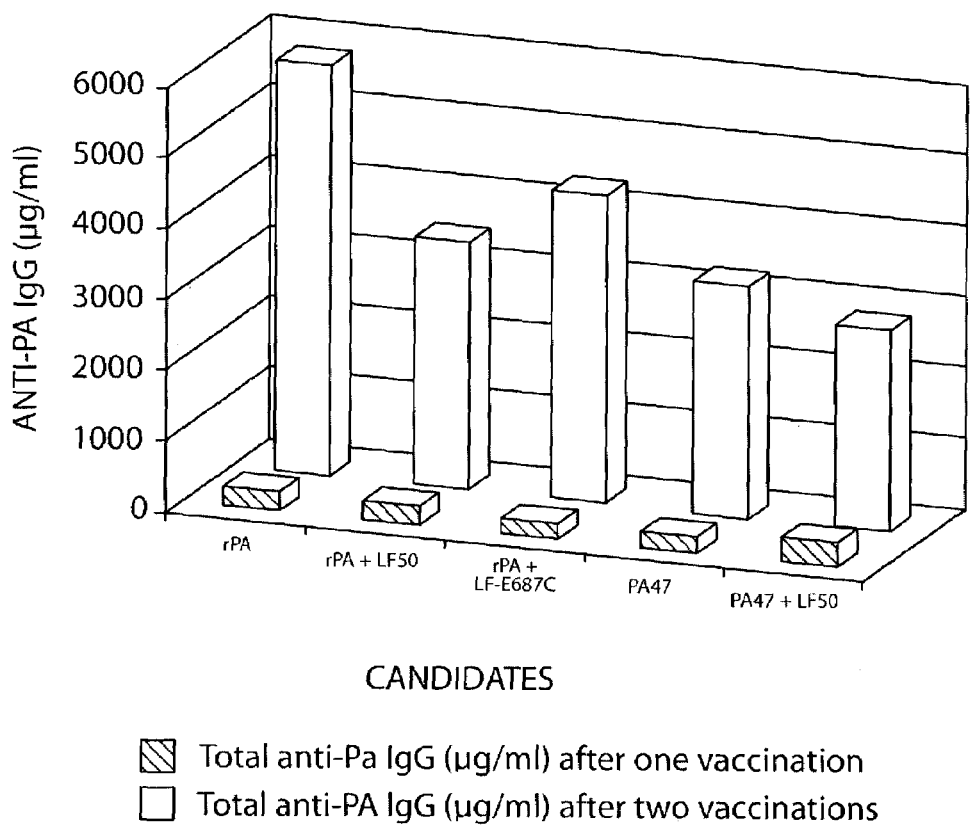
FIG. 18 illustrates the amount of total anti-PA IgG from CD1 mice vaccinated with either 1 or 2 doses of corresponding vaccine samples, wherein each 0.5 ml dose consists of 25 µg of each antigen adsorbed to 1.4 µg of aluminum hydroxide in a preservative solution (9.36 g/L NaCl, 0.033 g/L phenol, and 281 µl/L formaldehyde), and the vaccination was done by the intraperitoneal route in days 0 and 28 and the bleedings were done in days 28 and 42, respectively.
Figure 19:
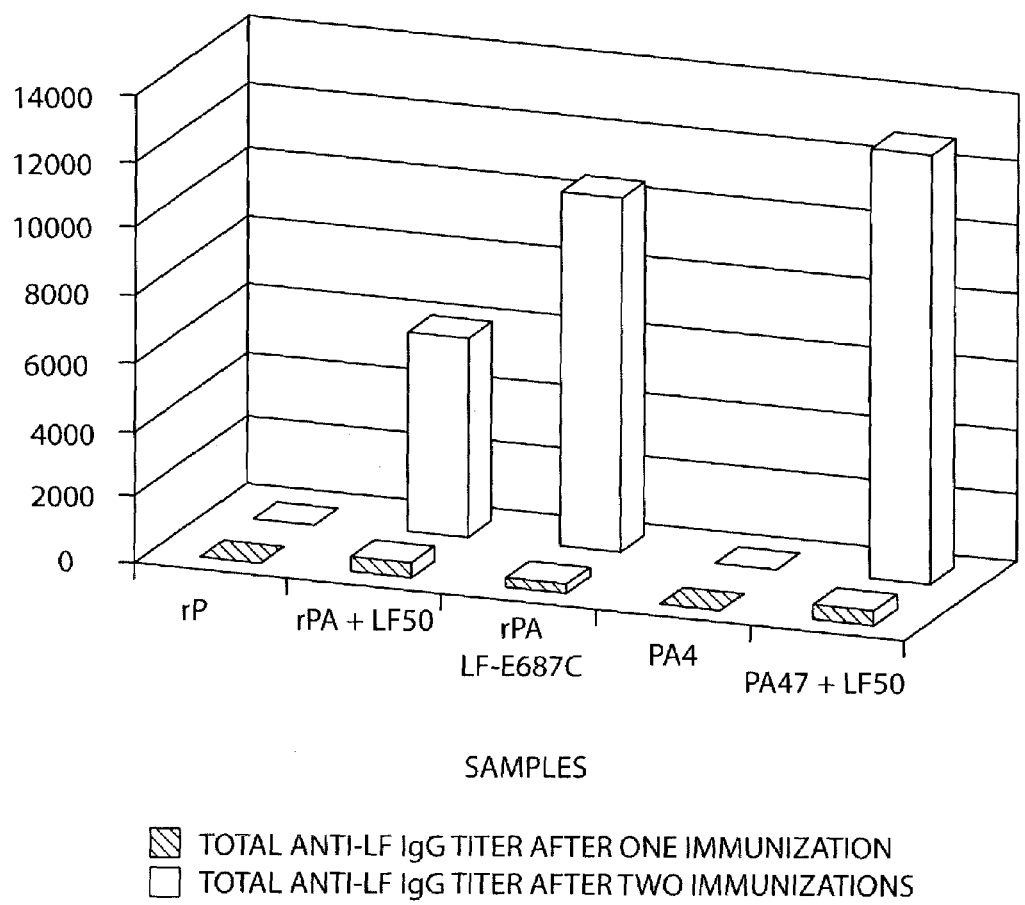
FIG. 19 illustrates the total anti-LF IgG titers from CD1 with either 1 or 2 doses of corresponding vaccine samples; each 0.5 ml dose consists of 25 µg of each antigen adsorbed to 1.4 µg of aluminum hydroxide in a preservative solution (9.36 g/L NaCl, 0.033 g/L phenol, and 281 µl/L formaldehyde), the vaccination was done by the intraperitoneal route in days 0 and 28 and the bleedings were done in days 28 and 42, respectively.

The results of the immunogenicity study indicate that both PA and LF can induce strong immune responses after two vaccinations (FIGS. 18 and 19). Additionally, the amounts of total anti-PA IgG were statistically not different when different sizes of PA variants were used indicating smaller PA deletion mutant can generate as strong immune responses as the wild-type PA protein (FIG. 18).

TABLE 2

| | | Anti-PA IgG (µg/ml) | | Anti-LF Titer | |
|---|---|---|---|---|---|
| Candidate | | 1 Dose | 2 Doses | 1 Dose | 2 Doses |
| rPA | N | 10 | 11 | NA | NA |
| | Log Mean | 2.439 | 3.762 | | |
| | SD | 0.162 | 0.312 | | |
| | GM | 275 | 5775 | | |
| | MIN | 146 | 1329 | | |
| | MAX | 437 | 14224 | | |
| rPA + LF$_{50}$ | N | 10 | 11 | 10 | 11 |
| | Log Mean | 2.452 | 3.539 | 3.662 | 4.779 |
| | SD | 0.160 | 0.195 | 0.277 | 0.342 |
| | GM | 283 | 3462 | 4595 | 60092 |
| | MIN | 176 | 1152 | 2000 | 8000 |
| | MAX | 482 | 5750 | 8000 | 128000 |
| rPA + LF-E687C | N | 10 | 11 | 10 | 11 |
| | Log Mean | 2.308 | 3.634 | 3.482 | 5.025 |
| | SD | 0.236 | 0.163 | 0.210 | 0.195 |
| | GM | 203 | 4308 | 3031 | 105952 |
| | MIN | 74 | 2893 | 2000 | 64000 |
| | MAX | 369 | 9264 | 8000 | 256000 |
| rPA47 | N | 11 | 11 | NA | NA |
| | Log Mean | 2.370 | 3.515 | | |
| | SD | 0.180 | 0.130 | | |
| | GM | 235 | 3272 | | |
| | MIN | 153 | 2107 | | |
| | MAX | 613 | 6029 | | |
| rPA47 + LF$_{50}$ | N | 9 | 11 | 9 | 11 |
| | Log Mean | 2.492 | 3.449 | 3.636 | 5.107 |
| | SD | 0.187 | 0.244 | 0.317 | 0.233 |
| | GM | 310 | 2810 | 4320 | 128000 |
| | MIN | 158 | 633 | 2000 | 64000 |
| | MAX | 682 | 4770 | 16000 | 256000 |

Similarly, the titers of total anti-LF IgG were statistically not different when different sizes of LF variants were used, indicating smaller LF deletion mutant can generate as strong immune responses as the wild-type LF protein (FIG. 19).

These results support the idea that two antigens derived from PA and LF can be used together to induce stronger immune responses than either PA or LF alone, possibly resulting in a better and faster protection against anthrax infection.

The present invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and examples is hereby incorporated herein by reference.

SEQUENCE LISTING

<160> NUMBER OF SEQ ID NOS: 34

<210> SEQ ID NO 1
<211> LENGTH: 6694
<212> TYPE: DNA
<213> ORGANISM: Artificial
<220> FEATURE:
<221> NAME/KEY:
<222> LOCATION:
<223> OTHER INFORMATION: Artificial DNA sequence to be used as one of the two backbones of the E. coli-Bacillus anthracis shuttle vectors. Designated as pBP I.

<400> SEQUENCE: 1

```
catatgggat cccgggtaag aattcggctg ctaacaaagc ccgaaaggaa gctgagttgg     60
ctgctgccac cgctgagcaa taactagcat aaccccttgg ggcctctaaa cgggtcttga    120
ggggtttttt gctgaaagga ggaactatat ccggatcgag atcaattctg gcgtaatagc    180
gaagaggccc gcaccgatcg cccttcccaa cagttgcgca gcctgaatgg cgaatgggac    240
gcgccctgta gcggcgcatt aagcgcggcg ggtgtggtgg ttacgcgcag cgtgaccgct    300
acacttgcca gcgccctagc gcccgctcct ttcgctttct tcccttcctt tctcgccacg    360
ttcgccggct ttccccgtca agctctaaat cgggggctcc ctttagggtt ccgatttagt    420
gctttacggc acctcgaccc caaaaaactt gattagggtg atggttcacg tagtgggcca    480
tcgccctgat agacggtttt tcgccctttg acgttggagt ccacgttctt taatagtgga    540
ctcttgttcc aaactggaac aacactcaac cctatctcgg tctattcttt tgatttataa    600
gggattttgc cgatttcggc ctattggtta aaaaatgagc tgatttaaca aaaatttaac    660
gcgaatttta acaaaatatt aacgcttaca atttaggtgg cacttttcgg ggaaatgtgc    720
gcggaacccc tatttgttta tttttctaaa tacattcaaa tatgtatccg ctcatgagac    780
aataaccctg ataaatgctt caataatatt gaaaaaggaa gagtatgagt attcaacatt    840
tccgtgtcgc ccttattccc ttttttgcgg cattttgcct tcctgttttt gctcacccag    900
aaacgctggt gaaagtaaaa gatgctgaag atcagttggg tgcacgagtg ggttacatcg    960
aactggatct caacagcggt aagatccttg agagttttcg ccccgaagaa cgttttccaa   1020
tgatgagcac ttttaaagtt ctgctatgtg gcgcggtatt atcccgtatt gacgccgggc   1080
aagagcaact cggtcgccgc atacactatt ctcagaatga cttggttgag tactcaccag   1140
tcacagaaaa gcatcttacg gatggcatga cagtaagaga attatgcagt gctgccataa   1200
ccatgagtga taacactgcg gccaacttac ttctgacaac gatcggagga ccgaaggagc   1260
taaccgcttt tttgcacaac atgggggatc atgtaactcg ccttgatcgt tgggaaccgg   1320
agctgaatga agccatacca aacgacgagc gtgacaccac gatgcctgta gcaatggcaa   1380
caacgttgcg caaactatta actggcgaac tacttactct agcttcccgg caacaattaa   1440
tagactggat ggaggcggat aaagttgcag gaccacttct gcgctcggcc cttccggctg   1500
gctggtttat tgctgataaa tctggagccg gtgagcgtgg gtctcgcggt atcattgcag   1560
cactggggcc agatggtaag ccctcccgta tcgtagttat ctacacgacg gggagtcagg   1620
caactatgga tgaacgaaat agacagatcg ctgagatagg tgcctcactg attaagcatt   1680
ggtaactgtc agaccaagtt tactcatata tactttagat tgatttaaaa cttcattttt   1740
aatttaaaag gatctaggtg aagatccttt ttgataatct catgaccaaa atcccttaac   1800
gtgagttttc gttccactga gcgtcagacc ccgtagaaaa gatcaaagga tcttcttgag   1860
```

```
atccttttt   tctgcgcgta   atctgctgct   tgcaaacaaa   aaaaccaccg   ctaccagcgg   1920
tggtttgttt   gccggatcaa   gagctaccaa   ctcttttcc    gaaggtaact   ggcttcagca   1980
gagcgcagat   accaaatact   gttcttctag   tgtagccgta   gttaggccac   cacttcaaga   2040
actctgtagc   accgcctaca   tacctcgctc   tgctaatcct   gttaccagtg   gctgctgcca   2100
gtggcgataa   gtcgtgtctt   accgggttgg   actcaagacg   atagttaccg   gataaggcgc   2160
agcggtcggg   ctgaacgggg   ggttcgtgca   cacagcccag   cttggagcga   acgacctaca   2220
ccgaactgag   atacctacag   cgtgagctat   gagaaagcgc   cacgcttccc   gaagggagaa   2280
aggcggacag   gtatccggta   agcggcaggg   tcggaacagg   agagcgcacg   agggagcttc   2340
caggggggaaa  cgcctggtat   ctttatagtc   ctgtcgggtt   tcgccacctc   tgacttgagc   2400
gtcgatttt   gtgatgctcg   tcagggggc    ggagcctatg   gaaaaacgcc   agcaacgcgg   2460
ccttttacg   gttcctggcc   ttttgctggc   cttttgctca   catgttcttt   cctgcgttat   2520
ccctgattc   tgtggataac   cgtattaccg   cctttgagtg   agctgatacc   gctcgccgca   2580
gccgaacgac   cgagcgcagc   gagtcagtga   gcgaggaagc   ggaagagcgc   ctgatgcggt   2640
attttctcct   tacgcatctg   tgcggtattt   cacaccgcaa   tggtgcactc   tcagtacaat   2700
ctgctctgat   gccgcatagt   taagccagta   tacactccgc   tatcgctacg   tgactgcaag   2760
gagatggcgc   ccaacagtcc   cccggccacg   gggcctgcca   ccatacccac   gccgaaacaa   2820
gcgctcatga   gcccgaagtg   gcgagcccga   tcttccccat   cggtgatgtc   ggcgatatag   2880
gcgccagcaa   ccgcacctgt   ggcgccggtg   atgccggcca   cgatgcgtcc   ggcgtagagg   2940
atcgagatcc   aggagaacaa   aaacgatttt   tgaggaaag    ttataaatta   ttttccgaac   3000
gatatggcaa   gcaaatatt    gcttatgcaa   cagttcataa   tgatgagcaa   acccctcaca   3060
tgcatttagg   tgttgtgcct   atgcgtgatg   gaaaactgca   aggaaaaaat   gtgtttaatc   3120
gtcaagaact   gttatggcta   caagataaat   tccccgagca   catgaaaaaa   cagggttttg   3180
agttgaagcg   tggtgaacgt   ggctctgacc   gtaaacatat   tgagacagct   aaatttaaaa   3240
aacaaacttt   ggaaaagag   attgattttc    tagaaaaaaa   tttagcagtt   aaaaagatg   3300
aatggactgc   ttatagcgat   aaagttaaat   cagatttaga   agtaccagcg   aaacgacaca   3360
tgaaaagtgt   tgaagtgcca   acgggtgaaa   agtccatgtt   tggtttggga   aaagaaataa   3420
tgaaaacaga   aagaaaccaa   accaaaaatg   ttgttatatc   ggagcgtgat   tataaaaact   3480
tagtgactgc   tgcgagagat   aacgataggt   aaaacagca    tgttagaaat   ctcatgagta   3540
ctgatatggc   gagagaatat   aaaaaattaa   gtaaagaaca   tgggcaagtt   aaagaaaaat   3600
atagtggtct   tgtagagcga   tttaatgaaa   atgtaaatga   ttataatgag   ttgcttgaag   3660
aaaacaagtc   tttaaagtct   aaaataagcg   atttaaagcg   tgatgtgagt   ttaatctatg   3720
aaagcactaa   ggaattcctt   aaggaacgta   cagacggctt   aaaagccttt   aaaaacgttt   3780
ttaagggggtt  tgtagacaag   gtaaaggata   aacagcaca    attccaagaa   aaacacgatt   3840
tagaacctaa   aaagaacgaa   tttgaactaa   ctcataaccg   agaggtaaaa   aaagaacgaa   3900
gtcgagatca   gggaatgagt   ttataaaata   aaaaagcac    ctgaaaaggt   gtctttttt   3960
gatggttttg   aacttgttct   ttcttatctt   gatacatata   gaataacgt    cattttatt   4020
ttagttgctg   aaaggtgcgt   tgaagtgttg   gtatgtatgt   gttttaaagt   attgaaaacc   4080
cttaaaattg   gttgcacaga   aaaaccccat   ctgttaaagt   tataagtgac   taaacaaata   4140
actaaataga   tgggggtttc   ttttaatatt   atgtgtccta   atagtagcat   ttattcagat   4200
```

| | |
|---|---|
| gaaaaatcaa gggttttagt ggacaagaca aaaagtggaa aagtgagacc atggagagaa | 4260 |
| aagaaaatcg ctaatgttga ttactttgaa cttctgcata ttcttgaatt taaaaaggct | 4320 |
| gaaagagtaa aagattgtgc tgaaatatta gagtataaac aaaatcgtga acaggcgaa | 4380 |
| agaaagttgt atcgagtgtg gttttgtaaa tccaggcttt gtccaatgtg caactggagg | 4440 |
| agagcaatga acatggcat tcagtcacaa aaggttgttg ctgaagttat taaacaaaag | 4500 |
| ccaacagttc gttggttgtt ctcacatta acagttaaaa atgtttatga tggcgaagaa | 4560 |
| ttaaataaga gtttgtcaga tatggctcaa ggatttcgcc gaatgatgca atataaaaaa | 4620 |
| attaataaaa atcttgttgg ttttatgcgt gcaacgaag tgacaataaa taataaagat | 4680 |
| aattcttata atcagcacat gcatgtattg gtatgtgtgg aaccaactta ttttaagaat | 4740 |
| acagaaaact acgtgaatca aaacaatgg attcaatttt ggaaaaaggc aatgaaatta | 4800 |
| gactatgatc caaatgtaaa agttcaaatg attcgaccga aaataaata taaatcggat | 4860 |
| atacaatcgg caattgacga aactgcaaaa tatcctgtaa aggatacgga ttttatgacc | 4920 |
| gatgatgaag aaaagaattt gaaacgtttg tctgatttgg aggaaggttt acaccgtaaa | 4980 |
| aggttaatct cctatggtgg tttgttaaaa gaaatacata aaaaattaaa ccttgatgac | 5040 |
| acagaagaag gcgatttgat tcatacagat gatgacgaaa aagccgatga agatggattt | 5100 |
| tctattattg caatgtggaa ttgggaacgg aaaaattatt ttattaaaga gtagttcaac | 5160 |
| aaacgggcca gtttgttgaa gattagatgc tataattgtt attaaaagga ttgaaggatg | 5220 |
| cttaggaaga cgagttatta atagctgaat aagaacggtg ctctccaaat attcttattt | 5280 |
| agaaaagcaa atctaaaatt atctgaaaag ggaatgagaa tagtgaatgg accaataata | 5340 |
| atgactagaa aagaaagaat gaagattgtt catgaaatta aggaacgaat attggataaa | 5400 |
| tatggggatg atgttaaggc tattggtgtt tatggctctc ttggtcgtca gactgatggg | 5460 |
| ccctattcgg atattgagat gatgtgtgtc atgtcaacag aggaagcaga gttcagccat | 5520 |
| gaatggacaa ccggtgagtg aaggtggaa gtgaattttg atagcgaaga gattctacta | 5580 |
| gattatgcat ctcaggtgga atcagattgg ccgcttacac atggtcaatt tttctctatt | 5640 |
| ttgccgattt atgattcagg tggatactta gagaaagtgt atcaaactgc taaatcggta | 5700 |
| gaagcccaaa cgttccacga tgcgatttgt gcccttatcg tagaagagct gttttgaatat | 5760 |
| gcaggcaaat ggcgtaatat tcgtgtgcaa ggaccgacaa catttctacc atccttgact | 5820 |
| gtacaggtag caatggcagg tgccatgttg attggtctgc atcatcgcat ctgttatacg | 5880 |
| acgagcgctt cggtcttaac tgaagcagtt aagcaatcag atcttccttc aggttatgac | 5940 |
| catctgtgcc agttcgtaat gtctggtcaa ctttccgact ctgagaaact tctggaatcg | 6000 |
| ctagagaatt tctggaatgg gattcaggag tggacagaac gacacggata tatagtggat | 6060 |
| gtgtcaaaac gcataccatt ttgaacgatg acctctaata attgttaatc atgttggtta | 6120 |
| cgtatttatt aacttctcct agtattagta attatcatg ctgtcatggc gcattaacgg | 6180 |
| aataaagggt gtgcttaaat cgggccattt tgcgtaataa gaaaaaggat taattatgag | 6240 |
| cgaattgaat taataataag gtaatagatt tacattagaa aatgaaaggg gattttatgc | 6300 |
| gtgagaatgt tacagtctat cccggcattg ccagtcgggg atattaaaaa gagtataggt | 6360 |
| ttttattgcg ataaactagg tttcactttg gttcaccatg aagatggatt cgcagttcta | 6420 |
| atgtgtaatg aggttcggat tcatctatta aacatataaa ttcttttta tgttatatat | 6480 |
| ttataaagt tctgttttaaa aagccaaaaa taaataatta tctcttttta tttatattat | 6540 |
| attgaaacta agtttattta atttcaatat aatataaatt taatttata caaaaaggag | 6600 |

```
aacgtatatg aaaaaacgaa aagtgttaat accattaatg gcattgtcta cgatattagt   6660
ttcaagcaca ggtaatttag aggtgattca ggca                               6694

<210> SEQ ID NO 2
<211> LENGTH: 5865
<212> TYPE: DNA
<213> ORGANISM: Artificial
<220> FEATURE:
<221> NAME/KEY:
<222> LOCATION:
<223> OTHER INFORMATION: Artificial DNA sequence to be used as one of
      the two backbones of the
      E. coli-Bacillus anthracis shuttle vectors.  Designated as pBP II.

<400> SEQUENCE: 2
catatgggat ccggctgcta acaaagcccg aaaggaagct gagttggctg ctgccaccgc     60
tgagcaataa ctagcataac cccttggggc ctctaaacgg gtcttgaggg gttttttgct   120
gaaaggagga actatatccg gatatcccgc aagaggcccg gcagtaccgg cataaccaag   180
cctatgccta cagcatccag ggtgacggtg ccgaggatga cgatgagcgc attgttagat   240
ttcatacacg gtgcctgact cgttagcaa tttaactgtg ataaactacc gcattaaagc    300
ttatcgatga taagctgtca acatgagaa ttcttgaaga cgaaagggcc tcgtgatacg    360
cctattttta taggttaatg tcatgataat aatggtttct tagacgtcag gtggcacttt   420
tcggggaaat gtgcgcggaa cccctatttg tttatttttc taaatacatt caaatatgta   480
tccgctcatg agacaataac cctgataaat gcttcaataa tattgaaaaa ggaagagtat   540
gagtattcaa catttccgtg tcgcccttat tccctttttt gcggcatttt gccttcctgt   600
ttttgctcac ccagaaacgc tggtgaaagt aaaagatgct gaagatcagt tgggtgcacg   660
agtgggttac atcgaactgg atctcaacag cggtaagatc cttgagagtt ttcgccccga   720
agaacgtttt ccaatgatga gcactttttaa agttctgcta tgtggcgcgg tattatcccg   780
tgttgacgcc gggcaagagc aactcggtcg ccgcatacac tattctcaga atgacttggt   840
tgagtactca ccagtcacag aaaagcatct tacggatggc atgacagtaa gagaattatg   900
cagtgctgcc ataaccatga gtgataacac tgcggccaac ttacttctga caacgatcgg   960
aggaccgaag gagctaaccg cttttttgca acatggggg atcatgtaa ctcgccttga   1020 tcgttgggaa ccggagctga atgaagccat accaaacgac gagcgtgaca ccacgatgcc   1080
tgcagcaatg gcaacaacgt tgcgcaaact attaactggc gaactactta ctctagcttc   1140
ccggcaacaa ttaatagact ggatggaggc ggataaagtt gcaggaccac ttctgcgctc   1200
ggcccttccg gctggctggt ttattgctga taaatctgga gccggtgagc gtgggtctcg   1260
cggtatcatt gcagcactgg ggccagatgg taagccctcc cgtatcgtag ttatctacac   1320
gacggggagt caggcaacta tggatgaacg aaatagacag atcgctgaga taggtgcctc   1380
actgattaag cattggtaac tgtcagacca gtttactca tatatacttt agattgattt   1440
aaaacttcat ttttaattta aaaggatcta ggtgaagatc cttttttgata atctcatgac   1500 caaaatccct taacgtgagt tttcgttcca ctgagcgtca gaccccgtag aaaagatcaa   1560
aggatcttct tgagatcctt ttttttctgcg cgtaatctgc tgcttgcaaa caaaaaaacc   1620
accgctacca gcggtggttt gtttgccgga tcaagagcta ccaactcttt ttccgaaggt   1680
aactggcttc agcagagcgc agataccaaa tactgtcctt ctagtgtagc cgtagttagg   1740
ccaccacttc aagaactctg tagcaccgcc tacatacctc gctctgctaa tcctgttacc   1800
```

```
agtggctgct gccagtggcg ataagtcgtg tcttaccggg ttggactcaa gacgatagtt    1860
accggataag gcgcagcggt cgggctgaac gggggggttcg tgcacacagc ccagcttgga   1920
gcgaacgacc tacaccgaac tgagatacct acagcgtgag ctatgagaaa gcgccacgct    1980
tcccgaaggg agaaaggcgg acaggtatcc ggtaagcggc agggtcggaa caggagagcg    2040
cacgagggag cttccagggg gaaacgcctg gtatctttat agtcctgtcg ggtttcgcca    2100
cctctgactt gagcgtcgat ttttgtgatg ctcgtcaggg gggcggagcc tatgaaaaaa    2160
cgccagcaac gcggcctttt tacggttcct ggccttttgc tggccttttg ctcacatgtt    2220
ctttcctgcg ttatccctg attctgtgga taaccgtatt accgcctttg agtgagctga     2280
taccgctcgc cgcagccgaa cgaccgagcg cagcgagtca gtgagcgagg aagcggaaga    2340
gcgcctgatg cggtattttc tccttacgca tctgtgcggt atttcacacc gcaatggtgc    2400
actctcagta caatctgctc tgatgccgca tagttaagcc agtaaaaaaa atttagcagt    2460
taaaaaagat gaatggactg cttatagcga taaagttaaa tcagatttag aagtaccagc    2520
gaaacgacac atgaaaagtg ttgaagtgcc aacgggtgaa aagtccatgt ttggtttggg    2580
aaaagaaata atgaaaacag aaaagaaacc aaccaaaaat gttgttatat cggagcgtga    2640
ttataaaaac ttagtgactg ctgcgagaga taacgatagg ttaaaacagc atgttagaaa    2700
tctcatgagt actgatatgg cgagagaata taaaaaatta agtaaagaac atgggcaagt    2760
taaagaaaaa tatagtggtc ttgtagagcg atttaatgaa aatgtaaatg attataatga    2820
gttgcttgaa gaaacaagt ctttaaagtc taaaataagc gatttaaagc gtgatgtgag     2880
tttaatctat gaaagcacta aggaattcct taaggaacgt acagacggct taaaagcctt    2940
taaaaacgtt tttaagggt ttgtagacaa ggtaaaggat aaaacagcac aattccaaga     3000
aaaacacgat ttagaaccta aaaagaacga atttgaacta actcataacc gagaggtaaa    3060
aaaagaacga agtcgagatc agggaatgag tttataaaat aaaaaaagca cctgaaaagg    3120
tgtcttttt tgatggtttt gaacttgttc tttcttatct tgatacatat agaaataacg     3180
tcatttttat tttagttgct gaaaggtgcg ttgaagtgtt ggtatgtatg tgttttaaag    3240
tattgaaaac ccttaaaatt ggttgcacag aaaaacccca tctgttaaag ttataagtga    3300
ctaaacaaat aactaaatag atgggggttt cttttaatat tatgtgtcct aatagtagca    3360
tttattcaga tgaaaaatca agggttttag tggacaagac aaaaagtgga aaagtgagac    3420
catggagaga aaagaaaatc gctaatgttg attactttga acttctgcat attcttgaat    3480
ttaaaaaggc tgaaagagta aaagattgtg ctgaaatatt agagtataaa caaaatcgtg    3540
aaacaggcga agaaagttg tatcgagtgt ggttttgtaa atccaggctt tgtccaatgt     3600
gcaactggag gagagcaatg aaacatggca ttcagtcaca aaaggttgtt gctgaagtta    3660
ttaaacaaaa gccaacagtt cgttggttgt ttctcacatt aacagttaaa aatgtttatg    3720
atggcgaaga attaaataag agtttgtcag atatggctca aggatttcgc cgaatgatgc    3780
aatataaaaa aattaataaa aatcttgttg gttttatgcg tgcaacggaa gtgacaataa    3840
ataataaaga taattcttat aatcagcaca tgcatgtatt ggtatgtgtg gaaccaactt    3900
attttaagaa tacagaaaac tacgtgaatc aaaaacaatg gattcaattt tggaaaaagg    3960
caatgaaaatt agactatgat ccaaatgtaa aagttcaaat gattcgaccg aaaaataaat   4020
ataaatcgga tatacaatcg gcaattgacg aaactgcaaa atatcctgta aaggatacgg    4080
attttatgac cgatgatgaa gaaagaatt tgaaacgttt gtctgatttg gaggaaggtt     4140
tacaccgtaa aaggttaatc tcctatggtg gtttgttaaa agaaatacat aaaaaattaa    4200
```

```
accttgatga cacagaagaa ggcgatttga ttcatacaga tgatgacgaa aaagccgatg    4260
aagatggatt ttctattatt gcaatgtgga attgggaacg gaaaaattat tttattaaag    4320
agtagttcaa caaacgggcc agtttgttga agattagatg ctataattgt tattaaaagg    4380
attgaaggat gcttaggaag acgagttatt aatagctgaa taagaacggt gctctccaaa    4440
tattcttatt tagaaaagca aatctaaaat tatctgaaaa gggaatgaga atagtgaatg    4500
gaccaataat aatgactaga gaagaaagaa tgaagattgt tcatgaaatt aaggaacgaa    4560
tattggataa atatggggat gatgttaagg ctattggtgt ttatggctct cttggtcgtc    4620
agactgatgg gccctattcg gatattgaga tgatgtgtgt catgtcaaca gaggaagcag    4680
agttcagcca tgaatggaca accggtgagt ggaaggtgga agtgaatttt gatagcgaag    4740
agattctact agattatgca tctcaggtgg aatcagattg gccgcttaca catggtcaat    4800 tttctctat tttgccgatt tatgattcag gtggatactt agagaaagtg tatcaaactg     4860
ctaaatcggt agaagcccaa acgttccacg atgcgatttg tgcccttatc gtagaagagc    4920
tgtttgaata tgcaggcaaa tggcgtaata ttcgtgtgca aggaccgaca acatttctac    4980
catccttgac tgtacaggta gcaatggcag gtgccatgtt gattggtctg catcatcgca    5040
tctgttatac gacgagcgct tcggtcttaa ctgaagcagt taagcaatca gatcttcctt    5100
caggttatga ccatctgtgc cagttcgtaa tgtctggtca actttccgac tctgagaaac    5160
ttctggaatc gctagagaat ttctggaatg ggattcagga gtggacagaa cgacacggat    5220
atatagtgga tgtgtcaaaa cgcataccat tttgaacgat gacctctaat aattgttaat    5280
catgttggtt acgtatttat taacttctcc tagtattagt aattatcatg gctgtcatgg    5340
cgcattaacg gaataaaggg tgtgcttaaa tcgggccatt ttgcgtaata agaaaaagga    5400
ttaattatga gcgaattgaa ttaataataa ggtaatagat ttacattaga aaatgaaagg    5460
ggattttatg cgtgagaatg ttacagtcta tcccggcatt gccagtcggg gatattaaaa    5520
agagtatagg ttttttattgc gataaactag gtttcacttt ggttcaccat gaagatggat    5580
tcgcagttct aatgtgtaat gaggttcgga ttcatctatt aaacatataa attctttttt    5640
atgttatata tttataaaag ttctgtttaa aaagccaaaa ataaataatt atctcttttt    5700
atttatatta tattgaaact aaagtttatt aatttcaata taatataaat ttaattttat    5760
acaaaaagga gaacgtatat gaaaaaacga aaagtgttaa taccattaat ggcattgtct    5820
acgatattag tttcaagcac aggtaattta gaggtgattc aggca                    5865
```

<210> SEQ ID NO 3
<211> LENGTH: 771
<212> TYPE: DNA
<213> ORGANISM: Bacillus anthracis
<220> FEATURE:
<221> NAME/KEY: CDS
<222> LOCATION:
<223> OTHER INFORMATION: DNA coding sequence from pBP101 corresponding to LF30 protein.

<400> SEQUENCE: 3

```
catatggcgg gcggtcatgg tgatgtaggt atgcacgtaa aagagaaaga gaaaataaaa     60
gatgagaata agagaaaaga tgaagaacga aataaaacac aggaagagca tttaaaggaa    120
atcatgaaac acattgtaaa aatagaagta aaggggagg aagctgttaa aaaagaggca    180
gcagaaaagc tacttgagaa agtaccatct gatgttttag agatgtataa agcaattgga    240
ggaaagatat atattgtgga tggtgatatt acaaaacata tatctttaga agcattatct    300
```

```
gaagataaga aaaaaataaa agacatttat gggaaagatg ccttattaca tgaacattat    360
gtatatgcaa agaaggata tgaacccgta cttgtaatcc aatcttcgga agattatgta     420
gaaaatactg aaaaggcact gaacgtttat tatgaaatag gtaagatatt atcaagggat    480 atttaagta aaattaatca accatatcag aaattttag atgtattaaa taccattaaa     540
aatgcatctg attcagatgg acaagatctt ttatttacta atcagcttaa ggaacatccc    600
acagactttt ctgtagaatt cttggaacaa aatagcaatg aggtacaaga agtatttgcg    660
aaagcttttg catattatat cgagccacag catcgtgatg ttttacagct ttatgcaccg    720
gaagctttta attcatgga taaatttaac gaacaagaaa taaatctata a              771
```

<210> SEQ ID NO 4
<211> LENGTH: 256
<212> TYPE: PRT
<213> ORGANISM: Bacillus anthracis
<220> FEATURE:
<221> NAME/KEY: MUTAGEN
<222> LOCATION:
<223> OTHER INFORMATION: Amino acid sequence corresponding to LF30 protein.

<400> SEQUENCE: 4

```
His Met Ala Gly Gly His Gly Asp Val Gly Met His Val Lys Glu Lys
  1               5                  10                  15

Glu Lys Asn Lys Asp Glu Asn Lys Arg Lys Asp Glu Glu Arg Asn Lys
             20                  25                  30

Thr Gln Glu Glu His Leu Lys Glu Ile Met Lys His Ile Val Lys Ile
         35                  40                  45

Glu Val Lys Gly Glu Glu Ala Val Lys Lys Glu Ala Ala Glu Lys Leu
     50                  55                  60

Leu Glu Lys Val Pro Ser Asp Val Leu Glu Met Tyr Lys Ala Ile Gly
 65                  70                  75                  80

Gly Lys Ile Tyr Ile Val Asp Gly Asp Ile Thr Lys His Ile Ser Leu
                 85                  90                  95

Glu Ala Leu Ser Glu Asp Lys Lys Lys Ile Lys Asp Ile Tyr Gly Lys
            100                 105                 110

Asp Ala Leu Leu His Glu His Tyr Val Tyr Ala Lys Glu Gly Tyr Glu
        115                 120                 125

Pro Val Leu Val Ile Gln Ser Ser Glu Asp Tyr Val Glu Asn Thr Glu
    130                 135                 140

Lys Ala Leu Asn Val Tyr Tyr Glu Ile Gly Lys Ile Leu Ser Arg Asp
145                 150                 155                 160

Ile Leu Ser Lys Ile Asn Gln Pro Tyr Gln Lys Phe Leu Asp Val Leu
                165                 170                 175

Asn Thr Ile Lys Asn Ala Ser Asp Ser Asp Gly Gln Asp Leu Leu Phe
            180                 185                 190

Thr Asn Gln Leu Lys Glu His Pro Thr Asp Phe Ser Val Glu Phe Leu
        195                 200                 205

Glu Gln Asn Ser Asn Glu Val Gln Glu Val Phe Ala Lys Ala Phe Ala
    210                 215                 220

Tyr Tyr Ile Glu Pro Gln His Arg Asp Val Leu Gln Leu Tyr Ala Pro
225                 230                 235                 240

Glu Ala Phe Asn Tyr Met Asp Lys Phe Asn Glu Gln Glu Ile Asn Leu
                245                 250                 255
```

-continued

```
<210> SEQ ID NO 5
<211> LENGTH: 2337
<212> TYPE: DNA
<213> ORGANISM: Bacillus anthracis
<220> FEATURE:
<221> NAME/KEY: CDS
<222> LOCATION:
<223> OTHER INFORMATION: DNA coding sequence for B. anthracis Lethal
      Factor (LF) with additional CATATG at its N terminus.

<400> SEQUENCE: 5
```

| | | | | | |
|---|---|---|---|---|---|
| catatggcgg | gcggtcatgg | tgatgtaggt | atgcacgtaa | aagagaaaga | gaaaaataaa | 60 |
| gatgagaata | agagaaaaga | tgaagaacga | ataaaacac | aggaagagca | tttaaaggaa | 120 |
| atcatgaaac | acattgtaaa | aatagaagta | aaaggggagg | aagctgttaa | aaaagaggca | 180 |
| gcagaaaagc | tacttgagaa | agtaccatct | gatgttttag | agatgtataa | agcaattgga | 240 |
| ggaaagatat | atattgtgga | tggtgatatt | acaaaacata | tatctttaga | agcattatct | 300 |
| gaagataaga | aaaaataaa | agacatttat | gggaaagatg | ccttattaca | tgaacattat | 360 |
| gtatatgcaa | agaaggata | tgaacccgta | cttgtaatcc | aatcttcgga | agattatgta | 420 |
| gaaaatactg | aaaaggcact | gaacgtttat | tatgaaaatg | gtaagatatt | atcaagggat | 480 |
| atttttaagta | aaattaatca | accatatcag | aaattttag | atgtattaaa | taccattaaa | 540 |
| aatgcatctg | attcagatgg | acaagatctt | ttatttacta | atcagcttaa | ggaacatccc | 600 |
| acagactttt | ctgtagaatt | cttggaacaa | aatagcaatg | aggtacaaga | agtatttgcg | 660 |
| aaagcttttg | catattatat | cgagccacag | catcgtgatg | ttttacagct | ttatgcaccg | 720 |
| gaagctttta | attacatgga | taaatttaac | gaacaagaaa | taaatctatc | cttggaagaa | 780 |
| cttaaagatc | aacggatgct | gtcaagatat | gaaaaatggg | aaaagataaa | acagcactat | 840 |
| caacactgga | gcgattcttt | atctgaagaa | ggaagaggac | ttttaaaaaa | gctgcagatt | 900 |
| cctattgagc | aaagaaaga | tgacataatt | cattctttat | ctcaagaaga | aaagagctt | 960 |
| ctaaaagaa | tacaaattga | tagtagtgat | tttttatcta | ctgaggaaaa | agagttttta | 1020 |
| aaaaagctac | aaattgatat | cgtgattct | ttatctgaag | aagaaaaaga | gcttttaaat | 1080 |
| agaatacagg | tggatagtag | taatcctta | tctgaaaaag | aaaaagagtt | tttaaaaaag | 1140 |
| ctgaaacttg | atattcaacc | atacgatatt | aatcaaaggt | tgcaagatac | aggagggtta | 1200 |
| attgatagtc | cgtcaattaa | tcttgatgta | agaaagcagt | ataaaaggga | tattcaaaat | 1260 |
| attgatgctt | tattacatca | atccattgga | agtaccttgt | acaataaaat | ttatttgtat | 1320 |
| gaaaatatga | atatcaataa | ccttacagca | accctaggtg | cggatttagt | tgattccact | 1380 |
| gataatacta | aaattaatag | aggtatttc | aatgaattca | aaaaaattt | caaatatagt | 1440 |
| atttctagta | actatatgat | tgttgatata | atgaaaggc | ctgcattaga | taatgagcgt | 1500 |
| ttgaaatgga | gaatccaatt | atcaccagat | actcgagcag | gatatttaga | aaatggaaag | 1560 |
| cttatattac | aagaaacat | cggtctgaa | ataaaggatg | tacaaataat | taagcaatcc | 1620 |
| gaaaaagaat | atataaggat | tgatgcgaaa | gtagtgccaa | agagtaaaat | agatacaaaa | 1680 |
| attcaagaag | cacagttaaa | tataaatcag | gaatggaata | agcattagg | gttaccaaaa | 1740 |
| tatacaaagc | ttattacatt | caacgtgcat | aatagatatg | catccaatat | tgtagaaagt | 1800 |
| gcttatttaa | tattgaatga | atggaaaaat | aatattcaaa | gtgatcttat | aaaaaaggta | 1860 |
| acaaattact | tagttgatgg | taatggaaga | tttgtttta | ccgatattac | tctccctaat | 1920 |
| atagctgaac | aatatacaca | tcaagatgag | atatatgagc | aagttcattc | aaaagggtta | 1980 |
| tatgttccag | aatcccgttc | tatattactc | catggacctt | caaaaggtgt | agaattaagg | 2040 |

-continued

```
aatgatagtg agggtttat acacgaattt ggacatgctg tggatgatta tgctggatat    2100
ctattagata agaaccaatc tgatttagtt acaaattcta aaaaattcat tgatatttt    2160 aaggaagaag ggagtaattt aacttcgtat gggagaacaa atgaagcgga atttttgca    2220 gaagcctta ggttaatgca ttctacggac catgctgaac gtttaaaagt tcaaaaaat    2280 gctccgaaaa ctttccaatt tattaacgat cagattaagt tcattattaa ctcataa     2337
```

<210> SEQ ID NO 6
<211> LENGTH: 778
<212> TYPE: PRT
<213> ORGANISM: Bacillus anthracis
<220> FEATURE:
<221> NAME/KEY: MUTAGEN
<222> LOCATION:
<223> OTHER INFORMATION: Amino acid sequence of B. anthracis Lethal
      Factor (LF) with additional His and Met at its N terminus.

<400> SEQUENCE: 6

```
His Met Ala Gly Gly His Gly Asp Val Gly Met His Val Lys Glu Lys
  1               5                  10                  15

Glu Lys Asn Lys Asp Glu Asn Lys Arg Lys Asp Glu Glu Arg Asn Lys
             20                  25                  30

Thr Gln Glu Glu His Leu Lys Glu Ile Met Lys His Ile Val Lys Ile
         35                  40                  45

Glu Val Lys Gly Glu Glu Ala Val Lys Lys Glu Ala Ala Glu Lys Leu
     50                  55                  60

Leu Glu Lys Val Pro Ser Asp Val Leu Glu Met Tyr Lys Ala Ile Gly
 65                  70                  75                  80

Gly Lys Ile Tyr Ile Val Asp Gly Asp Ile Thr Lys His Ile Ser Leu
                 85                  90                  95

Glu Ala Leu Ser Glu Asp Lys Lys Lys Ile Lys Asp Ile Tyr Gly Lys
            100                 105                 110

Asp Ala Leu Leu His Glu His Tyr Val Tyr Ala Lys Glu Gly Tyr Glu
        115                 120                 125

Pro Val Leu Val Ile Gln Ser Ser Glu Asp Tyr Val Glu Asn Thr Glu
    130                 135                 140

Lys Ala Leu Asn Val Tyr Tyr Glu Ile Gly Lys Ile Leu Ser Arg Asp
145                 150                 155                 160

Ile Leu Ser Lys Ile Asn Gln Pro Tyr Gln Lys Phe Leu Asp Val Leu
                165                 170                 175

Asn Thr Ile Lys Asn Ala Ser Asp Ser Asp Gly Gln Asp Leu Leu Phe
            180                 185                 190

Thr Asn Gln Leu Lys Glu His Pro Thr Asp Phe Ser Val Glu Phe Leu
        195                 200                 205

Glu Gln Asn Ser Asn Glu Val Gln Glu Val Phe Ala Lys Ala Phe Ala
    210                 215                 220

Tyr Tyr Ile Glu Pro Gln His Arg Asp Val Leu Gln Leu Tyr Ala Pro
225                 230                 235                 240

Glu Ala Phe Asn Tyr Met Asp Lys Phe Asn Glu Gln Glu Ile Asn Leu
                245                 250                 255

Ser Leu Glu Glu Leu Lys Asp Gln Arg Met Leu Ser Arg Tyr Glu Lys
            260                 265                 270

Trp Glu Lys Ile Lys Gln His Tyr Gln His Trp Ser Asp Ser Leu Ser
        275                 280                 285

Glu Glu Gly Arg Gly Leu Leu Lys Lys Leu Gln Ile Pro Ile Glu Pro
```

-continued

```
                290                 295                 300
Lys Lys Asp Asp Ile Ile His Ser Leu Ser Gln Glu Lys Glu Leu
305                 310                 315                 320

Leu Lys Arg Ile Gln Ile Asp Ser Ser Asp Phe Leu Ser Thr Glu Glu
                325                 330                 335

Lys Glu Phe Leu Lys Lys Leu Gln Ile Asp Ile Arg Asp Ser Leu Ser
                340                 345                 350

Glu Glu Glu Lys Glu Leu Leu Asn Arg Ile Gln Val Asp Ser Ser Asn
                355                 360                 365

Pro Leu Ser Glu Lys Glu Lys Glu Phe Leu Lys Leu Lys Leu Asp
370                 375                 380

Ile Gln Pro Tyr Asp Ile Asn Gln Arg Leu Gln Asp Thr Gly Gly Leu
385                 390                 395                 400

Ile Asp Ser Pro Ser Ile Asn Leu Asp Val Arg Lys Gln Tyr Lys Arg
                405                 410                 415

Asp Ile Gln Asn Ile Asp Ala Leu Leu His Gln Ser Ile Gly Ser Thr
                420                 425                 430

Leu Tyr Asn Lys Ile Tyr Leu Tyr Glu Asn Met Asn Ile Asn Asn Leu
                435                 440                 445

Thr Ala Thr Leu Gly Ala Asp Leu Val Asp Ser Thr Asp Asn Thr Lys
450                 455                 460

Ile Asn Arg Gly Ile Phe Asn Glu Phe Lys Lys Asn Phe Lys Tyr Ser
465                 470                 475                 480

Ile Ser Ser Asn Tyr Met Ile Val Asp Ile Asn Glu Arg Pro Ala Leu
                485                 490                 495

Asp Asn Glu Arg Leu Lys Trp Arg Ile Gln Leu Ser Pro Asp Thr Arg
                500                 505                 510

Ala Gly Tyr Leu Glu Asn Gly Lys Leu Ile Leu Gln Arg Asn Ile Gly
                515                 520                 525

Leu Glu Ile Lys Asp Val Gln Ile Ile Lys Gln Ser Glu Lys Glu Tyr
                530                 535                 540

Ile Arg Ile Asp Ala Lys Val Val Pro Lys Ser Lys Ile Asp Thr Lys
545                 550                 555                 560

Ile Gln Glu Ala Gln Leu Asn Ile Asn Gln Glu Trp Asn Lys Ala Leu
                565                 570                 575

Gly Leu Pro Lys Tyr Thr Lys Leu Ile Thr Phe Asn Val His Asn Arg
                580                 585                 590

Tyr Ala Ser Asn Ile Val Glu Ser Ala Tyr Leu Ile Leu Asn Glu Trp
                595                 600                 605

Lys Asn Asn Ile Gln Ser Asp Leu Ile Lys Lys Val Thr Asn Tyr Leu
                610                 615                 620

Val Asp Gly Asn Gly Arg Phe Val Phe Thr Asp Ile Thr Leu Pro Asn
625                 630                 635                 640

Ile Ala Glu Gln Tyr Thr His Gln Asp Glu Ile Tyr Glu Gln Val His
                645                 650                 655

Ser Lys Gly Leu Tyr Val Pro Glu Ser Arg Ser Ile Leu Leu His Gly
                660                 665                 670

Pro Ser Lys Gly Val Glu Leu Arg Asn Asp Ser Glu Gly Phe Ile His
                675                 680                 685

Glu Phe Gly His Ala Val Asp Asp Tyr Ala Gly Tyr Leu Leu Asp Lys
                690                 695                 700

Asn Gln Ser Asp Leu Val Thr Asn Ser Lys Lys Phe Ile Asp Ile Phe
705                 710                 715                 720
```

-continued

```
Lys Glu Glu Gly Ser Asn Leu Thr Ser Tyr Gly Arg Thr Asn Glu Ala
            725                 730                 735
Glu Phe Phe Ala Glu Ala Phe Arg Leu Met His Ser Thr Asp His Ala
        740                 745                 750
Glu Arg Leu Lys Val Gln Lys Asn Ala Pro Lys Thr Phe Gln Phe Ile
    755                 760                 765
Asn Asp Gln Ile Lys Phe Ile Ile Asn Ser
    770                 775
```

<210> SEQ ID NO 7
<211> LENGTH: 8198
<212> TYPE: DNA
<213> ORGANISM: Bacillus anthracis
<220> FEATURE:
<221> NAME/KEY:
<222> LOCATION:
<223> OTHER INFORMATION: Expression vector for B. anthracis Protective
      Antigen (PA). Entire sequence is shown since the vector sequence
      is different from the rest
      of the pBP vectors. The PA coding sequence is from 3735 to 5942.

<400> SEQUENCE: 7

```
tcgtcagggg ggcggagcct atggaaaaac gccagcaacg cggcctttttt acggttcctg      60
gccttttgct ggccttttgc tcacatgttc tttcctgcgt tatcccctga ttctgtggat     120
aaccgtatta ccgcctttga gtgagctgat accgctcgcc gcagccgaac gaccgagcgc     180
agcgagtcag tgagcgagga agcggaagag cgcctgatgc ggtattttct ccttacgcat     240
ctgtgcggta tttcacaccg caatggtgca ctctcagtac aatctgctct gatgccgcat     300
agttaagcca gtaaaaaaaa tttagcagtt aaaaagatg aatggactgc ttatagcgat     360
aaagttaaat cagatttaga agtaccagcg aaacgacaca tgaaagtgt tgaagtgcca     420
acgggtgaaa agtccatgtt tggtttggga aagaaataa tgaaaacaga aagaaacca     480
accaaaaatg ttgttatatc ggagcgtgat tataaaaact tagtgactgc tgcgagagat     540
aacgataggt taaacagca tgttagaaat ctcatgagta ctgatatggc gagagaatat     600
aaaaaattaa gtaaagaaca tgggcaagtt aaagaaaaat atagtggtct tgtagagcga     660
tttaatgaaa atgtaaatga ttataatgag ttgcttgaag aaaacaagtc tttaaagtct     720
aaaataagcg atttaaagcg tgatgtgagt ttaatctatg aaagcactaa ggaattcctt     780
aaggaacgta cagacggctt aaaagccttt aaaaacgttt ttaaggggtt tgtagacaag     840
gtaaaggata aacagcaca attccaagaa aaacacgatt tagaacctaa aagaacgaa     900
tttgaactaa ctcataaccg agaggtaaaa aagaacgaa gtcgagatca gggaatgagt     960
ttataaaata aaaaaagcac ctgaaaaggt gtcttttttt gatggttttg aacttgttct    1020
ttcttatctt gatacatata gaaataacgt catttttatt ttagttgctg aaaggtgcgt    1080
tgaagtgttg gtatgtatgt gttttaaagt attgaaaacc cttaaaattg gttgcacaga    1140
aaaaccccat ctgttaaagt tataagtgac taaacaaata actaaataga tgggggttc    1200
ttttaatatt atgtgtccta atagtagcat ttattcagat gaaaaatcaa gggttttagt    1260
ggacaagaca aaaagtggaa aagtgagacc atggagagaa aagaaaatcg ctaatgttga    1320
ttactttgaa cttctgcata ttcttgaatt taaaaggct gaaagagtaa agattgtgc    1380
tgaaatatta gagtataaac aaatcgtga acaggcgaa agaaagttgt atcgagtgtg    1440
gttttgtaaa tccaggcttt gtccaatgtg caactgagg agagcaatga acatgcat    1500
tcagtcacaa aaggttgttg ctgaagttat taaacaaaag ccaacagttc gttggttgtt    1560
```

-continued

```
tctcacatta acagttaaaa atgtttatga tggcgaagaa ttaaataaga gtttgtcaga   1620
tatggctcaa ggatttcgcc gaatgatgca atataaaaaa attaataaaa atcttgttgg   1680
ttttatgcgt gcaacggaag tgacaataaa taataaagat aattcttata atcagcacat   1740
gcatgtattg gtatgtgtgg aaccaactta ttttaagaat acagaaaact acgtgaatca   1800
aaaacaatgg attcaattt ggaaaaaggc aatgaaatta gactatgatc aaatgtaaa   1860 agttcaaatg attcgaccga aaaataaata taaatcggat atacaatcgg caattgacga   1920
aactgcaaaa tatcctgtaa aggatacgga ttttatgacc gatgatgaag aaaagaattt   1980
gaaacgtttg tctgatttgg aggaaggttt acaccgtaaa aggttaatct cctatggtgg   2040
tttgttaaaa gaaatacata aaaaattaaa ccttgatgac acagaagaag gcgatttgat   2100
tcatacagat gatgacgaaa aagccgatga agatggattt tctattattg caatgtggaa   2160
ttgggaacgg aaaaattatt ttattaaaga gtagttcaac aaacgggcca gtttgttgaa   2220
gattagatgc tataattgtt attaaaagga ttgaaggatg cttaggaaga cgagttatta   2280
atagctgaat aagaacggtg ctctccaaat attcttattt agaaaagcaa atctaaaatt   2340
atctgaaaag ggaatgagaa tagtgaatgg accaataata atgactagag aagaaagaat   2400
gaagattgtt catgaaatta aggaacgaat attggataaa tatggggatg atgttaaggc   2460
tattggtgtt tatggctctc ttggtcgtca gactgatggg ccctattcgg atattgagat   2520
gatgtgtgtc atgtcaacag aggaagcaga gttcagccat gaatggacaa ccggtgagtg   2580
gaaggtggaa gtgaattttg atagcgaaga gattctacta gattatgcat ctcaggtgga   2640
atcagattgg ccgcttacac atggtcaatt tttctctatt ttgccgattt atgattcagg   2700
tggatactta gagaaagtgt atcaaactgc taaatcggta gaagcccaaa cgttccacga   2760
tgcgatttgt gcccttatcg tagaagagct gtttgaatat gcaggcaaat ggcgtaatat   2820
tcgtgtgcaa ggaccgacaa catttctacc atccttgact gtacaggtag caatggcagg   2880
tgccatgttg attggtctgc atcatcgcat ctgttatacg acgagcgctt cggtcttaac   2940
tgaagcagtt aagcaatcag atcttccttc aggttatgac catctgtgcc agttcgtaat   3000
gtctggtcaa cttttccgact ctgagaaact tctggaatcg ctagagaatt tctggaatgg   3060
gattcaggag tggacagaac gacacggata tatagtggat gtgtcaaaac gcataccatt   3120
ttgaacgatg acctctaata attgttaatc atgttggtta cgtatttatt aacttctcct   3180
agtattagta attatcatgg ctgtcatggc gcattaacgg aataaagggt gtgcttaaat   3240
cgggccattt tgcgtaataa gaaaaaggat taattatgag cgaattgaat taataataag   3300
gtaatagatt tacattagaa aatgaaaggg gatttttatgc gtgagaatgt tacagtctat   3360
cccggcattg ccagtcgggg atattaaaaa gagtataggt ttttattgcg ataaactagg   3420
tttcactttg gttcaccatg aagatggatt cgcagttcta atgtgtaatg aggttcggat   3480
tcatctatta aacatataaa ttcttttttta tgttatatat ttataaaagt tctgtttaaa   3540
aagccaaaaa taaataatta tctcttttta tttatattat attgaaacta agtttatta   3600 atttcaatat aatataaatt taattttata caaaaaggag aacgtatatg aaaaaacgaa   3660
aagtgttaat accattaatg gcattgtcta cgatatagt ttcaagcaca ggtaatttag   3720
aggtgattca ggcagaagtt aaacaggaga accggttatt aaatgaatca gaatcaagtt   3780
cccaggggtt actaggatac tatttttagt atttgaattt tcaagcaccc atggtggtta   3840
cctcttctac tacaggggat ttatctattc ctagttctga gttagaaaat attccatcgg   3900
```

-continued

```
aaaaccaata ttttcaatct gctatttggt caggatttat caaagttaag aagagtgatg    3960
aatatacatt tgctacttcc gctgataatc atgtaacaat gtgggtagat gaccaagaag    4020
tgattaataa agcttctaat tctaacaaaa tcagattaga aaaggaaga ttatatcaaa     4080 taaaaattca atatcaacga gaaaatccta ctgaaaaagg attggatttc aagttgtact   4140
ggaccgattc tcaaaataaa aaagaagtga tttctagtga taacttacaa ttgccagaat   4200
taaaacaaaa atcttcgaac tcaagaaaaa agcgaagtac aagtgctgga cctacggttc   4260
cagaccgtga caatgatgga atccctgatt cattagaggt agaaggatat acggttgatg   4320
tcaaaaataa aagaactttt ctttcaccat ggatttctaa tattcatgaa agaaaggat    4380 taaccaaata taaatcatct cctgaaaaat ggagcacggc ttctgatccg tacagtgatt   4440
tcgaaaaggt tacaggacgg attgataaga atgtatcacc agaggcaaga cacccccttg   4500
tggcagctta tccgattgta catgtagata tggagaatat tattctctca aaaaatgagg   4560
atcaatccac acagaatact gatagtcaaa cgagaacaat aagtaaaaat acttctacaa   4620
gtaggacaca tactagtgaa gtacatggaa atgcagaagt gcatgcgtcg ttctttgata   4680
ttggtgggag tgtatctgca ggatttagta attcgaattc aagtacggtc gcaattgatc   4740
attcactatc tctagcaggg gaaagaactt gggctgaaac aatgggttta aataccgctg   4800
atacagcaag attaaatgcc aatattagat atgtaaatac tgggacggct ccaatctaca   4860
acgtgttacc aacgacttcg ttagtgttag gaaaaaatca aacactcgcg acaattaaag   4920
ctaaggaaaa ccaattaagt caaatacttg cacctaataa ttattatcct tctaaaaact   4980
tggcgccaat cgcattaaat gcacaagacg atttcagttc tactccaatt acaatgaatt   5040
acaatcaatt tcttgagtta gaaaaaacga acaattaag attagatacg gatcaagtat    5100
atgggaatat agcaacatac aattttgaaa atggaagagt gagggtggat acaggctcga   5160
actggagtga agtgttaccg caaattcaag aaacaactgc acgtatcatt tttaatggaa   5220
aagatttaaa tctggtagaa aggcggatag cggcggttaa tcctagtgat ccattagaaa   5280
cgactaaacc ggatatgaca ttaaaagaag cccttaaaat agcatttgga tttaacgaac   5340
cgaatggaaa cttacaatat caagggaaag acataaccga atttgatttt aatttcgatc   5400
aacaaacatc tcaaaatatc aagaatcagt tagcggaatt aaacgcaact aacatatata   5460
ctgtattaga taaaatcaaa ttaaatgcaa aaatgaatat tttaataaga gataaacgtt   5520
ttcattatga tagaaataac atagcagttg gggcggatga gtcagtagtt aaggaggctc   5580
atagagaagt aattaattcg tcaacagagg gattattgtt aaatattgat aaggatataa   5640 gaaaatatt atcaggttat attgtagaaa ttgaagatac tgaagggctt aaagaagtta   5700
taaatgacag atatgatatg ttgaatattt ctagtttacg gcaagatgga aaaacattta   5760
tagattttaa aaaatataat gataaattac cgttatatat aagtaatccc aattataagg   5820
taaatgtata tgctgttact aaagaaaaca ctattattaa tcctagtgag aatggggata   5880
ctagtaccaa cgggatcaag aaaattttaa tcttttctaa aaaaggctat gagataggat   5940 aagtaattc taggtgattt ttaaattatc taaaaaacag taaaattaaa acatactctt   6000
tttgtaagaa atacaaggag agtatgtttt aaacagtaat ctaaatcatc ataatccttt   6060
gagattgttt gtaggatccg gctgctaaca aagcccgaaa ggaagctgag ttggctgctg   6120
ccaccgctga gcaataacta gcataacccc ttggggcctc taaacgggtc ttgaggggtt   6180
ttttgctgaa aggaggaact atatccggat atcccgcaag aggcccggca gtaccggcat   6240
aaccaagcct atgcctacag catccagggt gacggtgccg aggatgacga tgagcgcatt   6300
```

```
gttagatttc atacacggtg cctgactgcg ttagcaattt aactgtgata aactaccgca    6360
ttaaagctta tcgatgataa gctgtcaaac atgagaattc ttgaagacga aagggcctcg    6420
tgatacgcct atttttatag gttaatgtca tgataataat ggtttcttag acgtcaggtg    6480
gcactttccg gggaaatgtg cgcggaaccc ctatttgttt attttctaa atacattcaa     6540 atatgtatcc gctcatgaga caataaccct gataaatgct tcaataatat tgaaaaagga    6600
agagtatgag tattcaacat ttccgtgtcg cccttattcc cttttttgcg gcattttgcc    6660
ttcctgtttt tgctcaccca gaaacgctgg tgaaagtaaa agatgctgaa gatcagttgg    6720
gtgcacgagt gggttacatc gaactggatc tcaacagcgg taagatcctt gagagttttc    6780
gccccgaaga acgttttcca atgatgagca cttttaaagt tctgctatgt ggcgcggtat    6840
tatcccgtgt tgacgccggg caagagcaac tcggtcgccg catacactat tctcagaatg    6900
acttggttga gtactcacca gtcacagaaa agcatcttac ggatggcatg acagtaagag    6960
aattatgcag tgctgccata accatgagtg ataacactgc ggccaactta cttctgacaa    7020
cgatcggagg accgaaggag ctaaccgctt ttttgcacaa catgggggat catgtaactc    7080
gccttgatcg ttgggaaccg gagctgaatg aagccatacc aaacgacgag cgtgacacca    7140
cgatgcctgc agcaatggca acaacgttgc gcaaactatt aactggcgaa ctacttactc    7200
tagcttcccg gcaacaatta atagactgga tggaggcgga taaagttgca ggaccacttc    7260
tgcgctcggc ccttccggct ggctggttta ttgctgataa atctggagcc ggtgagcgtg    7320
ggtctcgcgg tatcattgca gcactggggc cagatggtaa gccctcccgt atcgtagtta    7380
tctacacgac ggggagtcag gcaactatgg atgaacgaaa tagacagatc gctgagatag    7440
gtgcctcact gattaagcat tggtaactgt cagaccaagt ttactcatat atactttaga    7500
ttgatttaaa acttcatttt taatttaaaa ggatctaggt gaagatcctt tttgataatc    7560
tcatgaccaa aatcccttaa cgtgagtttt cgttccactg agcgtcagac cccgtagaaa    7620
agatcaaagg atcttcttga gatccttttt ttctgcgcgt aatctgctgc ttgcaaacaa    7680
aaaaaccacc gctaccagcg gtggtttgtt tgccggatca agagctacca actcttttc    7740 cgaaggtaac tggcttcagc agagcgcaga taccaaatac tgtccttcta gtgtagccgt    7800
agttaggcca ccacttcaag aactctgtag caccgcctac atacctcgct ctgctaatcc    7860
tgttaccagt ggctgctgcc agtggcgata agtcgtgtct taccgggttg gactcaagac    7920
gatagttacc ggataaggcg cagcggtcgg gctgaacggg gggttcgtgc acacagccca    7980
gcttggagcg aacgacctac accgaactga gatacctaca gcgtgagcta tgagaaagcg    8040
ccacgcttcc cgaagggaga aaggcggaca ggtatccggt aagcggcagg gtcggaacag    8100
gagagcgcac gagggagctt ccagggggaa acgcctggta tctttatagt cctgtcgggt    8160
ttcgccacct ctgacttgag cgtcgatttt tgtgatgc                            8198
```

<210> SEQ ID NO 8
<211> LENGTH: 2208
<212> TYPE: DNA
<213> ORGANISM: Bacillus anthracis
<220> FEATURE:
<221> NAME/KEY: CDS
<222> LOCATION:
<223> OTHER INFORMATION: DNA coding sequence for B. anthracis PA.

<400> SEQUENCE: 8

```
gaagttaaac aggagaaccg gttattaaat gaatcagaat caagttccca ggggttacta      60
```

| | |
|---|---|
| ggatactatt ttagtgattt gaattttcaa gcacccatgg tggttacctc ttctactaca | 120 |
| ggggatttat ctattcctag ttctgagtta gaaaatattc catcggaaaa ccaatatttt | 180 |
| caatctgcta tttggtcagg atttatcaaa gttaagaaga gtgatgaata tacatttgct | 240 |
| acttccgctg ataatcatgt aacaatgtgg gtagatgacc aagaagtgat taataaagct | 300 |
| tctaattcta caaaatcag attagaaaaa ggaagattat atcaaataaa aattcaatat | 360 |
| caacgagaaa atcctactga aaaggattg gatttcaagt tgtactggac cgattctcaa | 420 |
| aataaaaaag aagtgatttc tagtgataac ttacaattgc cagaattaaa acaaaaatct | 480 |
| tcgaactcaa gaaaaagcg aagtacaagt gctggaccta cggttccaga ccgtgacaat | 540 |
| gatggaatcc ctgattcatt agaggtagaa ggatatacgg ttgatgtcaa aaataaaaga | 600 |
| acttttcttt caccatggat ttctaatatt catgaaagaa aaggattaac caaatataaa | 660 |
| tcatctcctg aaaaatggag cacggcttct gatccgtaca gtgatttcga aaaggttaca | 720 |
| ggacggattg ataagaatgt atcaccagag caagcacc cccttgtggc agcttatccg | 780 |
| attgtacatg tagatatgga gaatattatt ctctcaaaaa atgaggatca atccacacag | 840 |
| aatactgata gtcaaacgag aacaataagt aaaaatactt ctacaagtag gacacatact | 900 |
| agtgaagtac atggaaatgc agaagtgcat gcgtcgttct ttgatattgg tgggagtgta | 960 |
| tctgcaggat ttagtaattc gaattcaagt acggtcgcaa ttgatcattc actatctcta | 1020 |
| gcagggaaa gaacttgggc tgaaacaatg gtttaaata ccgctgatac agcaagatta | 1080 |
| aatgccaata ttagatatgt aaatactggg acggctccaa tctacaacgt gttaccaacg | 1140 |
| acttcgttag tgttaggaaa aaatcaaaca ctcgcgacaa ttaaagctaa ggaaaaccaa | 1200 |
| ttaagtcaaa tacttgcacc taataattat tatccttcta aaaacttggc gccaatcgca | 1260 |
| ttaaatgcac aagacgattt cagttctact ccaattacaa tgaattacaa tcaatttctt | 1320 |
| gagttagaaa aaacgaaaca attaagatta gatacggatc aagtatatgg gaatatagca | 1380 |
| acatacaatt ttgaaaatgg aagagtgagg gtggatacag gctcgaactg gagtgaagtg | 1440 |
| ttaccgcaaa ttcaagaaac aactgcacgt atcattttta atggaaaaga tttaaatctg | 1500 |
| gtagaaaggc ggatagcggc ggttaatcct agtgatccat tagaaacgac taaaccggat | 1560 |
| atgacattaa agaagccct taaaatagca tttggattta acgaaccgaa tggaaactta | 1620 |
| caatatcaag ggaaagacat aaccgaattt gattttaatt tcgatcaaca acatctcaa | 1680 |
| aatatcaaga atcagttagc ggaattaaac gcaactaaca tatatactgt attagataaa | 1740 |
| atcaaattaa atgcaaaaat gaatatttta ataagagata acgttttca ttatgataga | 1800 |
| aataacatag cagttgggc ggatgagtca gtagttaagg aggctcatag agaagtaatt | 1860 |
| aattcgtcaa cagagggatt attgttaaat attgataagg atataagaaa atatattca | 1920 |
| ggttatattg tagaaattga agatactgaa gggcttaaag aagttataaa tgacagatat | 1980 |
| gatatgttga atatttctag tttacggcaa gatggaaaaa catttataga ttttaaaaaa | 2040 |
| tataatgata aattaccgtt atatataagt aatcccaatt ataaggtaaa tgtatatgct | 2100 |
| gttactaaag aaaacactat tattaatcct agtgagaatg gggatactag taccaacggg | 2160 |
| atcaagaaaa ttttaatctt ttctaaaaaa ggctatgaga taggataa | 2208 |

<210> SEQ ID NO 9
<211> LENGTH: 735
<212> TYPE: PRT
<213> ORGANISM: Bacillus anthracis
<220> FEATURE:
<221> NAME/KEY:

-continued

```
<222> LOCATION:
<223> OTHER INFORMATION: Amino acid sequence of B. anthracis PA.

<400> SEQUENCE: 9
```

| | | | | | | | | | | | | | | |
|---|---|---|---|---|---|---|---|---|---|---|---|---|---|---|
| Glu | Val | Lys | Gln | Glu | Asn | Arg | Leu | Leu | Asn | Glu | Ser | Glu | Ser | Ser |
| 1 | | | | 5 | | | | | 10 | | | | | 15 |
| Gln | Gly | Leu | Leu | Gly | Tyr | Tyr | Phe | Ser | Asp | Leu | Asn | Phe | Gln | Ala | Pro |
| | | | 20 | | | | | 25 | | | | | 30 | |
| Met | Val | Thr | Ser | Ser | Thr | Thr | Gly | Asp | Leu | Ser | Ile | Pro | Ser | Ser |
| | | 35 | | | | 40 | | | | | 45 | | | |
| Glu | Leu | Glu | Asn | Ile | Pro | Ser | Glu | Asn | Gln | Tyr | Phe | Gln | Ser | Ala | Ile |
| 50 | | | | | 55 | | | | | 60 | | | | | |
| Trp | Ser | Gly | Phe | Ile | Lys | Val | Lys | Lys | Ser | Asp | Glu | Tyr | Thr | Phe | Ala |
| 65 | | | | | 70 | | | | | 75 | | | | | 80 |
| Thr | Ser | Ala | Asp | Asn | His | Val | Thr | Met | Trp | Val | Asp | Asp | Gln | Glu | Val |
| | | | | 85 | | | | | 90 | | | | | 95 | |
| Ile | Asn | Lys | Ala | Ser | Asn | Ser | Asn | Lys | Ile | Arg | Leu | Glu | Lys | Gly | Arg |
| | | | 100 | | | | | 105 | | | | | 110 | | |
| Leu | Tyr | Gln | Ile | Lys | Ile | Gln | Tyr | Gln | Arg | Glu | Asn | Pro | Thr | Glu | Lys |
| | | 115 | | | | 120 | | | | | 125 | | | | |
| Gly | Leu | Asp | Phe | Lys | Leu | Tyr | Trp | Thr | Asp | Ser | Gln | Asn | Lys | Lys | Glu |
| 130 | | | | | 135 | | | | | 140 | | | | | |
| Val | Ile | Ser | Ser | Asp | Asn | Leu | Gln | Leu | Pro | Glu | Leu | Lys | Gln | Lys | Ser |
| 145 | | | | | 150 | | | | | 155 | | | | | 160 |
| Ser | Asn | Ser | Arg | Lys | Lys | Arg | Ser | Thr | Ser | Ala | Gly | Pro | Thr | Val | Pro |
| | | | | 165 | | | | | 170 | | | | | 175 | |
| Asp | Arg | Asp | Asn | Asp | Gly | Ile | Pro | Asp | Ser | Leu | Glu | Val | Glu | Gly | Tyr |
| | | | 180 | | | | | 185 | | | | | 190 | | |
| Thr | Val | Asp | Val | Lys | Asn | Lys | Arg | Thr | Phe | Leu | Ser | Pro | Trp | Ile | Ser |
| | | 195 | | | | 200 | | | | | 205 | | | | |
| Asn | Ile | His | Glu | Lys | Lys | Gly | Leu | Thr | Lys | Tyr | Lys | Ser | Ser | Pro | Glu |
| | 210 | | | | | 215 | | | | | 220 | | | | |
| Lys | Trp | Ser | Thr | Ala | Ser | Asp | Pro | Tyr | Ser | Asp | Phe | Glu | Lys | Val | Thr |
| 225 | | | | | 230 | | | | | 235 | | | | | 240 |
| Gly | Arg | Ile | Asp | Lys | Asn | Val | Ser | Pro | Glu | Ala | Arg | His | Pro | Leu | Val |
| | | | | 245 | | | | | 250 | | | | | 255 | |
| Ala | Ala | Tyr | Pro | Ile | Val | His | Val | Asp | Met | Glu | Asn | Ile | Ile | Leu | Ser |
| | | | 260 | | | | | 265 | | | | | 270 | | |
| Lys | Asn | Glu | Asp | Gln | Ser | Thr | Gln | Asn | Thr | Asp | Ser | Gln | Thr | Arg | Thr |
| | | 275 | | | | 280 | | | | | 285 | | | | |
| Ile | Ser | Lys | Asn | Thr | Ser | Thr | Ser | Arg | Thr | His | Thr | Ser | Glu | Val | His |
| | 290 | | | | | 295 | | | | | 300 | | | | |
| Gly | Asn | Ala | Glu | Val | His | Ala | Ser | Phe | Phe | Asp | Ile | Gly | Gly | Ser | Val |
| 305 | | | | | 310 | | | | | 315 | | | | | 320 |
| Ser | Ala | Gly | Phe | Ser | Asn | Ser | Asn | Ser | Ser | Thr | Val | Ala | Ile | Asp | His |
| | | | | 325 | | | | | 330 | | | | | 335 | |
| Ser | Leu | Ser | Leu | Ala | Gly | Glu | Arg | Thr | Trp | Ala | Glu | Thr | Met | Gly | Leu |
| | | | 340 | | | | | 345 | | | | | 350 | | |
| Asn | Thr | Ala | Asp | Thr | Ala | Arg | Leu | Asn | Ala | Asn | Ile | Arg | Tyr | Val | Asn |
| | | 355 | | | | 360 | | | | | 365 | | | | |
| Thr | Gly | Thr | Ala | Pro | Ile | Tyr | Asn | Val | Leu | Pro | Thr | Thr | Ser | Leu | Val |
| | 370 | | | | | 375 | | | | | 380 | | | | |
| Leu | Gly | Lys | Asn | Gln | Thr | Leu | Ala | Thr | Ile | Lys | Ala | Lys | Glu | Asn | Gln |
| 385 | | | | | 390 | | | | | 395 | | | | | 400 |

```
Leu Ser Gln Ile Leu Ala Pro Asn Asn Tyr Tyr Pro Ser Lys Asn Leu
                405                 410                 415
Ala Pro Ile Ala Leu Asn Ala Gln Asp Asp Phe Ser Ser Thr Pro Ile
            420                 425                 430
Thr Met Asn Tyr Asn Gln Phe Leu Glu Leu Glu Lys Thr Lys Gln Leu
        435                 440                 445
Arg Leu Asp Thr Asp Gln Val Tyr Gly Asn Ile Ala Thr Tyr Asn Phe
    450                 455                 460
Glu Asn Gly Arg Val Arg Val Asp Thr Gly Ser Asn Trp Ser Glu Val
465                 470                 475                 480
Leu Pro Gln Ile Gln Glu Thr Thr Ala Arg Ile Ile Phe Asn Gly Lys
                485                 490                 495
Asp Leu Asn Leu Val Glu Arg Arg Ile Ala Ala Val Asn Pro Ser Asp
            500                 505                 510
Pro Leu Glu Thr Thr Lys Pro Asp Met Thr Leu Lys Glu Ala Leu Lys
        515                 520                 525
Ile Ala Phe Gly Phe Asn Glu Pro Asn Gly Asn Leu Gln Tyr Gln Gly
    530                 535                 540
Lys Asp Ile Thr Glu Phe Asp Phe Asn Phe Asp Gln Gln Thr Ser Gln
545                 550                 555                 560
Asn Ile Lys Asn Gln Leu Ala Glu Leu Asn Ala Thr Asn Ile Tyr Thr
                565                 570                 575
Val Leu Asp Lys Ile Lys Leu Asn Ala Lys Met Asn Ile Leu Ile Arg
            580                 585                 590
Asp Lys Arg Phe His Tyr Asp Arg Asn Asn Ile Ala Val Gly Ala Asp
        595                 600                 605
Glu Ser Val Val Lys Glu Ala His Arg Glu Val Ile Asn Ser Ser Thr
    610                 615                 620
Glu Gly Leu Leu Leu Asn Ile Asp Lys Asp Ile Arg Lys Ile Leu Ser
625                 630                 635                 640
Gly Tyr Ile Val Glu Ile Glu Asp Thr Glu Gly Leu Lys Glu Val Ile
                645                 650                 655
Asn Asp Arg Tyr Asp Met Leu Asn Ile Ser Ser Leu Arg Gln Asp Gly
            660                 665                 670
Lys Thr Phe Ile Asp Phe Lys Lys Tyr Asn Asp Lys Leu Pro Leu Tyr
        675                 680                 685
Ile Ser Asn Pro Asn Tyr Lys Val Asn Val Tyr Ala Val Thr Lys Glu
    690                 695                 700
Asn Thr Ile Ile Asn Pro Ser Glu Asn Gly Asp Thr Ser Thr Asn Gly
705                 710                 715                 720
Ile Lys Lys Ile Leu Ile Phe Ser Lys Lys Gly Tyr Glu Ile Gly
                725                 730                 735

<210> SEQ ID NO 10
<211> LENGTH: 9286
<212> TYPE: DNA
<213> ORGANISM: Bacillus anthracis
<220> FEATURE:
<221> NAME/KEY:
<222> LOCATION:
<223> OTHER INFORMATION: Dual expression vector pBP105 for B. anthracis
      PA and LF30. Entire sequence is shown since the vector sequence
      contains two coding regions. The coding region for PA is from
      3735 to 5942 and the coding region for LF30 is from 6391 to 7161.

<400> SEQUENCE: 10
tcgtcagggg ggcggagcct atggaaaaac gccagcaacg cggccttttt acggttcctg      60
```

-continued

```
gccttttgct ggccttttgc tcacatgttc tttcctgcgt tatcccctga ttctgtggat      120
aaccgtatta ccgcctttga gtgagctgat accgctcgcc gcagccgaac gaccgagcgc      180
agcgagtcag tgagcgagga agcggaagag cgcctgatgc ggtattttct ccttacgcat      240
ctgtgcggta tttcacaccg caatggtgca ctctcagtac aatctgctct gatgccgcat      300
agttaagcca gtaaaaaaaa tttagcagtt aaaaagatg  aatggactgc ttatagcgat      360
aaagttaaat cagatttaga agtaccagcg aaacgacaca tgaaagtgtt gaagtgcca       420 acgggtgaaa agtccatgtt tggtttggga aagaaataa  tgaaaacaga aagaaaccaa       480
accaaaaatg ttgttatatc ggagcgtgat tataaaaact tagtgactgc tgcgagagat      540
aacgataggt taaacagca  tgttagaaat ctcatgagta ctgatatggc gagagaatat      600
aaaaaattaa gtaaagaaca tgggcaagtt aaagaaaaat atagtggtct tgtagagcga      660
tttaatgaaa atgtaaatga ttataatgag ttgcttgaag aaaacaagtc tttaaagtct      720
aaaataagcg atttaaagcg tgatgtgagt ttaatctatg aaagcactaa ggaattcctt      780
aaggaacgta cagacggctt aaaagccttt aaaaacgttt ttaaggggtt tgtagacaag      840
gtaaaggata aacagcaca  attccaagaa aaacacgatt tagaacctaa aaagaacgaa      900
tttgaactaa ctcataaccg agaggtaaaa aagaacgaa  gtcgagatca gggaatgagt      960
ttataaaata aaaaaagcac ctgaaaaggt gtctttttt  gatggttttg aacttgttct     1020
ttcttatctt gatacatata gaaataacgt catttttatt ttagttgctg aaaggtgcgt     1080
tgaagtgttg gtatgtatgt gttttaaagt attgaaaacc cttaaaattg gttgcacaga     1140
aaaaccccat ctgttaaagt tataagtgac taaacaaata actaaataga tgggggtttc     1200
ttttaatatt atgtgtccta atagtagcat ttattcagat gaaaaatcaa gggttttagt     1260
ggacaagaca aaaagtggaa aagtgagacc atggagagaa aagaaaatcg ctaatgttga     1320
ttactttgaa cttctgcata ttcttgaatt taaaaaggct gaaagagtaa agattgtgc      1380 tgaaatatta gagtataaac aaaatcgtga acaggcgaa  agaaagttgt atcgagtgtg     1440
gttttgtaaa tccaggcttt gtccaatgtg caactggagg agagcaatga acatggcat      1500 tcagtcacaa aaggttgttg ctgaagttat taaacaaaag ccaacagttc gttggttgtt     1560
tctcacatta acagttaaaa atgtttatga tggcgaagaa ttaaataaga gtttgtcaga     1620
tatggctcaa ggatttcgcc gaatgatgca atataaaaaa attaataaaa atcttgttgg     1680
ttttatgcgt gcaacggaag tgacaataaa taataaagat aattcttata atcagcacat     1740
gcatgtattg gtatgtgtgg aaccaactta ttttaagaat acagaaaact acgtgaatca     1800
aaaacaatgg attcaattt  ggaaaaaggc aatgaaatta gactatgatc caaatgtaaa     1860
agttcaaatg attcgaccga aaaataaata taaatcggat atacaatcgg caattgacga     1920
aactgcaaaa tatcctgtaa aggatacgga ttttatgacc gatgatgaag aaaagaattt     1980
gaaacgtttg tctgatttgg aggaaggttt acaccgtaaa aggttaatct cctatggtgg     2040
tttgttaaaa gaaatacata aaaaattaaa ccttgatgac acagaagaag gcgatttgat     2100
tcatacagat gatgacgaaa aagccgatga agatggattt tctattattg caatgtggaa     2160
ttgggaacgg aaaaattatt ttattaaaga gtagttcaac aaacgggcca gtttgttgaa     2220
gattagatgc tataattgtt attaaaagga ttgaaggatg cttaggaaga cgagttatta     2280
atagctgaat aagaacggtg ctctccaaat attcttattt agaaaagcaa atctaaaatt     2340
atctgaaaag ggaatgagaa tagtgaatgg accaataata atgactagag aagaaagaat     2400
```

```
gaagattgtt catgaaatta aggaacgaat attggataaa tatggggatg atgttaaggc    2460
tattggtgtt tatggctctc ttggtcgtca gactgatggg ccctattcgg atattgagat    2520
gatgtgtgtc atgtcaacag aggaagcaga gttcagccat gaatggacaa ccggtgagtg    2580
gaaggtggaa gtgaattttg atagcgaaga gattctacta gattatgcat ctcaggtgga    2640
atcagattgg ccgcttacac atggtcaatt tttctctatt ttgccgattt atgattcagg    2700
tggatactta gagaaagtgt atcaaactgc taaatcggta gaagcccaaa cgttccacga    2760
tgcgatttgt gcccttatcg tagaagagct gtttgaatat gcaggcaaat ggcgtaatat    2820
tcgtgtgcaa ggaccgacaa catttctacc atccttgact gtacaggtag caatggcagg    2880
tgccatgttg attggtctgc atcatcgcat ctgttatacg acgagcgctt cggtcttaac    2940
tgaagcagtt aagcaatcag atcttccttc aggttatgac catctgtgcc agttcgtaat    3000
gtctggtcaa ctttccgact ctgagaaact tctggaatcg ctagagaatt ctggaatgg     3060 gattcaggag tggacagaac gacacggata tatagtggat gtgtcaaaac gcataccatt    3120
ttgaacgatg acctctaata attgttaatc atgttggtta cgtatttatt aacttctcct    3180
agtattagta attatcatgg ctgtcatggc gcattaacgg aataaagggt gtgcttaaat    3240
cgggccattt tgcgtaataa gaaaaaggat taattatgag cgaattgaat taataataag    3300
gtaatagatt tacattagaa aatgaaaggg gatttttatgc gtgagaatgt tacagtctat    3360
cccggcattg ccagtcgggg atattaaaaa gagtataggt ttttattgcg ataaactagg    3420
tttcactttg gttcaccatg aagatggatt cgcagttcta atgtgtaatg aggttcggat    3480
tcatctatta aacatataaa ttctttttta tgttatatat ttataaaagt tctgtttaaa    3540
aagccaaaaa taaataatta tctcttttta tttatattat attgaaacta agtttatta     3600 atttcaatat aatataaatt taattttata caaaaaggag aacgtatatg aaaaaacgaa    3660
aagtgttaat accattaatg gcattgtcta cgatattagt ttcaagcaca ggtaatttag    3720
aggtgattca ggcagaagtt aaacaggaga accggttatt aaatgaatca gaatcaagtt    3780
cccaggggtt actaggatac tattttagtg atttgaattt tcaagcaccc atggtggtta    3840
cctcttctac tacagggggat ttatctattc ctagttctga gttagaaaat attccatcgg    3900
aaaaccaata ttttcaatct gctatttggt caggatttat caaagttaag aagagtgatg    3960
aatatacatt tgctacttcc gctgataatc atgtaacaat gtgggtagat gaccaagaag    4020
tgattaataa agcttctaat tctaacaaaa tcagattaga aaaggaaga ttatatcaaa     4080 taaaaattca atatcaacga gaaaatccta ctgaaaaagg attggattc aagttgtact     4140 ggaccgattc tcaaaataaa aaagaagtga tttctagtga taacttacaa ttgccagaat    4200
taaaacaaaa atcttcgaac tcaagaaaaa agcgaagtac aagtgctgga cctacggttc    4260
cagaccgtga caatgatgga atccctgatt cattagaggt agaaggatat acggttgatg    4320
tcaaaaataa aagaactttt ctttcaccat ggatttctaa tattcatgaa agaaaggat     4380 taaccaaata taaatcatct cctgaaaaat ggagcacggc ttctgatccg tacagtgatt    4440
tcgaaaaggt tacaggacgg attgataaga atgtatcacc agaggcaaga caccccttg     4500 tggcagctta tccgattgta catgtagata tggagaatat tattctctca aaaaatgagg    4560
atcaatccac acagaatact gatagtcaaa cgagaacaat aagtaaaaat acttctacaa    4620
gtaggacaca tactagtgaa gtacatggaa atgcagaagt gcatgcgtcg ttctttgata    4680
ttggtgggag tgtatctgca ggatttagta attcgaattc aagtacggtc gcaattgatc    4740
attcactatc tctagcaggg gaaagaactt gggctgaaac aatggggttta aataccgctg    4800
```

```
atacagcaag attaaatgcc aatattagat atgtaaatac tgggacggct ccaatctaca      4860
acgtgttacc aacgacttcg ttagtgttag gaaaaaatca aacactcgcg acaattaaag      4920
ctaaggaaaa ccaattaagt caaatacttg cacctaataa ttattatcct tctaaaaact      4980
tggcgccaat cgcattaaat gcacaagacg atttcagttc tactccaatt acaatgaatt      5040
acaatcaatt tcttgagtta gaaaaaacga acaattaaag attagatacg gatcaagtat      5100
atgggaatat agcaacatac aattttgaaa atggaagagt gagggtggat acaggctcga      5160
actggagtga agtgttaccg caaattcaag aaacaactgc acgtatcatt tttaatggaa      5220
aagatttaaa tctggtagaa aggcggatag cggcggttaa tcctagtgat ccattagaaa      5280
cgactaaacc ggatatgaca ttaaaagaag cccttaaaat agcatttgga tttaacgaac      5340
cgaatggaaa cttacaatat caagggaaag acataaccga atttgatttt aatttcgatc      5400
aacaaacatc tcaaaatatc aagaatcagt tagcggaatt aaacgcaact aacatatata      5460
ctgtattaga taaaatcaaa ttaaatgcaa aatgaatat tttaataaga gataaacgtt      5520
ttcattatga tagaaataac atagcagttg gggcggatga gtcagtagtt aaggaggctc      5580
atagagaagt aattaattcg tcaacagagg gattattgtt aaatattgat aaggatataa      5640 gaaaatatt atcaggttat attgtagaaa ttgaagatac tgaagggctt aaagaagtta      5700
taaatgacag atatgatatg ttgaatatt ctagtttacg gcaagatgga aaaacattta      5760 tagatttta aaaatataat gataaattac cgttatatat aagtaatccc aattataagg      5820
taaatgtata tgctgttact aaagaaaaca ctattattaa tcctagtgag aatggggata      5880
ctagtaccaa cgggatcaag aaaattttaa tcttttctaa aaaaggctat gagataggat      5940 aagtaattc taggtgattt ttaaattatc taaaaaacag taaaattaaa acatactctt      6000
tttgtaagaa atacaaggag agtatgtttt aaacagtaat ctaaatcatc ataatcccttt      6060 gagattgttt gtaggatccc actttggttc accatgaaga tggattcgca gttctaatgt      6120
gtaatgaggt tcggattcat ctattaaaca tataaattct tttttatgtt atatatttat      6180
aaaagttctg tttaaaaagc caaaaataaa taattatctc ttttttattta tattatattg      6240 aaactaaagt ttattaattt caatataata taaatttaat tttatacaaa aaggagaacg      6300
tatatgaaaa aacgaaaagt gttaatacca ttaatggcat tgtctacgat attagtttca      6360
agcacaggta atttagaggt gattcaggca catatggcgg gcggtcatgg tgatgtaggt      6420
atgcacgtaa aagagaaaga gaaaaataaa gatgagaata agagaaaaga tgaagaacga      6480
aataaaacac aggaagagca tttaaaggaa atcatgaaac acattgtaaa aatagaagta      6540
aaaggggagg aagctgttaa aaaagaggca gcagaaaagc tacttgagaa agtaccatct      6600
gatgttttag agatgtataa agcaattgga ggaaagatat atattgtgga tggtgatatt      6660
acaaaacata tatctttaga agcattatct gaagataaga aaaaaataaa agacatttat      6720
gggaaagatg ccttattaca tgaacattat gtatatgcaa agaaggata tgaacccgta      6780 cttgtaatcc aatcttcgga agattatgta gaaaatactg aaaaggcact gaacgttttat      6840 tatgaaatag gtaagatatt atcaagggat attttaagta aaattaatca accatatcag      6900 aaattttag atgtattaaa taccattaaa aatgcatctg attcagatgg acaagatctt      6960
ttatttacta atcagcttaa ggaacatccc acagactttt ctgtagaatt cttggaacaa      7020
aatagcaatg aggtacaaga agtatttgcg aaagcttttg catattatat cgagccacag      7080
catcgtgatg ttttacagct ttatgcaccg gaagcttta attacatgga taaatttaac      7140
```

```
gaacaagaaa taaatctata aggatccggc tgctaacaaa gcccgaaagg aagctgagtt   7200
ggctgctgcc accgctgagc aataactagc ataacccctt ggggcctcta acgggtctt    7260 gagggtttt ttgctgaaag gaggaactat atccggatat cccgcaagag gcccggcagt    7320
accggcataa ccaagcctat gcctacagca tccagggtga cggtgccgag gatgacgatg   7380
agcgcattgt tagatttcat acacggtgcc tgactgcgtt agcaatttaa ctgtgataaa   7440
ctaccgcatt aaagcttatc gatgataagc tgtcaaacat gagaattctt gaagacgaaa   7500
gggcctcgtg atacgccat ttttataggt taatgtcatg ataataatgg tttcttagac    7560
gtcaggtggc acttttcggg gaaatgtgcg cggaaccct atttgtttat ttttctaaat    7620
acattcaaat atgtatccgc tcatgagaca ataaccctga taaatgcttc aataatattg   7680 aaaaggaag agtatgagta ttcaacattt ccgtgtcgcc cttattccct ttttttgcggc   7740 attttgcctt cctgttttg ctcacccaga acgctggtg aaagtaaaag atgctgaaga    7800
tcagttgggt gcacgagtgg gttacatcga actggatctc aacagcggta agatccttga   7860
gagttttcgc cccgaagaac gttttccaat gatgagcact tttaaagttc tgctatgtgg   7920
cgcggtatta tcccgtgttg acgccgggca agagcaactc ggtcgccgca tacactattc   7980
tcagaatgac ttggttgagt actcaccagt cacagaaaag catcttacgg atggcatgac   8040
agtaagagaa ttatgcagtg ctgccataac catgagtgat aacactgcgg ccaacttact   8100
tctgacaacg atcggaggac cgaaggagct aaccgctttt ttgcacaaca tgggggatca   8160
tgtaactcgc cttgatcgtt gggaaccgga gctgaatgaa gccataccaa acgacgagcg   8220
tgacaccacg atgcctgcag caatggcaac aacgttgcgc aaactattaa ctggcgaact   8280
acttactcta gcttcccggc aacaattaat agactggatg gaggcggata agttgcagg    8340 accacttctg cgctcggccc ttccggctgg ctggtttatt gctgataaat ctggagccgg   8400
tgagcgtggg tctcgcggta tcattgcagc actggggcca gatggtaagc cctcccgtat   8460
cgtagttatc tacacgacgg ggagtcaggc aactatggat gaacgaaata gacagatcgc   8520
tgagataggt gcctcactga ttaagcattg gtaactgtca gaccaagttt actcatatat   8580
actttagatt gatttaaaac ttcatttta atttaaaagg atctaggtga agatcctttt   8640
tgataatctc atgaccaaaa tcccttaacg tgagttttcg ttccactgag cgtcagaccc   8700
cgtagaaaag atcaaaggat cttcttgaga tccttttttt ctgcgcgtaa tctgctgctt   8760
gcaaacaaaa aaaccaccgc taccagcggt ggtttgtttg ccggatcaag agctaccaac   8820 tcttttccg aaggtaactg gcttcagcag agcgcagata ccaaatactg tccttctagt    8880
gtagccgtag ttaggccacc acttcaagaa ctctgtagca ccgcctacat acctcgctct   8940
gctaatcctg ttaccagtgg ctgctgccag tggcgataag tcgtgtctta ccgggttgga   9000
ctcaagacga tagttaccgg ataaggcgca gcggtcgggc tgaacggggg gttcgtgcac   9060
acagcccagc ttggagcgaa cgacctacac cgaactgaga tacctacagc gtgagctatg   9120
agaaagcgcc acgcttcccg aagggagaaa ggcggacagg tatccggtaa gcggcagggt   9180
cggaacagga gagcgcacga gggagcttcc agggggaaac gcctggtatc tttatagtcc   9240
tgtcgggttt cgccacctct gacttgagcg tcgattttg tgatgc                  9286
```

<210> SEQ ID NO 11
<211> LENGTH: 2208
<212> TYPE: DNA
<213> ORGANISM: Bacillus anthracis
<220> FEATURE:
<221> NAME/KEY: CDS
<222> LOCATION:
<223> OTHER INFORMATION: DNA coding sequence from pBP105 for B.
     anthracis PA. The DNA coding
     sequences for rPA (2208 bases) is identical to Sequence 8.

<400> SEQUENCE: 11

| | | | | | |
|---|---|---|---|---|---|
| gaagttaaac | aggagaaccg | gttattaaat | gaatcagaat | caagttccca | ggggttacta | 60 |
| ggatactatt | ttagtgattt | gaattttcaa | gcacccatgg | tggttacctc | ttctactaca | 120 |
| ggggatttat | ctattcctag | ttctgagtta | gaaaatattc | catcggaaaa | ccaatatttt | 180 |
| caatctgcta | tttggtcagg | atttatcaaa | gttaagaaga | gtgatgaata | catttgct | 240 |
| acttccgctg | ataatcatgt | aacaatgtgg | gtagatgacc | aagaagtgat | taataaagct | 300 |
| tctaattcta | acaaaatcag | attagaaaaa | ggaagattat | atcaaataaa | aattcaatat | 360 |
| caacgagaaa | atcctactga | aaaggattg | gatttcaagt | tgtactggac | cgattctcaa | 420 |
| aataaaaaag | aagtgatttc | tagtgataac | ttacaattgc | agaattaaa | acaaaaatct | 480 |
| tcgaactcaa | gaaaaagcg | aagtacaagt | gctggaccta | cggttccaga | ccgtgacaat | 540 |
| gatggaatcc | ctgattcatt | agaggtagaa | ggatatacgg | ttgatgtcaa | aaataaaaga | 600 |
| acttttcttt | caccatggat | ttctaatatt | catgaaaaga | aggattaac | caaatataaa | 660 |
| tcatctcctg | aaaaatggag | cacggcttct | gatccgtaca | gtgatttcga | aaaggttaca | 720 |
| ggacggattg | ataagaatgt | atcaccagag | gcaagacacc | cccttgtggc | agcttatccg | 780 |
| attgtacatg | tagatatgga | gaatattatt | ctctcaaaaa | atgaggatca | atccacacag | 840 |
| aatactgata | gtcaaacgag | aacaataagt | aaaaatactt | ctacaagtag | gacacatact | 900 |
| agtgaagtac | atggaaatgc | agaagtgcat | gcgtcgttct | ttgatattgg | tgggagtgta | 960 |
| tctgcaggat | ttagtaattc | gaattcaagt | acggtcgcaa | ttgatcattc | actatctcta | 1020 |
| gcagggggaaa | gaacttgggc | tgaaacaatg | ggtttaaata | ccgctgatac | agcaagatta | 1080 |
| aatgccaata | ttagatatgt | aaatactggg | acggctccaa | tctacaacgt | gttaccaacg | 1140 |
| acttcgttag | tgttaggaaa | aaatcaaaca | ctcgcgacaa | ttaaagctaa | ggaaaaccaa | 1200 |
| ttaagtcaaa | tacttgcacc | taataattat | tatccttcta | aaaacttggc | gccaatcgca | 1260 |
| ttaaatgcac | aagacgattt | cagttctact | ccaattacaa | tgaattacaa | tcaatttctt | 1320 |
| gagttagaaa | aaacgaaaca | attaagatta | gatacggatc | aagtatatgg | aatatagca | 1380 |
| acatacaatt | ttgaaaatgg | aagagtgagg | gtggatacag | gctcgaactg | gagtgaagtg | 1440 |
| ttaccgcaaa | ttcaagaaac | aactgcacgt | atcatttta | atggaaaaga | tttaaatctg | 1500 |
| gtagaaaggc | ggatagcggc | ggttaatcct | agtgatccat | agaaacgac | taaaccggat | 1560 |
| atgcacattaa | aagaagccct | taaaatagca | tttggattta | acgaaccgaa | tggaaactta | 1620 |
| caatatcaag | ggaaagacat | aaccgaattt | gattttaatt | tcgatcaaca | aacatctcaa | 1680 |
| aatatcaaga | atcagttagc | ggaattaaac | gcaactaaca | tatatactgt | attagataaa | 1740 |
| atcaaattaa | atgcaaaaat | gaatatttta | ataagagata | aacgttttca | ttatgataga | 1800 |
| aataacatag | cagttgggggc | ggatgagtca | gtagttaagg | aggctcatag | agaagtaatt | 1860 |
| aattcgtcaa | cagagggatt | attgttaaat | attgataagg | atataagaaa | aatattatca | 1920 |
| ggttatattg | tagaaattga | agatactgaa | gggcttaaag | aagttataaa | tgacagatat | 1980 |
| gatatgttga | atatttctag | tttacggcaa | gatggaaaaa | catttataga | ttttaaaaaa | 2040 |
| tataatgata | aattaccgtt | atatataagt | aatcccaatt | ataagtaaa | tgtatatgct | 2100 |
| gttactaaag | aaaacactat | tattaatcct | agtgagaatg | gggatactag | taccaacggg | 2160 |

```
atcaagaaaa ttttaatctt ttctaaaaaa ggctatgaga taggataa        2208
```

<210> SEQ ID NO 12
<211> LENGTH: 771
<212> TYPE: DNA
<213> ORGANISM: Bacillus anthracis
<220> FEATURE:
<221> NAME/KEY: CDS
<222> LOCATION:
<223> OTHER INFORMATION: DNA coding sequence from pBP105 corresponding
      to LF30 protein. The DNA coding sequence for LF30 (771 bases) is
      identical to Sequence 3.

<400> SEQUENCE: 12

```
catatggcgg gcggtcatgg tgatgtaggt atgcacgtaa aagagaaaga gaaaaataaa    60
gatgagaata agagaaaaga tgaagaacga aataaaacac aggaagagca tttaaaggaa   120
atcatgaaac acattgtaaa aatagaagta aaaggggagg aagctgttaa aaaagaggca   180
gcagaaaagc tacttgagaa agtaccatct gatgttttag agatgtataa agcaattgga   240
ggaaagatat atattgtgga tggtgatatt acaaaacata tatctttaga agcattatct   300
gaagataaga aaaaaataaa agacatttat gggaaagatg ccttattaca tgaacattat   360
gtatatgcaa aagaaggata tgaacccgta cttgtaatcc aatcttcgga agattatgta   420
gaaaatactg aaaaggcact gaacgtttat tatgaaatag gtaagatatt atcaagggat   480
atttaagta aaattaatca accatatcag aaattttag atgtattaaa taccattaaa   540
aatgcatctg attcagatgg acaagatctt ttatttacta atcagcttaa ggaacatccc   600
acagactttt ctgtagaatt cttggaacaa aatagcaatg aggtacaaga agtatttgcg   660
aaagctttg catattatat cgagccacag catcgtgatg ttttacagct ttatgcaccg   720
gaagctttta attcatgga taaatttaac gaacaagaaa taaatctata a             771
```

<210> SEQ ID NO 13
<211> LENGTH: 735
<212> TYPE: PRT
<213> ORGANISM: Bacillus anthracis
<220> FEATURE:
<221> NAME/KEY:
<222> LOCATION:
<223> OTHER INFORMATION: Amino acid sequence of B. anthracis PA.
      Amino acids sequence of PA
      (735 amino acids) is identical to Sequence 9.

<400> SEQUENCE: 13

```
Glu Val Lys Gln Glu Asn Arg Leu Leu Asn Glu Ser Glu Ser Ser Ser
  1               5                  10                  15

Gln Gly Leu Leu Gly Tyr Tyr Phe Ser Asp Leu Asn Phe Gln Ala Pro
              20                  25                  30

Met Val Val Thr Ser Ser Thr Thr Gly Asp Leu Ser Ile Pro Ser Ser
          35                  40                  45

Glu Leu Glu Asn Ile Pro Ser Glu Asn Gln Tyr Phe Gln Ser Ala Ile
     50                  55                  60

Trp Ser Gly Phe Ile Lys Val Lys Lys Ser Asp Glu Tyr Thr Phe Ala
 65                  70                  75                  80

Thr Ser Ala Asp Asn His Val Thr Met Trp Val Asp Asp Gln Glu Val
                 85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125
```

```
Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Gln Thr Arg Thr
        275                 280                 285

Ile Ser Lys Asn Thr Ser Thr Ser Arg Thr His Thr Ser Glu Val His
    290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
        355                 360                 365

Thr Gly Thr Ala Pro Ile Tyr Asn Val Leu Pro Thr Thr Ser Leu Val
    370                 375                 380

Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
                405                 410                 415

Ala Pro Ile Ala Leu Asn Ala Gln Asp Asp Phe Ser Ser Thr Pro Ile
            420                 425                 430

Thr Met Asn Tyr Asn Gln Phe Leu Glu Leu Glu Lys Thr Lys Gln Leu
        435                 440                 445

Arg Leu Asp Thr Asp Gln Val Tyr Gly Asn Ile Ala Thr Tyr Asn Phe
    450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
        515                 520                 525

Ile Ala Phe Gly Phe Asn Glu Pro Asn Gly Asn Leu Gln Tyr Gln Gly
    530                 535                 540
```

-continued

```
Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
        595                 600                 605

Glu Ser Val Val Lys Glu Ala His Arg Glu Val Ile Asn Ser Ser Thr
    610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
        675                 680                 685

Ile Ser Asn Pro Asn Tyr Lys Val Asn Val Tyr Ala Val Thr Lys Glu
    690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735

<210> SEQ ID NO 14
<211> LENGTH: 256
<212> TYPE: PRT
<213> ORGANISM: Bacillus anthracis
<220> FEATURE:
<221> NAME/KEY: MUTAGEN
<222> LOCATION:
<223> OTHER INFORMATION: Amino acid sequence corresponding to LF30
      protein.  Amino acids sequence of LF30 (256 amino acids) is
      identical to Sequence 4.

<400> SEQUENCE: 14

His Met Ala Gly Gly His Gly Asp Val Gly Met His Val Lys Glu Lys
1               5                   10                  15

Glu Lys Asn Lys Asp Glu Asn Lys Arg Lys Asp Glu Glu Arg Asn Lys
            20                  25                  30

Thr Gln Glu Glu His Leu Lys Glu Ile Met Lys His Ile Val Lys Ile
        35                  40                  45

Glu Val Lys Gly Glu Glu Ala Val Lys Lys Glu Ala Ala Glu Lys Leu
    50                  55                  60

Leu Glu Lys Val Pro Ser Asp Val Leu Glu Met Tyr Lys Ala Ile Gly
65                  70                  75                  80

Gly Lys Ile Tyr Ile Val Asp Gly Asp Ile Thr Lys His Ile Ser Leu
                85                  90                  95

Glu Ala Leu Ser Glu Asp Lys Lys Lys Ile Lys Asp Ile Tyr Gly Lys
            100                 105                 110

Asp Ala Leu Leu His Glu His Tyr Val Tyr Ala Lys Glu Gly Tyr Glu
        115                 120                 125

Pro Val Leu Val Ile Gln Ser Ser Glu Asp Tyr Val Glu Asn Thr Glu
    130                 135                 140

Lys Ala Leu Asn Val Tyr Tyr Glu Ile Gly Lys Ile Leu Ser Arg Asp
145                 150                 155                 160
```

```
Ile Leu Ser Lys Ile Asn Gln Pro Tyr Gln Lys Phe Leu Asp Val Leu
            165                 170                 175

Asn Thr Ile Lys Asn Ala Ser Asp Ser Asp Gly Gln Asp Leu Leu Phe
        180                 185                 190

Thr Asn Gln Leu Lys Glu His Pro Thr Asp Phe Ser Val Glu Phe Leu
        195                 200                 205

Glu Gln Asn Ser Asn Glu Val Gln Glu Val Phe Ala Lys Ala Phe Ala
        210                 215                 220

Tyr Tyr Ile Glu Pro Gln His Arg Asp Val Leu Gln Leu Tyr Ala Pro
225                 230                 235                 240

Glu Ala Phe Asn Tyr Met Asp Lys Phe Asn Glu Gln Glu Ile Asn Leu
                245                 250                 255

<210> SEQ ID NO 15
<211> LENGTH: 1515
<212> TYPE: DNA
<213> ORGANISM: Bacillus anthracis
<220> FEATURE:
<221> NAME/KEY: CDS
<222> LOCATION:
<223> OTHER INFORMATION: DNA coding sequence from pBP107 for an
      artificial LF-PA fusion protein BP107.

<400> SEQUENCE: 15
catatggcgg gcggtcatgg tgatgtaggt atgcacgtaa agagaaaga gaaaataaa       60 gatgagaata gagaaaaga tgaagaacga ataaaacac aggaagagca tttaaaggaa     120
atcatgaaac acattgtaaa aatagaagta aaaggggagg aagctgttaa aaaagaggca     180
gcagaaaagc tacttgagaa agtaccatct gatgttttag atgtataa agcaattgga      240 ggaaagatat atattgtgga tggtgatatt acaaaacata tatctttaga agcattatct     300
gaagataaga aaaaaataaa agacatttat gggaaagatg ccttattaca tgaacattat     360
gtatatgcaa agaaggata tgaacccgta cttgtaatcc aatcttcgga agattatgta       420
gaaaatactg aaaaggcact gaacgttat tatgaaatag gtaagatatt atcaagggat      480 atttaagta aaattaatca accatatcag aaattttag atgtatataa taccattaaa      540
aatgcatctg attcagatgg acaagatctt ttatttacta atcagcttaa ggaacatccc      600
acagactttt ctgtagaatt cttggaacaa atagcaatg aggtacaaga agtatttgcg     660
aaagcttttg catattatat cgagccacag catcgtgatg ttttacagct ttatgcaccg     720
gaagctttta attacatgga taaatttaac gaacaagaaa taaatctaac tgcacgtatc      780 attttttaatg gaaagatttt aatctggta gaaaggcgga tagcggcggt taatcctagt      840
gatccattag aaacgactaa accggatatg acattaaag aagcccttaa aatagcatt       900 ggatttaacg aaccgaatgg aaacttacaa tatcaaggga agacataac cgaatttgat      960 tttaatttcg atcaacaaac atctcaaaat atcaagaatc agttagcgga attaaacgca    1020
actaacatat atactgtat agataaaatc aaattaaatg caaaaatgaa tattttaata      1080
agagataaac gttttcatta tgatagaat aacatagcag ttggggcgga tgagtcagta    1140
gttaaggagg ctcatagaga agtaattaat tcgtcaacag agggattatt gttaaatatt    1200
gataaggata taagaaaaat attatcaggt tatattgtag aaattgaaga tactgaaggg     1260
cttaaagaag ttataaatga cagatatgat atgttgaata tttctagttt acggcaagat    1320
ggaaaaacat ttagagattt taaaaatat aatgataaat taccgttata taagtaat      1380 cccaattata aggtaaatgt atatgctgtt actaaagaaa acactattat taatcctagt   1440
```

```
gagaatgggg atactagtac aacgggatc aagaaaattt taatcttttc taaaaaaggc    1500
tatgagatag gataa                                                    1515
```

<210> SEQ ID NO 16
<211> LENGTH: 504
<212> TYPE: PRT
<213> ORGANISM: Bacillus anthracis
<220> FEATURE:
<221> NAME/KEY: MUTAGEN
<222> LOCATION:
<223> OTHER INFORMATION: Amino acid sequence for an artificial LF-PA
      fusion protein BP107.

<400> SEQUENCE: 16

```
His Met Ala Gly Gly His Gly Asp Val Gly Met His Val Lys Glu Lys
 1               5                  10                  15

Glu Lys Asn Lys Asp Glu Asn Lys Arg Lys Asp Glu Glu Arg Asn Lys
            20                  25                  30

Thr Gln Glu Glu His Leu Lys Glu Ile Met Lys His Ile Val Lys Ile
        35                  40                  45

Glu Val Lys Gly Glu Glu Ala Val Lys Lys Glu Ala Ala Glu Lys Leu
    50                  55                  60

Leu Glu Lys Val Pro Ser Asp Val Leu Glu Met Tyr Lys Ala Ile Gly
65                  70                  75                  80

Gly Lys Ile Tyr Ile Val Asp Gly Asp Ile Thr Lys His Ile Ser Leu
                85                  90                  95

Glu Ala Leu Ser Glu Asp Lys Lys Lys Ile Lys Asp Ile Tyr Gly Lys
            100                 105                 110

Asp Ala Leu Leu His Glu His Tyr Val Tyr Ala Lys Glu Gly Tyr Glu
        115                 120                 125

Pro Val Leu Val Ile Gln Ser Ser Glu Asp Tyr Val Glu Asn Thr Glu
    130                 135                 140

Lys Ala Leu Asn Val Tyr Tyr Glu Ile Gly Lys Ile Leu Ser Arg Asp
145                 150                 155                 160

Ile Leu Ser Lys Ile Asn Gln Pro Tyr Gln Lys Phe Leu Asp Val Leu
                165                 170                 175

Asn Thr Ile Lys Asn Ala Ser Asp Ser Asp Gly Gln Asp Leu Leu Phe
            180                 185                 190

Thr Asn Gln Leu Lys Glu His Pro Thr Asp Phe Ser Val Glu Phe Leu
        195                 200                 205

Glu Gln Asn Ser Asn Glu Val Gln Glu Val Phe Ala Lys Ala Phe Ala
    210                 215                 220

Tyr Tyr Ile Glu Pro Gln His Arg Asp Val Leu Gln Leu Tyr Ala Pro
225                 230                 235                 240

Glu Ala Phe Asn Tyr Met Asp Lys Phe Asn Glu Gln Glu Ile Asn Leu
                245                 250                 255

Thr Ala Arg Ile Ile Phe Asn Gly Lys Asp Leu Asn Leu Val Glu Arg
            260                 265                 270

Arg Ile Ala Ala Val Asn Pro Ser Asp Pro Leu Glu Thr Thr Lys Pro
        275                 280                 285

Asp Met Thr Leu Lys Glu Ala Leu Lys Ile Ala Phe Gly Phe Asn Glu
    290                 295                 300

Pro Asn Gly Asn Leu Gln Tyr Gln Gly Lys Asp Ile Thr Glu Phe Asp
305                 310                 315                 320

Phe Asn Phe Asp Gln Gln Thr Ser Gln Asn Ile Lys Asn Gln Leu Ala
```

|  | 325 |  | 330 |  | 335 |  |
|---|---|---|---|---|---|---|

Glu Leu Asn Ala Thr Asn Ile Tyr Thr Val Leu Asp Lys Ile Lys Leu
    340      345      350

Asn Ala Lys Met Asn Ile Leu Ile Arg Asp Lys Arg Phe His Tyr Asp
   355      360      365

Arg Asn Ile Ala Val Gly Ala Asp Glu Ser Val Val Lys Glu Ala
  370      375      380

His Arg Glu Val Ile Asn Ser Ser Thr Glu Gly Leu Leu Leu Asn Ile
385      390      395      400

Asp Lys Asp Ile Arg Lys Ile Leu Ser Gly Tyr Ile Val Glu Ile Glu
     405      410      415

Asp Thr Glu Gly Leu Lys Glu Val Ile Asn Asp Arg Tyr Asp Met Leu
    420      425      430

Asn Ile Ser Ser Leu Arg Gln Asp Gly Lys Thr Phe Ile Asp Phe Lys
   435      440      445

Lys Tyr Asn Asp Lys Leu Pro Leu Tyr Ile Ser Asn Pro Asn Tyr Lys
   450      455      460

Val Asn Val Tyr Ala Val Thr Lys Glu Asn Thr Ile Ile Asn Pro Ser
465      470      475      480

Glu Asn Gly Asp Thr Ser Thr Asn Gly Ile Lys Lys Ile Leu Ile Phe
     485      490      495

Ser Lys Lys Gly Tyr Glu Ile Gly
   500

<210> SEQ ID NO 17
<211> LENGTH: 1974
<212> TYPE: DNA
<213> ORGANISM: Bacillus anthracis
<220> FEATURE:
<221> NAME/KEY: CDS
<222> LOCATION:
<223> OTHER INFORMATION: DNA coding sequence from pBP108 for an
   artificial LF-PA fusion protein BP108.

<400> SEQUENCE: 17

| | |
|---|---:|
| catatggcgg gcggtcatgg tgatgtaggt atgcacgtaa agagaaaga gaaaataaa | 60 |
| gatgagaata agagaaaaga tgaagaacga aataaaacac aggaagagca tttaaaggaa | 120 |
| atcatgaaac acattgtaaa aatagaagta aaaggggagg aagctgttaa aaagaggca | 180 |
| gcagaaaagc tacttgagaa agtaccatct gatgttttag atgtgtataa agcaattgga | 240 |
| ggaaagatat atattgtgga tggtgatatt acaaaacata tatctttaga agcattatct | 300 |
| gaagataaga aaaaataaa agacatttat gggaaagatg ctttattaca tgaacattat | 360 |
| gtatatgcaa agaaggata tgaacccgta cttgtaatcc aatcttcgga agattatgta | 420 |
| gaaaatactg aaaaggcact gaacgtttat tatgaaatag gtaagatatt atcaagggat | 480 |
| attttaagta aaattaatca accatatcag aaattttag atgtattaaa taccattaaa | 540 |
| aatgcatctg attcagatgg acaagatctt ttatttacta atcagcttaa ggaacatccc | 600 |
| acagactttt ctgtagaatt cttggaacaa aatagcaatg aggtacaaga agtattttgcg | 660 |
| aaagcttttg catattatat cgagccacag catcgtgatg ttttacagct ttatgcaccg | 720 |
| gaagcttta attacatgga taaatttaac gaacaagaaa taaatctatc cttggaagaa | 780 |
| cttaaagatc aacggatgct gtcaagatat gaaaaatggg aaaagataaa acagcactat | 840 |
| caacactgga gcgattcttt atctgaagaa ggaagaggac ttttaaaaaa gctgcagatt | 900 |
| cctattgagc caagaaaaga tgacataatt cattctttat ctcaagaaga aaagagctt | 960 |

-continued

```
ctaaaaagaa tacaaattga tagtagtgat tttttatcta ctgaggaaaa agagttttta    1020
aaaaagctac aaattgatat tcgtgattct ttatctgaag aagaaaaaga gcttttaaat    1080
agaatacagg tggatagtag taatccttta tctgaaaaag aaaaagagtt tttaaaaaag    1140
ctgaaacttg atattcaacc atacgatatt aatcaaaggt tgcaagatac aggagggtta    1200
attgatagtc cgccaattaa tcttgaaact gcacgtatca ttttttaatgg aaaagattta    1260 aatctggtag aaaggcggat agcggcggtt aatcctagtg atccattaga aacgactaaa    1320
ccggatatga cattaaaaga agcccttaaa atagcatttg gatttaacga accgaatgga    1380
aacttacaat atcaagggaa agacataacc gaatttgatt ttaatttcga tcaacaaaca    1440
tctcaaaata tcaagaatca gttagcggaa ttaaacgcaa ctaacatata tactgtatta    1500
gataaaatca aattaaatgc aaaaatgaat attttaataa gagataaacg ttttcattat    1560
gatagaaata acatagcagt tggggcggat gagtcagtag ttaaggaggc tcatagagaa    1620
gtaattaatt cgtcaacaga gggattattg ttaaatattg ataaggatat aagaaaaata    1680
ttatcaggtt atattgtaga aattgaagat actgaagggc ttaaagaagt tataaatgac    1740
agatatgata tgttgaatat ttctagttta cggcaagatg gaaaaacatt tatagatttt    1800
aaaaaatata atgataaatt accgttatat ataagtaatc ccaattataa ggtaaatgta    1860
tatgctgtta ctaaagaaaa cactattatt aatcctagtg agaatgggga tactagtacc    1920
aacgggatca agaaaatttt aatcttttct aaaaaaggct atgagatagg ataa          1974
```

<210> SEQ ID NO 18
<211> LENGTH: 657
<212> TYPE: PRT
<213> ORGANISM: Bacillus anthracis
<220> FEATURE:
<221> NAME/KEY: MUTAGEN
<222> LOCATION:
<223> OTHER INFORMATION: Amino acid sequence for an artificial LF-PA fusion protein BP109.

<400> SEQUENCE: 18

```
His Met Ala Gly Gly His Gly Asp Val Gly Met His Val Lys Glu Lys
  1               5                  10                  15

Glu Lys Asn Lys Asp Glu Asn Lys Arg Lys Asp Glu Glu Arg Asn Lys
             20                  25                  30

Thr Gln Glu Glu His Leu Lys Glu Ile Met Lys His Ile Val Lys Ile
         35                  40                  45

Glu Val Lys Gly Glu Glu Ala Val Lys Lys Glu Ala Ala Glu Lys Leu
     50                  55                  60

Leu Glu Lys Val Pro Ser Asp Val Leu Glu Met Tyr Lys Ala Ile Gly
 65                  70                  75                  80

Gly Lys Ile Tyr Ile Val Asp Gly Asp Ile Thr Lys His Ile Ser Leu
                 85                  90                  95

Glu Ala Leu Ser Glu Asp Lys Lys Lys Ile Lys Asp Ile Tyr Gly Lys
            100                 105                 110

Asp Ala Leu Leu His Glu His Tyr Val Tyr Ala Lys Glu Gly Tyr Glu
        115                 120                 125

Pro Val Leu Val Ile Gln Ser Ser Glu Asp Tyr Val Glu Asn Thr Glu
    130                 135                 140

Lys Ala Leu Asn Val Tyr Tyr Glu Ile Gly Lys Ile Leu Ser Arg Asp
145                 150                 155                 160

Ile Leu Ser Lys Ile Asn Gln Pro Tyr Gln Lys Phe Leu Asp Val Leu
```

```
                165                 170                 175
Asn Thr Ile Lys Asn Ala Ser Asp Ser Asp Gly Gln Asp Leu Leu Phe
                180                 185                 190

Thr Asn Gln Leu Lys Glu His Pro Thr Asp Phe Ser Val Glu Phe Leu
                195                 200                 205

Glu Gln Asn Ser Asn Glu Val Gln Glu Val Phe Ala Lys Ala Phe Ala
                210                 215                 220

Tyr Tyr Ile Glu Pro Gln His Arg Asp Val Leu Gln Leu Tyr Ala Pro
225                 230                 235                 240

Glu Ala Phe Asn Tyr Met Asp Lys Phe Asn Glu Gln Glu Ile Asn Leu
                245                 250                 255

Ser Leu Glu Glu Leu Lys Asp Gln Arg Met Leu Ser Arg Tyr Glu Lys
                260                 265                 270

Trp Glu Lys Ile Lys Gln His Tyr Gln His Trp Ser Asp Ser Leu Ser
                275                 280                 285

Glu Glu Gly Arg Gly Leu Leu Lys Lys Leu Gln Ile Pro Ile Glu Pro
                290                 295                 300

Lys Lys Asp Asp Ile Ile His Ser Leu Ser Gln Glu Glu Lys Glu Leu
305                 310                 315                 320

Leu Lys Arg Ile Gln Ile Asp Ser Ser Asp Phe Leu Ser Thr Glu Glu
                325                 330                 335

Lys Glu Phe Leu Lys Lys Leu Gln Ile Asp Ile Arg Asp Ser Leu Ser
                340                 345                 350

Glu Glu Glu Lys Glu Leu Leu Asn Arg Ile Gln Val Asp Ser Ser Asn
                355                 360                 365

Pro Leu Ser Glu Lys Glu Lys Glu Phe Leu Lys Lys Leu Lys Leu Asp
370                 375                 380

Ile Gln Pro Tyr Asp Ile Asn Gln Arg Leu Gln Asp Thr Gly Gly Leu
385                 390                 395                 400

Ile Asp Ser Pro Pro Ile Asn Leu Glu Thr Ala Arg Ile Ile Phe Asn
                405                 410                 415

Gly Lys Asp Leu Asn Leu Val Glu Arg Arg Ile Ala Ala Val Asn Pro
                420                 425                 430

Ser Asp Pro Leu Glu Thr Thr Lys Pro Asp Met Thr Leu Lys Glu Ala
                435                 440                 445

Leu Lys Ile Ala Phe Gly Phe Asn Glu Pro Asn Gly Asn Leu Gln Tyr
                450                 455                 460

Gln Gly Lys Asp Ile Thr Glu Phe Asp Phe Asn Phe Asp Gln Gln Thr
465                 470                 475                 480

Ser Gln Asn Ile Lys Asn Gln Leu Ala Glu Leu Asn Ala Thr Asn Ile
                485                 490                 495

Tyr Thr Val Leu Asp Lys Ile Lys Leu Asn Ala Lys Met Asn Ile Leu
                500                 505                 510

Ile Arg Asp Lys Arg Phe His Tyr Asp Arg Asn Asn Ile Ala Val Gly
                515                 520                 525

Ala Asp Glu Ser Val Val Lys Glu Ala His Arg Glu Val Ile Asn Ser
                530                 535                 540

Ser Thr Glu Gly Leu Leu Leu Asn Ile Asp Lys Asp Ile Arg Lys Ile
545                 550                 555                 560

Leu Ser Gly Tyr Ile Val Glu Ile Glu Asp Thr Glu Gly Leu Lys Glu
                565                 570                 575

Val Ile Asn Asp Arg Tyr Asp Met Leu Asn Ile Ser Ser Leu Arg Gln
                580                 585                 590
```

-continued

```
Asp Gly Lys Thr Phe Ile Asp Phe Lys Lys Tyr Asn Asp Lys Leu Pro
        595                 600                 605

Leu Tyr Ile Ser Asn Pro Asn Tyr Lys Val Asn Val Tyr Ala Val Thr
    610                 615                 620

Lys Glu Asn Thr Ile Ile Asn Pro Ser Glu Asn Gly Asp Thr Ser Thr
625                 630                 635                 640

Asn Gly Ile Lys Lys Ile Leu Ile Phe Ser Lys Lys Gly Tyr Glu Ile
                645                 650                 655

Gly
```

<210> SEQ ID NO 19
<211> LENGTH: 2289
<212> TYPE: DNA
<213> ORGANISM: Bacillus anthracis
<220> FEATURE:
<221> NAME/KEY: CDS
<222> LOCATION:
<223> OTHER INFORMATION: DNA coding sequence from pBP109 for an artificial LF-PA fusion protein BP109.

<400> SEQUENCE: 19

| | |
|---|---|
| catatggcgg gcggtcatgg tgatgtaggt atgcacgtaa agagaaaga gaaaaataaa | 60 |
| gatgagaata gagaaaaga tgaagaacga aataaaacac aggaagagca tttaaaggaa | 120 |
| atcatgaaac acattgtaaa aatagaagta aaaggggagg aagctgttaa aaagaggca | 180 |
| gcagaaaagc tacttgagaa agtaccatct gatgttttag agatgtataa agcaattgga | 240 |
| ggaaagatat atattgtgga tggtgatatt acaaaacata tatctttaga agcattatct | 300 |
| gaagataaga aaaaaataaa agacatttat gggaaagatg ctttattaca tgaacattat | 360 |
| gtatatgcaa agaaggata tgaacccgta cttgtaatcc aatcttcgga agattatgta | 420 |
| gaaaatactg aaaaggcact gaacgtttat tatgaaatag gtaagatatt atcaagggat | 480 |
| attttaagta aaattaatca accatatcag aaatttttag atgtattaaa taccattaaa | 540 |
| aatgcatctg attcagatgg acaagatctt ttatttacta atcagcttaa ggaacatccc | 600 |
| acagactttt ctgtagaatt cttggaacaa aatagcaatg aggtacaaga agtatttgcg | 660 |
| aaagcttttg catattatat cgagccacag catcgtgatg ttttacagct ttatgcaccg | 720 |
| gaagctttta attacatgga taatttaac gaacaagaaa taaatctatc cttggaagaa | 780 |
| cttaaagatc aacggatgct gtcaagatat gaaaaatggg aaaagataaa acagcactat | 840 |
| caacactgga gcgattcttt atctgaagaa ggaagaggac ttttaaaaa gctgcagatt | 900 |
| cctattgagc aaagaagaa tgacataatt cattctttat ctcaagaaga aaaagagctt | 960 |
| ctaaaaagaa tacaaattga tagtagtgat ttttatctca ctgaggaaaa agagtttta | 1020 |
| aaaaagctac aaattgatat tcgtgattct ttatctgaag aagaaaaaga gctttaaat | 1080 |
| agaatacagg tggatagtag taatccttta tctgaaaaag aaaaagagtt tttaaaaaag | 1140 |
| ctgaaacttg atattcaacc atacgatatt aatcaaaggt tgcaagatac aggagggtta | 1200 |
| attgatagtc cgccaattaa tcttgatgta agaaagcagt ataaaggga tattcaaaat | 1260 |
| attgatgctt tattacatca atccattgga agtaccttgt acaataaaat ttatttgtat | 1320 |
| gaaaatatga atatcaataa ccttacagca acctaggtg cggatttagt tgattccact | 1380 |
| gataatacta aaattaatag aggtatttc aatgaattca aaaaaattt caaatatagt | 1440 |
| atttctagta actatatgat tgttgatata atgaaaggc ctgcattaga taatgagcgt | 1500 |
| ttgaaatgga gaatccaatt atcaccagat actcgagcag gaactgcacg tatcattttt | 1560 |

```
aatggaaaag atttaaatct ggtagaaagg cggatagcgg cggttaatcc tagtgatcca   1620
ttagaaacga ctaaaccgga tatgacatta aagaagccc ttaaaatagc atttggattt    1680
aacgaaccga atggaaactt acaatatcaa gggaaagaca taaccgaatt tgattttaat   1740
ttcgatcaac aaacatctca aaatatcaag aatcagttag cggaattaaa cgcaactaac   1800
atatatactg tattagataa aatcaaatta atgcaaaaa tgaatatttt aataagagat    1860
aaacgttttc attatgatag aaataacata gcagttgggg cggatgagtc agtagttaag   1920
gaggctcata gagaagtaat taattcgtca acagagggat tattgttaaa tattgataag   1980
gatataagaa aaatattatc aggttatatt gtagaaattg aagatactga agggcttaaa   2040
gaagttataa atgacagata tgatatgttg aatatttcta gtttacggca agatggaaaa   2100
acatttatag attttaaaaa atataatgat aaattaccgt tatatataag taatcccaat   2160
tataaggtaa atgtatatgc tgttactaaa gaaaacacta ttattaatcc tagtgagaat   2220
ggggatacta gtaccaacgg gatcaagaaa attttaatct tttctaaaaa aggctatgag   2280
ataggataa                                                          2289
```

<210> SEQ ID NO 20
<211> LENGTH: 762
<212> TYPE: PRT
<213> ORGANISM: Artificial
<220> FEATURE:
<221> NAME/KEY: MUTAGEN
<222> LOCATION:
<223> OTHER INFORMATION: Amino acid sequence for an artificial LF-PA
      fusion protein BP109.

<400> SEQUENCE: 20

```
His Met Ala Gly Gly His Gly Asp Val Gly Met His Val Lys Glu Lys
  1               5                  10                  15

Glu Lys Asn Lys Asp Glu Asn Lys Arg Lys Asp Glu Glu Arg Asn Lys
             20                  25                  30

Thr Gln Glu Glu His Leu Lys Glu Ile Met Lys His Ile Val Lys Ile
         35                  40                  45

Glu Val Lys Gly Glu Glu Ala Val Lys Lys Glu Ala Glu Lys Leu
     50                  55                  60

Leu Glu Lys Val Pro Ser Asp Val Leu Glu Met Tyr Lys Ala Ile Gly
 65                  70                  75                  80

Gly Lys Ile Tyr Ile Val Asp Gly Asp Ile Thr Lys His Ile Ser Leu
                 85                  90                  95

Glu Ala Leu Ser Glu Asp Lys Lys Ile Lys Asp Ile Tyr Gly Lys
            100                 105                 110

Asp Ala Leu Leu His Glu His Tyr Val Tyr Ala Lys Glu Gly Tyr Glu
        115                 120                 125

Pro Val Leu Val Ile Gln Ser Ser Glu Asp Tyr Val Glu Asn Thr Glu
    130                 135                 140

Lys Ala Leu Asn Val Tyr Tyr Glu Ile Gly Lys Ile Leu Ser Arg Asp
145                 150                 155                 160

Ile Leu Ser Lys Ile Asn Gln Pro Tyr Gln Lys Phe Leu Asp Val Leu
                165                 170                 175

Asn Thr Ile Lys Asn Ala Ser Asp Ser Asp Gly Gln Asp Leu Leu Phe
            180                 185                 190

Thr Asn Gln Leu Lys Glu His Pro Thr Asp Phe Ser Val Glu Phe Leu
        195                 200                 205
```

-continued

```
Glu Gln Asn Ser Asn Glu Val Gln Glu Val Phe Ala Lys Ala Phe Ala
    210                 215                 220

Tyr Tyr Ile Glu Pro Gln His Arg Asp Val Leu Gln Leu Tyr Ala Pro
225                 230                 235                 240

Glu Ala Phe Asn Tyr Met Asp Lys Phe Asn Glu Gln Glu Ile Asn Leu
                245                 250                 255

Ser Leu Glu Glu Leu Lys Asp Gln Arg Met Leu Ser Arg Tyr Glu Lys
            260                 265                 270

Trp Glu Lys Ile Lys Gln His Tyr Gln His Trp Ser Asp Ser Leu Ser
        275                 280                 285

Glu Glu Gly Arg Gly Leu Leu Lys Lys Leu Gln Ile Pro Ile Glu Pro
    290                 295                 300

Lys Lys Asp Asp Ile Ile His Ser Leu Ser Gln Glu Glu Lys Glu Leu
305                 310                 315                 320

Leu Lys Arg Ile Gln Ile Asp Ser Ser Asp Phe Leu Ser Thr Glu Glu
                325                 330                 335

Lys Glu Phe Leu Lys Lys Leu Gln Ile Asp Ile Arg Asp Ser Leu Ser
            340                 345                 350

Glu Glu Glu Lys Glu Leu Leu Asn Arg Ile Gln Val Asp Ser Ser Asn
        355                 360                 365

Pro Leu Ser Glu Lys Glu Lys Glu Phe Leu Lys Lys Leu Lys Leu Asp
370                 375                 380

Ile Gln Pro Tyr Asp Ile Asn Gln Arg Leu Gln Asp Thr Gly Gly Leu
385                 390                 395                 400

Ile Asp Ser Pro Pro Ile Asn Leu Asp Val Arg Lys Gln Tyr Lys Arg
                405                 410                 415

Asp Ile Gln Asn Ile Asp Ala Leu Leu His Gln Ser Ile Gly Ser Thr
            420                 425                 430

Leu Tyr Asn Lys Ile Tyr Leu Tyr Glu Asn Met Asn Ile Asn Asn Leu
        435                 440                 445

Thr Ala Thr Leu Gly Ala Asp Leu Val Asp Ser Thr Asp Asn Thr Lys
    450                 455                 460

Ile Asn Arg Gly Ile Phe Asn Glu Phe Lys Lys Asn Phe Lys Tyr Ser
465                 470                 475                 480

Ile Ser Ser Asn Tyr Met Ile Val Asp Ile Asn Glu Arg Pro Ala Leu
                485                 490                 495

Asp Asn Glu Arg Leu Lys Trp Arg Ile Gln Leu Ser Pro Asp Thr Arg
            500                 505                 510

Ala Gly Thr Ala Arg Ile Ile Phe Asn Gly Lys Asp Leu Asn Leu Val
        515                 520                 525

Glu Arg Arg Ile Ala Ala Val Asn Pro Ser Asp Pro Leu Glu Thr Thr
    530                 535                 540

Lys Pro Asp Met Thr Leu Lys Glu Ala Leu Lys Ile Ala Phe Gly Phe
545                 550                 555                 560

Asn Glu Pro Asn Gly Asn Leu Gln Tyr Gln Gly Lys Asp Ile Thr Glu
                565                 570                 575

Phe Asp Phe Asn Phe Asp Gln Gln Thr Ser Gln Asn Ile Lys Asn Gln
            580                 585                 590

Leu Ala Glu Leu Asn Ala Thr Asn Ile Tyr Thr Val Leu Asp Lys Ile
        595                 600                 605

Lys Leu Asn Ala Lys Met Asn Ile Leu Ile Arg Asp Lys Arg Phe His
    610                 615                 620

Tyr Asp Arg Asn Asn Ile Ala Val Gly Ala Asp Glu Ser Val Val Lys
```

```
                625                 630                 635                 640
       Glu Ala His Arg Glu Val Ile Asn Ser Ser Thr Glu Gly Leu Leu Leu
                       645                 650                 655

Asn Ile Asp Lys Asp Ile Arg Lys Ile Leu Ser Gly Tyr Ile Val Glu
                       660                 665                 670

Ile Glu Asp Thr Glu Gly Leu Lys Glu Val Ile Asn Asp Arg Tyr Asp
                       675                 680                 685

Met Leu Asn Ile Ser Ser Leu Arg Gln Asp Gly Lys Thr Phe Ile Asp
                       690                 695                 700

Phe Lys Lys Tyr Asn Asp Lys Leu Pro Leu Tyr Ile Ser Asn Pro Asn
       705                 710                 715                 720

Tyr Lys Val Asn Val Tyr Ala Val Thr Lys Glu Asn Thr Ile Ile Asn
                       725                 730                 735

Pro Ser Glu Asn Gly Asp Thr Ser Thr Asn Gly Ile Lys Lys Ile Leu
                       740                 745                 750

Ile Phe Ser Lys Lys Gly Tyr Glu Ile Gly
                       755                 760

<210> SEQ ID NO 21
<211> LENGTH: 1722
<212> TYPE: DNA
<213> ORGANISM: Bacillus anthracis
<220> FEATURE:
<221> NAME/KEY: CDS
<222> LOCATION:
<223> OTHER INFORMATION: DNA coding sequence from pBP111 for a
      PA deletion mutant PA64.

<400> SEQUENCE: 21
catatgaaaa agcgaagtac aagtgctgga cctacggttc cagaccgtga caatgatgga        60
atccctgatt cattagaggt agaaggatat acggttgatg tcaaaaataa agaactttt        120 cttcaccat ggatttctaa tattcatgaa agaaaggat taaccaaata taatcatct          180 cctgaaaaat ggagcacggc ttctgatccg tacagtgatt tcgaaaaggt tacaggacgg       240
attgataaga atgtatcacc agaggcaaga cacccccttg tggcagctta tccgattgta       300
catgtagata tggagaatat tattctctca aaaaatgagg atcaatccac acagaatact       360
gatagtcaaa cgagaacaat aagtaaaaat acttctacaa gtaggacaca tactagtgaa       420
gtacatggaa atgcagaagt gcatgcgtcg ttctttgata ttggtgggag tgtatctgca       480
ggatttagta attcgaattc aagtacggtc gcaattgatc attcactatc tctagcaggg       540
gaaagaactt gggctgaaac aatgggttta ataccgctg atacagcaag attaaatgcc       600
atatattgat atgtaaatac tgggacggct ccaatctaca acgtgttacc aacgacttcg       660
ttagtgttag gaaaaaatca aacactcgcg acaattaaag ctaaggaaaa ccaattaagt       720
caaatacttg cacctaataa ttattatcct tctaaaaact ggcgccaat cgcattaaat        780 gcacaagacg atttcagttc tactccaatt acaatgaatt acaatcaatt tcttgagtta       840
gaaaaaacga acaattaag attagatacg gatcaagtat atgggaatat agcaacatac       900
aattttgaaa atggaagagt gagggtggat acaggctcga actggagtga agtgttaccg       960
caaattcaag aaacaactgc acgtatcatt tttaatggaa aagatttaaa tctggtagaa      1020
aggcggatag cggcggttaa tcctagtgat ccattagaaa cgactaaacc ggatatgaca      1080 ttaaagaag ccctaaaat agcatttgga tttaacgaac cgaatggaaa cttacaatat       1140
caagggaaag acataaccga atttgatttt aatttcgatc aacaaacatc tcaaaatatc      1200
```

-continued

```
aagaatcagt tagcggaatt aaacgcaact aacatatata ctgtattaga taaaatcaaa    1260
ttaaatgcaa aaatgaatat tttaataaga gataaacgtt ttcattatga tagaaataac    1320
atagcagttg gggcggatga gtcagtagtt aaggaggctc atagagaagt aattaattcg    1380
tcaacagagg gattattgtt aaatattgat aaggataaa gaaaaatatt atcaggttat    1440
attgtagaaa ttgaagatac tgaagggctt aaagaagtta taaatgacag atatgatatg    1500
ttgaatattt ctagtttacg gcaagatgga aaaacattta tagattttaa aaaatataat    1560
gataaattac cgttatatat aagtaatccc aattataagg taaatgtata tgctgttact    1620
aaagaaaaca ctattattaa tcctagtgag aatggggata ctagtaccaa cgggatcaag    1680 aaaatttaa tcttttctaa aaaaggctat gagataggat aa                       1722
```

<210> SEQ ID NO 22
<211> LENGTH: 573
<212> TYPE: PRT
<213> ORGANISM: Bacillus anthracis
<220> FEATURE:
<221> NAME/KEY: MUTAGEN
<222> LOCATION:
<223> OTHER INFORMATION: Amino acid sequence for a PA deletion mutant PA64

<400> SEQUENCE: 22

```
His Met Lys Lys Arg Ser Thr Ser Ala Gly Pro Thr Val Pro Asp Arg
  1               5                  10                  15

Asp Asn Asp Gly Ile Pro Asp Ser Leu Glu Val Glu Gly Tyr Thr Val
             20                  25                  30

Asp Val Lys Asn Lys Arg Thr Phe Leu Ser Pro Trp Ile Ser Asn Ile
         35                  40                  45

His Glu Lys Lys Gly Leu Thr Lys Tyr Lys Ser Ser Pro Glu Lys Trp
     50                  55                  60

Ser Thr Ala Ser Asp Pro Tyr Ser Asp Phe Glu Lys Val Thr Gly Arg
 65                  70                  75                  80

Ile Asp Lys Asn Val Ser Pro Glu Ala Arg His Pro Leu Val Ala Ala
                 85                  90                  95

Tyr Pro Ile Val His Val Asp Met Glu Asn Ile Ile Leu Ser Lys Asn
            100                 105                 110

Glu Asp Gln Ser Thr Gln Asn Thr Asp Ser Gln Thr Arg Thr Ile Ser
        115                 120                 125

Lys Asn Thr Ser Thr Ser Arg Thr His Thr Ser Glu Val His Gly Asn
    130                 135                 140

Ala Glu Val His Ala Ser Phe Phe Asp Ile Gly Gly Ser Val Ser Ala
145                 150                 155                 160

Gly Phe Ser Asn Ser Asn Ser Ser Thr Val Ala Ile Asp His Ser Leu
                165                 170                 175

Ser Leu Ala Gly Glu Arg Thr Trp Ala Glu Thr Met Gly Leu Asn Thr
            180                 185                 190

Ala Asp Thr Ala Arg Leu Asn Ala Asn Ile Arg Tyr Val Asn Thr Gly
        195                 200                 205

Thr Ala Pro Ile Tyr Asn Val Leu Pro Thr Thr Ser Leu Val Leu Gly
    210                 215                 220

Lys Asn Gln Thr Leu Ala Thr Ile Lys Ala Lys Glu Asn Gln Leu Ser
225                 230                 235                 240

Gln Ile Leu Ala Pro Asn Asn Tyr Tyr Pro Ser Lys Asn Leu Ala Pro
                245                 250                 255
```

-continued

Ile Ala Leu Asn Ala Gln Asp Asp Phe Ser Ser Thr Pro Ile Thr Met
                260                 265                 270

Asn Tyr Asn Gln Phe Leu Glu Leu Glu Lys Thr Lys Gln Leu Arg Leu
            275                 280                 285

Asp Thr Asp Gln Val Tyr Gly Asn Ile Ala Thr Tyr Asn Phe Glu Asn
        290                 295                 300

Gly Arg Val Arg Val Asp Thr Gly Ser Asn Trp Ser Glu Val Leu Pro
305                 310                 315                 320

Gln Ile Gln Glu Thr Thr Ala Arg Ile Ile Phe Asn Gly Lys Asp Leu
                325                 330                 335

Asn Leu Val Glu Arg Arg Ile Ala Ala Val Asn Pro Ser Asp Pro Leu
            340                 345                 350

Glu Thr Thr Lys Pro Asp Met Thr Leu Lys Glu Ala Leu Lys Ile Ala
        355                 360                 365

Phe Gly Phe Asn Glu Pro Asn Gly Asn Leu Gln Tyr Gln Gly Lys Asp
370                 375                 380

Ile Thr Glu Phe Asp Phe Asn Phe Asp Gln Gln Thr Ser Gln Asn Ile
385                 390                 395                 400

Lys Asn Gln Leu Ala Glu Leu Asn Ala Thr Asn Ile Tyr Thr Val Leu
                405                 410                 415

Asp Lys Ile Lys Leu Asn Ala Lys Met Asn Ile Leu Ile Arg Asp Lys
            420                 425                 430

Arg Phe His Tyr Asp Arg Asn Asn Ile Ala Val Gly Ala Asp Glu Ser
        435                 440                 445

Val Val Lys Glu Ala His Arg Glu Val Ile Asn Ser Ser Thr Glu Gly
    450                 455                 460

Leu Leu Leu Asn Ile Asp Lys Asp Ile Arg Lys Ile Leu Ser Gly Tyr
465                 470                 475                 480

Ile Val Glu Ile Glu Asp Thr Glu Gly Leu Lys Glu Val Ile Asn Asp
                485                 490                 495

Arg Tyr Asp Met Leu Asn Ile Ser Ser Leu Arg Gln Asp Gly Lys Thr
            500                 505                 510

Phe Ile Asp Phe Lys Lys Tyr Asn Asp Lys Leu Pro Leu Tyr Ile Ser
        515                 520                 525

Asn Pro Asn Tyr Lys Val Asn Val Tyr Ala Val Thr Lys Glu Asn Thr
    530                 535                 540

Ile Ile Asn Pro Ser Glu Asn Gly Asp Thr Ser Thr Asn Gly Ile Lys
545                 550                 555                 560

Lys Ile Leu Ile Phe Ser Lys Lys Gly Tyr Glu Ile Gly
                565                 570

<210> SEQ ID NO 23
<211> LENGTH: 1272
<212> TYPE: DNA
<213> ORGANISM: Bacillus anthracis
<220> FEATURE:
<221> NAME/KEY: CDS
<222> LOCATION:
<223> OTHER INFORMATION: DNA coding sequence from pBP113 for a PA
      deletion mutant PA47.

<400> SEQUENCE: 23
catatggata ttggtgggag tgtatctgca ggatttagta attcgaattc aagtacggtc      60
gcaattgatc attcactatc tctagcaggg gaaagaactt gggctgaaac aatgggttta     120
aataccgctg atacagcaag attaaatgcc aatattgat atgtaaatac tgggacggct     180

-continued

```
ccaatctaca acgtgttacc aacgacttcg ttagtgttag gaaaaaatca aacactcgcg    240
acaattaaag ctaaggaaaa ccaattaagt caaatacttg cacctaataa ttattatcct    300
tctaaaaact tggcgccaat cgcattaaat gcacaagacg atttcagttc tactccaatt    360
acaatgaatt acaatcaatt tcttgagtta gaaaaaacga aacaattaag attagatacg    420
gatcaagtat atgggaatat agcaacatac aattttgaaa atggaagagt gagggtggat    480
acaggctcga actggagtga agtgttaccg caaattcaag aaacaactgc acgtatcatt    540
tttaatggaa aagatttaaa tctggtagaa aggcggatag cggcggttaa tcctagtgat    600
ccattagaaa cgactaaacc ggatatgaca ttaaaagaag cccttaaaat agcatttgga    660
tttaacgaac cgaatggaaa cttacaatat caagggaaag ataaccga atttgatttt     720 aatttcgatc aacaaacatc tcaaaatatc aagaatcagt tagcggaatt aaacgcaact    780
aacatatata ctgtattaga taaaatcaaa ttaaatgcaa aatgaatat tttaataaga     840 gataaacgtt ttcattatga tagaaataac atagcagttg gggcggatga gtcagtagtt    900
aaggaggctc atagagaagt aattaattcg tcaacagagg gattattgtt aaatattgat    960
aaggatataa gaaaaatatt atcaggttat attgtagaaa ttgaagatac tgaagggctt   1020
aaagaagtta taaatgacag atatgatatg ttgaatattt ctagtttacg gcaagatgga   1080
aaaacattta tagattttaa aaaatataat gataaattac cgttatatat aagtaatccc   1140
aattataagg taaatgtata tgctgttact aaagaaaaca ctattattaa tcctagtgag   1200
aatggggata ctagtaccaa cgggatcaag aaaattttaa tcttttctaa aaaaggctat   1260
gagataggat aa                                                       1272
```

<210> SEQ ID NO 24
<211> LENGTH: 423
<212> TYPE: PRT
<213> ORGANISM: Bacillus anthracis
<220> FEATURE:
<221> NAME/KEY: MUTAGEN
<222> LOCATION:
<223> OTHER INFORMATION: Amino acid sequence for a PA deletion mutant PA47.

<400> SEQUENCE: 24

```
His Met Asp Ile Gly Gly Ser Val Ser Ala Gly Phe Ser Asn Ser Asn
  1               5                  10                  15

Ser Ser Thr Val Ala Ile Asp His Ser Leu Ser Leu Ala Gly Glu Arg
             20                  25                  30

Thr Trp Ala Glu Thr Met Gly Leu Asn Thr Ala Asp Thr Ala Arg Leu
         35                  40                  45

Asn Ala Asn Ile Arg Tyr Val Asn Thr Gly Thr Ala Pro Ile Tyr Asn
     50                  55                  60

Val Leu Pro Thr Thr Ser Leu Val Leu Gly Lys Asn Gln Thr Leu Ala
 65                  70                  75                  80

Thr Ile Lys Ala Lys Glu Asn Gln Leu Ser Gln Ile Leu Ala Pro Asn
                 85                  90                  95

Asn Tyr Tyr Pro Ser Lys Asn Leu Ala Pro Ile Ala Leu Asn Ala Gln
            100                 105                 110

Asp Asp Phe Ser Ser Thr Pro Ile Thr Met Asn Tyr Asn Gln Phe Leu
        115                 120                 125

Glu Leu Glu Lys Thr Lys Gln Leu Arg Leu Asp Thr Asp Gln Val Tyr
    130                 135                 140

Gly Asn Ile Ala Thr Tyr Asn Phe Glu Asn Gly Arg Val Arg Val Asp
```

```
145                 150                 155                 160
Thr Gly Ser Asn Trp Ser Glu Val Leu Pro Gln Ile Gln Glu Thr Thr
                165                 170                 175
Ala Arg Ile Ile Phe Asn Gly Lys Asp Leu Asn Leu Val Glu Arg Arg
            180                 185                 190
Ile Ala Ala Val Asn Pro Ser Asp Pro Leu Glu Thr Thr Lys Pro Asp
        195                 200                 205
Met Thr Leu Lys Glu Ala Leu Lys Ile Ala Phe Gly Phe Asn Glu Pro
    210                 215                 220
Asn Gly Asn Leu Gln Tyr Gln Gly Lys Asp Ile Thr Glu Phe Asp Phe
225                 230                 235                 240
Asn Phe Asp Gln Gln Thr Ser Gln Asn Ile Lys Asn Gln Leu Ala Glu
                245                 250                 255
Leu Asn Ala Thr Asn Ile Tyr Thr Val Leu Asp Lys Ile Lys Leu Asn
            260                 265                 270
Ala Lys Met Asn Ile Leu Ile Arg Asp Lys Arg Phe His Tyr Asp Arg
        275                 280                 285
Asn Asn Ile Ala Val Gly Ala Asp Glu Ser Val Val Lys Glu Ala His
290                 295                 300
Arg Glu Val Ile Asn Ser Ser Thr Glu Gly Leu Leu Leu Asn Ile Asp
305                 310                 315                 320
Lys Asp Ile Arg Lys Ile Leu Ser Gly Tyr Ile Val Glu Ile Glu Asp
                325                 330                 335
Thr Glu Gly Leu Lys Glu Val Ile Asn Asp Arg Tyr Asp Met Leu Asn
            340                 345                 350
Ile Ser Ser Leu Arg Gln Asp Gly Lys Thr Phe Ile Asp Phe Lys Lys
        355                 360                 365
Tyr Asn Asp Lys Leu Pro Leu Tyr Ile Ser Asn Pro Asn Tyr Lys Val
    370                 375                 380
Asn Val Tyr Ala Val Thr Lys Glu Asn Thr Ile Ile Asn Pro Ser Glu
385                 390                 395                 400
Asn Gly Asp Thr Ser Thr Asn Gly Ile Lys Lys Ile Leu Ile Phe Ser
                405                 410                 415
Lys Lys Gly Tyr Glu Ile Gly
            420
```

<210> SEQ ID NO 25
<211> LENGTH: 723
<212> TYPE: DNA
<213> ORGANISM: Bacillus anthracis
<220> FEATURE:
<221> NAME/KEY: CDS
<222> LOCATION:
<223> OTHER INFORMATION: DNA coding sequence from pBP115 for a PA deletion mutant PA27.

<400> SEQUENCE: 25

```
catatgttaa atctggtaga aaggcggata gcggcggtta atcctagtga tccattagaa      60
acgactaaac cggatatgac attaaaagaa gcccttaaaa tagcatttgg atttaacgaa     120
ccgaatggaa acttacaata tcaagggaaa gacataaccg aatttgattt taatttcgat     180
caacaaacat ctcaaaatat caagaatcag ttagcggaat aaacgcaac taacatatat     240
actgtattag ataaaatcaa attaaatgca aaaatgaata ttttaataag agataaacgt     300
tttcattatg atagaaataa catagcagtt ggggcggatg agtcagtagt taaggaggct     360
catagagaag taattaattc gtcaacagag ggattattgt taaatattga taaggatata     420
```

```
agaaaaatat tatcaggtta tattgtagaa attgaagata ctgaagggct taaagaagtt     480
ataaatgaca gatatgatat gttgaatatt tctagtttac ggcaagatgg aaaaacattt     540
atagatttta aaaatataa tgataaatta ccgttatata taagtaatcc caattataag     600
gtaaatgtat atgctgttac taaagaaaac actattatta atcctagtga gaatggggat     660
actagtacca acgggatcaa gaaaatttta atcttttcta aaaaaggcta tgagatagga     720
taa                                                                   723
```

```
<210> SEQ ID NO 26
<211> LENGTH: 240
<212> TYPE: PRT
<213> ORGANISM: Bacillus anthracis
<220> FEATURE:
<221> NAME/KEY: MUTAGEN
<222> LOCATION:
<223> OTHER INFORMATION: Amino acid sequence of a PA deletion mutant
      PA27.

<400> SEQUENCE: 26
```

```
His Met Leu Asn Leu Val Glu Arg Arg Ile Ala Ala Val Asn Pro Ser
1               5                   10                  15

Asp Pro Leu Glu Thr Thr Lys Pro Asp Met Thr Leu Lys Glu Ala Leu
            20                  25                  30

Lys Ile Ala Phe Gly Phe Asn Glu Pro Asn Gly Asn Leu Gln Tyr Gln
        35                  40                  45

Gly Lys Asp Ile Thr Glu Phe Asp Phe Asn Phe Asp Gln Gln Thr Ser
    50                  55                  60

Gln Asn Ile Lys Asn Gln Leu Ala Glu Leu Asn Ala Thr Asn Ile Tyr
65                  70                  75                  80

Thr Val Leu Asp Lys Ile Lys Leu Asn Ala Lys Met Asn Ile Leu Ile
                85                  90                  95

Arg Asp Lys Arg Phe His Tyr Asp Arg Asn Asn Ile Ala Val Gly Ala
            100                 105                 110

Asp Glu Ser Val Val Lys Glu Ala His Arg Glu Val Ile Asn Ser Ser
        115                 120                 125

Thr Glu Gly Leu Leu Leu Asn Ile Asp Lys Asp Ile Arg Lys Ile Leu
    130                 135                 140

Ser Gly Tyr Ile Val Glu Ile Glu Asp Thr Glu Gly Leu Lys Glu Val
145                 150                 155                 160

Ile Asn Asp Arg Tyr Asp Met Leu Asn Ile Ser Ser Leu Arg Gln Asp
                165                 170                 175

Gly Lys Thr Phe Ile Asp Phe Lys Lys Tyr Asn Asp Lys Leu Pro Leu
            180                 185                 190

Tyr Ile Ser Asn Pro Asn Tyr Lys Val Asn Val Tyr Ala Val Thr Lys
        195                 200                 205

Glu Asn Thr Ile Ile Asn Pro Ser Glu Asn Gly Asp Thr Ser Thr Asn
    210                 215                 220

Gly Ile Lys Lys Ile Leu Ile Phe Ser Lys Lys Gly Tyr Glu Ile Gly
225                 230                 235                 240
```

```
<210> SEQ ID NO 27
<211> LENGTH: 2070
<212> TYPE: DNA
<213> ORGANISM: Bacillus anthracis
<220> FEATURE:
<221> NAME/KEY: CDS
<222> LOCATION:
```

-continued

<223> OTHER INFORMATION: DNA coding sequence from pBP116 for a LF deletion mutant LF80.

<400> SEQUENCE: 27

```
catatggcgg gcggtcatgg tgatgtaggt atgcacgtaa aagagaaaga gaaaaataaa     60
gatgagaata agagaaaaga tgaagaacga aataaaacac aggaagagca tttaaaggaa    120
atcatgaaac acattgtaaa aatagaagta aaaggggagg aagctgttaa aaaagaggca    180
gcagaaaagc tacttgagaa agtaccatct gatgttttag agatgtataa agcaattgga    240
ggaaagatat atattgtgga tggtgatatt acaaaacata tatctttaga agcattatct    300
gaagataaga aaaaaataaa agacatttat gggaaagatg ctttattaca tgaacattat    360
gtatatgcaa aagaaggata tgaacccgta cttgtaatcc aatcttcgga agattatgta    420
gaaaatactg aaaaggcact gaacgtttat tatgaaatag gtaagatatt atcaagggat    480
attttaagta aaattaatca accatatcag aaatttttag atgtattaaa taccattaaa    540
aatgcatctg attcagatgg acaagatctt ttatttacta atcagcttaa ggaacatccc    600
acagactttt ctgtagaatt cttggaacaa aatagcaatg aggtacaaga agtatttgcg    660
aaagcttttg catattatat cgagccacag catcgtgatg ttttacagct ttatgcaccg    720
gaagctttta attacatgga taaatttaac gaacaagaaa taaatctatc cttggaagaa    780
cttaaagatc aacggatgct gtcaagatat gaaaaatggg aaaagataaa acagcactat    840
caacactgga gcgattcttt atctgaagaa ggaagaggac ttttaaaaaa gctgcagatt    900
cctattgagc caaagaaaga tgacataatt cattctttat ctcaagaaga aaaagagctt    960
ctaaaaagaa tacaaattga tagtagtgat tttttatcta ctgaggaaaa agagttttta   1020
aaaaagctac aaattgatat tcgtgattct ttatctgaag aagaaaaaga gcttttaaat   1080
agaatacagg tggatagtag taatccttta tctgaaaaag aaaaagagtt tttaaaaaag   1140
ctgaaacttg atattcaacc atacgatatt aatcaaaggt tgcaagatac aggagggtta   1200
attgatagtc cgccaattaa tcttgatgta agaaagcagt ataaaaggga tattcaaaat   1260
attgatgctt tattacatca atccattgga agtaccttgt acaataaaat ttatttgtat   1320
gaaaatatga atatcaataa ccttacagca accctaggtg cggatttagt tgattccact   1380
gataatacta aaattaatag aggtattttc aatgaattca aaaaaaattt caaatatagt   1440
atttctagta actatatgat tgttgatata aatgaaaggc ctgcattaga taatgagcgt   1500
ttgaaatgga gaatccaatt atcaccagat actcgagcag gatatttaga aaatggaaag   1560
cttatattac aaagaaacat cggtctggaa ataaaggatg tacaaataat taagcaatcc   1620
gaaaaagaat atataaggat tgatgcgaaa gtagtgccaa agagtaaaat agatacaaaa   1680
attcaagaag cacagttaaa tataaatcag gaatggaata aagcattagg gttaccaaaa   1740
tatacaaagc ttattacatt caacgtgcat aatagatatg catccaatat tgtagaaagt   1800
gcttatttaa tattgaatga atggaaaaat aatattcaaa gtgatcttat aaaaaaggta   1860
acaaattact tagttgatgg taatggaaga tttgttttta ccgatattac tctccctaat   1920
atagctgaac aatatacaca tcaagatgag atatatgagc aagttcattc aaaagggtta   1980
tatgttccag aatcccgttc tatattactc catggacctt caaaaggtgt agaattaagg   2040
aatgatagtg agggttttat acacgaataa                                    2070
```

<210> SEQ ID NO 28
<211> LENGTH: 689
<212> TYPE: PRT

```
<213> ORGANISM: Bacillus anthracis
<220> FEATURE:
<221> NAME/KEY: MUTAGEN
<222> LOCATION:
<223> OTHER INFORMATION: Amino acid sequence of a LF deletion mutant
      LF80.

<400> SEQUENCE: 28
```

| | | | | | | | | | | | | | | | |
|---|---|---|---|---|---|---|---|---|---|---|---|---|---|---|---|
| His | Met | Ala | Gly | Gly | His | Gly | Asp | Val | Gly | Met | His | Val | Lys | Glu | Lys |
| 1 | | | | 5 | | | | | 10 | | | | | 15 | |
| Glu | Lys | Asn | Lys | Asp | Glu | Asn | Lys | Arg | Lys | Asp | Glu | Glu | Arg | Asn | Lys |
| | | | 20 | | | | | 25 | | | | | 30 | | |
| Thr | Gln | Glu | Glu | His | Leu | Lys | Glu | Ile | Met | Lys | His | Ile | Val | Lys | Ile |
| | | | 35 | | | | | 40 | | | | | 45 | | |
| Glu | Val | Lys | Gly | Glu | Glu | Ala | Val | Lys | Lys | Glu | Ala | Ala | Glu | Lys | Leu |
| | | 50 | | | | | 55 | | | | | 60 | | | |
| Leu | Glu | Lys | Val | Pro | Ser | Asp | Val | Leu | Glu | Met | Tyr | Lys | Ala | Ile | Gly |
| 65 | | | | | 70 | | | | | 75 | | | | | 80 |
| Gly | Lys | Ile | Tyr | Ile | Val | Asp | Gly | Asp | Ile | Thr | Lys | His | Ile | Ser | Leu |
| | | | | 85 | | | | | 90 | | | | | 95 | |
| Glu | Ala | Leu | Ser | Glu | Asp | Lys | Lys | Lys | Ile | Lys | Asp | Ile | Tyr | Gly | Lys |
| | | | | 100 | | | | | 105 | | | | | 110 | |
| Asp | Ala | Leu | Leu | His | Glu | His | Tyr | Val | Tyr | Ala | Lys | Glu | Gly | Tyr | Glu |
| | | | 115 | | | | | 120 | | | | | 125 | | |
| Pro | Val | Leu | Val | Ile | Gln | Ser | Ser | Glu | Asp | Tyr | Val | Glu | Asn | Thr | Glu |
| | | 130 | | | | | 135 | | | | | 140 | | | |
| Lys | Ala | Leu | Asn | Val | Tyr | Tyr | Glu | Ile | Gly | Lys | Ile | Leu | Ser | Arg | Asp |
| 145 | | | | | 150 | | | | | 155 | | | | | 160 |
| Ile | Leu | Ser | Lys | Ile | Asn | Gln | Pro | Tyr | Gln | Lys | Phe | Leu | Asp | Val | Leu |
| | | | | 165 | | | | | 170 | | | | | 175 | |
| Asn | Thr | Ile | Lys | Asn | Ala | Ser | Asp | Ser | Asp | Gly | Gln | Asp | Leu | Leu | Phe |
| | | | 180 | | | | | 185 | | | | | 190 | | |
| Thr | Asn | Gln | Leu | Lys | Glu | His | Pro | Thr | Asp | Phe | Ser | Val | Glu | Phe | Leu |
| | | | 195 | | | | | 200 | | | | | 205 | | |
| Glu | Gln | Asn | Ser | Asn | Glu | Val | Gln | Glu | Val | Phe | Ala | Lys | Ala | Phe | Ala |
| | | | 210 | | | | | 215 | | | | | 220 | | |
| Tyr | Tyr | Ile | Glu | Pro | Gln | His | Arg | Asp | Val | Leu | Gln | Leu | Tyr | Ala | Pro |
| 225 | | | | | 230 | | | | | 235 | | | | | 240 |
| Glu | Ala | Phe | Asn | Tyr | Met | Asp | Lys | Phe | Asn | Glu | Gln | Glu | Ile | Asn | Leu |
| | | | | 245 | | | | | 250 | | | | | 255 | |
| Ser | Leu | Glu | Glu | Leu | Lys | Asp | Gln | Arg | Met | Leu | Ser | Arg | Tyr | Glu | Lys |
| | | | 260 | | | | | 265 | | | | | 270 | | |
| Trp | Glu | Lys | Ile | Lys | Gln | His | Tyr | Gln | His | Trp | Ser | Asp | Ser | Leu | Ser |
| | | 275 | | | | | 280 | | | | | 285 | | | |
| Glu | Glu | Gly | Arg | Gly | Leu | Leu | Lys | Lys | Leu | Gln | Ile | Pro | Ile | Glu | Pro |
| | | 290 | | | | | 295 | | | | | 300 | | | |
| Lys | Lys | Asp | Asp | Ile | Ile | His | Ser | Leu | Ser | Gln | Glu | Glu | Lys | Glu | Leu |
| 305 | | | | | 310 | | | | | 315 | | | | | 320 |
| Leu | Lys | Arg | Ile | Gln | Ile | Asp | Ser | Ser | Asp | Phe | Leu | Ser | Thr | Glu | Glu |
| | | | | 325 | | | | | 330 | | | | | 335 | |
| Lys | Glu | Phe | Leu | Lys | Lys | Leu | Gln | Ile | Asp | Ile | Arg | Asp | Ser | Leu | Ser |
| | | | 340 | | | | | 345 | | | | | 350 | | |
| Glu | Glu | Glu | Lys | Glu | Leu | Leu | Asn | Arg | Ile | Gln | Val | Asp | Ser | Ser | Asn |
| | | | 355 | | | | | 360 | | | | | 365 | | |
| Pro | Leu | Ser | Glu | Lys | Glu | Lys | Glu | Phe | Leu | Lys | Lys | Leu | Lys | Leu | Asp |

```
                370             375             380
Ile Gln Pro Tyr Asp Ile Asn Gln Arg Leu Gln Asp Thr Gly Gly Leu
385                 390                 395                 400

Ile Asp Ser Pro Ser Ile Asn Leu Asp Val Arg Lys Gln Tyr Lys Arg
                405                 410                 415

Asp Ile Gln Asn Ile Asp Ala Leu Leu His Gln Ser Ile Gly Ser Thr
            420                 425                 430

Leu Tyr Asn Lys Ile Tyr Leu Tyr Glu Asn Met Asn Ile Asn Asn Leu
        435                 440                 445

Thr Ala Thr Leu Gly Ala Asp Leu Val Asp Ser Thr Asp Asn Thr Lys
    450                 455                 460

Ile Asn Arg Gly Ile Phe Asn Glu Phe Lys Lys Asn Phe Lys Tyr Ser
465                 470                 475                 480

Ile Ser Ser Asn Tyr Met Ile Val Asp Ile Asn Glu Arg Pro Ala Leu
                485                 490                 495

Asp Asn Glu Arg Leu Lys Trp Arg Ile Gln Leu Ser Pro Asp Thr Arg
            500                 505                 510

Ala Gly Tyr Leu Glu Asn Gly Lys Leu Ile Leu Gln Arg Asn Ile Gly
        515                 520                 525

Leu Glu Ile Lys Asp Val Gln Ile Ile Lys Gln Ser Glu Lys Glu Tyr
    530                 535                 540

Ile Arg Ile Asp Ala Lys Val Val Pro Lys Ser Lys Ile Asp Thr Lys
545                 550                 555                 560

Ile Gln Glu Ala Gln Leu Asn Ile Asn Gln Glu Trp Asn Lys Ala Leu
                565                 570                 575

Gly Leu Pro Lys Tyr Thr Lys Leu Ile Thr Phe Asn Val His Asn Arg
            580                 585                 590

Tyr Ala Ser Asn Ile Val Glu Ser Ala Tyr Leu Ile Leu Asn Glu Trp
        595                 600                 605

Lys Asn Asn Ile Gln Ser Asp Leu Ile Lys Lys Val Thr Asn Tyr Leu
    610                 615                 620

Val Asp Gly Asn Gly Arg Phe Val Phe Thr Asp Ile Thr Leu Pro Asn
625                 630                 635                 640

Ile Ala Glu Gln Tyr Thr His Gln Asp Glu Ile Tyr Glu Gln Val His
                645                 650                 655

Ser Lys Gly Leu Tyr Val Pro Glu Ser Arg Ser Ile Leu Leu His Gly
            660                 665                 670

Pro Ser Lys Gly Val Glu Leu Arg Asn Asp Ser Glu Gly Phe Ile His
        675                 680                 685

Glu

<210> SEQ ID NO 29
<211> LENGTH: 1497
<212> TYPE: DNA
<213> ORGANISM: Bacillus anthracis
<220> FEATURE:
<221> NAME/KEY: CDS
<222> LOCATION:
<223> OTHER INFORMATION: DNA coding sequence from pBP118 for a LF
      deletion mutant LF60.

<400> SEQUENCE: 29
catatggcgg gcggtcatgg tgatgtaggt atgcacgtaa aagagaaaga gaaaataaa      60 gatgagaata agagaaaaga tgaagaacga aataaaacac aggaagagca tttaaggaa    120 atcatgaaac acattgtaaa aatagaagta aaaggggagg aagctgttaa aaaagaggca   180
```

-continued

```
gcagaaaagc tacttgagaa agtaccatct gatgttttag agatgtataa agcaattgga    240
ggaaagatat atattgtgga tggtgatatt acaaaacata tatctttaga agcattatct    300
gaagataaga aaaaataaa agacatttat gggaaagatg ctttattaca tgaacattat    360
gtatatgcaa agaaggata tgaacccgta cttgtaatcc aatcttcgga agattatgta    420
gaaaatactg aaaaggcact gaacgtttat tatgaaatag gtaagatatt atcaagggat    480
attttaagta aaattaatca accatatcag aaattttag atgtattaaa taccattaaa    540
aatgcatctg attcagatgg acaagatctt ttatttacta atcagcttaa ggaacatccc    600
acagactttt ctgtagaatt cttggaacaa aatagcaatg aggtacaaga agtatttgcg    660
aaagcttttg catattatat cgagccacag catcgtgatg ttttacagct ttatgcaccg    720 gaagcttta attacatgga taaatttaac gaacaagaaa taaatctatc cttggaagaa    780
cttaaagatc aacggatgct gtcaagatat gaaaatggg aaaagataaa acagcactat    840
caacactgga gcgattcttt atctgaagaa ggaagaggac ttttaaaaaa gctgcagatt    900
cctattgagc caagaaaga tgacataatt cattctttat ctcaagaaga aaaagagctt    960
ctaaaaagaa tacaaattga tagtagtgat tttttatcta ctgaggaaaa agagttttta   1020
aaaaagctac aaattgatat tcgtgattct ttatctgaag aagaaaaaga gcttttaaat   1080
agaatacagg tggatagtag taatccttta tctgaaaaag aaaaagagtt tttaaaaaag   1140
ctgaaacttg atattcaacc atacgatatt aatcaaaggt tgcaagatac aggagggtta   1200
attgatagtc cgccaattaa tcttgatgta agaaagcagt ataaaaggga tattcaaaat   1260
attgatgctt tattacatca atccattgga agtaccttgt acaataaaat ttatttgtat   1320
gaaaatatga atatcaataa ccttacagca accctaggtg cggatttagt tgattccact   1380
gataatacta aaattaatag aggtattttc aatgaattca aaaaaatttt caaatatagt   1440
atttctagta actatatgat tgttgatata aatgaaaggc ctgcattaga taattaa       1497
```

<210> SEQ ID NO 30
<211> LENGTH: 498
<212> TYPE: PRT
<213> ORGANISM: Bacillus anthracis
<220> FEATURE:
<221> NAME/KEY: MUTAGEN
<222> LOCATION:
<223> OTHER INFORMATION: Amino acid sequence of a LF deletion mutant LF60.

<400> SEQUENCE: 30

```
His Met Ala Gly Gly His Gly Asp Val Gly Met His Val Lys Glu Lys
 1               5                  10                  15

Glu Lys Asn Lys Asp Glu Asn Lys Arg Lys Asp Glu Glu Arg Asn Lys
            20                  25                  30

Thr Gln Glu Glu His Leu Lys Glu Ile Met Lys His Ile Val Lys Ile
        35                  40                  45

Glu Val Lys Gly Glu Glu Ala Val Lys Lys Glu Ala Ala Glu Lys Leu
    50                  55                  60

Leu Glu Lys Val Pro Ser Asp Val Leu Glu Met Tyr Lys Ala Ile Gly
65                  70                  75                  80

Gly Lys Ile Tyr Ile Val Asp Gly Asp Ile Thr Lys His Ile Ser Leu
                85                  90                  95

Glu Ala Leu Ser Glu Asp Lys Lys Lys Ile Lys Asp Ile Tyr Gly Lys
            100                 105                 110
```

```
Asp Ala Leu Leu His Glu His Tyr Val Tyr Ala Lys Glu Gly Tyr Glu
        115                 120                 125

Pro Val Leu Val Ile Gln Ser Ser Glu Asp Tyr Val Glu Asn Thr Glu
    130                 135                 140

Lys Ala Leu Asn Val Tyr Tyr Glu Ile Gly Lys Ile Leu Ser Arg Asp
145                 150                 155                 160

Ile Leu Ser Lys Ile Asn Gln Pro Tyr Gln Lys Phe Leu Asp Val Leu
                165                 170                 175

Asn Thr Ile Lys Asn Ala Ser Asp Ser Asp Gly Gln Asp Leu Leu Phe
            180                 185                 190

Thr Asn Gln Leu Lys Glu His Pro Thr Asp Phe Ser Val Glu Phe Leu
        195                 200                 205

Glu Gln Asn Ser Asn Glu Val Gln Glu Val Phe Ala Lys Ala Phe Ala
    210                 215                 220

Tyr Tyr Ile Glu Pro Gln His Arg Asp Val Leu Gln Leu Tyr Ala Pro
225                 230                 235                 240

Glu Ala Phe Asn Tyr Met Asp Lys Phe Asn Glu Gln Glu Ile Asn Leu
                245                 250                 255

Ser Leu Glu Glu Leu Lys Asp Gln Arg Met Leu Ser Arg Tyr Glu Lys
            260                 265                 270

Trp Glu Lys Ile Lys Gln His Tyr Gln His Trp Ser Asp Ser Leu Ser
        275                 280                 285

Glu Glu Gly Arg Gly Leu Leu Lys Lys Leu Gln Ile Pro Ile Glu Pro
    290                 295                 300

Lys Lys Asp Asp Ile Ile His Ser Leu Ser Gln Glu Glu Lys Glu Leu
305                 310                 315                 320

Leu Lys Arg Ile Gln Ile Asp Ser Ser Asp Phe Leu Ser Thr Glu Glu
                325                 330                 335

Lys Glu Phe Leu Lys Lys Leu Gln Ile Asp Ile Arg Asp Ser Leu Ser
            340                 345                 350

Glu Glu Glu Lys Glu Leu Leu Asn Arg Ile Gln Val Asp Ser Ser Asn
        355                 360                 365

Pro Leu Ser Glu Lys Glu Lys Glu Phe Leu Lys Lys Leu Lys Leu Asp
    370                 375                 380

Ile Gln Pro Tyr Asp Ile Asn Gln Arg Leu Gln Asp Thr Gly Gly Leu
385                 390                 395                 400

Ile Asp Ser Pro Ser Ile Asn Leu Asp Val Arg Lys Gln Tyr Lys Arg
                405                 410                 415

Asp Ile Gln Asn Ile Asp Ala Leu Leu His Gln Ser Ile Gly Ser Thr
            420                 425                 430

Leu Tyr Asn Lys Ile Tyr Leu Tyr Glu Asn Met Asn Ile Asn Asn Leu
        435                 440                 445

Thr Ala Thr Leu Gly Ala Asp Leu Val Asp Ser Thr Asp Asn Thr Lys
    450                 455                 460

Ile Asn Arg Gly Ile Phe Asn Glu Phe Lys Lys Asn Phe Lys Tyr Ser
465                 470                 475                 480

Ile Ser Ser Asn Tyr Met Ile Val Asp Ile Asn Glu Arg Pro Ala Leu
                485                 490                 495

Asp Asn
```

<210> SEQ ID NO 31
<211> LENGTH: 1206
<212> TYPE: DNA
<213> ORGANISM: Bacillus anthracis
<220> FEATURE:
<221> NAME/KEY: CDS
<222> LOCATION:
<223> OTHER INFORMATION: DNA coding sequence from pBP119 for a LF
      deletion mutant LF50.

<400> SEQUENCE: 31

| catatggcgg | gcggtcatgg | tgatgtaggt | atgcacgtaa | aagagaaaga | gaaaaataaa | 60 |
| gatgagaata | agagaaaaga | tgaagaacga | aataaaacac | aggaagagca | tttaaaggaa | 120 |
| atcatgaaac | acattgtaaa | aatagaagta | aaaggggagg | aagctgttaa | aaaagaggca | 180 |
| gcagaaaagc | tacttgagaa | agtaccatct | gatgttttag | agatgtataa | agcaattgga | 240 |
| ggaaagatat | atattgtgga | tggtgatatt | acaaaacata | tatctttaga | agcattatct | 300 |
| gaagataaga | aaaaaataaa | agacatttat | gggaaagatg | ctttattaca | tgaacattat | 360 |
| gtatatgcaa | agaaggata | tgaacccgta | cttgtaatcc | aatcttcgga | agattatgta | 420 |
| gaaaatactg | aaaaggcact | gaacgtttat | tatgaaatag | gtaagatatt | atcaagggat | 480 |
| attttaagta | aaattaatca | accatatcag | aaattttag | atgtattaaa | taccattaaa | 540 |
| aatgcatctg | attcagatgg | acaagatctt | ttatttacta | atcagcttaa | ggaacatccc | 600 |
| acagactttt | ctgtagaatt | cttggaacaa | aatagcaatg | aggtacaaga | agtatttgcg | 660 |
| aaagcttttg | catattatat | cgagccacag | catcgtgatg | ttttacagct | ttatgcaccg | 720 |
| gaagctttta | attacatgga | taaatttaac | gaacaagaaa | taaatctatc | cttggaagaa | 780 |
| cttaaagatc | aacggatgct | gtcaagatat | gaaaaatggg | aaaagataaa | acagcactat | 840 |
| caacactgga | gcgattcttt | atctgaagaa | ggaagaggac | ttttaaaaaa | gctgcagatt | 900 |
| cctattgagc | caaagaaaga | tgacataatt | cattctttat | ctcaagaaga | aaaagagctt | 960 |
| ctaaaaagaa | tacaaattga | tagtagtgat | ttttttatcta | ctgaggaaaa | agagtttta | 1020 |
| aaaaagctac | aaattgatat | tcgtgattct | ttatctgaag | aagaaaaaga | gcttttaaat | 1080 |
| agaatacagg | tggatagtag | taatcccttta | tctgaaaaag | aaaaagagtt | tttaaaaaag | 1140 |
| ctgaaacttg | atattcaacc | atacgatatt | aatcaaaggt | tgcaagatac | aggagggtta | 1200 |
| atttaa | | | | | | 1206 |

<210> SEQ ID NO 32
<211> LENGTH: 401
<212> TYPE: PRT
<213> ORGANISM: Bacillus anthracis
<220> FEATURE:
<221> NAME/KEY: MUTAGEN
<222> LOCATION:
<223> OTHER INFORMATION: Amino acid sequence of a LF deletion mutant
      LF50.

<400> SEQUENCE: 32

```
His Met Ala Gly Gly His Gly Asp Val Gly Met His Val Lys Glu Lys
  1               5                  10                  15

Glu Lys Asn Lys Asp Glu Asn Lys Arg Lys Asp Glu Glu Arg Asn Lys
             20                  25                  30

Thr Gln Glu Glu His Leu Lys Glu Ile Met Lys His Ile Val Lys Ile
         35                  40                  45

Glu Val Lys Gly Glu Glu Ala Val Lys Lys Glu Ala Ala Glu Lys Leu
     50                  55                  60

Leu Glu Lys Val Pro Ser Asp Val Leu Glu Met Tyr Lys Ala Ile Gly
 65                  70                  75                  80

Gly Lys Ile Tyr Ile Val Asp Gly Asp Ile Thr Lys His Ile Ser Leu
```

|   |   | 85 |   |   |   | 90 |   |   |   | 95 |   |
|---|---|---|---|---|---|---|---|---|---|---|---|

Glu Ala Leu Ser Glu Asp Lys Lys Ile Lys Asp Ile Tyr Gly Lys
    100      105      110

Asp Ala Leu Leu His Glu His Tyr Val Tyr Ala Lys Glu Gly Tyr Glu
   115      120      125

Pro Val Leu Val Ile Gln Ser Ser Glu Asp Tyr Val Glu Asn Thr Glu
   130      135      140

Lys Ala Leu Asn Val Tyr Tyr Glu Ile Gly Lys Ile Leu Ser Arg Asp
145      150      155      160

Ile Leu Ser Lys Ile Asn Gln Pro Tyr Gln Lys Phe Leu Asp Val Leu
    165      170      175

Asn Thr Ile Lys Asn Ala Ser Asp Ser Asp Gly Gln Asp Leu Leu Phe
   180      185      190

Thr Asn Gln Leu Lys Glu His Pro Thr Asp Phe Ser Val Glu Phe Leu
   195      200      205

Glu Gln Asn Ser Asn Glu Val Gln Glu Val Phe Ala Lys Ala Phe Ala
210      215      220

Tyr Tyr Ile Glu Pro Gln His Arg Asp Val Leu Gln Leu Tyr Ala Pro
225      230      235      240

Glu Ala Phe Asn Tyr Met Asp Lys Phe Asn Glu Gln Glu Ile Asn Leu
    245      250      255

Ser Leu Glu Glu Leu Lys Asp Gln Arg Met Leu Ser Arg Tyr Glu Lys
   260      265      270

Trp Glu Lys Ile Lys Gln His Tyr Gln His Trp Ser Asp Ser Leu Ser
   275      280      285

Glu Glu Gly Arg Gly Leu Leu Lys Lys Leu Gln Ile Pro Ile Glu Pro
290      295      300

Lys Lys Asp Asp Ile Ile His Ser Leu Ser Gln Glu Glu Lys Glu Leu
305      310      315      320

Leu Lys Arg Ile Gln Ile Asp Ser Ser Asp Phe Leu Ser Thr Glu Glu
    325      330      335

Lys Glu Phe Leu Lys Lys Leu Gln Ile Asp Ile Arg Asp Ser Leu Ser
   340      345      350

Glu Glu Glu Lys Glu Leu Leu Asn Arg Ile Gln Val Asp Ser Ser Asn
   355      360      365

Pro Leu Ser Glu Lys Glu Lys Glu Phe Leu Lys Lys Leu Lys Leu Asp
   370      375      380

Ile Gln Pro Tyr Asp Ile Asn Gln Arg Leu Gln Asp Thr Gly Gly Leu
385      390      395      400

Ile

<210> SEQ ID NO 33
<211> LENGTH: 924
<212> TYPE: DNA
<213> ORGANISM: Bacillus anthracis
<220> FEATURE:
<221> NAME/KEY: CDS
<222> LOCATION:
<223> OTHER INFORMATION: DNA coding sequence from pBP120 for a LF
   deletion mutant LF40.

<400> SEQUENCE: 33
catatggcgg gcggtcatgg tgatgtaggt atgcacgtaa aagagaaaga gaaaaataaa  60
gatgagaata agagaaaaga tgaagaacga aataaaacac aggaagagca tttaaaggaa 120
atcatgaaac acattgtaaa aatagaagta aaaggggagg aagctgttaa aaaagaggca 180

```
gcagaaaagc tacttgagaa agtaccatct gatgttttag agatgtataa agcaattgga    240
ggaaagatat atattgtgga tggtgatatt acaaaacata tatctttaga agcattatct    300
gaagataaga aaaaaataaa agacatttat gggaaagatg ctttattaca tgaacattat    360
gtatatgcaa agaaggata tgaacccgta cttgtaatcc aatcttcgga agattatgta    420
gaaaatactg aaaaggcact gaacgtttat tatgaaatag gtaagatatt atcaagggat    480 atttttaagta aaattaatca accatatcag aaattttag atgtattaaa taccattaaa    540
aatgcatctg attcagatgg acaagatctt ttatttacta atcagcttaa ggaacatccc    600
acagactttt ctgtagaatt cttggaacaa aatagcaatg aggtacaaga agtatttgcg    660
aaagcttttg catattatat cgagccacag catcgtgatg ttttacagct ttatgcaccg    720 gaagcttta attacatgga taaatttaac gaacaagaaa taaatctatc cttggaagaa    780
cttaaagatc aacggatgct gtcaagatat gaaaaatggg aaaagataaa acagcactat    840
caacactgga gcgattcttt atctgaagaa ggaagaggac tttaaaaaa gctgcagatt    900 cctattgagc aaagaaaga ttaa                                           924
```

<210> SEQ ID NO 34
<211> LENGTH: 307
<212> TYPE: PRT
<213> ORGANISM: Bacillus anthracis
<220> FEATURE:
<221> NAME/KEY: MUTAGEN
<222> LOCATION:
<223> OTHER INFORMATION: Amino acid sequence of a LF deletion mutant LF40.

<400> SEQUENCE: 34

```
His Met Ala Gly Gly His Gly Asp Val Gly Met His Val Lys Glu Lys
 1               5                  10                  15

Glu Lys Asn Lys Asp Glu Asn Lys Arg Lys Asp Glu Glu Arg Asn Lys
             20                  25                  30

Thr Gln Glu Glu His Leu Lys Glu Ile Met Lys His Ile Val Lys Ile
         35                  40                  45

Glu Val Lys Gly Glu Glu Ala Val Lys Lys Glu Ala Ala Glu Lys Leu
     50                  55                  60

Leu Glu Lys Val Pro Ser Asp Val Leu Glu Met Tyr Lys Ala Ile Gly
 65                  70                  75                  80

Gly Lys Ile Tyr Ile Val Asp Gly Asp Ile Thr Lys His Ile Ser Leu
                 85                  90                  95

Glu Ala Leu Ser Glu Asp Lys Lys Lys Ile Lys Asp Ile Tyr Gly Lys
            100                 105                 110

Asp Ala Leu Leu His Glu His Tyr Val Tyr Ala Lys Glu Gly Tyr Glu
        115                 120                 125

Pro Val Leu Val Ile Gln Ser Ser Glu Asp Tyr Val Glu Asn Thr Glu
    130                 135                 140

Lys Ala Leu Asn Val Tyr Tyr Glu Ile Gly Lys Ile Leu Ser Arg Asp
145                 150                 155                 160

Ile Leu Ser Lys Ile Asn Gln Pro Tyr Gln Lys Phe Leu Asp Val Leu
                165                 170                 175

Asn Thr Ile Lys Asn Ala Ser Asp Ser Asp Gly Gln Asp Leu Leu Phe
            180                 185                 190

Thr Asn Gln Leu Lys Glu His Pro Thr Asp Phe Ser Val Glu Phe Leu
        195                 200                 205
```

-continued

```
Glu Gln Asn Ser Asn Glu Val Gln Glu Val Phe Ala Lys Ala Phe Ala
    210                 215                 220

Tyr Tyr Ile Glu Pro Gln His Arg Asp Val Leu Gln Leu Tyr Ala Pro
225                 230                 235                 240

Glu Ala Phe Asn Tyr Met Asp Lys Phe Asn Glu Gln Glu Ile Asn Leu
                245                 250                 255

Ser Leu Glu Glu Leu Lys Asp Gln Arg Met Leu Ser Arg Tyr Glu Lys
            260                 265                 270

Trp Glu Lys Ile Lys Gln His Tyr Gln His Trp Ser Asp Ser Leu Ser
        275                 280                 285

Glu Glu Gly Arg Gly Leu Leu Lys Lys Leu Gln Ile Pro Ile Glu Pro
    290                 295                 300

Lys Lys Asp
305
```

We claim:

1. An immunogenic composition comprising a recombinant *B. anthracis* PA (rPA) protein comprising the amino acid sequence set forth in SEQ ID NO: 9 and a recombinant *B. anthracis* LF (rLF) protein comprising the amino acid sequence set forth in SEQ ID NO: 6.

2. The composition of claim 1, further comprising at least one adjuvant.

3. The immunogenic composition of claim 2, wherein said adjuvant is aluminum hydroxide, an immunostimulatory sequence (ISS), CpG, or calcium phosphate.

4. A method of producing an immunogenic response in an animal comprising the step of: administering to an animal the immunogenic composition of claim 1.

5. The method of claim 4, wherein the composition comprises rPA to rLF at a ratio of 5:2.

6. The method of claim 4, further comprising the step of administering at least one adjuvant to the animal.

7. The method of claim 5, wherein said adjuvant is aluminum hydroxide, an immunostimulatory sequence (ISS), CpG, or calcium phosphate.

8. The method of claim 7, wherein the composition comprises 50 μg rPA and 20 μg rLF per 0.5 ml of the aluminum hydroxide.

* * * * *